US011939586B2

(12) United States Patent
De Veylder et al.

(10) Patent No.: US 11,939,586 B2
(45) Date of Patent: Mar. 26, 2024

(54) MEANS AND METHODS FOR IMPROVED REGENERATION

(71) Applicants: VIB VZW, Ghent (BE); UNIVERSITEIT GENT, Ghent (BE)

(72) Inventors: Lieven De Veylder, Drongen (BE); Jefri Heyman, Roosdaal (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 384 days.

(21) Appl. No.: 16/340,949

(22) PCT Filed: Oct. 11, 2017

(86) PCT No.: PCT/EP2017/075937
§ 371 (c)(1),
(2) Date: Apr. 10, 2019

(87) PCT Pub. No.: WO2018/069392
PCT Pub. Date: Apr. 19, 2018

(65) Prior Publication Data
US 2019/0225976 A1    Jul. 25, 2019

(30) Foreign Application Priority Data
Oct. 11, 2016  (EP) ..................................... 16193308

(51) Int. Cl.
| | | |
|---|---|---|
| *C12N 15/82* | (2006.01) | |
| *C07K 14/415* | (2006.01) | |
| *C12N 9/00* | (2006.01) | |
| *C12N 15/113* | (2010.01) | |

(52) U.S. Cl.
CPC ........ *C12N 15/8241* (2013.01); *C07K 14/415* (2013.01); *C12N 9/00* (2013.01); *C12N 15/113* (2013.01); *C12N 2800/24* (2013.01); *C12N 2800/30* (2013.01); *C12N 2820/65* (2013.01); *C12N 2830/50* (2013.01); *C12N 2830/65* (2013.01)

(58) Field of Classification Search
None
See application file for complete search history.

(56) References Cited

U.S. PATENT DOCUMENTS 10,968,458 B2 *  4/2021  Gordon-Kamm ...........................
                                                C12N 15/8262

FOREIGN PATENT DOCUMENTS

| EP | 2719763 A1 * | 4/2014 | ......... C12N 15/8286 |
|---|---|---|---|
| EP | 2719763 A1 | 4/2014 | |

OTHER PUBLICATIONS

Bolle et al. PAT1, a new member of the GRAS family, is involved in phytochrome A signal transduction. Genes Dev. May 15, 2000; 14(10):1269-78. (Year: 2000).*
Torres-Galea et al. Two GRAS proteins, Scarecrow-LIKE21 and Phytochrome A Signal TRANSDUCTION1, function cooperatively in phytochrome A signal transduction. Plant Physiol. Jan. 2013;161(1):291-304. Epub Oct. 29, 2012. (Year: 2013).*
Jones et al. Transient transformation of plants. Methods Mol. Biol.513, 131-152 (2009). (Year: 2009).*
Karimi et al. Gateway vectors for transformation of cereals. Trends Plant Sci. Jan. 2013;18(1):1-4. Epub Oct. 30, 2012. (Year: 2013).*
Heyman et al. ERF115 controls root quiescent center cell division and stem cell replenishment. Science. Nov. 15, 2013;342(6160):860-3. Epub Oct. 24, 2013 (Year: 2013).*
Feng. Advances in AP2/ERF super-family transcription factors in plant. Critical Reviews in Biotechnology, 2020, vol. 40, No. 6, 750-776. (Year: 2020).*
Bolle C et al., "PAT1, a new member of the GRAS family, is involved in phytochrome A signal transduction", Genes and Development, Cold Spring Harbor Laboratory Press, Plainview, NY, US, vol. 14, No. 10, May 1, 2002 (May 1, 2002 ), pp. 1269-1278, XP002965851, ISSN: 0890-9369.
Heyman et al., "ERF115 Controls Root Quiescent Center Cell Division and Stem Cell Replenishment", Science, vol. 342, No. 6160, Nov. 15, 2013 (Nov. 15, 2013), pp. 860-863, XP055431874, ISSN: 0036-8075, DOI: 10.1126/science.1240667.
Huang et al., "A Root-Knot Nematode Secretory Peptide Functions as a Ligand for a Plant Transcription Factor", Molecular Plant-Microbe Interactions, vol. 19, No. 5, May 1, 2006 (May 1, 2006 ), pp. 463-470, XP055431911, US ISSN: 0894-0282, DOI: 10.1094/MPMI-19-0463.
PCT International Search Report and Written Opinion, Application No. PCT/EP2017/075937, dated Dec. 22, 2017, 10 pages.
Torres-Galea et al., "Two GRAS Proteins, Scarecrow-LIKE21 and Phytochrome A Signal TRANSDUCTION1 , Function Cooperatively in Phytochrome A Signal Transduction", Plant Physiology, vol. 161, No. 1, Jan. 1, 2013 (Jan. 1, 2013), pp. 291-304, XP055432062, Rockville, Md, USA ISSN: 0032-0889, DOI: 10.1104/pp.112.206607.

* cited by examiner

Primary Examiner — Cynthia E Collins
(74) Attorney, Agent, or Firm — Patent Law Works LLP

(57) ABSTRACT

The present invention relates to the field of plant genetic engineering, particularly the modulation of gene expression in plant cells for improved regeneration competence. The invention discloses means and methods wherein the Ethylene Response Factor (ERF) and Phytochrome A Signal Transduction 1 (PAT1) transcription factor complex activity in plant cells grants increased regeneration.

16 Claims, 15 Drawing Sheets
(14 of 15 Drawing Sheet(s) Filed in Color)
Specification includes a Sequence Listing.

SEQUENCE LISTING

<160> NUMBER OF SEQ ID NOS: 245

<210> SEQ ID NO 1
<211> LENGTH: 263

```
<212> TYPE: PRT
<213> ORGANISM: Arabidopsis thaliana

<400> SEQUENCE: 1

Met Ala Asn Ser Gly Asn Tyr Gly Lys Arg Pro Phe Arg Gly Asp Glu
1               5                   10                  15

Ser Asp Glu Lys Lys Glu Ala Asp Asp Glu Asn Ile Phe Pro Phe
            20                  25                  30

Phe Ser Ala Arg Ser Gln Tyr Asp Met Arg Ala Met Val Ser Ala Leu
            35                  40                  45

Thr Gln Val Ile Gly Asn Gln Ser Ser Ser His Asp Asn Asn Gln His
    50                  55                  60

Gln Pro Val Val Tyr Asn Gln Asp Pro Asn Pro Ala Pro Pro
65                  70                  75                  80

Thr Gln Asp Gln Gly Leu Leu Arg Lys Arg His Tyr Arg Gly Val Arg
                85                  90                  95

Gln Arg Pro Trp Gly Lys Trp Ala Ala Glu Ile Arg Asp Pro Gln Lys
            100                 105                 110

Ala Ala Arg Val Trp Leu Gly Thr Phe Glu Thr Ala Glu Ala Ala Ala
        115                 120                 125

Leu Ala Tyr Asp Asn Ala Ala Leu Lys Phe Lys Gly Ser Lys Ala Lys
    130                 135                 140

Leu Asn Phe Pro Glu Arg Ala Gln Leu Ala Ser Asn Thr Ser Thr Thr
145                 150                 155                 160

Thr Gly Pro Pro Asn Tyr Tyr Ser Ser Asn Asn Gln Ile Tyr Tyr Ser
                165                 170                 175

Asn Pro Gln Thr Asn Pro Gln Thr Ile Pro Tyr Phe Asn Gln Tyr Tyr
            180                 185                 190

Tyr Asn Gln Tyr Leu His Gln Gly Gly Asn Ser Asn Asp Ala Leu Ser
        195                 200                 205

Tyr Ser Leu Ala Gly Gly Glu Thr Gly Ser Met Tyr Asn His Gln
    210                 215                 220

Thr Leu Ser Thr Thr Asn Ser Ser Ser Gly Gly Ser Ser Arg Gln
225                 230                 235                 240

Gln Asp Asp Glu Gln Asp Tyr Ala Arg Tyr Leu Arg Phe Gly Asp Ser
                245                 250                 255

Ser Pro Pro Asn Ser Gly Phe
            260

<210> SEQ ID NO 2
<211> LENGTH: 422
<212> TYPE: PRT
<213> ORGANISM: Zea mays

<400> SEQUENCE: 2

Met Glu Arg Val Lys Tyr Cys Asp Cys Thr Val Cys Ser Val Gln Arg
1               5                   10                  15

Ser Leu Cys Ser Thr Arg Arg Arg Arg Arg Arg Gln Ile Asp
            20                  25                  30

Arg Gln Leu Thr Lys Val Asp Pro Arg Arg His Gly Lys Arg Pro
            35                  40                  45

Leu Pro Ala Ala Glu Val Glu Glu Glu Glu Glu Ala Leu Pro
    50                  55                  60

Pro Gly Pro Pro Pro Ala Lys His Glu Gln Leu Glu Glu Pro His His
65                  70                  75                  80
```

```
Ala Ala Val Ser Gln Leu Gln Gly Ala Thr Phe Ser Gly Gly Gly
                85                  90                  95

Ser Ser Ser Ser Ser Val Ile Gly Gly Pro Ser Pro Gln Ala Tyr
            100                 105                 110

Ala Gln Tyr Tyr Tyr Ser Ala Arg Ala Asp Asn Asp Ala Ser Ala Val
        115                 120                 125

Ala Ser Ala Leu Ala His Val Ile Arg Ala Ser Pro Asp Gln Leu Pro
    130                 135                 140

Pro Gln Gln Ala Pro Ala Leu Tyr Gly Ala Gly Val Pro Gly Ser Leu
145                 150                 155                 160

Arg Leu Gly Asp His Pro Gln Ala Ser Ala His His Tyr Pro Gly Pro
                165                 170                 175

Gly Gly His Val Ala Ala Ala Glu Glu Glu Gln Gly Arg Arg Arg His
            180                 185                 190

Tyr Arg Gly Val Arg Gln Arg Pro Trp Gly Lys Trp Ala Ala Glu Ile
        195                 200                 205

Arg Asp Pro Lys Lys Ala Ala Arg Val Trp Leu Gly Thr Phe Asp Thr
    210                 215                 220

Ala Glu Asp Ala Ala Ile Ala Tyr Asp Glu Ala Ala Leu Arg Phe Lys
225                 230                 235                 240

Gly Thr Lys Ala Lys Leu Asn Phe Pro Glu Arg Val Gln Gly Arg Thr
                245                 250                 255

Asp Leu Gly Phe Leu Val Thr Arg Gly Ile Pro Asp His Arg His Pro
            260                 265                 270

Ser Ala Ala Val Thr Leu Ala Ala Met Pro Pro Pro His His Gln His
        275                 280                 285

Gly His Gln Thr Val Val Pro Tyr Pro Asp Leu Met Gln Tyr Ala Gln
    290                 295                 300

Leu Leu Gln Gly Gly Arg Gly Gly Gly His Ala Glu Ala Ala Val
305                 310                 315                 320

Gln Gln Ala His Arg Gln Gln Gln Gln Gln Leu Met Thr Met Met
                325                 330                 335

Gly Gly Arg Pro Gly Val Asn Leu Pro Ser Thr Phe Ser Pro Ser Ser
            340                 345                 350

Ser Ala Ser Ala Pro Gln Ile Leu Asp Phe Ser Thr Gln Gln Leu Ile
        355                 360                 365

Arg Pro Gly Pro Pro Ser Pro Ser Pro Arg Ala Ala Met Pro
    370                 375                 380

Ser Ser Ser Ala Ala Ala Ala Pro Ser Thr Pro Ser Ser Thr Thr Thr
385                 390                 395                 400

Ala Ser Ser Pro Ser Gly Gly Ala Trp Pro Tyr Gly Gly Glu Arg His
                405                 410                 415

Arg Asn Lys Lys Asp Ala
            420

<210> SEQ ID NO 3
<211> LENGTH: 443
<212> TYPE: PRT
<213> ORGANISM: Zea mays

<400> SEQUENCE: 3

Met Arg Ile Ser Leu Arg Val Leu Ile Ser Ser Glu Leu Gly Thr Ser
1               5                   10                  15

Leu Cys Thr Ala Ala Pro Ser Leu Ala Arg Ala Ser Val Arg Lys Ser
            20                  25                  30
```

```
Lys Ser Ser Ala Leu Ser Leu Thr His Ala Arg Ile Asp Arg Ser Ser
            35                  40                  45

Ser Thr His Arg Arg Arg Gln Ile Asn Gly Gln Leu Thr Lys Val
    50                  55                  60

Asp Pro Arg Arg His Gly Lys Arg Pro Leu Pro Ala Asp Glu Glu
65              70                  75                  80

Glu Glu Glu Glu Glu Leu Pro Pro Pro Ala Lys Tyr Glu Gln
                85                  90                  95

Leu Asp Gln Glu Glu Lys His His Val Val Ser Gln Leu Gln Ala
                100             105                 110

Gly Ala Thr Phe Ser Gly Gly Arg Gly Ser Ser Ser Ser Val Ala
            115                 120                 125

Gly Pro Ser Pro Glu Ala Tyr Ala Gln Tyr Tyr Tyr Ser Ala Arg Ala
        130                 135                 140

Asp His Asp Ala Ser Ala Val Ala Ser Ala Leu Ala His Val Ile Arg
145                 150                 155                 160

Ala Ser Pro Asp Gln Leu Pro Pro Gln Gln Ala Ala Cys Leu Tyr Gly
                165                 170                 175

Ala Ala Gly Ala Pro Val Leu Arg Gln Gly Glu Gly Asp His Pro Gln
            180                 185                 190

Pro Gln Ala Ala His His His Pro Gly Gly His Val Ala Ala Glu
        195                 200                 205

Glu Glu Gln Gly Leu Arg Arg His Tyr Arg Gly Val Arg Gln Arg Pro
        210                 215                 220

Trp Gly Lys Trp Ala Ala Glu Ile Arg Asp Pro Lys Lys Ala Ala Arg
225                 230                 235                 240

Val Trp Leu Gly Thr Phe Asp Thr Ala Glu Asp Ala Ala Ile Ala Tyr
                245                 250                 255

Asp Glu Ala Ala Leu Arg Phe Lys Gly Thr Lys Ala Lys Leu Asn Phe
                260                 265                 270

Pro Glu Arg Val Gln Gly Arg Thr Asp Leu Gly Phe Val Val Thr Arg
        275                 280                 285

Gly Ile Pro Asp His His Arg His Pro Arg Ala Ala Val Asn Leu
        290                 295                 300

Ala Ala Met Pro Gln Ala Gln Ala Gln Pro His Leu Gln His Gly Arg
305                 310                 315                 320

Pro Thr Val Met Pro Tyr Pro Tyr Pro Tyr Pro Asp Leu Met Gln Tyr
                325                 330                 335

Ala Gln Leu Leu Gln Gly Gly Arg Gly Gly Asp His Ala Ala
            340                 345                 350

Val Gln Gln Gln Leu Met Met Met Gly Gly Arg Gly Gly Asn Leu Pro
        355                 360                 365

Phe Ser Phe Ser Pro Pro Ser Ser Trp Ser Ala Pro Pro Gln Ile Leu
        370                 375                 380

Asp Phe Ser Ala Arg Gln Leu Ile Thr Gln Pro Gly Pro Pro Ser Ser
385                 390                 395                 400

Pro Ala Ala Pro Gly Gly Ala Ala Pro Ser Thr Pro Ser Ser Thr
            405                 410                 415

Thr Ala Ser Ser Pro Ser Ala Ser Ala Ser Gly Ser Ala Trp Pro Tyr
                420                 425                 430

Gly Gly Glu His His Arg Asn Lys Lys Asp Ala
            435                 440
```

<210> SEQ ID NO 4
<211> LENGTH: 357
<212> TYPE: PRT
<213> ORGANISM: Zea mays

<400> SEQUENCE: 4

```
Met Cys Phe Glu Leu Ala Asp Gln Arg Gly Pro Gln Gly Gly Gly Gly
1               5                   10                  15

Ala Gly Trp Pro Ala Lys Arg Arg Ala Gly Val Gln Asp Glu Gly
            20                  25                  30

Ala Ala Ala Ala Ala Gly Met Ala Met Ala Ala Gly Pro Gly Glu
        35                  40                  45

Val Met Ser Glu Tyr Tyr Gln Ala Gln Glu Leu Ser Thr Met Val Ser
    50                  55                  60

Ala Leu Thr His Val Val Ala Gly Ala Pro Met Gly Ser Ala Pro Ala
65                  70                  75                  80

Gln Arg Pro Met His Gly Ala Ser Gly Tyr Tyr Ala His Glu Met Gly
                85                  90                  95

Ser Tyr Arg Gly Ala Pro Ser Pro Glu Leu Ala Gly Ser Glu Leu Ser
            100                 105                 110

Ser Asp Thr Gln Ser Ala Gly Ala Ala Met Glu Glu His Gln Ser
        115                 120                 125

Ala Ala Ala Leu Ser Ser Gln Glu Gly Pro Glu Thr Pro Arg Arg Arg
130                 135                 140

Tyr Arg Gly Val Arg Gln Arg Pro Trp Gly Lys Trp Ala Ala Glu Ile
145                 150                 155                 160

Arg Asp Pro His Lys Ala Ala Arg Val Trp Leu Gly Thr Phe Glu Thr
                165                 170                 175

Ala Glu Ala Ala Ala Arg Ala Tyr Asp Glu Ala Ala Leu Arg Phe Arg
            180                 185                 190

Gly Ser Arg Ala Lys Leu Asn Phe Pro Glu Asp Ala Arg Leu Tyr Pro
        195                 200                 205

Ala Ser Thr Ala Gly Ala Ala Pro Leu Ala Ala Ala Ser Thr
    210                 215                 220

Ser Pro Pro Val Tyr Ser Gly Gly Val Gln Gly Ser Ser Asp Tyr Leu
225                 230                 235                 240

Arg Tyr His Gln Met Leu Leu Gln Ala Ser Thr Gly Ser Gln Gly Thr
                245                 250                 255

Leu Leu Pro Phe Tyr Gly Gly Met Ser Asn Pro Tyr Gly Gly
            260                 265                 270

Ala Ala Met Thr Gly Ser Tyr Gly Gly Ala Gly Gly Asn Thr Ser
        275                 280                 285

Gly Ser Leu Gly Ser Tyr Tyr Ser Phe Pro Ala Ser Ser Val Ser Val
290                 295                 300

Ala Thr Val Pro Ser Ser Thr Ser Ser Ala Ser Gly Tyr Tyr Tyr Ser
305                 310                 315                 320

Ser Pro His Asp Ser Gln His Ser Glu Ala Ser Ala Ala Asp Trp
                325                 330                 335

Asn Trp Glu Ser Ala Leu Ala Trp Pro Asp Ser Gly Tyr Pro Pro
            340                 345                 350

Pro Pro His Thr Gln
        355
```

<210> SEQ ID NO 5

<211> LENGTH: 134
<212> TYPE: PRT
<213> ORGANISM: Vitis vinifera

<400> SEQUENCE: 5

```
Met Ser Ala Met Val Ser Ala Leu Thr Gln Val Ile Gly Asn Thr Asp
1               5                   10                  15

Lys Asn Pro Leu His Asp Leu Gly Asn Pro Ser Pro Ile Ser His His
            20                  25                  30

Ser Ala Thr Thr Pro His Asp Gln Pro Ser Gln Leu Leu Gln Asp Gln
        35                  40                  45

Gly Asn Gln Leu Arg Arg Arg His Tyr Arg Gly Val Arg Gln Arg Pro
    50                  55                  60

Trp Gly Lys Trp Ala Ala Glu Ile Arg Asp Pro Asn Lys Ala Ala Arg
65                  70                  75                  80

Val Trp Leu Gly Thr Phe Asp Thr Ala Glu Asp Ala Ala Leu Ala Tyr
                85                  90                  95

Asp Glu Ala Ala Leu Arg Phe Lys Gly Asn Lys Ala Lys Leu Asn Phe
            100                 105                 110

Pro Glu Arg Val Gln Gly Arg Ser Glu Leu Gly Tyr Leu Thr Asn Pro
        115                 120                 125

Pro Ser Arg Trp Arg Trp
        130
```

<210> SEQ ID NO 6
<211> LENGTH: 246
<212> TYPE: PRT
<213> ORGANISM: Vitis vinifera

<400> SEQUENCE: 6

```
Met Ser Ala Met Val Ser Ala Leu Thr Gln Val Ile Gly Asn Thr Asp
1               5                   10                  15

Lys Asn Pro Leu His Asp Leu Gly Asn Pro Ser Pro Ile Ser His His
            20                  25                  30

Ser Ala Thr Thr Pro His Asp Gln Pro Ser Gln Leu Leu Gln Asp Gln
        35                  40                  45

Gly Asn Gln Leu Arg Arg Arg His Tyr Arg Gly Val Arg Gln Arg Pro
    50                  55                  60

Trp Gly Lys Trp Ala Ala Glu Ile Arg Asp Pro Asn Lys Ala Ala Arg
65                  70                  75                  80

Val Trp Leu Gly Thr Phe Asp Thr Ala Glu Asp Ala Ala Leu Ala Tyr
                85                  90                  95

Asp Glu Ala Ala Leu Arg Phe Lys Gly Asn Lys Ala Lys Leu Asn Phe
            100                 105                 110

Pro Glu Arg Val Gln Gly Arg Ser Glu Leu Gly Tyr Leu Thr Asn Arg
        115                 120                 125

Gln Asp Phe Leu Leu Pro Gln Gln Gln Leu Pro Asn Pro Ala Val
    130                 135                 140

Pro Pro Leu Pro His Pro Ser Leu Pro Arg Pro Ser Tyr Pro Asn Leu
145                 150                 155                 160

His His Tyr Ala Gln Leu Leu Pro Gly Gly Gly Asp Leu Asn His
                165                 170                 175

Ala Met Ser Ser Leu Tyr Gly Arg Glu Ala Ser Thr Thr Gln Ser Leu
            180                 185                 190

Ser Thr Thr Ser Ser Ser Ser Thr Thr Ser His Pro Gln His His
        195                 200                 205
```

Gln Arg Arg Arg Gln Arg Glu Glu Glu Leu Gln Gln Pro Gln Leu
    210                 215                 220

Leu Gln Phe Ser Ser Leu Phe Gly Ser Ser Ser Asn Asp Pro His
225                 230                 235                 240

Asn Asn Arg Arg Asp Asp
            245

<210> SEQ ID NO 7
<211> LENGTH: 240
<212> TYPE: PRT
<213> ORGANISM: Populus trichocarpa

<400> SEQUENCE: 7

Met Asp Val Met Val Ser Ala Leu Ala Gln Val Ile Gly Ser Ser His
1               5                   10                  15

Asn Ser Ser Ala Gln Val Gln Glu Asn Pro Leu Thr Ser Thr Gln Ser
                20                  25                  30

Ser Thr Glu Asn Asp Gln Thr Gln Pro Ala Val Gln Asp Gln Gly Asn
            35                  40                  45

Ala Arg Arg Arg His Tyr Arg Gly Val Arg Gln Arg Pro Trp Gly Lys
        50                  55                  60

Trp Ala Ala Glu Ile Arg Asp Pro Lys Lys Ala Ala Arg Val Trp Leu
65                  70                  75                  80

Gly Thr Phe Glu Thr Ala Glu Ala Ala Ala Leu Ala Tyr Asp Glu Ala
                85                  90                  95

Ala Leu Arg Phe Lys Gly Ser Lys Ala Lys Leu Asn Phe Pro Glu Arg
                100                 105                 110

Val Pro Ser Gly Gly Thr Glu Leu Gly Phe Phe Thr Arg Gly Gln Gly
            115                 120                 125

Leu His Thr Val Thr Glu Pro Val Ser Asn His Ile Met Ala Pro Leu
130                 135                 140

Ala Arg Ser Gln Arg Ser Gln Glu Ala Tyr Asn Pro Asn Asn Phe Gln
145                 150                 155                 160

Tyr Pro Gln Phe Leu Gly Thr Thr Ser Gly Tyr Gly Leu Ser His Val
                165                 170                 175

Met Pro Pro Ala Val Pro Phe Gly Gly Glu Thr Phe Leu Ser Pro Thr
                180                 185                 190

Ser Ser Ser Ala Ser Ser Asn Ser Trp Pro Ile Ser Ser Gln Gln Gln
            195                 200                 205

Gln Gln Gln Gln Glu Glu Leu Leu Arg Leu Ser Met Gln Phe Gly Ser
        210                 215                 220

Ser Tyr Asn Ser Arg Tyr Asp Pro Ser Lys Tyr Lys Asp Glu Gly Leu
225                 230                 235                 240

<210> SEQ ID NO 8
<211> LENGTH: 289
<212> TYPE: PRT
<213> ORGANISM: Solanum lycopersicum

<400> SEQUENCE: 8

Met Asp Arg Ile Arg Arg Gly Lys Arg Arg Tyr Glu Ser Glu Glu Lys
1               5                   10                  15

Glu Asp Arg Asn Tyr Asn His Met Tyr Ser Ser Ala Arg Ser Gln His
                20                  25                  30

Asp Met Ser Thr Met Val Ala Val Leu Ser Gln Val Ile Gly Asn Lys
            35                  40                  45

Ser Thr Thr Asn Thr Asn Ser Ser Ser Ser Ser Ala His His Lys
    50                      55                      60

Pro Leu Leu Thr Leu Asn His Gln Ser Asn Thr Ala Ala Met Gln
65                      70                      75                  80

Asn Gln Leu Pro Gln Leu Asn Gln Gln Gln Gly Asn Asn Glu Lys Arg
                    85                      90                      95

Arg Arg Gln Tyr Arg Gly Val Arg Gln Arg Pro Trp Gly Lys Trp Ala
                100                     105                     110

Ala Glu Ile Arg Asp Pro Glu Lys Ala Ala Arg Val Trp Leu Gly Thr
            115                     120                     125

Phe His Thr Ala Glu Asp Ala Ala Ile Ala Tyr Asp Glu Ala Ala Leu
        130                     135                     140

Lys Phe Lys Gly Asn Lys Ala Lys Leu Asn Phe Pro Glu Arg Val Gln
145                     150                     155                     160

Ser Thr Thr Asp Gln Phe Gly Ile Ser Tyr Leu Ile Thr Asn Thr Asn
                    165                     170                     175

His Gln Gln His Gln Phe Gln Pro Thr Asn Phe Leu Pro Asn Ser Asp
                180                     185                     190

Gln Leu Gln Gln His His Tyr Ser Asn His Asn Ala Asp Asp Leu Lys
            195                     200                     205

Phe Gly Val Ser Pro Ser Phe Tyr His Pro Thr Gly Phe Asn Pro Lys
        210                     215                     220

Ala Leu Asp Leu Val Glu Pro Ser Lys Ser Ser Ser Met Thr Tyr Leu
225                     230                     235                     240

Val Gln Gln Ala Ser Ser His Gln Val Gln Glu Glu Pro Arg Tyr Ile
                    245                     250                     255

Asn His Gln Gln Glu Asp Glu Asn Asn Leu Lys Phe Ser Ser Tyr Phe
                260                     265                     270

Gly Thr Tyr Ser Ser Ser Gly Pro Thr Leu Gly Glu Phe Glu Asp Gln
            275                     280                     285

Lys

<210> SEQ ID NO 9
<211> LENGTH: 244
<212> TYPE: PRT
<213> ORGANISM: Solanum lycopersicum

<400> SEQUENCE: 9

Met Lys Arg Ser Ser Asn Asn Asp Gln Arg Asp Glu Lys Asp Thr
1               5                       10                      15

Ser Asn Ile Phe Pro Ile Tyr Ser Ser Ala Arg Ser Gln His Asp Met
                    20                      25                      30

Ser Ala Met Val Ser Ala Leu Ser Gln Val Ile Gly Asn Ser Ser Ser
            35                      40                      45

Ser Ala Ser Gly Asp Ser Ser Val His Val Asn Pro Leu Thr Leu
        50                      55                      60

Ile Gln Gln His Gln Ser Gln Ser Ser Thr Gln Asp Gln Glu Arg Arg
65                      70                      75                      80

Arg Tyr Arg Gly Val Arg Gln Arg Pro Trp Gly Lys Trp Ala Ala Glu
                    85                      90                      95

Ile Arg Asp Pro Lys Lys Ala Ala Arg Val Trp Leu Gly Thr Phe Glu
            100                     105                     110

Thr Ala Glu Gly Ala Ala Leu Ala Tyr Asp Glu Ala Ala Leu Arg Phe
        115                     120                     125

```
Lys Gly Asn Lys Ala Lys Leu Asn Phe Pro Glu Arg Val Gln Gly Gln
            130                 135                 140

Phe Phe Gln Cys Tyr Asp Gln Pro Ala Thr Ser Ser Asn Asn Thr Ser
145                 150                 155                 160

Glu Gln Asn Tyr Pro Asn Val His His Tyr Ala Asp Leu Leu Leu Arg
                165                 170                 175

Thr Asp Asn Asn Ile Asp Leu Asn Phe Asp Val Ser Pro Asn Thr Phe
            180                 185                 190

Tyr His Ser Phe Asp Ile Ser Gln Ser Ser Met Glu Val Pro Val Tyr
        195                 200                 205

His Glu Glu Gln Gln Val Ile Thr Thr His Glu Glu Glu Glu
    210                 215                 220

Asp Phe Val Lys Tyr Arg Gly Ser His Phe Gly Asn Ser Thr Ser Ser
225                 230                 235                 240

Gly Gly Thr Lys

<210> SEQ ID NO 10
<211> LENGTH: 230
<212> TYPE: PRT
<213> ORGANISM: Solanum tuberosum

<400> SEQUENCE: 10

Met Asp Arg Thr Arg His Gly Lys Arg Pro Tyr Glu Ser Glu Glu Lys
1               5                   10                  15

Glu Asp Thr Asn Asn Asn Gln Met Tyr Ser Ser Ala Arg Ser Gln His
            20                  25                  30

Asp Met Ser Thr Met Val Ser Val Leu Ser Gln Val Ile Gly Asn Lys
        35                  40                  45

Ser Arg Thr Asn Thr Asn Ser Ser Ser Ser Ser Ala His His Lys
    50                  55                  60

Pro Leu Leu Thr Leu Asn His Arg Ser Ser Thr Thr Ala Ala Met Gln
65                  70                  75                  80

Asn Gln Leu Pro Gln Leu Asn Gln Gln Gln Gly Asn Asn Glu Arg Arg
                85                  90                  95

Arg Arg Gln Tyr Arg Gly Val Arg Gln Arg Pro Trp Gly Lys Trp Ala
            100                 105                 110

Ala Glu Ile Arg Asp Pro Glu Lys Ala Ala Arg Val Trp Leu Gly Thr
        115                 120                 125

Phe His Thr Ala Glu Asp Ala Ala Ile Ala Tyr Asp Glu Ala Ala Leu
    130                 135                 140

Lys Phe Lys Gly Asn Lys Ala Lys Leu Asn Phe Pro Glu Arg Val Gln
145                 150                 155                 160

Ser Ala Thr Asp Gln Phe Gly Ile Ser Tyr Leu Ile Thr Thr Thr Asn
                165                 170                 175

Gln Phe Pro Ala Asn Lys Phe Leu Pro Asn Ser Asp Gln Leu Gln His
            180                 185                 190

His Tyr Ala Pro Ala Gly Gly Ser Asn His Asn Ala Asp Asp Leu Asn
        195                 200                 205

Phe Gly Val Ser Pro Ser Ser Tyr His Pro Thr Gly Lys Ser Thr Val
    210                 215                 220

Asn Asp Leu Ser Thr Gln
225                 230

<210> SEQ ID NO 11
```

```
<211> LENGTH: 269
<212> TYPE: PRT
<213> ORGANISM: Glycine max

<400> SEQUENCE: 11

Met Glu Gly Arg Ser Ile Ser His Ser Ser Glu Arg Glu Glu Tyr
1               5                   10                  15

Asp Leu Phe Pro Ile Tyr Ser Glu Arg Ser Gln Gln Asp Met Ser Ala
                20                  25                  30

Met Val Ser Ala Leu Thr Gln Val Ile Gly Gly Ser Asn Ser Asp Ser
            35                  40                  45

Leu Gln Gln His Glu Gly Leu Leu Thr Ser Ser His Asn Asn Thr Ser
    50                  55                  60

Thr Gln Asn Asn Asn Glu Gln Ser Gln Ala Pro Gln Gln Glu Gln Gly
65                  70                  75                  80

Ser Val Arg Arg Arg His Tyr Arg Gly Val Arg Gln Arg Pro Trp Gly
                85                  90                  95

Lys Trp Ala Ala Glu Ile Arg Asp Pro Lys Lys Ala Ala Arg Val Trp
                100                 105                 110

Leu Gly Thr Phe Glu Thr Ala Glu Ala Ala Leu Ala Tyr Asp Glu
            115                 120                 125

Ala Ala Leu Arg Phe Lys Gly Ser Lys Ala Lys Leu Asn Phe Pro Glu
    130                 135                 140

Arg Val Gln Gly Thr Ala Ser Glu Phe Gly Tyr His Leu Thr Asn Gln
145                 150                 155                 160

His Ser Thr Ser Ser His Asp Gln Gln Ala Ser Asn Pro Ile Ile Thr
                165                 170                 175

Pro His Phe Ala Thr Thr Gln Glu Thr Tyr Ser Pro Ser His His Phe
            180                 185                 190

Gln Tyr Ala Gln Gln Gln Leu Met Gly Gly Gly Ser Asn Ser Phe Asn
    195                 200                 205

Asn Asn Gln Asp Met Leu Arg Phe Tyr Gly Gly His Asn Met Phe Val
210                 215                 220

Ser Ser Gln Gln Ser Ala Ser Ser Ser Ser Thr Ala Leu Ser Gln
225                 230                 235                 240

Asn Gln Gln Asp Glu Leu Leu Arg Phe Ser Met Gln Phe Gly Ala Ser
                245                 250                 255

Ser His Ser Asp His Ser Gly Asn Trp Arg Gly Gly Gln
            260                 265

<210> SEQ ID NO 12
<211> LENGTH: 233
<212> TYPE: PRT
<213> ORGANISM: Gossypium raimondii

<400> SEQUENCE: 12

Met Asn Ala Met Val His Ala Leu Ala Gln Val Ile Gly Asn Asn
1               5                   10                  15

Ser Asn Pro Leu Leu Gln Leu His Asp Asp Gln His Pro Asn Pro Thr
                20                  25                  30

Ala Gln Gln Asn Gln Ser His Gln Gln Pro Gln Asp Gln Gly
            35                  40                  45

Asn Ala Arg Arg Arg His Tyr Arg Gly Val Arg Gln Arg Pro Trp Gly
    50                  55                  60

Lys Trp Ala Ala Glu Ile Arg Asp Pro Lys Lys Ala Ala Arg Val Trp
65                  70                  75                  80
```

-continued

```
Leu Gly Thr Phe Glu Thr Ala Glu Ala Ala Leu Ala Tyr Asp Asp
            85                  90                  95

Ala Ala Leu Arg Phe Lys Gly Ser Lys Ala Lys Leu Asn Phe Pro Glu
            100                 105                 110

Arg Val Gln Gly Arg Leu Glu Ser Ser Tyr Leu Thr Thr Thr Arg Gln
            115                 120                 125

Glu Leu Glu Arg Thr Glu Ala Pro Pro His Pro Pro Thr Tyr Pro
130                 135                 140

Asn Ile Ser Gln Tyr Ala Gln Leu Leu Ser Gly Gly Leu Pro Asn Thr
145                 150                 155                 160

Ala Phe Asn Tyr Ala Met Pro Ser Gly Ala Ala Tyr Gly Ser Trp Pro
                    165                 170                 175

Ala Phe Thr Thr Ser Ser His Ser Ser Ser Ser Ser Ser Ser Ser Thr
                    180                 185                 190

Thr Leu Thr Ser Gln Gln Gly Tyr Met Gly Gly Phe Ser Leu His
            195                 200                 205

Phe Gly Gly Ser Ser Pro Thr Ser Asp His Thr Asn Asn Met Gly Asp
            210                 215                 220

Tyr Asp Tyr Tyr Tyr Ser Arg Asp Gln
225                 230
```

<210> SEQ ID NO 13
<211> LENGTH: 255
<212> TYPE: PRT
<213> ORGANISM: Brassica rapa

<400> SEQUENCE: 13

```
Met Asn Asn Gly Lys Arg Pro Phe Arg Ala Gly Glu Ser Glu Lys
1               5                   10                  15

Lys Glu Ala Asp Asp Glu Asn Ile Phe Pro Phe Phe Ser Ala Arg
                20                  25                  30

Ser Glu Tyr Asp Thr Arg Ala Met Val Ser Ala Leu Thr Gln Val Ile
            35                  40                  45

Gly Asn Gln Ser Ser Thr His Asp Asn Asn Leu His His Pro Val Glu
50                  55                  60

Tyr Asp Gln Gln Asp Pro Ile Gln His Val Pro Pro Thr Gln Asp His
65                  70                  75                  80

Gly Asn Leu Arg Lys Ile His Tyr Arg Gly Val Arg Gln Arg Pro Trp
                    85                  90                  95

Gly Lys Trp Ala Ala Glu Ile Arg Asp Pro Gln Lys Ala Ala Arg Val
                    100                 105                 110

Trp Leu Gly Thr Phe Glu Thr Ala Glu Ala Ala Leu Ala Tyr Asp
            115                 120                 125

Glu Ala Ala Leu Lys Phe Lys Gly Ser Lys Ala Lys Leu Asn Phe Pro
130                 135                 140

Glu Arg Ala Gln Leu Ala Ser Asn Thr Ser Thr Ile Thr Gly Leu Pro
145                 150                 155                 160

Asn Tyr Tyr Ser Ser Asn Asn Gln Thr Tyr Tyr Ser Asn Pro Gln Thr
                    165                 170                 175

Asn Pro Gln Asn Ile Pro Tyr Tyr Asn Gln Tyr Tyr Asn Gln Tyr
            180                 185                 190

Leu Gln Gln Gly Gly Asn Ser Asn Asp Ala Leu Ser Tyr Ser Leu Ala
            195                 200                 205

Gly Gly Glu Thr Gly Gly Ser Ile Tyr Ser His Gln Thr Leu Ser Asn
```

```
                210              215                220
Thr Thr Ser Ser Pro Ala Gly Gly Ser Leu Arg Gln Gln Glu Asp Tyr
225                 230                 235                 240

Thr Arg Phe Trp His Phe Gly Asp Ser Ser Pro Asn Ser Gly Val
                245                 250                 255

<210> SEQ ID NO 14
<211> LENGTH: 253
<212> TYPE: PRT
<213> ORGANISM: Brassica rapa

<400> SEQUENCE: 14

Met Met Pro Phe Gly Ala Gly Glu Ser Asp Glu Arg Lys Glu Ala Asp
1               5                   10                  15

Asp Glu Glu Asn Ile Phe Pro Phe Leu Ser Ala Arg Ser Gln Tyr Asp
                20                  25                  30

Thr Arg Ala Met Val Ser Ala Leu Thr Gln Val Ile Gly Asn Gln Ser
            35                  40                  45

Ser Thr His Asp Ser Asn Gln His His Pro Val Glu Tyr Asn Gln Gln
        50                  55                  60

Asp Pro Ile Gln His Val Pro Pro Thr Gln Asp Gln Gly Asn Leu Arg
65                  70                  75                  80

Lys Arg His Tyr Arg Gly Val Arg Gln Arg Pro Trp Gly Lys Trp Ala
                85                  90                  95

Ala Glu Ile Arg Asp Pro Gln Lys Ala Ala Arg Val Trp Leu Gly Thr
                100                 105                 110

Phe Glu Thr Ala Glu Ala Ala Ala Leu Ala Tyr Asp Glu Ala Ala Leu
            115                 120                 125

Lys Phe Lys Gly Ser Lys Ala Lys Leu Asn Phe Pro Glu Arg Ala Gln
130                 135                 140

Leu Ala Ser Asn Ala Ser Thr Ile Thr Gly Leu Pro Asn Tyr His Ser
145                 150                 155                 160

Ser Asn Asn Gln Met Tyr Tyr Ser Asn Pro Gln Thr Asn Pro Gln Thr
                165                 170                 175

Met Pro Tyr Tyr Asn Gln Tyr Tyr Tyr Asn Gln Tyr Leu Gln Gln Gly
            180                 185                 190

Gly Asn Ser Asn Asp Ala Leu Ser Tyr Ser Leu Ala Gly Gly Glu Thr
        195                 200                 205

Gly Gly Ser Met Tyr Asn His Gln Ser Ile Ser Asn Thr Thr Ser Ser
    210                 215                 220

Ser Ser Gly Gly Ser Ser Arg Pro Gln Gln Glu Gln Asp Tyr Ala Arg
225                 230                 235                 240

Phe Trp His Phe Gly Asp Ser Ser Pro Ser Ser Gly Phe
                245                 250

<210> SEQ ID NO 15
<211> LENGTH: 250
<212> TYPE: PRT
<213> ORGANISM: Hordeum vulgare

<400> SEQUENCE: 15

Met Val Ser Ala Leu Ser His Val Ile Arg Ala Thr Pro Asp Gln Glu
1               5                   10                  15

Pro Ala Tyr Tyr Pro Ala Gly Pro Ala Ala Val Ser Arg Glu Gln Gln
                20                  25                  30

His Gln His Ala Ala Ala Ile Ala Glu Glu Gln Gly Arg Lys Arg His
```

```
            35                  40                  45
Tyr Arg Gly Val Arg Gln Arg Pro Trp Gly Lys Trp Ala Ala Glu Ile
 50                  55                  60

Arg Asp Pro Lys Lys Ala Ala Arg Val Trp Leu Gly Thr Phe Asp Thr
 65                  70                  75                  80

Ala Glu Asp Ala Ala Ile Ala Tyr Asp Glu Ala Ala Leu Arg Phe Lys
                 85                  90                  95

Gly Thr Lys Ala Lys Leu Asn Phe Pro Glu Arg Val Gln Gly Arg Thr
            100                 105                 110

Asp Leu Gly Phe Val Val Thr Arg Gly Ile Pro Asp Arg Leu Gln Gln
            115                 120                 125

Gln Gln His Tyr Pro Ala Ala Val Gly Ala Pro Ala Met Arg Pro Pro
        130                 135                 140

Leu His Gln Gln Gln Ala Val Val Pro Tyr Pro Asp Leu Leu Arg Tyr
145                 150                 155                 160

Ala Gln Leu Leu Gln Gly Ala Gly Ser Ala Gly Gly Ala Val Asn Leu
                165                 170                 175

Pro Phe Gly Ala Met Ser Pro Pro Ser Met Ser Ser Ser Ser Ser Pro
            180                 185                 190

His Ile Leu Asp Phe Ser Thr Gln Gln Leu Ile Arg Val Ser Pro Ala
        195                 200                 205

Ser Pro Ala Ala Ala Ile Ser Gly Ser Ala Thr Thr Gly Pro Ser Thr
210                 215                 220

Ser Ser Ser Thr Thr Thr Ala Ser Ser Pro Gly Ala Ala Trp Pro Tyr
225                 230                 235                 240

Thr Gly Glu Gln Lys Asn Asn Lys Asp Ser
                245                 250

<210> SEQ ID NO 16
<211> LENGTH: 269
<212> TYPE: PRT
<213> ORGANISM: Oryza sativa ssp. Indica

<400> SEQUENCE: 16

Met Val Thr Ala Leu Ala His Val Ile Arg Ala Ala Pro Asp Leu His
  1               5                  10                  15

Leu Pro His His Pro Ser Ser Ser Ala Ser Ala Ala His Pro Gln
             20                  25                  30

Gln Ala Ser Ser Phe Tyr Pro Thr Ala Ala Ala Ala Ser Ser Pro
         35                  40                  45

Ser Asp Gln Leu Ala Ala Ala Ala Ala Ala Glu Glu Gln Gly Arg
 50                  55                  60

Arg Arg His Tyr Arg Gly Val Arg Gln Arg Pro Trp Gly Lys Trp Ala
 65                  70                  75                  80

Ala Glu Ile Arg Asp Pro Lys Lys Ala Ala Arg Val Trp Leu Gly Thr
                 85                  90                  95

Phe Asp Thr Ala Glu Asp Ala Ala Ile Ala Tyr Asp Glu Ala Ala Leu
            100                 105                 110

Arg Phe Lys Gly Thr Lys Ala Lys Leu Asn Phe Pro Glu Arg Val Gln
            115                 120                 125

Gly Arg Thr Asp Leu Gly Phe Leu Val Thr Arg Gly Ile Pro Pro Ala
        130                 135                 140

Ala Thr His Gly Gly Gly Tyr Tyr Pro Ser Ser Ser Pro Ala Ala Gly
145                 150                 155                 160
```

```
Ala Cys Pro Pro Pro Arg Gln Gln Gln Thr Val Val Pro Tyr Pro Asp
                165                 170                 175

Leu Met Arg Tyr Ala Gln Leu Leu Gln Gly Gly Val Gly Gly Ser Tyr
            180                 185                 190

Met Pro Phe Gly Gly Ala Ala Thr Met Ser Ser Ser Thr Val Ser Ser
        195                 200                 205

Ser Ser Ala Pro Gln Ile Leu Asp Phe Ser Thr Gln Gln Leu Ile Arg
    210                 215                 220

Ala Gly Pro Pro Ser Pro Met Pro Ser Ser Gly Ser Gly Ser Ala Thr
225                 230                 235                 240

Ala Ala Ala Ser Ser Thr Thr Ser Ala Ser Ser Pro Gly Ala Trp Pro
                245                 250                 255

Tyr Gly Gly Ser Glu Arg Lys Lys Lys Asp Ser Ser Ser
            260                 265

<210> SEQ ID NO 17
<211> LENGTH: 269
<212> TYPE: PRT
<213> ORGANISM: Oryza sativa ssp. Japonica

<400> SEQUENCE: 17

Met Val Thr Ala Leu Ala His Val Ile Arg Ala Ala Pro Asp Leu His
1               5                   10                  15

Leu Pro His His Pro Ser Ser Ser Ala Ser Ala Ala Ala His Pro Gln
            20                  25                  30

Gln Ala Ser Ser Phe Tyr Pro Thr Ala Ala Ala Ala Ser Ser Pro
        35                  40                  45

Ser Asp Gln Leu Ala Ala Ala Ala Ala Ala Glu Glu Gln Gly Arg
    50                  55                  60

Arg Arg His Tyr Arg Gly Val Arg Gln Arg Pro Trp Gly Lys Trp Ala
65                  70                  75                  80

Ala Glu Ile Arg Asp Pro Lys Lys Ala Ala Arg Val Trp Leu Gly Thr
                85                  90                  95

Phe Asp Thr Ala Glu Asp Ala Ala Ile Ala Tyr Asp Glu Ala Ala Leu
            100                 105                 110

Arg Phe Lys Gly Thr Lys Ala Lys Leu Asn Phe Pro Glu Arg Val Gln
        115                 120                 125

Gly Arg Thr Asp Leu Gly Phe Leu Val Thr Arg Gly Ile Pro Pro Ala
    130                 135                 140

Ala Thr His Gly Gly Tyr Tyr Pro Ser Ser Pro Ala Ala Gly
145                 150                 155                 160

Ala Cys Pro Pro Pro Arg Gln Gln Gln Thr Val Val Pro Tyr Pro Asp
                165                 170                 175

Leu Met Arg Tyr Ala Gln Leu Leu Gln Gly Gly Val Gly Gly Ser Tyr
            180                 185                 190

Met Pro Phe Gly Gly Ala Ala Thr Met Ser Ser Ser Thr Val Ser Ser
        195                 200                 205

Ser Ser Ala Pro Gln Ile Leu Asp Phe Ser Thr Gln Gln Leu Ile Arg
    210                 215                 220

Ala Gly Pro Pro Ser Pro Met Pro Ser Ser Gly Ser Gly Ser Ala Thr
225                 230                 235                 240

Ala Ala Ala Ser Ser Thr Thr Ser Ala Ser Ser Pro Gly Ala Trp Pro
                245                 250                 255

Tyr Gly Gly Ser Glu Arg Lys Lys Lys Asp Ser Ser Ser
            260                 265
```

<210> SEQ ID NO 18
<211> LENGTH: 393
<212> TYPE: PRT
<213> ORGANISM: Setaria italica

<400> SEQUENCE: 18

```
Met Pro Gly Ser Ile Asp Pro Ala Pro Ser Ala Asp Gly Arg Arg
1               5                   10                  15

Arg Arg Gln Ile Asp Arg Gln Leu Thr Lys Val Asp Pro Arg Arg His
                20                  25                  30

Gly Lys Arg Pro Leu Pro Ala Asp Lys Glu Glu Glu Asp Gln Pro Pro
            35                  40                  45

Pro Pro Pro Ala Lys His Glu Gln Leu Glu Ile Glu Glu His Arg
50                  55                  60

Tyr His Val Ser Gln Leu Gln Gln Gly Ala Thr Phe Ser Ala Gly Gly
65                  70                  75                  80

Gly Gly Gly Gly Ser Ser Ser Ser Ala Ala Gly Ala Ala Ala Gly
                85                  90                  95

Pro Ser Pro Glu Ala Tyr Ala Gln Tyr Tyr Tyr Ser Ala Arg Ala Asp
            100                 105                 110

His Asp Ala Ser Ala Val Ala Ser Ala Leu Ala His Val Ile Arg Ala
        115                 120                 125

Ser Pro Asp Gln Leu Pro Pro His Ala Phe Gly Gly Gly Ala Pro
130                 135                 140

Pro Gly Gln Gly Asp Tyr Gln Gln Ala Ala Pro Pro Ala Ala Ala Ala
145                 150                 155                 160

Ala Ala Ala Glu Glu Glu Gln Ala Ala Gly Arg Arg Arg His Tyr Arg
                165                 170                 175

Gly Val Arg Gln Arg Pro Trp Gly Lys Trp Ala Ala Glu Ile Arg Asp
            180                 185                 190

Pro Lys Lys Ala Ala Arg Val Trp Leu Gly Thr Phe Asp Thr Ala Glu
        195                 200                 205

Asp Ala Ala Ile Ala Tyr Asp Glu Ala Ala Leu Arg Phe Lys Gly Thr
210                 215                 220

Lys Ala Lys Leu Asn Phe Pro Glu Arg Val Gln Gly Arg Thr Asp Met
225                 230                 235                 240

Gly Phe Leu Val Thr Arg Gly Ile Pro Asp Arg His His His Gln Gly
                245                 250                 255

Gly Ala Ala Val Thr Leu Ala Ala Met Pro Pro Pro His Arg Gln His
            260                 265                 270

His Gln Thr Val Val Pro Tyr Pro Asp Leu Met Gln Tyr Ala Gln Leu
        275                 280                 285

Leu Gln Gly Gly Gly Arg Gly Gly Gly Ala Gly Asp His His Ala
290                 295                 300

Glu Ala Ala Ala Gln Gln Ala Gln Ala Arg Leu Met Met Met Ala Arg
305                 310                 315                 320

Gly Gly Val Ser Leu Pro Phe Gly Ala Ala Ser Phe Ser Ser Ser Ser
                325                 330                 335

Ser Ser Ala Pro Gln Ile Leu Asp Phe Ser Thr Gln Leu Ile Arg
            340                 345                 350

Pro Gly Pro Pro Ser Pro Ala Ala Ala Ala Pro Ser Thr Pro Ser Ser
        355                 360                 365

Thr Thr Thr Ala Ser Ser Pro Gly Gly Ser Ala Trp Pro Tyr Gly Gly
```

```
                    370                 375                 380
Glu His His Arg Asn Lys Lys Asp Ala
385                 390

<210> SEQ ID NO 19
<211> LENGTH: 294
<212> TYPE: PRT
<213> ORGANISM: Sorghum bicolor

<400> SEQUENCE: 19

Met Thr Lys Lys Leu Ile Ser Ala Met Ala Gly Lys Gln Gly Phe Lys
1               5                   10                  15

Glu Gln Gln Phe Asn Asp Gln Arg Gln Gln Ala Ser Ile Gln Gly
            20                  25                  30

Asp Asp Ile Ala Lys Ser Leu Val Gly Phe Gly Gly Gly Gly Arg
        35                  40                  45

Leu Ile Ser His Glu Gln Glu Asp Ala Ile Ile Val Ala Ala Leu Arg
    50                  55                  60

His Val Val Ser Gly Tyr Ser Thr Pro Pro Glu Val Val Thr Val
65                  70                  75                  80

Ala Gly Gly Glu Pro Cys Gly Val Cys Gly Ile Asp Gly Cys Leu Gly
                85                  90                  95

Cys Asp Phe Phe Gly Ala Ala Pro Glu Leu Thr Gln Gln Glu Ala Val
                100                 105                 110

Asn Phe Gly Thr Gly Gln Met Val Ala Thr Ala Ala Ala Ala Ala
            115                 120                 125

Gly Gly Glu His Gly Gln Arg Thr Arg Arg Arg Lys Lys Asn Met
130                 135                 140

Tyr Arg Gly Val Arg Gln Arg Pro Trp Gly Lys Trp Ala Ala Glu Ile
145                 150                 155                 160

Arg Asp Pro Arg Arg Ala Ala Arg Val Trp Leu Gly Thr Phe Asp Thr
                165                 170                 175

Ala Glu Glu Ala Ala Arg Ala Tyr Asp Cys Ala Ala Ile Glu Phe Arg
                180                 185                 190

Gly Ala Arg Ala Lys Leu Asn Phe Pro Gly His Glu Ala Leu Leu Pro
            195                 200                 205

Phe Gln Gly His Gly His Gly Gly Asp Ala Cys Ala Thr Ala Ala Ala
    210                 215                 220

Asn Ala Glu Thr Gln Thr Thr Pro Met Leu Met Thr Pro Ser Pro Cys
225                 230                 235                 240

Ser Ala Asp Ala Ala Ala Ala Pro Gly Asp Trp Gln Leu Gly Gly
                245                 250                 255

Gly Val Asp Gly Gly Glu Gly Asp Glu Val Trp Glu Gly Leu Leu Gln
            260                 265                 270

Asp Leu Met Lys Gln Asp Glu Ala Asp Leu Trp Phe Leu Pro Phe Ser
    275                 280                 285

Gly Ala Ala Ser Ser Phe
            290

<210> SEQ ID NO 20
<211> LENGTH: 236
<212> TYPE: PRT
<213> ORGANISM: Theobroma cacao

<400> SEQUENCE: 20

Met Thr Ala Met Val Thr Ala Leu Thr His Val Met Gly Thr Gly Gly
```

-continued

```
1               5                   10                  15
Ser Asp Glu Gln Leu Ser Phe Thr Pro Ser Ser Val Pro Leu Ser Gln
            20                  25                  30

Ser Ala Val Lys Glu Glu Pro Asp Pro Gln Pro Val Gln Asp Gln
            35                  40                  45

Glu Asn Thr Arg Arg His Tyr Arg Gly Val Arg Gln Arg Pro Trp
        50                  55                  60

Gly Lys Trp Ala Ala Glu Ile Arg Asp Pro Lys Lys Ala Ala Arg Val
65                  70                  75                  80

Trp Leu Gly Thr Phe Asp Thr Ala Glu Asp Ala Ala Leu Ala Tyr Asp
                85                  90                  95

Arg Ala Ala Leu Lys Phe Lys Gly Thr Lys Ala Lys Leu Asn Phe Pro
            100                 105                 110

Glu Arg Val Gln Gly Asn Thr Glu Val Ser Tyr Phe Thr Gly His Gly
            115                 120                 125

Asp Ser Ser Thr Val Arg Pro Asp Gln Asn Pro Thr Pro Ala Ala Thr
        130                 135                 140

Pro Pro Ser Trp Ser Gln Asp Ser Tyr Pro His Leu Phe Gln Tyr Ala
145                 150                 155                 160

Gln Leu Leu Ser Ser Asn Asp Ala Asp Ile Ser Tyr Tyr Thr Ser
                165                 170                 175

Asn Leu Phe Asn Gln Glu Pro Leu Ser Pro Gln Phe Pro Ser Met Ala
            180                 185                 190

Ala Ser Pro Asn Ile Ser Ser Gln Tyr His His Gln Asp Gln Thr Arg
            195                 200                 205

Phe Ser Thr Lys Tyr Glu Ser Ser Ser Gly Ser Asp Tyr Pro Glu Gln
        210                 215                 220

Tyr Gly Lys Asp Ser Asp Pro Ser Asn Arg Ser Glu
225                 230                 235

<210> SEQ ID NO 21
<211> LENGTH: 232
<212> TYPE: PRT
<213> ORGANISM: Elaeis guineensis

<400> SEQUENCE: 21

Met Val Ser Ala Leu Ala His Val Ile Ser Ser Leu Ser Gly Val
1               5                   10                  15

Gly Val Gly Val Gly Arg Ser Glu Ser Val Val Ile Gln Ser Glu Leu
            20                  25                  30

Asn Pro Ala Met Ala Gly Pro Glu Ser Gly Ser Met Glu Arg Glu Leu
            35                  40                  45

Ser Gln Pro Ser Glu Glu Gln Gly Asn Val Arg Arg Arg His Tyr Arg
        50                  55                  60

Gly Val Arg Gln Arg Pro Trp Gly Lys Trp Ala Ala Glu Ile Arg Asp
65                  70                  75                  80

Pro Arg Lys Ala Ala Arg Val Trp Leu Gly Thr Tyr Asn Thr Ala Glu
                85                  90                  95

Glu Ala Ala Ile Ala Tyr Asp Glu Ala Ala Leu Arg Phe Lys Gly Thr
            100                 105                 110

Lys Ala Lys Leu Asn Phe Pro Glu Arg Val Gln Gly Arg Thr Asp Leu
            115                 120                 125

Gly Phe Leu Val Ser Arg Gly Ile Pro Glu Arg Pro Gln Pro Ile
        130                 135                 140
```

```
Thr Pro Pro Pro Thr Ala Ser Tyr Pro Asp Leu Leu Gln Tyr Ala Gln
145                 150                 155                 160

Leu Leu Gln Ser Arg Asp Glu Asp Leu His Ser Val Ala Ser Gly Leu
            165                 170                 175

Phe Val Thr Asp Ser Phe Thr Ser Gly Ser Ser Gln Val Ser Tyr His
        180                 185                 190

Ser Thr Ser Gly Ser Ser Gln Glu Phe Leu Asp Phe Phe Ser Gln Met
    195                 200                 205

Arg Ser Ser Ser Ser Ser Ser Arg Gln Pro Arg Gly Asp Gln Lys
    210                 215                 220

Asp Lys Asp Ser Asn Gln Gln Gln
225                 230

<210> SEQ ID NO 22
<211> LENGTH: 234
<212> TYPE: PRT
<213> ORGANISM: Elaeis guineensis

<400> SEQUENCE: 22

Met Val Ser Ala Leu Ala His Val Ile Ser Ser Ser Pro Gly Val
1               5                   10                  15

Gly Val Gly Val Gly Val Gly Gly Glu Thr Arg Glu Ile Gln Pro
            20                  25                  30

Glu Leu Ser Pro Ala Met Ala Gly Thr Gly Ser Gly Ser Met Glu Ile
        35                  40                  45

Arg Glu Leu Ser Gln Pro Ser Gln Gln Gly Asn Val Arg Arg Arg
    50                  55                  60

His Tyr Arg Gly Val Arg Gln Arg Pro Trp Gly Lys Trp Ala Ala Glu
65                  70                  75                  80

Ile Arg Asp Pro Lys Lys Ala Ala Arg Val Trp Leu Gly Thr Phe Asp
                85                  90                  95

Thr Ala Glu Gln Ala Ala Ile Ala Tyr Asp Glu Ala Ala Leu Arg Phe
            100                 105                 110

Lys Gly Thr Lys Ala Lys Leu Asn Phe Pro Glu Arg Val Gln Gly Arg
        115                 120                 125

Thr Asp Leu Gly Phe Leu Leu Ser Arg Gly Ile Pro Glu Arg Gln Pro
    130                 135                 140

Glu Pro Ile Thr Pro Ser Ala Ala Thr Tyr Pro Asp Leu Leu Gln
145                 150                 155                 160

Tyr Ala Gln Leu Leu Gln Ser Arg Asp Glu Asp Phe His Asn Val Ala
                165                 170                 175

Ser Gly Leu Tyr Ile Gly Gly Ser Phe Ala Ser Gly Ser Ser Gln Met
            180                 185                 190

Ser Pro Ala Ser Met Ser Gly Ser Gln Glu Phe Leu Asp Phe Ser
        195                 200                 205

Ser Gln Phe Gly Thr Ser Ser Ser Thr Ser Trp Pro His Gly Asp
    210                 215                 220

Gln Lys Asp Lys Asp Ser Ser Gln His Pro
225                 230

<210> SEQ ID NO 23
<211> LENGTH: 244
<212> TYPE: PRT
<213> ORGANISM: Malus domestica

<400> SEQUENCE: 23
```

```
Met Ser Ala Met Val Ser Ala Leu Thr Gln Val Ile Gly Thr Thr Asp
1               5                   10                  15

Asp His Ala Ala Val Gln Pro Asn Pro Thr Ser Ile Ser Asp Ser Ser
            20                  25                  30

Leu Leu Val Lys Gln Glu Pro Asp Arg Ser Gln Pro Val Gln Asp Gln
        35                  40                  45

Glu Pro Val Arg Arg His Tyr Arg Gly Val Arg Gln Arg Pro Trp
    50                  55                  60

Gly Lys Trp Ala Ala Glu Ile Arg Asp Pro Lys Ala Ala Arg Val
65                  70                  75                  80

Trp Leu Gly Thr Phe Glu Thr Ala Glu Asp Ala Ala Ile Ala Tyr Asp
                85                  90                  95

Asn Ala Ala Leu Lys Phe Lys Gly Thr Lys Ala Lys Leu Asn Phe Pro
            100                 105                 110

Glu Arg Val Gln Gly Lys Thr Asp Leu Gly Ile Leu Met Gly Ser Ser
            115                 120                 125

Gly Ser Gly Ala Ala Ser Thr Gln Arg Thr Gln Asn Leu Met Thr Pro
        130                 135                 140

Ala Gly His Ile Val Asn Pro Gln Pro Ala Pro Ala Pro Leu Met Met
145                 150                 155                 160

Ser Gln Gln Pro Glu Thr Phe Pro Asp Leu Tyr Gln Tyr Ala Arg Leu
                165                 170                 175

Leu Ser Gly Asn Asp Ala Asp Phe Tyr Asn Tyr Ser Tyr Pro Phe
            180                 185                 190

Asn Gln Asp Pro Arg Phe Thr Ser Arg Phe Leu Pro Ser Ser Thr His
            195                 200                 205

Phe Ser Ser Ser Thr Ala Ser Gln Asp Ser Gln Pro Pro Gln Gln Gly
        210                 215                 220

Gln Gln Asp His Glu Glu Asp Gly Gly Asn Glu Asp Arg Asn Trp Ser
225                 230                 235                 240

Asn Pro Arg Glu

<210> SEQ ID NO 24
<211> LENGTH: 268
<212> TYPE: PRT
<213> ORGANISM: Malus domestica

<400> SEQUENCE: 24

Met Ile Phe Asp Pro Phe Cys Ser Ser Ala Arg Ser Gln His Glu Met
1               5                   10                  15

Ser Ala Met Val Ser Ala Leu Ala Gln Val Leu Gly Ser Asn Asn Ser
            20                  25                  30

Gln Thr Pro Ala Val Gln Glu Pro Val Glu Pro Pro Leu Ile Thr Pro
        35                  40                  45

Gln Ser Ser Ala Met Glu Leu His Asp Gly Gln Ser Pro Gln Gln Ala
    50                  55                  60

Gln Asp Gln Gly Asn Val Arg Arg His Tyr Arg Gly Val Arg Gln
65                  70                  75                  80

Arg Pro Trp Gly Lys Trp Ala Ala Glu Ile Arg Asp Pro Lys Lys Ala
                85                  90                  95

Ala Arg Val Trp Leu Gly Thr Phe Glu Thr Ala Glu Ala Ala Ala Ile
            100                 105                 110

Ser Tyr Asp Glu Ala Ala Leu Arg Phe Lys Gly Ser Lys Ala Lys Leu
        115                 120                 125
```

```
Asn Phe Pro Glu Arg Val Gln Gly Arg Ile Thr Glu Leu Gly Tyr Leu
        130                 135                 140

Thr Thr Thr Ser Thr Gln Gln Asn Leu Pro Ala Glu Ala Gln Ser Ile
145                 150                 155                 160

Thr Asp His His Gln Pro Leu Pro Asp His Gln Tyr Gln Leu Gln Ala
                165                 170                 175

Phe Pro Asn Asn Val Ala Thr Pro His Asp Gln Tyr Ala Pro Tyr Phe
                180                 185                 190

Leu Ser Gly Asn Glu Gly Val Asn Tyr Asp Asp Leu Pro Thr Asn Leu
            195                 200                 205

Ser Glu Arg Glu Arg Phe Ala Phe Gln Thr Ser Glu Thr Thr Ser Ser
210                 215                 220

Ser Leu Leu Pro Phe Leu Pro Ser His Gln Gln Glu Asp Gln His
225                 230                 235                 240

Pro Leu Asn Tyr Ser Met Pro Ala Phe Gly Ser Ser Ser Ser Ser
                245                 250                 255

Ser Asn Pro Pro Pro Arg Asn Arg Asn Arg Arg Pro
            260                 265
```

<210> SEQ ID NO 25
<211> LENGTH: 272
<212> TYPE: PRT
<213> ORGANISM: Malus domestica
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid

<400> SEQUENCE: 25

```
Met Ile Phe Glu Pro Phe Cys Ser Ser Ala Arg Ser Gln His Glu Met
1               5                   10                  15

Ser Ala Met Val Ser Ala Leu Ser Gln Val Leu Gly Ser Thr Asn Asn
            20                  25                  30

Gln Thr Pro Ala Val Gln Val Pro Met Glu Pro Pro Met Ile Ala Pro
        35                  40                  45

Gln Ser Ser Ala Met Glu Ser His Asp Asp Gln Ser Pro Gln His Ala
    50                  55                  60

Arg Asp Gln Gly Thr Ala Arg Arg Arg His Tyr Arg Gly Val Arg Gln
65                  70                  75                  80

Arg Pro Trp Gly Lys Trp Ala Ala Glu Ile Arg Asp Pro Lys Lys Ala
                85                  90                  95

Ala Arg Val Trp Leu Gly Thr Phe Glu Thr Asp Glu Ala Ala Ala Leu
            100                 105                 110

Ala Tyr Asp Glu Ala Ala Leu Arg Phe Lys Gly Ser Lys Ala Lys Leu
        115                 120                 125

Asn Phe Pro Glu Arg Val Gln Gly Arg Ile Thr Glu Leu Gly Ser Leu
    130                 135                 140

Thr Ala Thr Ser Thr Gln Gln Asn Leu Pro Ala Gly Thr Ser Gln Gly
145                 150                 155                 160

Val Ile Thr Asp His His His Pro Leu Ser Asp Xaa Gln Tyr Gln Leu
                165                 170                 175

Gln Ala Phe Pro Asn Asn Val Val Thr Pro Pro His Asp Gln Tyr Ala
            180                 185                 190
```

```
Gln Tyr Phe Arg Ser Gly His Glu Cys Ile Ser Tyr Asp Leu Pro Ala
            195                 200                 205

Thr Leu Tyr Glu Arg Glu Ile Phe Ala Xaa Gln Thr Ser Glu Thr Thr
    210                 215                 220

Thr Ser Ser Ser Leu Leu Pro Phe Leu Pro Ser His Gln Gln Glu
225                 230                 235                 240

Asp Gln Gln His Pro Leu Ser Tyr Ser Met Pro Gly Phe Gly Ser Ser
                245                 250                 255

Ser Ser Ser Ser Asn Pro Pro Arg Asn Arg Asn Arg Arg Pro
            260                 265                 270
```

<210> SEQ ID NO 26
<211> LENGTH: 264
<212> TYPE: PRT
<213> ORGANISM: Malus domestica
<220> FEATURE:
<221> NAME/KEY: misc_feature
<222> LOCATION: (115)..(115)
<223> OTHER INFORMATION: Xaa can be any naturally occurring amino acid

<400> SEQUENCE: 26

```
Met Tyr Asp Ile Ala Thr Asn Ser Gln Phe Asp Val His Lys Val Asp
1               5                   10                  15

Arg Lys His Gly Lys Arg Leu Leu Ala Ser Val Glu Ser Glu Glu Lys
            20                  25                  30

Glu Glu Asp Gln Ile Phe Pro Val Tyr Ser Thr Arg Ser Gln Gln Asp
        35                  40                  45

Thr Ser Ala Met Val Ser Ala Leu Ala Gln Val Ile Gly Lys Asn Ser
50                  55                  60

Asp Gln Ile Asn Asn Pro Leu Asp Gln Val Gln Gly Ile Asn Pro Leu
65                  70                  75                  80

Ile Thr Ser Gln Ser Ser Pro Thr Glu Thr Gln Ser Gln Thr Val Leu
                85                  90                  95

Gln Asp Gln Gly Asn Leu Arg Arg Gln His Tyr Arg Gly Val Arg Arg
            100                 105                 110

Arg Pro Xaa Gly Lys Trp Ala Ala Glu Ile Arg Asp Pro Val Lys Ala
        115                 120                 125

Ala Arg Val Trp Leu Gly Thr Phe Asp Thr Ala Glu Ala Ala Ala Leu
130                 135                 140

Ala Tyr Asp Lys Ala Ala Leu Lys Phe Lys Gly Ser Lys Ala Lys Leu
145                 150                 155                 160

Asn Phe Pro Glu Arg Val Gln Gly Ile Ser Glu Ser Gly Cys Leu Ala
                165                 170                 175

Leu Ile Thr Thr Asp Gln Gln Asp Ser Leu Asn Ile Asn Pro Pro Gln
            180                 185                 190

Pro Asn Ile Thr Arg Pro Thr Ser Ser Val Phe Asp Cys Thr Gln
        195                 200                 205

Tyr Asn Asn Val Thr Ser Thr Ser Leu Leu Ser Ser Ser Ser Met
210                 215                 220

Pro Ser Gln Gln Ala Ala Glu Leu Pro Ser Phe Ser Met Gln Phe Gly
225                 230                 235                 240

Ser Ser Phe Ser Ser Ser Ser Gly Pro Pro His Lys Tyr Arg Lys
                245                 250                 255

Asp Phe Asp Ser Ser His Ser Arg
            260
```

```
<210> SEQ ID NO 27
<211> LENGTH: 214
<212> TYPE: PRT
<213> ORGANISM: Malus domestica
<220> FEATURE:
<221> NAME/KEY: misc_feature
<222> LOCATION: (110)..(110)
<223> OTHER INFORMATION: Xaa can be any naturally occurring amino acid

<400> SEQUENCE: 27
```

Met Val Ser Ala Leu Ala Gln Val Ile Gly Lys Asn Ser Asp Gln Ile
1               5                   10                  15

Asn Asn Pro Leu Gly Gln Val Gln Gly Ile Asn Pro Leu Thr Thr Ser
            20                  25                  30

Gln Ser Ser Pro Thr Glu Thr Gln Ser Gln Pro Val Leu Leu Gln Asp
        35                  40                  45

Gln Gly Asn Leu Arg Arg Gln His Tyr Arg Gly Val Arg Arg Arg Pro
    50                  55                  60

Ser Gly Lys Trp Ala Ala Glu Ile Arg Asp Pro Val Lys Ala Ala Arg
65                  70                  75                  80

Val Trp Leu Gly Thr Phe Asp Thr Ala Glu Ala Ala Leu Ala Tyr
                85                  90                  95

Asp Lys Ala Ala Leu Lys Phe Lys Gly Ser Lys Ala Lys Xaa Asn Phe
                100                 105                 110

Pro Glu Arg Val Gln Gly Ser Ser Glu Ser Gly Cys Leu Thr Leu Ile
            115                 120                 125

Thr Thr Asp Gln Gln Asp Ser Leu Asn Ile Asn Pro Pro Gln Pro Asn
        130                 135                 140

Ile Thr Arg Pro Thr Ser Ser Val Phe Asp Cys Thr Gln His Asn
145                 150                 155                 160

Asn Val Ile Tyr Cys Thr Ser Leu Leu Ser Ser Ser Met Pro Ser
                165                 170                 175

Gln Gln Ala Ala Glu Leu Pro Ser Phe Ser Met Gln Phe Gly Ser Ser
            180                 185                 190

Phe Ser Ser Ser Ser Gly Pro Pro His Lys Tyr Arg Lys Asp Phe
        195                 200                 205

Asp Ser Arg His Ser Arg
        210

```
<210> SEQ ID NO 28
<211> LENGTH: 304
<212> TYPE: PRT
<213> ORGANISM: Malus domestica

<400> SEQUENCE: 28
```

Met Phe Phe Arg Tyr Thr Phe Leu Leu Gly Ile Arg Ala Val Ser Ser
1               5                   10                  15

Val Val Phe Arg Ser Ser Val Val Glu Ala Ile Leu Val Thr Thr Thr
            20                  25                  30

Ala Leu Gln Tyr Val Gln Thr Thr Arg Thr Thr Ile Ser Ala Ala Thr
        35                  40                  45

Ser Thr Cys Ser Arg Val Lys Leu Asp Lys Val Asp Leu Lys His Gly
    50                  55                  60

Lys Arg Pro Leu Ala Ser Val Glu Ser Glu Glu Lys Glu Glu Asp Gln
65                  70                  75                  80

Ile Phe Pro Val Tyr Ser Ala Arg Ser Gln Gln Asp Thr Ser Ala Met
                85                  90                  95

```
Val Ser Ala Leu Ala Gln Val Ile Gly Asn Asn Ser Asp Gln Ile Asn
            100                 105                 110

Asn Pro Leu Asp Gln Val Gln Gly Ile Ser Ser Leu Ile Thr Ser Gln
            115                 120                 125

Ser Ser Pro Thr Glu Thr Gln Ser Gln Pro Val Leu Leu Gln Asp Gln
            130                 135                 140

Gly Asn Leu Arg Arg Gln His Tyr Arg Gly Val Arg Arg Pro Trp
145                 150                 155                 160

Gly Lys Trp Ala Ala Glu Ile Arg Asp Pro Ile Lys Ala Ala Arg Val
                    165                 170                 175

Trp Leu Gly Thr Phe Asn Thr Ala Glu Ala Ala Leu Ala Tyr Asp
                180                 185                 190

Gly Ala Ala Leu Arg Phe Lys Gly Ser Lys Ala Lys Leu Asn Phe Pro
            195                 200                 205

Glu Arg Val Val Gln Gly Ser Ser Glu Ser Gly Cys Leu Thr Ile Thr
            210                 215                 220

Thr Gln Leu Gln His Ser Leu Asn Asn Ile Pro Pro Glu Ala Asn Ile
225                 230                 235                 240

Ser Arg Pro Thr Tyr Ser Asn Val Phe Asp Tyr Ala Arg Tyr Asn Asn
                    245                 250                 255

Val Thr Ser Thr Ser Ser Ser Ser Met Pro Ser Gln Gln Ala Ala Glu
                260                 265                 270

Leu Arg Ser Phe Ser Met Gln Phe Gly Ser Ser Ser Ser Ser Ser Ser
            275                 280                 285

Gly Pro Pro Tyr Lys Tyr Arg Lys Asp Phe Asp Arg Ser His Ser Arg
290                 295                 300
```

<210> SEQ ID NO 29
<211> LENGTH: 243
<212> TYPE: PRT
<213> ORGANISM: Fragaria vesca

<400> SEQUENCE: 29

```
Met Ser Ala Met Val Ser Ala Leu Thr Gln Val Ile Gly Asn Pro Glu
1               5                   10                  15

Glu Asp Asn Lys Gln Val Gln Ser Asn Pro Ala Ser Val Lys Asp Glu
                20                  25                  30

Pro Asp Arg Ser Gln Pro Val Gln Asp Gln Glu Ser Thr Val Arg Arg
            35                  40                  45

Arg His Tyr Arg Gly Val Arg Gln Arg Pro Trp Gly Lys Trp Ala Ala
        50                  55                  60

Glu Ile Arg Asp Pro Lys Lys Ala Ala Arg Val Trp Leu Gly Thr Phe
65                  70                  75                  80

Glu Thr Ala Glu Asp Ala Ala Ile Ala Tyr Asp Asn Ala Ala Leu Lys
                85                  90                  95

Phe Lys Gly Thr Lys Ala Lys Leu Asn Phe Pro Glu Arg Val Gln Gly
            100                 105                 110

Asn Ser Ser Ile Leu Ile Gln Gly Ser Ser Gly Thr Ser Ser Gly
            115                 120                 125

Ser Ser Val Ser Thr Glu Arg Asn Arg Ser Arg Pro Ala Leu Thr Val
            130                 135                 140

Pro His His Asp Ala Ser Tyr Val Ala Pro Ser Gln Pro Gln Gln Glu
145                 150                 155                 160

Ser Ser Ser Phe Pro Asp Leu Tyr Gln Tyr Ala Gln Leu Leu Gln Ser
                165                 170                 175
```

```
Asn Asp Ile Asp Phe Ser Ser Asn Tyr Gln Tyr Pro Pro Asn Asn Pro
            180                 185                 190

Phe Asn Gln Asp Tyr His Pro Gln Tyr Ser Thr Pro Gln Phe Pro Pro
            195                 200                 205

Ser Thr Tyr Tyr Pro Ser His Gln Gln Gln Gly Gln Gln Asp Asp His
            210                 215                 220

Val Gln Glu Asp His Gln Asn Glu Asn Lys Asn Trp Asn Arg Arg Asn
225                 230                 235                 240

Pro Ser Glu

<210> SEQ ID NO 30
<211> LENGTH: 240
<212> TYPE: PRT
<213> ORGANISM: Fragaria vesca

<400> SEQUENCE: 30

Met Ser Ala Met Val Ser Val Leu Ser Arg Val Ile Ser Gly Asp Ser
1               5                   10                  15

Ser Thr Asp Thr Asp Pro Asn Pro Ala Leu Leu Gln Leu Pro Gln Gln
            20                  25                  30

Ser Ser Thr Ala Thr Pro Glu Leu Asp Gln Ser His Gln Gln Ala Ala
            35                  40                  45

Pro Asp Gln Ala Gly Ser Val Arg Arg Arg His Tyr Arg Gly Val Arg
    50                  55                  60

Gln Arg Pro Trp Gly Lys Trp Ala Ala Glu Ile Arg Asp Pro Lys Lys
65                  70                  75                  80

Ala Ala Arg Val Trp Leu Gly Thr Phe Glu Thr Ala Glu Ala Ala Ala
                85                  90                  95

Leu Ala Tyr Asp Glu Ala Ala Leu Arg Phe Lys Gly Ser Lys Ala Lys
            100                 105                 110

Leu Asn Phe Pro Glu Arg Val Gln Gly Thr Ser Glu Ser Gly Gly Tyr
        115                 120                 125

Leu Thr Thr Gln Thr Val Ala His Gln Pro Leu Ile Ser Asp Tyr His
    130                 135                 140

Gln Gln Gln Leu Val Tyr Pro Asn Asn Ile Thr Thr Thr Asp Gln Tyr
145                 150                 155                 160

Tyr Pro Gln Phe Tyr Gly Asn Leu Asn Tyr Gly Gln Pro Asp Pro Arg
                165                 170                 175

Phe Tyr Asn Gln Pro Ala Thr Ser Ser Tyr Pro Pro Phe Ile Pro Ile
            180                 185                 190

Ser Gln Ala Gln Glu Glu Asp Arg Gln Gln Gln Pro Ala Leu Ser Ser
        195                 200                 205

Pro Met Pro Asp Phe Gly Ser Pro Ser Ser Ser Leu His Pro Glu Tyr
    210                 215                 220

Pro Gln Tyr Asp Thr Thr Arg Asn Phe Asp Asn Ser His Trp Arg Gly
225                 230                 235                 240

<210> SEQ ID NO 31
<211> LENGTH: 224
<212> TYPE: PRT
<213> ORGANISM: Fragaria vesca

<400> SEQUENCE: 31

Met Ala Lys Glu Gln Glu His Ala Ile Met Val Ser Ala Leu Glu Gln
1               5                   10                  15
```

```
Val Ile Gly Gly Gly Ile Ala Thr Arg Thr Ser Gly Thr Ser Gln Asn
             20                  25                  30

His Cys Gln Tyr Ala Thr Ser Ala Ala Glu Ala Gly Thr Asn Lys Lys
         35                  40                  45

Val Val Ile Leu Val Ser Asp Gly Asp Thr Cys Gln Val Cys Lys Ile
 50                  55                  60

Asp Gly Cys Leu Gly Cys Glu Phe Phe Pro Pro Ser Asn Lys His Gly
 65                  70                  75                  80

Lys Gly Lys Arg Val Lys Lys Ser Lys Tyr Arg Gly Val Arg Gln Arg
                 85                  90                  95

Pro Trp Gly Lys Trp Ala Ala Glu Ile Arg Asp Pro Arg Arg Ala Val
             100                 105                 110

Arg Val Trp Leu Gly Thr Phe Gln Thr Ala Glu Glu Ala Ala Arg Ala
             115                 120                 125

Tyr Asp Lys Ala Ala Val Glu Phe Arg Gly Glu Lys Ala Lys Leu Asn
         130                 135                 140

Phe Pro Arg Ile Ser Ser Glu Ala Gly Thr Ser Thr Ala Ala Leu Thr
145                 150                 155                 160

Lys Gln Ser Met Glu Thr Asp Asp Glu Val His Asn Gln Val Asn Pro
                 165                 170                 175

Ser Asn Glu Lys Ser Ala Asn Gln Glu Leu Gly Gln Gly Ser Asp Val
             180                 185                 190

Lys Asp Asp Glu Ile Asp Arg Phe Ile Trp Lys Met Leu Lys Asp Asp
             195                 200                 205

Asp Gly Asp Glu Asp Leu Ser Thr Met Val Asn Ser Asn Met Leu Asn
210                 215                 220

<210> SEQ ID NO 32
<211> LENGTH: 255
<212> TYPE: PRT
<213> ORGANISM: Fragaria vesca

<400> SEQUENCE: 32

Met Val Ser Ala Leu Thr Gln Val Ile Gly Asn Thr Thr His Glu Gln
1               5                   10                  15

Asn Pro Leu Gln Val Ile Asp His Gln Val Leu Gly Asn Pro Gln Val
             20                  25                  30

Phe Ser Ala Glu Asn Pro Val Glu Gln Ser Pro Ala Val Val Leu
         35                  40                  45

Gln Ala Gln Gly Asn Val Arg Gln His Tyr Arg Gly Val Arg Arg Arg
 50                  55                  60

Pro Trp Gly Lys Trp Ala Ala Glu Ile Arg Asp Pro His Lys Ala Ala
 65                  70                  75                  80

Arg Val Trp Leu Gly Thr Phe Glu Thr Ala Glu Ala Ala Leu Ala
                 85                  90                  95

Tyr Asp Glu Ala Ala Leu Arg Phe Lys Gly Ser Lys Ala Lys Leu Asn
             100                 105                 110

Phe Pro Glu Arg Val Gln Gly Ile Ser Pro Ser Thr Ser Ser Gly Leu
             115                 120                 125

Tyr Leu Ala Ile Ser Thr Ser Thr Gly His Asp His Arg Leu Ala Asn
         130                 135                 140

Ser Ala Pro Pro Ala Ala Pro Ile Ser Arg Pro Thr Thr Tyr Ser Ile
145                 150                 155                 160

Asn Pro Asn Asn Val Asn Ile Asp Tyr Asp Ala Leu Val Ser Ser Ser
                 165                 170                 175
```

```
Gln Asn His Gly Gln Glu Arg Thr Met Pro Gln Ile Asn Val Gln Thr
            180                 185                 190

Thr Leu Ser Ser Thr Ser Ser Ala Ser Ser Met Pro Ser His His Gln
        195                 200                 205

Gln Glu Arg Val Gln Gln Glu Asp Gln Gln Leu Leu Lys Phe
    210                 215                 220

Pro Ile Met Pro Phe Gly Gly Ser Ser Ser Ser Ser Asp Pro Pro
225                 230                 235                 240

Thr Lys Tyr Arg Arg Asp Ser Ser Gly Ser Gly Asp Phe Arg Arg
            245                 250                 255

<210> SEQ ID NO 33
<211> LENGTH: 239
<212> TYPE: PRT
<213> ORGANISM: Eucalyptus grandis

<400> SEQUENCE: 33

Met Val Ser Ala Leu Ser Arg Val Ile Ser Thr Ser Asp Asp Ala Pro
1               5                   10                  15

Ser Ser Ala Asp Asp Pro Ala Ala Pro Val Gln Glu Glu His Gly Asp
            20                  25                  30

Pro Pro Gln Gln Ala Pro Asp Gln Glu Ser Val Arg Lys Lys His Tyr
        35                  40                  45

Arg Gly Val Arg Gln Arg Pro Trp Gly Lys Trp Ala Ala Glu Ile Arg
    50                  55                  60

Asp Pro Lys Lys Ala Ala Arg Val Trp Leu Gly Thr Phe Glu Thr Ala
65                  70                  75                  80

Glu Asp Ala Ala Leu Ala Tyr Asp Arg Ala Ala Leu Lys Phe Lys Gly
                85                  90                  95

Thr Lys Ala Lys Leu Asn Phe Pro Glu Arg Val Gln Gly Lys Pro Glu
            100                 105                 110

Tyr Ala Ala Tyr Ser Asn Pro Ser His Gln Asn Ser Gly Val Asn Val
        115                 120                 125

Leu Pro Glu Gln Ile Asn Pro Gln Pro Ala Pro Phe Val Pro Tyr Pro
    130                 135                 140

His Ala Ala Phe Pro Asp Leu Ala Gln Tyr Ala Gln Leu Leu Ser Ser
145                 150                 155                 160

Asn Asp Ala Glu Phe Pro Tyr Tyr Val Ser Asn Leu Tyr Gly Gln Glu
                165                 170                 175

Pro Phe Gly Ser Gln Gln Ser Ser Thr Ser Ser Ser Ser Ile Ser
            180                 185                 190

Ser Ser Ser Tyr His Tyr Asn Gln Gln Gln Gln Gln Glu Pro Gln
        195                 200                 205

Asn Glu Pro Ser Arg Thr Ser Phe Gly Trp Ser Pro Ser Asn Tyr Asp
    210                 215                 220

Phe Gln Gly Tyr Gly Asp Gly Phe Asp Pro Arg Asn Gln Gly Gln
225                 230                 235

<210> SEQ ID NO 34
<211> LENGTH: 267
<212> TYPE: PRT
<213> ORGANISM: Eucalyptus grandis

<400> SEQUENCE: 34

Met Glu Gly Arg Asn Trp Lys Arg Ser Lys Ser Gln Ala Gly His Val
1               5                   10                  15
```

```
Ser Glu Glu Thr Glu Asp Gly Asp Arg Lys Arg Asn Asn Tyr Ala Tyr
            20                  25                  30

Pro Ser Ser Leu Met Glu Thr Ala Arg Ser Gln Gln Asp Thr Ser Ala
        35                  40                  45

Ile Val Ser Ala Leu Ala Gln Val Ile Ala Asn Pro Ala Ala Ala Ala
 50                  55                  60

Ser His His Ala Ser Leu Ser Ser Ser Ala Ser Leu Ser Gln Ser Ser
 65                  70                  75                  80

Leu His Asp His Gln Ala Pro Asp Ala Gln Val Gly Lys Asn Lys Lys
                 85                  90                  95

Leu Glu Val Ser Arg Asn Tyr Arg Gly Val Arg Gln Arg Pro Trp Gly
            100                 105                 110

Lys Tyr Ala Ala Glu Ile Arg Asp Pro Lys Lys Ala Ala Arg Val Trp
                115                 120                 125

Leu Gly Thr Phe Asp Thr Ala Glu Gly Ala Ala Leu Ala Tyr Asp Glu
        130                 135                 140

Ala Ala Leu Arg Phe Lys Gly Asn Lys Ala Lys Leu Asn Phe Pro Glu
145                 150                 155                 160

Arg Val His Ser Leu Pro Pro Tyr Gly Pro Ala Cys Asn Ala Ser
                165                 170                 175

Gln Pro Gln Ser Gln Leu Leu Pro Pro Ala Phe Ser Ser Cys Asp Asn
            180                 185                 190

His Val Gly Ala Gln Leu Met Asp Gly Cys Ala Met Pro Pro Pro Arg
        195                 200                 205

Pro Ser Tyr Val Arg Gly Gln Gly Pro Thr Ser Ser Ala Ser Ala Ser
    210                 215                 220

Asp Tyr Phe Gln Ser Leu Gln Pro Thr Pro Ser Leu Ser Ser Ser Ser
225                 230                 235                 240

Ser Met Pro Ser Pro Phe His Gln His Asp Pro Gln His Ser Phe Asp
                245                 250                 255

Gly Phe Ser Ser Ser Trp Arg Ser Ser His Glu
                260                 265

<210> SEQ ID NO 35
<211> LENGTH: 267
<212> TYPE: PRT
<213> ORGANISM: Eucalyptus grandis

<400> SEQUENCE: 35

Met Glu Gly Arg Asn Trp Lys Arg Ser Lys Ser Gln Ala Gly His Val
 1               5                   10                  15

Ser Ala Glu Arg Glu Asp Gly Asp Lys Lys Arg Asn Asn Tyr Ala Tyr
            20                  25                  30

Pro Ser Ser Leu Met Glu Thr Gly Arg Ser Gln Gln Asp Thr Ser Ala
        35                  40                  45

Ile Val Ser Ala Leu Ala Gln Val Ile Ala Asn Pro Ala Ala Ala Glu
 50                  55                  60

Ser His His Ala Ser Leu Ser Ser Ser Ala Ser Leu Ser Gln Ser Ser
 65                  70                  75                  80

Leu His Asp His Gln Ala Pro Asp Ala Gln Val Gly Lys Asn Lys Lys
                 85                  90                  95

Leu Glu Val Ser Arg Asn Tyr Arg Gly Val Arg Gln Arg Pro Trp Gly
            100                 105                 110

Lys Tyr Ala Ala Glu Ile Arg Asp Pro Lys Lys Ala Ala Arg Val Trp
```

```
                115                 120                 125
Leu Gly Thr Phe Asp Thr Ala Glu Gly Ala Ala Leu Ala Tyr Asp Glu
            130                 135                 140

Ala Ala Leu Arg Phe Lys Gly Asn Lys Ala Lys Leu Asn Phe Pro Glu
145                 150                 155                 160

Arg Val His Ser Leu Pro Pro Tyr Gly Pro Ala Ser Asn Ala Ser
                165                 170                 175

Gln Pro Gln Ser Gln Gln Leu Pro Pro Ala Phe Ser Ser Cys Asp Asn
            180                 185                 190

His Val Gly Ala Gln Leu Met Asp Gly Cys Ala Met Pro Pro Pro Cys
            195                 200                 205

Pro Ser Phe Val Arg Gly Gln Gly Pro Thr Ser Ser Ala Ser Ala Ser
            210                 215                 220

Asp Tyr Phe Gln Ser Leu Gln Pro Thr Pro Ser Ser Ser Ser Ser Ser
225                 230                 235                 240

Ser Thr Thr Ser Pro Phe His Gln His Asp Pro Gln His Ser Phe Asp
                245                 250                 255

Gly Phe Ser Ser Ser Trp Arg Ser Ser Gln Glu
            260                 265

<210> SEQ ID NO 36
<211> LENGTH: 282
<212> TYPE: PRT
<213> ORGANISM: Eucalyptus grandis

<400> SEQUENCE: 36

Met Ser Gly Leu Lys Val Ala Asp Arg Gly Asp Lys Ala Pro Ile Leu
1               5                   10                  15

Tyr Pro Gly Leu Asp Arg Glu Arg Glu Thr Ser Ala Met Val Leu Ala
            20                  25                  30

Leu Ala Arg Val Val Ala Gly Glu Val Pro Gly Asp Ala Glu Glu Ser
                35                  40                  45

Cys Pro Phe Pro Phe Pro Ser Gly Val Leu Arg Leu Lys Arg Gly His
        50                  55                  60

Gly Asp Leu Ser Ala Glu Pro Ser Ala Glu Ala Gln Leu Arg Arg Ala
65                  70                  75                  80

Pro Gly Arg Glu Ser Ser Val Asp Asp Ala Ala Arg Gly Ile Met Glu
                85                  90                  95

Gly Pro Ser Met Lys Thr Thr Asn His Ala Thr Pro Thr Tyr Glu Tyr
            100                 105                 110

Ser Asn Ser Thr Ala Ala Met Ser Met Ser Asn Asp Glu His Gln Pro
                115                 120                 125

Arg Arg Lys Tyr Arg Gly Val Arg Gln Arg Pro Trp Gly Lys Trp Ala
            130                 135                 140

Ala Glu Ile Arg Asp Pro Val Lys Ala Arg Val Trp Leu Gly Thr
145                 150                 155                 160

Phe Glu Thr Ala Glu Gly Ala Ala Gln Ala Tyr Asp Val Ala Ala Leu
                165                 170                 175

Lys Tyr Arg Gly Asn Lys Ala Lys Leu Asn Phe Pro Glu Asn Val Val
            180                 185                 190

Ala Arg Leu Ser Leu Ala Ala Pro Pro Ala Thr Gln Met Thr Val Pro
            195                 200                 205

Asp Ala Ala Arg Thr His Val Thr Val Pro Ala Asp Thr Glu His Gln
210                 215                 220
```

```
Leu Ala Ser Gly Pro Asp His Gly Cys Gly Glu Trp Cys Ser Trp Leu
225                 230                 235                 240

Ser Pro Asp Pro Asp Leu Ala His Ser Asn Leu Leu Pro Ser Ser Ser
            245                 250                 255

Ser Pro Ser Ser Ser Ser Ser Val Ser Lys Ala Ala Ser Phe Ala
        260                 265                 270

Phe Pro Thr Arg Ser Gly Ser Trp Pro Phe
        275                 280
```

<210> SEQ ID NO 37
<211> LENGTH: 387
<212> TYPE: PRT
<213> ORGANISM: Eucalyptus grandis

<400> SEQUENCE: 37

```
Met Glu Glu Ala Val Met Pro Met Tyr Ser Pro Tyr Cys Pro Pro Gly
1               5                   10                  15

Glu Thr Ser Ala Ile Val Ser Ala Leu Thr His Val Val Thr Gly Thr
            20                  25                  30

Arg Gly Gly Gln His Gly Gly Ala Tyr Gln Ser Thr Leu Ala Pro Ser
        35                  40                  45

Phe Ala Tyr Asp Ser Ala Ser Ala Gly Ser Ser Ser Gln Leu Pro Trp
    50                  55                  60

Thr Tyr Ile Gly Gln Lys Arg Glu Arg Asp Glu Ala Gly Ser Ser Ser
65                  70                  75                  80

Gln Phe Leu Ala Glu Pro Pro Leu Ser Gln Arg Asp Tyr Tyr Gly Ile
                85                  90                  95

Tyr Gly Gly Ser Phe Ala Leu Arg Glu Thr Ser Ala Ile Ser Ala Ser
            100                 105                 110

Leu Pro Gly Leu Gln Ala Arg Thr Val Ala Ala Thr Ser Asn Val Pro
        115                 120                 125

Pro Pro Pro Ser Gly Ala Gly Pro Pro Tyr Glu Gly Gly Glu Arg
    130                 135                 140

Arg Arg Arg Tyr Arg Gly Val Arg Gln Arg Pro Trp Gly Lys Trp Ala
145                 150                 155                 160

Ala Glu Ile Arg Asp Pro Gln Lys Ala Ala Arg Val Trp Leu Gly Thr
                165                 170                 175

Phe Asp Thr Ala Glu Ala Ala Ala Arg Ala Tyr Asp Glu Ala Ala Leu
            180                 185                 190

Arg Phe Arg Gly Asn Arg Ala Lys Leu Asn Phe Pro Glu Asn Val Arg
        195                 200                 205

Val Ile Pro Pro Asn Val Pro Thr Tyr Gly Ser Pro Ala Ala Ala Ala
    210                 215                 220

Ala Thr Leu Ala Ala Gly Ser Ala Pro Pro Ala Ile Ala Ala Gly Gln
225                 230                 235                 240

Leu Ala Pro Pro Tyr Ala Gly Ala Val Pro Leu Tyr Pro Arg Gly Ser
                245                 250                 255

Glu Gly Phe Asn Leu Gly Asp Tyr Trp Glu Tyr Ser Gln Leu Leu Gln
            260                 265                 270

Gly His His His Gln Pro Ala Ser Leu Met Glu Gln Met Met Tyr
        275                 280                 285

Ser Ser Gln Met Ala Ser Ser His Ser Ser Leu Ser Leu Pro Ser Ser
290                 295                 300

Ser Pro Pro Gln Pro Pro Pro Pro Pro Ser Phe Pro Ser Ser Asp
305                 310                 315                 320
```

```
Leu Tyr Gly Ser Ser Ser Ser Gly Phe Gly Ala Ser Ser Phe
                325                 330             335

Ser Ser Ser Val Pro Leu Phe Phe Pro Gln Gln Pro Leu Gly Tyr
            340             345             350

Phe Arg Pro Pro Pro Arg Pro Pro His Asp Gln Gly Ser Gly Gly
        355                 360             365

Glu Asp Ser Glu Pro Pro Ser Ser Asp Ser Ser His Tyr His Ser
    370             375             380

Ser Thr Ser
385

<210> SEQ ID NO 38
<211> LENGTH: 348
<212> TYPE: PRT
<213> ORGANISM: Eucalyptus grandis

<400> SEQUENCE: 38

Met Ser Ile Met Val Ser Ala Leu Arg Arg Val Val Ser Gly Glu Val
1               5                   10                  15

Leu Ser Gly Asp Asp Gln Gln Gln Phe Asn Leu Ser Gly Gly Tyr
            20                  25                  30

Glu Pro Ala Ala Leu Leu Gly Arg Ser Ser Leu Asp Ser Val Gly
            35                  40                  45

Val Gly Gln Lys Arg Gly Arg Gly Asp Ser Thr Ser Ser Ser Glu Phe
50                  55                  60

Leu Val Ser Gln Asp Ser Val Ala Phe Gly Gly Phe Pro Gln Ala Gly
65                  70                  75                  80

Ser Ser Ser Ser Asp Ala Arg Gly His Ala Gly Ser Thr Thr Val
                85                  90                  95

Glu Thr Ala Lys Ala Asp Thr Ala Asp Gly Thr Ala Pro Lys Tyr Glu
                100                 105                 110

Tyr Asn Tyr Glu Ala Pro Thr Thr Met Ala Ala Ser Arg Leu Asp Pro
            115                 120                 125

Thr Val Arg Arg Lys Tyr Arg Gly Val Arg Gln Arg Pro Trp Gly Lys
130                 135                 140

Trp Ala Ala Glu Ile Arg Asp Pro Phe Lys Ala Ser Arg Val Trp Leu
145                 150                 155                 160

Gly Thr Phe Asp Thr Ala Glu Gly Ala Ala Arg Ala Tyr Asp Arg Ala
                165                 170                 175

Ala Leu Gln Phe Arg Gly Ser Lys Ala Lys Leu Asn Phe Pro Glu Asn
            180                 185                 190

Val Arg Leu Arg Gln Gln Pro Ala Pro Val Ala Ser Ala Ala Phe Pro
            195                 200                 205

Ser Ala Thr His Phe Thr Ile Ser Arg Glu Leu Pro Ala Ser Gly Asn
210                 215                 220

Phe Asp Ala Thr Gly Tyr Asp Gly Gln Ala Pro Met Gln Gln Phe Pro
225                 230                 235                 240

Glu Asn Asp Phe Arg Glu Tyr His Arg Asp Val Ala Ala His Gln Glu
                245                 250                 255

Arg Leu Gln Gly Arg Thr Met Ser Leu Tyr Glu Gln Met Leu Phe Ser
            260                 265                 270

Asn Ser Ser Phe Gly Ser Gln Phe Gln Pro Ala Phe Ser Leu Ser Pro
            275                 280                 285

Ser Ser Ser Ser Ser Ser Ser Val Leu Ala Arg Ser Pro Asn Ser
```

```
                    290                 295                 300
Ser Leu Phe Met Pro Ser Pro Asn Val Thr Ser Arg Ser Gln Glu
305                 310                 315                 320

Ser Arg Arg Gly Ser Gly Asp Gly Ala Ala Val Phe Ser Gln His Pro
                325                 330                 335

Trp Thr Asp Ser Ser His Tyr Ser Ser Ser Gly
            340                 345

<210> SEQ ID NO 39
<211> LENGTH: 256
<212> TYPE: PRT
<213> ORGANISM: Eucalyptus grandis

<400> SEQUENCE: 39

Met Gln Gln Leu His Asp Leu Gly Met Thr Arg Asp Asp Glu His Gly
1               5                   10                  15

Ile Met Val Asn Ala Leu Gln His Val Ile Ser Gly Ser Ser Ser Thr
                20                  25                  30

Arg Pro Glu Pro Ile Pro Ala Phe Arg Ser Ser Thr Pro Ser His Leu
            35                  40                  45

Ser Ala Asp Gly Thr Ala Ala Glu Gln Arg Ala Pro Gly Leu Leu Ser
        50                  55                  60

Leu Pro Asp Val Ala Thr Cys Gln Val Cys Arg Ile Asp Gly Cys Leu
65                  70                  75                  80

Gly Cys Asn Phe Phe Ala Pro Gly Arg Val Ala Met Ala Val Gln Gly
                85                  90                  95

Gly Gly Asp Pro Ala Lys Ala Ala Gln Ala Leu Gly Val Gly Gln Ser
            100                 105                 110

Asn Lys Ser Ala Gly Arg Lys Arg Lys Gly Phe Tyr Arg Gly Val Arg
        115                 120                 125

Gln Arg Pro Trp Gly Lys Trp Ala Ala Glu Ile Arg Asp Pro Arg Arg
130                 135                 140

Ala Ala Arg Val Trp Leu Gly Thr Phe Glu Thr Ala Glu Gln Ala Ala
145                 150                 155                 160

Arg Ala Tyr Asp Arg Ala Ala Leu Glu Phe Arg Gly Ala Arg Ala Lys
                165                 170                 175

Leu Asn Phe Pro Leu Leu Pro Asn Asp Cys Thr Ser Thr Gly Ala Gly
            180                 185                 190

Lys Ser Arg Asp Met Met Glu Asp Gly Glu Ala Glu Thr Ile Lys
        195                 200                 205

Ala Arg Ala Glu Gly Gly Glu Ser Asn Asp Val Arg Glu Lys Ala Pro
210                 215                 220

Ser Phe Glu Arg Asp Asp Glu Arg Gly Ala Ser Glu Phe Trp Glu Lys
225                 230                 235                 240

Leu Glu Lys Glu Glu Leu Glu Gln Trp Pro Val Met His Leu Pro Pro
                245                 250                 255

<210> SEQ ID NO 40
<211> LENGTH: 246
<212> TYPE: PRT
<213> ORGANISM: Citrus sinensis

<400> SEQUENCE: 40

Met Tyr Gly Thr Ala Val Val Ser Ala Leu Ser Gln Val Ile Gly Asn
1               5                   10                  15

Thr Gln Asn Ser Pro Thr Ser Leu Gln Leu Ser Gln Asn Pro Asn Phe
```

```
                    20                  25                  30
Thr Thr Ser Ser Pro Asn Thr Ser Glu Arg Asp Leu Ser Gln Arg Val
             35                  40                  45

Glu Asp Gln Gly Asn Val Arg Arg His Tyr Arg Gly Val Arg Gln
 50                  55                  60

Arg Pro Trp Gly Lys Trp Ala Ala Glu Ile Arg Asp Pro Lys Lys Ala
 65                  70                  75                  80

Ala Arg Val Trp Leu Gly Thr Phe Asp Thr Ala Glu Ala Ala Leu
                 85                  90                  95

Ala Tyr Asp Glu Ala Ala Leu Arg Phe Lys Gly Ser Lys Ala Lys Leu
                100                 105                 110

Asn Phe Pro Glu Arg Val Gln Ala Asn Leu Thr Thr His Arg Tyr Gln
                115                 120                 125

Asp His Tyr Tyr His Ala Ala Ala Thr Thr Ser Gln Gln Val Ser
            130                 135                 140

Asn Pro Pro Pro Pro Pro Pro Arg Pro Leu Pro Leu Thr Gln Glu
145                 150                 155                 160

Val Met Tyr Ser Asn Leu Phe Gln Tyr Gln Gln Ala Asn Tyr Gly Ile
                165                 170                 175

Pro Ser Gly Phe Tyr Gly Glu Tyr Arg Tyr Leu Pro Val Thr Leu Pro
                180                 185                 190

Thr Thr Ser Ser Ser Ser Ser Ser Ser Ala Thr Ser Ser Gln Gln
                195                 200                 205

Pro Gln Gln His Glu Leu Leu Arg Tyr Gly Met Gln Leu Glu Ser Ser
            210                 215                 220

Ser Ser Ser Ala Ser Asp Pro His Glu Ser Thr Arg Arg Asn Ser Asp
225                 230                 235                 240

Thr Ser His Pro Gly Asp
                245

<210> SEQ ID NO 41
<211> LENGTH: 233
<212> TYPE: PRT
<213> ORGANISM: Citrus sinensis

<400> SEQUENCE: 41

Met Ser Ala Met Val Ser Ala Leu Thr Gln Val Ile Gly Thr Thr Thr
 1               5                  10                  15

Thr Asp Ala Asp Ala Asp Pro Ser Pro Ala Ala Val Lys Glu Glu Ser
                20                  25                  30

Ser Asp Asn Pro Leu Gln Gln Thr Gln Thr Gln Thr Gln Asp Gln Asp
             35                  40                  45

Gln Gly Thr Arg Arg Arg His Tyr Arg Gly Val Arg Gln Arg Pro Trp
 50                  55                  60

Gly Lys Trp Ala Ala Glu Ile Arg Asp Pro Lys Lys Ala Ala Arg Val
 65                  70                  75                  80

Trp Leu Gly Thr Phe Glu Thr Ala Glu Asp Ala Ala Met Ala Tyr Asp
                 85                  90                  95

Lys Ala Ala Leu Lys Phe Lys Gly Thr Lys Ala Lys Leu Asn Phe Pro
                100                 105                 110

Glu Arg Val Gln Gly Thr Thr Glu Phe Val Tyr Leu Asp Ser Ser Ser
            115                 120                 125

Ser Ser Ser Ala Phe His His His His Glu Ser Val Met Pro Ala Pro
            130                 135                 140
```

```
Pro Pro Arg Pro Thr Ser Met His His Gly Ala Tyr Pro Asp Leu Leu
145                 150                 155                 160

Gln Tyr Ala Gln Ile Leu Ser Ser Asp Asp Ala Thr Phe Asn Tyr Tyr
                165                 170                 175

Thr Ser Asn Leu Phe Asn Pro Gln Ser Ser Ser Ser Ser Ser Ser Thr
            180                 185                 190

Pro Ser Thr Phe Ser Ser Thr Thr Ser Leu Glu Gln Gln Gln Gln Glu
        195                 200                 205

Met Thr Arg Phe Ser Ser Asn Tyr Glu Ser Leu Ser Gly Ser Asp Phe
    210                 215                 220

Gln Asp His Ser Asn Asn Pro Asn Gly
225                 230
```

<210> SEQ ID NO 42
<211> LENGTH: 234
<212> TYPE: PRT
<213> ORGANISM: Citrus sinensis

<400> SEQUENCE: 42

```
Met Ser Ala Met Val Ser Ala Leu Thr Gln Val Ile Gly Thr Thr Thr
1               5                   10                  15

Thr Asp Ala Asp Ala Asp Pro Ser Pro Ala Ala Val Lys Glu Glu Ser
                20                  25                  30

Ser Asp Asn Pro Leu Gln Gln Thr Gln Thr Gln Thr Gln Asp Gln Asp
            35                  40                  45

Gln Glu Gly Thr Arg Arg Arg His Tyr Arg Gly Val Arg Gln Arg Pro
        50                  55                  60

Trp Gly Lys Trp Ala Ala Glu Ile Arg Asp Pro Lys Lys Ala Ala Arg
65                  70                  75                  80

Val Trp Leu Gly Thr Phe Glu Thr Ala Glu Asp Ala Ala Met Ala Tyr
                85                  90                  95

Asp Lys Ala Ala Leu Lys Phe Lys Gly Thr Lys Ala Lys Leu Asn Phe
                100                 105                 110

Pro Glu Arg Val Gln Gly Thr Thr Glu Phe Val Tyr Leu Asp Ser Ser
            115                 120                 125

Ser Ser Ser Ser Ala Phe His His His Glu Ser Val Met Pro Ala
        130                 135                 140

Pro Pro Pro Arg Pro Thr Ser Met His His Gly Ala Tyr Pro Asp Leu
145                 150                 155                 160

Leu Gln Tyr Ala Gln Ile Leu Ser Ser Asp Ala Thr Phe Asn Tyr
                165                 170                 175

Tyr Thr Ser Asn Leu Phe Asn Pro Gln Ser Ser Ser Ser Ser Ser Ser
            180                 185                 190

Thr Pro Ser Thr Phe Ser Ser Ser Thr Thr Ser Leu Glu Gln Gln Gln
        195                 200                 205

Glu Met Thr Arg Phe Ser Ser Asn Tyr Glu Ser Leu Ser Gly Ser Asp
    210                 215                 220

Phe Gln Asp His Ser Asn Asn Pro Asn Gly
225                 230
```

<210> SEQ ID NO 43
<211> LENGTH: 395
<212> TYPE: PRT
<213> ORGANISM: Carica papaya

<400> SEQUENCE: 43

```
Met Cys Gly Gly Ala Ile Ile Ser Asp Phe Ile Pro Thr Ala Thr Thr
1               5                   10                  15

Arg Ser Cys Lys Leu Thr Ala Asp Tyr Leu Trp Pro Asp Leu Asn Arg
            20                  25                  30

Asn Arg Lys Ser Lys Lys Ser Ser Lys Arg Ser Glu Val Val Asp Leu
                35                  40                  45

Asp Asp Asp Phe Glu Ala Asp Phe Gln Gly Phe Lys Asp Asp Glu Ser
50                          55                  60

Asp Ile Asp Val Asp Glu Asp Leu Asp Asp Ile Asp Ala Val Phe Ser
65                  70                  75                  80

Asp Ile Lys Pro Phe Ala Phe Ser Ala Thr Pro Leu Pro Arg Lys Thr
                85                  90                  95

Thr Ala Ser Ala Leu Ser Asn Gly Ser Lys Pro Val Lys Ala Val Glu
                100                 105                 110

Phe Asn Gly Leu Ala Glu Lys Ser Ala Lys Arg Lys Arg Lys Asn Gln
            115                 120                 125

Tyr Arg Gly Ile Arg Gln Arg Pro Trp Gly Lys Trp Ala Ala Glu Ile
            130                 135                 140

Arg Asp Arg Arg Lys Gly Val Arg Val Trp Leu Gly Thr Phe Asn Thr
145                 150                 155                 160

Ala Glu Glu Ala Ala Arg Ala Tyr Asp Ala Glu Ala Arg Arg Ile Arg
                165                 170                 175

Gly Lys Lys Ala Lys Val Asn Phe Pro Asp Glu Ser Pro Arg Ala Ser
                180                 185                 190

Pro Lys Arg Ala Val Asn Ser Met Lys Pro Val Ala Lys Ala Ile Leu
            195                 200                 205

Asn Ser Ala Gln Pro Asn Leu Ser Gln Asn Val Asn Tyr Phe Asn Asn
            210                 215                 220

Leu Gly Gln Asp Tyr Tyr Asn Thr Met Val Phe Val Asp Glu Lys Pro
225                 230                 235                 240

Gln Met Asn Gln Phe Ala Ser Met Asn Ser Phe Pro Pro Arg Arg Asn
                245                 250                 255

Ala Gly Val Lys Pro Phe Val Pro Ser Asp Asn Thr His Met Tyr Phe
                260                 265                 270

Ser Ser Asp Pro Gly Ser Asn Ser Phe Gly Cys Ser Glu Phe Gly Trp
            275                 280                 285

Gly Asp Gln Ala Thr Lys Thr Pro Glu Ile Ser Ser Val Leu Leu Asp
            290                 295                 300

Gln Pro Gln Phe Val Glu Asp Cys Asn Pro Glu Lys Lys Leu Lys Cys
305                 310                 315                 320

Ser Ser Glu Thr Met Val Pro Val Gln Gly Asn Ala Asn Lys Ser Leu
                325                 330                 335

Ser Glu Glu Leu Leu Ala Phe Asp Asn Gln Met Lys Tyr Leu Gln Val
            340                 345                 350

Pro His Leu Asp Ser Asn Trp Asp Ser Ser Leu Asp Ala Phe Leu Asn
            355                 360                 365

Gly Asp Ala Pro Gln Asp Ala Gly Asn Ser Met Asp Leu Trp Ala Phe
370                 375                 380

Asp Asp Leu Pro Ser Leu Val Gly Gly Val Phe
385                 390                 395

<210> SEQ ID NO 44
<211> LENGTH: 404
<212> TYPE: PRT
```

```
<213> ORGANISM: Musa acuminata subsp. malaccensis

<400> SEQUENCE: 44

Met Ala Ala Cys Ser Ser Gly Thr Ala Lys Trp Lys Leu Arg Glu Gly
 1               5                  10                  15

Lys Arg Lys Arg Ala Arg Gly Trp Glu Lys Ala Lys Ser Lys Gln Glu
            20                  25                  30

Cys Arg Ala His Gln Ser Arg Arg Pro Ala Gln Ser Ser Glu Arg Leu
        35                  40                  45

Phe Leu Ser Gln Ser Arg Ile Ile His Ser Leu Ser Phe Leu Leu Leu
    50                  55                  60

Arg Leu Leu Leu Asp Arg Leu Pro Leu Ser Pro Leu Ser Ala Val Asn
65                  70                  75                  80

Ile Ser Val Ser Leu Ser Arg Cys Cys Ile Tyr Leu Arg Leu Ser Val
                85                  90                  95

Val Phe Leu Cys Arg Arg Arg Cys His His Gln Arg Ile Ser Pro
            100                 105                 110

Asp Pro Leu Ser Gly Arg Arg Lys Glu Glu Arg Ser Arg Asn Asp
        115                 120                 125

Lys Val Asp Arg Arg Pro Gly Lys Arg Pro Leu Pro Pro Asp Glu Leu
130                 135                 140

Glu Lys Lys Glu Gly Asp Gln Gln Ala Val Ser Arg Phe Ala Ser
145                 150                 155                 160

Ser Arg Ala Asp His Asp Ala Ser Ala Met Val Ser Ala Leu Ala His
                165                 170                 175

Val Ile Ser Ser Ser Ser Val Val Asp Thr Arg Gly Gly Glu Pro
            180                 185                 190

Ala Ser Thr Gln Gln Gly Ile Lys Leu Glu Glu Ala Ala Gly Arg Gly
        195                 200                 205

Asp Thr Glu Ala Ala Gln Val Ser Glu Glu Gln Gly Asn Val Arg Arg
210                 215                 220

Arg His Tyr Arg Gly Val Arg Gln Arg Pro Trp Gly Lys Trp Ala Ala
225                 230                 235                 240

Glu Ile Arg Asp Pro Arg Lys Ala Ala Arg Val Trp Leu Gly Thr Phe
                245                 250                 255

Asp Thr Ala Glu Asp Ala Ala Val Ala Tyr Asp Glu Ala Ala Leu Arg
            260                 265                 270

Phe Lys Gly Thr Lys Ala Lys Leu Asn Phe Pro Glu Arg Val Gln Gly
        275                 280                 285

Arg Thr Asp Leu Gly Phe Leu Val Ser Pro Gly Val Pro Glu Arg Gln
290                 295                 300

Pro Pro Arg Val Pro Leu Gln Leu Pro Ala Thr Ser Tyr Pro Asp Leu
305                 310                 315                 320

Leu Gln Tyr Ala Gln Leu Leu Gln Ser Arg Asp Glu Asp Leu Gln Asn
                325                 330                 335

Val Ala Ser Gly Leu Tyr Val Gly Gly Thr Phe Thr Pro Val Ser Ser
            340                 345                 350

Gln Thr Pro Thr Thr Ser Ala Leu Gly Ser Ser Gln His Phe Leu Asp
        355                 360                 365

Phe Ser Ser Gln Ser Gln Tyr Thr Asn Phe Ser Ser Ser Ser Ser
370                 375                 380

Ser Ser Ser Ser Ser Trp Val His Gly Glu Gln Lys Asp Lys Asp Gly
385                 390                 395                 400
```

Ser Arg Pro Pro

<210> SEQ ID NO 45
<211> LENGTH: 227
<212> TYPE: PRT
<213> ORGANISM: Musa acuminata subsp. malaccensis

<400> SEQUENCE: 45

```
Met Val Ser Ala Leu Ser Arg Val Ile Ser Ser Ser Ser Val Ile
1               5                   10                  15

Asp Ala Ser Ala Gly Glu Pro Thr Val Asn Gln Gln Gly Ile Lys Leu
                20                  25                  30

Glu Gly Ala Asp Pro Gly Glu Lys Gln Ala Ile Gln Ile Ser Glu Glu
            35                  40                  45

Gln Gly Thr Val Arg Arg His Tyr Arg Gly Val Arg Gln Arg Pro Trp
50                  55                  60

Gly Lys Trp Ala Ala Glu Ile Arg Asp Pro Lys Lys Ala Ala Arg Val
65                  70                  75                  80

Trp Leu Gly Thr Phe Asp Thr Ala Glu Asp Ala Ala Val Ala Tyr Asp
                85                  90                  95

Glu Ala Ala Leu Arg Phe Lys Gly Ser Lys Ala Lys Leu Asn Phe Pro
            100                 105                 110

Gln Arg Val Gln Gly Arg Ala Glu Leu Ser Phe Leu Ala Ser Pro Gly
        115                 120                 125

Ile Pro Arg Arg Gln Pro Gln Pro Pro Thr Arg Pro Pro Ala Ser Ser
130                 135                 140

Tyr Pro Asp Leu Phe Arg Tyr Ala Gln Leu Leu Gln Ser Gly Asp Asp
145                 150                 155                 160

Asn Leu Gln Ser Val Ala Ser Gly Leu Tyr Val Gly Ser Ala Phe Thr
                165                 170                 175

Ser Ala Pro Ser Gln Ala Pro Pro Ser Ser Thr Ser Gly Ser Leu Pro
            180                 185                 190

Gln Phe Leu Gly Phe Ser Ser His Ser Pro Tyr Ser Ser Ser Ser Ser
        195                 200                 205

Ser Ser Gly Ser Trp Val Tyr Gly Asp His Lys Asp Lys Asp Ser Ser
210                 215                 220

Arg Pro Pro
225
```

<210> SEQ ID NO 46
<211> LENGTH: 256
<212> TYPE: PRT
<213> ORGANISM: Musa acuminata subsp. malaccensis

<400> SEQUENCE: 46

```
Met Asp Arg Arg His Gly Lys Arg Pro Leu Pro Asp Glu Ala Ala
1               5                   10                  15

Pro Glu Glu Lys Ala Gly Glu Leu Ser Cys Ser Pro Leu Ala Arg Ala
                20                  25                  30

Asp Gln Asp Ala Ser Ala Ile Val Ser Ala Leu Ala His Val Ile Gly
            35                  40                  45

Ser Cys Ser Pro Val Ala Gly Val Gly Gly Glu Met Arg Gln Asp
        50                  55                  60

Val Ser Gly Ser Gly Thr Gly Ser Val Glu Asn Arg Thr Gln Pro Ser
65                  70                  75                  80

Glu Glu Gln Gly Asn Ala Gly Arg Arg His Tyr Arg Gly Val Arg Gln
```

```
                    85                  90                  95
Arg Pro Trp Gly Lys Trp Ala Ala Glu Ile Arg Asp Pro Gln Lys Ala
                100                 105                 110

Ala Arg Val Trp Leu Gly Thr Phe Asp Thr Ala Val Asp Ala Ala Ile
            115                 120                 125

Ala Tyr Asp Glu Ala Ala Leu Arg Phe Lys Gly Cys Lys Ala Lys Leu
        130                 135                 140

Asn Phe Pro Glu Arg Val Gln Gly Arg Ser Asp Leu Gly Phe Leu Thr
145                 150                 155                 160

His Arg Trp Gln Ala Gln Pro Pro Val Gln Leu Pro Ala Thr Ser Tyr
                165                 170                 175

Pro Asp Leu Leu Arg Tyr Ala Arg Leu Leu Gln Ser Arg Asp Asp Asp
            180                 185                 190

Leu His Asn Arg Ala Val Gly Leu His Pro Ala Gly Ser Ser Phe Met
        195                 200                 205

Ser Thr Ser Ser His Thr Thr Pro Thr Ser Ser Leu Ser Gly Ser Ser
    210                 215                 220

Gln Glu Leu Val Gly Phe Ser His His Trp Gln Leu Arg Ser Ser Ser
225                 230                 235                 240

Ser Ser Ser Ser Trp Pro Gln Val Asp Leu Gln Asp Glu Asp Glu Asp
                245                 250                 255

<210> SEQ ID NO 47
<211> LENGTH: 229
<212> TYPE: PRT
<213> ORGANISM: Musa acuminata subsp. malaccensis

<400> SEQUENCE: 47

Met Val Ser Ala Leu Ser His Val Ile Ser Ser Arg Ser Pro Pro Val
1               5                   10                  15

Gly Ala Gly Gly Gly Glu Pro Val Met Val Gln His Asp Gly Lys Leu
            20                  25                  30

Ser Gly Ser Gly Ser Gly Ser Ala Glu Ile Arg Thr Gln Pro Ser Gly
        35                  40                  45

Glu Gln Gly Arg Arg His Tyr Arg Gly Val Arg Gln Arg Pro Trp Gly
    50                  55                  60

Lys Trp Ala Ala Glu Ile Arg Asp Pro Arg Lys Ala Ala Arg Val Trp
65                  70                  75                  80

Leu Gly Thr Phe Asp Thr Ala Glu Asp Ala Ala Ile Ala Tyr Asp Glu
                85                  90                  95

Ala Ala Leu Arg Phe Lys Gly Thr Lys Ala Lys Leu Asn Phe Pro Glu
            100                 105                 110

Arg Val Gln Gly Arg Thr Asp Leu Gly Phe Leu Val Ser Gly Gly Gly
        115                 120                 125

Ser Glu Arg Gln Pro Gln Pro Pro Thr Gln Arg Leu Pro Ala Ala Asn
    130                 135                 140

Ser Tyr Pro Asn Leu Leu Gln Tyr Ala Gln Leu Leu Gln Ser Arg Asp
145                 150                 155                 160

Gln Asp Leu His Gln Ala Ala Phe Gly Leu Tyr Ala Gly Ser Thr Phe
                165                 170                 175

Thr Ser Thr Ser Ser Gln Thr Ser Pro Thr Ser Met Ser Ala Ala Ser
            180                 185                 190

Ser Gln Glu Met Leu Asp Phe Thr Cys Gln Ser His Phe Lys Ser Ser
        195                 200                 205
```

```
Ser Ser Ser Ser Ser Trp Pro His Gly Gly His Lys His Glu Asp Gln
    210                 215                 220

Gln Pro Pro Gly Met
225

<210> SEQ ID NO 48
<211> LENGTH: 213
<212> TYPE: PRT
<213> ORGANISM: Musa acuminata subsp. malaccensis

<400> SEQUENCE: 48

Met Val Ser Ala Leu Thr His Val Ile Ser Val Ser Pro Val Val
1               5                   10                  15

Gly Ala Gly Gly Asp Glu Leu Val Ala Glu Pro Asp Ala Ser Cys Gly
                20                  25                  30

Ser Gly Pro Gly Ser Met Glu Ile Gly Thr Gln Ala Ser Glu Glu Gln
            35                  40                  45

Gly Arg Arg His Tyr Arg Gly Val Arg Gln Arg Pro Trp Gly Lys Trp
        50                  55                  60

Ala Ala Glu Ile Arg Asp Pro Lys Lys Ala Ala Arg Val Trp Leu Gly
65                  70                  75                  80

Thr Phe Asp Arg Ala Glu Asp Ala Ala Met Ala Tyr Asp Glu Ala Ala
                85                  90                  95

Leu Arg Phe Lys Gly Thr Lys Ala Lys Leu Asn Phe Pro Glu Arg Val
            100                 105                 110

Gln Gly Arg Thr Asp Leu Gly Phe Leu Val Thr Arg Ala Ala Pro Glu
        115                 120                 125

Arg Gln Pro Gln Pro Pro Ala Thr Ser Tyr Pro Asp Leu Arg Gln Tyr
    130                 135                 140

Ala Gln Leu Leu Gln Ser Gly Asp Ala Asp Val His Asn Ala Ala Leu
145                 150                 155                 160

Gly Leu Tyr Ala Gly Ser Thr Ile Thr Ser Thr Ser Leu Ser Gly Ser
                165                 170                 175

Ser Gln Glu Thr Gln Asp Leu Ser Ser Arg Ser Gln Phe Thr Ser Ser
            180                 185                 190

Ser Ala Ser Ser Ser Trp Pro Gln Ser Gly Gln Lys Glu Lys Asp Gln
        195                 200                 205

Arg Pro Pro Thr Met
    210

<210> SEQ ID NO 49
<211> LENGTH: 368
<212> TYPE: PRT
<213> ORGANISM: Musa acuminata subsp. malaccensis

<400> SEQUENCE: 49

Met Cys His Asn Val Ala Asn Pro His Gln Leu Pro Asp Asp Ser Phe
1               5                   10                  15

Ala Ala Glu Gly Ser Asp Gly Ala Pro Leu Ser Ser Tyr His Arg Ala
                20                  25                  30

Gln Glu Ile Ser Thr Ile Val Ser Ala Leu Ala His Val Met Ala Ser
            35                  40                  45

Glu Arg Arg Pro Arg Pro Val Gly Met Ala Val Asp Ser Val Ser Val
        50                  55                  60

Val Ser Ser Ser Ser Ser Ser Ser Ser Ser Ser Ser Ser Ser Leu Ser
65                  70                  75                  80
```

```
Cys Ile Ser Ser Ser Tyr Ser Ser Pro Ser Leu Gly Gly Gln Gly Gly
                85                  90                  95

Gly Ala Arg Ser Gln Asn Arg Thr Arg Val Pro Ser Pro Pro Asp
            100                 105                 110

Leu Ala Leu Arg His His Gln Gly Leu Gly Glu Phe Ala Arg Tyr Arg
            115                 120                 125

Gly Asp Ala Ser Pro Asp Val Ala Ala Thr Glu Gln Tyr Pro Gln Gly
            130                 135                 140

Gly Pro Leu Pro Ile Leu Gly Tyr Pro Val Ala Ala Ala Met Glu
145                 150                 155                 160

Glu Pro Ser Pro Ala Ser Ser Asn Pro Glu Glu Ala Glu Arg Ser Glu
                165                 170                 175

Pro Arg Arg Lys Tyr Arg Gly Val Arg Gln Arg Pro Trp Gly Lys Trp
            180                 185                 190

Ala Ala Glu Ile Arg Asp Pro His Lys Ala Ala Arg Val Trp Leu Gly
            195                 200                 205

Thr Phe Glu Thr Ala Glu Ala Ala Arg Ala Tyr Asp Ala Ala Ala
210                 215                 220

Leu Arg Phe Arg Gly Arg Arg Ala Lys Leu Asn Phe Pro Glu Asn Val
225                 230                 235                 240

Arg Leu Gln Pro Ser Leu Ser Val Pro Leu Ala Thr Ser Asn Ser Pro
                245                 250                 255

Ala Thr Thr Ser Asp Thr Ile Thr Asp Tyr Leu Ala Tyr Thr Arg Leu
            260                 265                 270

Leu Gln Gly Gly Glu Glu His Pro Arg Ile Pro Pro Thr Ser Leu Leu
            275                 280                 285

Asp Gln Tyr Met Tyr Ser Asn Tyr Ala Ser Pro Met Cys Ser Thr Val
290                 295                 300

Asn Asp Gly Ser Ser Leu Pro Ala Pro Ser Ile Pro Thr Tyr Ser Ser
305                 310                 315                 320

Val Val Ser Ser Ser Thr Pro Tyr Ser Pro Phe Tyr Ala Ser Ser
                325                 330                 335

Thr Thr Glu Gln Gln Thr Asn Trp Ser Gly Val Ser Asp Ile Pro Glu
            340                 345                 350

Thr Ser Trp Met Gly Ser Ser Gln Phe Pro Pro Ser Ser Ser Gly Ser
            355                 360                 365

<210> SEQ ID NO 50
<211> LENGTH: 387
<212> TYPE: PRT
<213> ORGANISM: Musa acuminata subsp. malaccensis

<400> SEQUENCE: 50

Met Cys Leu Lys Val Ala Asn Pro His Gln Ser Ser Asp Gly Ser Phe
1               5                   10                  15

Ala Ala Ala Gly Ser Asp Glu Met Glu Glu Asp Ala Ala Ala Ala
            20                  25                  30

Gly Met Met Tyr Ser Ser Val Thr Ala Gln Ala Ala Leu Leu Ser Gly
            35                  40                  45

His Arg Arg Ser Arg Glu Thr Ser Thr Met Val Ser Ala Leu Thr Arg
    50                  55                  60

Val Met Ala Gly Glu Gln Arg Pro Arg Pro Val Pro Met Ala Val Asp
65                  70                  75                  80

Ser Met Ser Ala Val Ser Ser Ser Ser Phe Ser Tyr Ile Phe Ser
            85                  90                  95
```

```
Pro Pro Pro Ser Tyr Ser Ser Pro Ser Thr Gly Gly Gln Ser Gly Gly
            100                 105                 110

Ala Ser Ser Gln Thr Arg Thr Arg Pro Glu Leu Pro Ser His Leu Ala
            115                 120                 125

Leu Arg Tyr Tyr Arg Cys Leu Gly Glu Phe Gly Ser Tyr Tyr Gly Gly
130                 135                 140

Ala Ser Pro Asp Val Ala Ala Val Glu Gln Tyr Pro Gln Ala Phe Leu
145                 150                 155                 160

Pro Met Leu Gln Ser Pro Ala Pro Ala Ala Ala Val Glu Glu Ala
            165                 170                 175

Ser Pro Ala Ser Ser Asn Gln Glu Glu Arg Glu Arg Ala Ala Pro Lys
            180                 185                 190

Arg Lys Tyr Arg Gly Val Arg Gln Arg Pro Trp Gly Lys Trp Ala Ala
            195                 200                 205

Glu Ile Arg Asp Pro Tyr Lys Ala Ala Arg Val Trp Leu Gly Thr Phe
            210                 215                 220

Glu Thr Ala Glu Glu Ala Ala Arg Ala Tyr Asp Glu Ala Ala Leu Arg
225                 230                 235                 240

Phe Arg Gly Ser Arg Ala Lys Leu Asn Phe Pro Glu Asn Val Arg Leu
            245                 250                 255

Gln Pro Ser His Ser Val Ala Leu Ala Ala Gln Val Pro Pro Ser Asn
            260                 265                 270

Ser Pro Ala Thr Ser Ser Gly Ala Val Ser Asp Tyr Leu Ala Tyr Ser
            275                 280                 285

Arg Leu Leu Gln Gly Ala Ser Glu Tyr Gln Arg Leu Pro Pro Ala Ser
            290                 295                 300

Leu Leu Asp Pro Phe Val His Ser Gly Val Asn Asp Ser Ser Ser Leu
305                 310                 315                 320

Pro Ala Ser Ser Phe His Ala Asn Ser Val Pro Ser Ser Thr Val Ile
            325                 330                 335

Ser Pro Ser Ser Ser Ser Ser Ser Tyr Pro Pro Ser Tyr Ala Ser
            340                 345                 350

Ser Thr Pro Thr Glu Arg Gln Met Ile Trp Gly Gly Ala Ser Gly Phe
            355                 360                 365

Pro Glu Thr Ser Trp Thr His Ser Ser Gln Phe Pro Pro Ser Ser Ser
            370                 375                 380

Gly Asp Ser
385

<210> SEQ ID NO 51
<211> LENGTH: 792
<212> TYPE: DNA
<213> ORGANISM: Arabidopsis thaliana

<400> SEQUENCE: 51
atggcgaatt caggaaatta tggaaagagg cccttcgag gcgatgaatc ggatgaaaag      60
aaagaagccg atgatgatga gaacatattc cctttcttct ctgcccgatc ccaatatgac    120
atgcgtgcca tggtctcagc cttgactcaa gtcattggaa accaaagcag ctctcatgat    180
aataaccaac atcaacctgt tgtgtataat caacaagatc ctaacccacc ggctcctcca    240
actcaagatc aagggctatt gaggaagagg cactatagag gggtaagaca acgaccatgg    300
ggaaagtggg cagctgaaat tcgggatccg caaaaggcag cacgggtgtg gctcgggaca    360
tttgagactg ctgaagctgc ggctttagct tatgataacg cagctcttaa gttcaaagga    420
```

| | |
|---|---|
| agcaaagcca aactcaattt ccctgagaga gctcaactag caagtaacac tagtacaact | 480 |
| accggtccac caaactatta ttcttctaat aatcaaattt actactcaaa tccgcagact | 540 |
| aatccgcaaa ccatacctta ttttaaccaa tactactata accaatatct tcatcaaggg | 600 |
| gggaatagta acgatgcatt aagttatagc ttggccggtg gagaaaccgg aggctcaatg | 660 |
| tataatcatc agacgttatc tactacaaat tcttcatctt ctggtggatc ttcaaggcaa | 720 |
| caagatgatg aacaagatta cgccagatat ttgcgttttg gggattcttc acctcctaat | 780 |
| tctggttttt ga | 792 |

<210> SEQ ID NO 52
<211> LENGTH: 1269
<212> TYPE: DNA
<213> ORGANISM: Zea mays

<400> SEQUENCE: 52

| | |
|---|---|
| atggagcgcg tgaagtattg tgattgtact gtgtgcagtg tgcagcggtc attgtgttct | 60 |
| acccgccgga ggaggaggag gaggaggcag atcgaccggc agctgactaa ggtggatcca | 120 |
| cggaggaggc atggcaagag gcccctaccc gccgccgagg tggaagagga ggaggaggag | 180 |
| gaggcgctgc ccccgggccc gccgcccgca aagcacgagc agctggagga gcctcaccac | 240 |
| gccgccgtct cgcagctgca aggagccacc tttagcggcg gcggagggtc gtcgtcgtct | 300 |
| tccgtgatcg gtggcccgtc gccgccgcag gcgtacgcgc agtactacta ctcggcgcgc | 360 |
| gccgacaacg acgcctccgc cgtggcctcc gcgcttgccc acgtcatccg ggcctcgcct | 420 |
| gaccagcttc cgccgcagca ggcgccggcc ttgtacggcg ccggcgtccc gggcagcctt | 480 |
| cggctgggag accacccgca agcgtctgcg caccactatc ccggtcccgg cggccacgtc | 540 |
| gccgccgccg aggaggagca aggtcggagg cggcactacc gggggtgag gcagcggccg | 600 |
| tggggcaagt gggcggcaga gatccgggac cccaagaagg cggcgcgggt gtggctcggc | 660 |
| accttcgaca cggcggagga cgccgccatc gcctacgacg aggcggcgct gcggttcaag | 720 |
| ggcaccaagg ccaagctcaa cttcccggag cgcgtgcagg gccgaaccga cctcggcttc | 780 |
| ctcgtcaccc gcggcatccc ggaccaccgg caccgtcgg cggcggtgac cctggcagca | 840 |
| atgccgccgc cgcaccacca gcacggccac cagaccgtcg tgccgtaccc cgacctcatg | 900 |
| cagtacgcgc agctgctgca gggcggccgg ggcggcggcg ccacgccga ggcggcggtc | 960 |
| cagcaggcgc accgtcagca gcagcagcag cagctcatga cgatgatggg cggtcggccg | 1020 |
| ggagtcaacc tgccctccac gttctcgccg tcgtcgtccg catcggcgcc gcagatactg | 1080 |
| gacttctcca cgcagcagct catccggccc ggcccgccgt cgccgtcgcc gccgcgggcc | 1140 |
| gcggcaatgc cgtcctcgtc ggccgctgcg gcgccgtcca cgccgtcgtc cacgaccaca | 1200 |
| gcgtcgtcgc ccagcggcgg tgcatggccg tacgcggggg agcgccacag gaataaaaaa | 1260 |
| gacgcgtga | 1269 |

<210> SEQ ID NO 53
<211> LENGTH: 1332
<212> TYPE: DNA
<213> ORGANISM: Zea mays

<400> SEQUENCE: 53

| | |
|---|---|
| atgcgcatct ctctccgcgt acttatcagt agcgagctcg gcacgtcatt gtgcactgct | 60 |
| gcaccgagcc tagcgcgagc ctccgtccga aagtccaaat cttcagctct ctccttgacg | 120 |

| | |
|---|---|
| catgcccgga tcgatcggtc cagctctacc caccggagga ggaggcagat caacgggcag | 180 |
| ctgactaagg tggatccacg gaggaggcat ggcaagaggc ccctacccgc cgacgaggag | 240 |
| gaggaagagg aggaggagct gcccccgccg ccggcaaagt acgagcagct ggatcaggag | 300 |
| gagaagcatc acgttgtcgt ctcgcagctg caagcaggag ctacctttag cggtggccga | 360 |
| gggtcttcgt cgtcttccgt ggccggccct tcgccggagg cgtacgcgca gtactactac | 420 |
| tcggcgcgcg ccgaccacga cgcctccgcc gtggcctccg cgctagccca tgtcatccgc | 480 |
| gcctcgcccg accaactccc gccgcagcag gccgcctgct tgtacggcgc cgccggcgcg | 540 |
| ccggtcctgc ggcagggaga gggagaccat ccgcaaccgc aagcggctgc gcaccaccat | 600 |
| cccggtggcc acgtcgccgc cgaggaggag caaggtctga ggcggcacta ccgaggggtg | 660 |
| aggcagcggc cgtggggcaa gtgggcggcg gagatccggg accccaagaa ggcggcgcgg | 720 |
| gtgtggctcg gcaccttcga cacggcggag gacgccgcca tcgcctacga cgaggcggcg | 780 |
| ctgcggttca agggcaccaa ggccaagctc aacttcccgg agcgcgtgca gggccgaacc | 840 |
| gacctcggct tcgtcgtcac ccgcggcatc ccggaccacc accggcaccc gcgggcggcg | 900 |
| gcggtgaacc tggcagcaat ccgcaggcg caggcgcagc cgcacttgca gcacggccgc | 960 |
| ccgaccgtca tgccgtaccc gtacccgtac cctgacctca tgcagtacgc gcagctgctg | 1020 |
| cagggcggcc ggggcggcgg cgaccacgcg gcggcggtcc agcagcagct catgatgatg | 1080 |
| ggcgggcggg gcgcaacct gcccttctcg ttctcgccgc cgtcgtcctg gagtgcgccg | 1140 |
| ccgcagatac tggacttctc ggcgcggcag ctcatcaccc agcccggccc gccgtcgtct | 1200 |
| ccggccgccc ccggcggcgc ggcgccgtcc acgccgtcgt ccacgaccac ggcgtcgtcg | 1260 |
| cccagcgcca gcgccagcgg cagtgcatgg ccgtacggtg gggagcacca caggaataaa | 1320 |
| aaggacgcgt ga | 1332 |

<210> SEQ ID NO 54
<211> LENGTH: 1074
<212> TYPE: DNA
<213> ORGANISM: Zea mays

<400> SEQUENCE: 54

| | |
|---|---|
| atgtgcttcg agctggcgga ccagcgcgga ccgcagggcg gcggcggagc ggggtggccg | 60 |
| gcgaagcggc gcgcgggagg cgtgcaggac gagggcgcgg ccgcggccgc ggggatggca | 120 |
| atggcggccg ccggccccgg ggaggtgatg tccgagtact accaggcgca ggagctgtcg | 180 |
| acgatggtgt cggcgctgac ccacgtcgtg gccggcgcgc cgatggggag cgcccctgcg | 240 |
| cagcggccaa tgcacggcgc ctccggctac tacgcgcacg agatggggag ctaccgcggc | 300 |
| gcgccatcgc cggagctcgc agggtcggag ctgagttcgg acacccagag cgcgggcgcg | 360 |
| gcggccatgg aggagcacca gtcggcagct gcgctgtcca gccaggaggg tcccgagacg | 420 |
| ccgcggaggc gctaccgcgg ggtgcgccag cggccgtggg gcaagtgggc cgccgagatc | 480 |
| cgggacccgc acaaggcggc gcgcgtctgg ctcggcacgt tcgagaccgc cgaggccgcg | 540 |
| gcgcgcgcct acgacgaggc cgcgctccgc ttccgcggca gccgcgccaa gctcaacttc | 600 |
| cccgaggacg cgcgcctcta ccggcgtcc acgcgggcg cggcggcgcc tctcgccgcg | 660 |
| gcggcctcga cctcccacc tgtctactcc ggtggcgtcc agggctcgtc ggactacctg | 720 |
| aggtaccacc agatgcttct gcaagcgtcc acgggcagcc agggcaccct gctcccgttc | 780 |
| tatggcggcg gcatgagcaa tccctacggc ggcggtgccg ccatgaccgg ttcctacggt | 840 |
| ggagccggcg gcggcaacac gagtggttcc ttgggctcct actactcgtt cccggcctcc | 900 |

```
tctgtttctg tcgccaccgt gccgtcctct acttcctctg cttcggggta ctactactcg      960
tcgccgcacg actcgcaaca cagcgaggcg tccgcggcgg cggactggaa ctgggagagc     1020
gcgctggcct ggcccgactc gagccagtac ccgccgccac ctcacactca gtag           1074
```

<210> SEQ ID NO 55
<211> LENGTH: 405
<212> TYPE: DNA
<213> ORGANISM: Vitis vinifera

<400> SEQUENCE: 55

```
atgtccgcta tggtttcagc tctcactcaa gtcattggaa acactgacaa aaacccactt       60
catgatcttg gaaacccatc accaatctcc caccactccg ccacaacccc acatgatcaa      120
ccttctcagc ttcttcaaga tcaagggaac cagctgagga aagacacta taggggagta       180
aggcaaagac cttgggggaa gtgggcagct gagatacgtg atccaaataa ggcagctcga      240
gtatggctgg gcactttcga cactgctgag gatgctgcac ttgcctatga tgaagctgct      300
cttaggttca aggaaacaa agccaagctt aacttccctg aaagagttca aggccgaagc       360
gaattaggtt acctcacaaa tcctccttcc aggtggaggt ggtga                     405
```

<210> SEQ ID NO 56
<211> LENGTH: 944
<212> TYPE: DNA
<213> ORGANISM: Vitis vinifera

<400> SEQUENCE: 56

```
atgtccgcta tggtttcagc tctcactcaa gtcattggaa acactgacaa aaacccactt       60
catgatcttg gaaacccatc accaatctcc caccactccg ccacaacccc acatgatcaa      120
ccttctcagc ttcttcaaga tcaagggaac cagctgagga agacacta taggggagta        180
aggcaaagac cttgggggaa gtgggcagct gagatacgtg atccaaataa ggcagctcga      240
gtatggctgg gcactttcga cactgctgag gatgctgcac ttgcctatga tgaagctgct      300
cttaggttca aggaaacaa agccaagctt aacttccctg aaagagttca aggccgaagc       360
gaattaggtt acctcacaaa tcgtcaagac ttccttcttc ctcagcaaca acagcttccc      420
aaccctgctg ttcctcctct tcctcatcca tccctccctc gaccgtcata tcccaatctt      480
catcactatg ctcagctcct tccaggtgga ggtggtgatt taaatcatgc tatgtccagt      540
ctttatggta gagaagcttc tactacgcag tctttgtcaa ctacatcttc atcttcttct      600
acaacctctc atccacaaca ccatcagcga agacgacaac gagaagaaga agaattacaa      660
caaccacaac ttctacaatt ttcatcactg tttggaagtt cttctagcaa cgaccctcac      720
aataacagga gagatgactg aaaaggtcag taaagagggt acttagtatt cccaataatc      780
cctttaagaa gggttgcagt aaaagatgtg aatttcggtt atgttgtctt attttatt        840
tttattttt attttaagc ttaaacccct gcctattgat ctttgtcttg agtttaagag         900
tgaaaaagag aacccacaat gcatggaagt gattctactc tata                      944
```

<210> SEQ ID NO 57
<211> LENGTH: 723
<212> TYPE: DNA
<213> ORGANISM: Populus trichocarpa

<400> SEQUENCE: 57

```
atggatgtga tggtttcagc tctagctcaa gtaattggaa gcagccacaa tagctcagct       60
```

```
caagtgcagg aaaatccatt gacctcaaca caatccagca cagaaaatga tcaaacccaa    120
ccagctgttc aagaccaagg gaatgcaagg agacgacatt atagaggagt taggcaaagg    180
ccttggggga atgggctgc tgagatccga gatcccaaga aggcagctcg agtgtggcta     240
ggcactttcg aaacggctga ggctgccgcc cttgcttacg atgaagcagc tcttaggttc    300
aaaggaagca aggctaagct caactttcct gaaagggttc catctggcgg gaccgaatta    360
ggtttcttta ctagaggcca aggtttgcat acggttactg aacctgtctc taatcacatt    420
atggctcctc tagctcgttc ccaacgatca caggaagcat ataatccaaa taattttcaa    480
tatccacaat ttcttggaac cacatcaggc tatggcttaa gccatgtcat gccgcctgca    540
gttccatttg gtggagaaac atttctttca ccgacttcct ccagtgcatc ttctaattcg    600
tggccgatat cttctcaaca gcagcagcag caacaagagg aacttttaag attatcaatg    660
cagtttggaa gttcttacaa ctctcgttat gatccttcta aatacaaaga cgaggggctt    720
tga                                                                  723
```

<210> SEQ ID NO 58
<211> LENGTH: 870
<212> TYPE: DNA
<213> ORGANISM: Solanum lycopersicum

<400> SEQUENCE: 58

```
atggaccgaa ttagacgtgg aaagaggcgc tatgaatccg aggaaaaaga agatagaaat     60
tacaatcaca tgtattcatc agctcgatct caacatgata tgtctactat ggttgcagtc    120
ctctctcaag ttattggcaa caaaagtact actaacacga attcttcttc ttcttcctcc    180
gcacatcata agccattatt aaccctaaat catcagtcta atactactgc agctatgcaa    240
aaccaattac ctcagctcaa tcaacaacaa gggaataatg agaagagaag aagacagtac    300
agaggtgtga ggcaaagacc atggggtaaa tgggcggccg aaatccgtga cccggaaaaa    360
gctgctcgtg tatggttggg tacttttcac actgcggaag atgctgcaat tgcatatgat    420
gaagctgcac ttaaatttaa aggaaacaaa gctaaactca actttccaga acgggttcaa    480
tccacaacgg atcaatttgg gatatcatac ctaattacta atacgaatca tcaacaacat    540
caatttcagc ccactaattt tctcccaaat tctgatcaat acaacaaca tcactacagt    600 aatcataatg ctgatgattt gaaatttggc gtctcgccga gttttttatca ccctacaggg    660 ttcaatccta aagcactcga tttagtggaa ccttcgaaat catcatcgat gacatatttg    720
gtacaacaag catcgtctca tcaggtacaa gaagaaccaa ggtatattaa tcaccagcaa    780
gaagatgaaa acaatctgaa attttcatct tattttggca cttattcaag ctcaggacca    840
actttggggg agtttgaaga tcaaaaataa                                     870
```

<210> SEQ ID NO 59
<211> LENGTH: 735
<212> TYPE: DNA
<213> ORGANISM: Solanum lycopersicum

<400> SEQUENCE: 59

```
atgaaaagat caagctctaa taatgatcag agggatgaaa aagacactag taacatattc     60
ccaatatact catcagctcg atctcaacat gacatgtctg ctatggtttc tgctctctct    120
caagtcattg gtaactcttc gtcttcagct agtggtgatt cctcctcagt gcatgttaat    180
ccactaaccc taattcagca acatcaatct caatcgtcta ctcaagatca agaaagaagg    240
cgatatagag gagttcgtca aaggccatgg ggtaaatggg cagcggaaat tcgggacccg    300
```

```
aaaaaggcag ctagggtttg gttaggtact tttgaaacag cggaaggtgc agcacttgct    360
tatgatgaag ctgctctaag attcaaagga aacaaagcta aactcaattt ccctgaaaga    420
gttcaaggac agttttcca atgctatgat caacctgcca cgtcatcaaa caacacatct     480
gaacaaaatt accctaatgt tcatcactat gctgatttat tacttcgtac tgacaataat    540
atcgatctaa atttcgatgt ttcaccaaat acttttatc actctttga tatttcacaa      600 tcatcaatgg aagttccagt ttatcatgag gagcagcaac aagttataac tacgcacgaa    660
gaagaagaag aagattttgt gaaatatcgt ggatcacatt ttggaaattc tacttcaagt    720
ggtggaacta aatag                                                     735
```

<210> SEQ ID NO 60
<211> LENGTH: 693
<212> TYPE: DNA
<213> ORGANISM: Solanum tuberosum

<400> SEQUENCE: 60

```
atggatcgaa ctagacatgg aagaggccc tatgaatcgg aggagaaaga agatacgaat     60
aataatcaaa tgtattcatc agctcgatct caacatgata tgtctactat ggtttctgtc    120
ctctctcaag ttattggcaa caaaagtagg actaacacaa attcttcttc ctcctcctcc    180
gcacatcata agccattatt aaccctaaat catcggtcta gtactactgc agctatgcaa    240
aaccaattac ctcagctcaa tcagcaacaa gggaataatg aaaggagaag aagacagtac    300
agaggtgtga ggcaaagacc ttggggtaaa tgggcggccg aaatccgtga cccggaaaaa    360
gctgctcgag tatggttggg tacttttcac actgcggaag atgctgcaat tgcatatgat    420
gaagctgcac ttaaatttaa aggaaacaaa gctaaactca actttccaga acgggttcaa    480
tccgcaactg atcaatttgg gatatcatac ctaattacta ctactaatca atttccagcc    540
aataaatttc tcccaaattc tgatcaatta caacatcact acgctcccgc aggtggaagt    600
aatcataatg ctgatgattt gaactttggc gtctcgccga gttcttatca ccctacaggt    660
aagagtactg taaatgattt gagtacgcag tag                                 693
```

<210> SEQ ID NO 61
<211> LENGTH: 810
<212> TYPE: DNA
<213> ORGANISM: Glycine max

<400> SEQUENCE: 61

```
atggaaggaa gatcaatatc acattcttct gaaagagaag aggaatatga tttgttccca     60
atatattctg aaaggtctca gcaagacatg tcagccatgg tttctgctct cacacaagtc    120
attggtggct ccaatagtga ttctcttcag cagcatgaag gccttttaac ttcttcacat    180
aacaacacct caacccagaa taataatgaa caatcccaag caccacaaca agaacaaggg    240
agtgtaagaa gaagacacta cagaggagtg aggcagcgtc catggggaaa gtgggctgca    300
gagattcgcg atccgaagaa agcagcgagg gtatggcttg gaacctttga aacagctgaa    360
gctgcagctc ttgcttatga tgaagctgct cttagattca aaggaagcaa agcaaaactc    420
aatttccctg aaagggttca aggcacagct agcgaatttg gttaccacct cacaaatcag    480
cacagcacta gtagtcatga tcagcaagct tctaacccta ttattactcc acactttgct    540
actactcaag aaacttattc accaagtcat cactttcaat atgcacaaca caactcatg     600 ggtggtggga gtaacagctt caataacaac caagatatgc ttcgtttcta tggggggacat   660
```

```
aacatgtttg tttcttctca gcaatctgca tcatcgtctt cttccactgc actgtctcag      720
aatcagcagg atgagttgct gagattttcg atgcaatttg agcttcttc tcattctgac      780 cattcaggga attggagggg tggacaatga                                      810

<210> SEQ ID NO 62
<211> LENGTH: 702
<212> TYPE: DNA
<213> ORGANISM: Gossypium raimondii

<400> SEQUENCE: 62
atgaacgcta tggttcatgc cctagctcaa gttattggaa acaataacag taaccctctt       60
cttcaacttc atgatgatca acatccaaac cccactgctc aacaaaacca atctcatcaa      120
cagcctcaac ctcaagatca ggggaacgcc aggagaagac actatagagg agtaaggcaa      180
agaccatggg ggaaatgggc ggccgaaatt cgtgacccga aaaaggcagc tcgggtttgg      240
cttggaacgt ttgaaacagc tgaagcagcg gccttagctt atgatgatgc agcacttagg      300
tttaaaggaa gcaaagcaaa gcttaacttc cctgaaagag ttcaaggaag attagaatcc      360
agttatctca aacaactcg tcaagaactg aacggacgg aggcgccacc tcatccgcca      420
ccaacctatc ctaatatttc tcagtacgcg cagctcctca gcggtggctt acccaatact      480
gctttcaact acgccatgcc aagtggtgct gcctatggat cctggccagc ttttactact      540
agttctcact cttcatcttc atcttcatct tccacaacgt taacttctca acaacaaggg      600
tatatgggtg gatttcatt gcactttggt ggttcatctc caacctcaga tcataccaac      660
aacatgggag attatgatta ttactattca agagatcaat ag                        702

<210> SEQ ID NO 63
<211> LENGTH: 768
<212> TYPE: DNA
<213> ORGANISM: Brassica rapa

<400> SEQUENCE: 63
atgaataatg ggaagagggcc ctttcgagct ggtgaatctg aggagaagaa agaagccgat       60
gacgacgaga acatatttcc gttcttctcg gctcgatctg aatacgacac gcgtgccatg      120
gtctcagcct tgactcaagt cattggaaac caaagcagca cgcatgataa taatctacat      180
caccctgttg agtatgatca gcaagatccc atccaacatg ttcctcctac tcaagatcat      240
ggaaacttga ggaaaataca ttatagaggg gtaaggcaac gaccatgggg aaaatgggct      300
gccgaaatta gggatccaca aaaggccgca cgcgtgtggc ttgggacatt tgagaccgct      360
gaagctgcgg ccttagctta tgatgaagca gctcttaagt tcaaaggaag caaagccaaa      420 cttaattcc ctgagagagc tcaactagca agtaacacta gtaccattac cggtctacca      480
aactattact cttctaataa tcaaacttac tactcaaatc cgcagactaa tccacaaaac      540
ataccatatt ataaccaata ctactataac caatatcttc agcaaggggg aaatagtaac      600
gatgcattaa gctatagtct ggcaggtggg gaaaccggag gctcaatata tagtcatcag      660
acattatcta ataccacttc ttccaccagct ggtggatctt taaggcaaca agaagattac      720
acaagatttt ggcattttgg ggattcttct cctaattctg ggtttga                   768

<210> SEQ ID NO 64
<211> LENGTH: 762
<212> TYPE: DNA
<213> ORGANISM: Brassica rapa

<400> SEQUENCE: 64
```

```
atgatgccct tggagcagg tgaatcggat gaaaggaaag aagccgatga tgaggagaac      60
atattccctt tcttatcagc ccgatcccaa tacgacacac gtgccatggt ctcagccttg     120
actcaagtca ttggaaacca aagcagcact catgatagta atcaacatca ccctgtagag     180
tataatcaac aagatcctat ccaacatgtt cctcctactc aagatcaagg aaacttgagg     240
aagaggcatt atagagggt aaggcaacgg ccatggggaa atgggctgc cgaaattcgg       300 gatccacaaa aggcagctcg agtgtggctc gggacatttg agaccgctga agctgcggcc    360
ttagcttatg atgaagcagc tcttaagttc aaaggaagca aagccaaact caatttccct    420
gagagagctc aactagcaag taacgctagt accattaccg gtctaccaaa ctatcactct    480
tctaataatc aaatgtatta ctcaaatccg cagaccaatc cacaaaccat gccatattat    540
aaccaatact actataacca atatcttcag caaggaggaa acagtaacga tgcattaagc    600
tatagtttgg ccggtgggga aactggaggt tcaatgtata atcatcagtc aatatctaat    660
acaacttctt catcttctgg tggatcttca aggccacaac aagaacaaga ttacgccaga    720
ttttggcatt ttggggattc ttctcccagt tcaggttttt ga                       762

<210> SEQ ID NO 65
<211> LENGTH: 653
<212> TYPE: DNA
<213> ORGANISM: Hordeum vulgare

<400> SEQUENCE: 65
atggtgtccg ctctgtccca cgtcatccgc gccacacccg accaggaacc agcctactac     60
cccgccggac ccgccgctgt ctctagagaa cagcagcatc agcacgctgc ggccatcgca    120
gaggaacaag ggaggaagcg tcactacaga ggggtgaggc agcggccatg ggaaagtgg     180 gcggcggaga tccggggaccc caagaaagcg gctcgtgtgt ggctcggcac cttcgacacg    240
gctgaggacg ccgccatcgc ctacgacgaa gcggcgctgc gcttcaaggg caccaaggcc    300 aagctaaaact tccccgagcg cgtccaggga cgcaccgacc tcggcttcgt cgtcacgcgc    360 ggcataccctg acagactgca gcaacaacag cactaccccg ccgccgtggg ggcgccggca    420
atgcggccgc cgctgcacca gcagcaggcc gtcgtgccgt accctgacct cctgcggtac    480
gcgcagctgt tgcagggcgc tggcagtgcc ggggcgctg tcaacctgcc gtttggggcc    540
atgtcgcccc cgtcgatgtc gtcctcgtcg tcgccccaca tactcgactt ctcgacacag    600
cagctcatcc gagtgagccc ggcgtccccc gccgcggcaa tatcaggttc agc            653

<210> SEQ ID NO 66
<211> LENGTH: 1321
<212> TYPE: DNA
<213> ORGANISM: Oryza sativa ssp. Indica

<400> SEQUENCE: 66
atggtcaccg cgctagccca cgtcatccgc gccgccccg acctgcacct ccccaccac       60 ccatcctcct ccgcctccgc cgccgcccac ccgcagcagg cttcttcctt ctacccgacc    120
gccgccgccg ccgcctcctc gccgtccgac cagctcgccg ccgccgccgc cgctgccgaa    180
gagcaaggta ccagctgatc cattcaccgc acaagtaaat tcctctctct caccgcgccg    240
cgtgccacgc cccgattgcg aaagcatggc acgcgcgagc gcgccataat ttggaagctt    300
cgcatccgcc aacgccaacg cccacgccgc cgtcgtcctc gtcctacgtt aatcccccatg   360 gctctagcta gctaattacc gggttaagta gcttcgaagc ttgcaatgca tgcttaatta    420
```

| | |
|---|---|
| gcggtaattg atccataatt aattaattag ttgaaccaaa cgagggttaa taagttaatt | 480 |
| aactcccaaa tcgttgccta tttcgtgccg gaagatacgc taaattaata gcgccatgtg | 540 |
| agtattttat gcacacaccg tattacgtta tccctgacga tcgaaggggg agtccgaatt | 600 |
| agtcacggat taattagcaa gttgcagtat tattattatt attattatgg gattaattag | 660 |
| tgggaattaa ttagcttagt gtgttttggt gggtgcaggg aggaggcggc actacagagg | 720 |
| tgttcgacag cggccatggg ggaagtgggc ggcggagata agggacccga agaaggcggc | 780 |
| gagggtgtgg ctggggacgt tcgacacggc ggaggacgcc gccatcgcct acgacgaggc | 840 |
| ggcgctccgg ttcaagggga ccaaggccaa gctcaacttc cccgagcgcg tccagggccg | 900 |
| caccgacctc ggcttcctcg tcacccgtgg catccccccc gccgccaccc acggtggcgg | 960 |
| ctactacccc tcgtcgtcgc cggcggcggg ggcatgcccc ccgccgcggc agcagcagac | 1020 |
| ggtcgtgccg tacccggacc tcatgcggta cgcgcagctg ctgcagggcg cgtcggcgg | 1080 |
| cagttacatg ccgttcggcg gcgccgcgac gatgtcgtcg tcgacggtgt cgtcctcgtc | 1140 |
| ggcgccgcag atactcgact tctcgacgca gcagctcatc cgggccggcc cgccgtcgcc | 1200 |
| aatgccatcg tcgggctccg gctcggcgac cgcggcggcg tcgtccacga cgtcggcgtc | 1260 |
| gtcgcccggt gcatggccgt acggcggctc ggagcgcaag aagaaggatt cgtcgtcgtg | 1320 |
| a | 1321 |

<210> SEQ ID NO 67
<211> LENGTH: 807
<212> TYPE: DNA
<213> ORGANISM: Oryza sativa ssp. Japonica

<400> SEQUENCE: 67

| | |
|---|---|
| atggtcaccg cgctagccca cgtcatccgc gccgcccccg acctgcacct ccccaccac | 60 |
| ccatcctcct ccgcctccgc cgccgcccac ccgcagcagg cttcttcctt ctacccgacc | 120 |
| gccgccgccg ccgcctcctc gccgtccgac cagctcgccg ccgccgccgc tgccgaagag | 180 |
| caagggagga ggcggcacta cagaggtgtt cgacagcggc catgggggaa gtgggcggcg | 240 |
| gagataaggg acccgaagaa ggcggcgagg gtgtggctgg ggacgttcga cacggcggag | 300 |
| gacgccgcca tcgcctacga cgaggcggcg ctccggttca aggggaccaa ggccaagctc | 360 |
| aacttccccg agcgcgtcca gggccgcacc gacctcggct tcctcgtcac ccgtggcatc | 420 |
| ccccccgccg ccacccacgg tggcggctac taccctcgt cgtcgccggc ggcggggca | 480 |
| tgccccccgc cgcggcagca gcagacggtc gtgccgtacc cggacctcat gcggtacgcg | 540 |
| cagctgctgc agggcggcgt cggcggcagt tacatgccgt tcggcggcgc cgcgacgatg | 600 |
| tcgtcgtcga cggtgtcgtc ctcgtcggcg ccgcagatac tcgacttctc gacgcagcag | 660 |
| ctcatccggg ccggcccgcc gtcaccaatg ccatcgtcgg gctccggctc ggcgaccgcg | 720 |
| gcggcgtcgt ccacgacgtc ggcgtcgtcg cccggtgcat ggccgtacgg cggctcggag | 780 |
| cgcaagaaga aggattcgtc gtcgtga | 807 |

<210> SEQ ID NO 68
<211> LENGTH: 1182
<212> TYPE: DNA
<213> ORGANISM: Setaria italica

<400> SEQUENCE: 68

| | |
|---|---|
| atgcccggat cgatcgatcc agctccatcg gccgacggga ggaggaggag gaggcagatc | 60 |
| gaccggcagc tgactaaggt ggatccccgg aggcatggca agaggcccct acccgccgac | 120 |

-continued

```
aaggaggaag aggatcagcc gccgcccccg ccgccggcga agcacgagca gctggagatc      180
gaggagcatc ggtaccacgt ctcgcagctg cagcaaggtg ctacctttag cgccggcggc      240
ggcggcggag ggtcgtcgtc gtcgtctgcc gccggcgccg cggctggtcc gtcgccggag      300
gcgtacgcgc agtactacta ctcggcgcgc gccgaccacg acgcctccgc cgtcgcctcc      360
gcgcttgccc acgtcatccg cgcctccccc gaccagctcc cgccgcacgc cttcggcggc      420
ggcggcgctc cgccgggcca gggagactac cagcaagcag cgccaccggc cgccgccgcc      480
gccgccgccg aggaggagca agcagcaggt cggaggcggc actaccgagg ggtgaggcag      540
cggccgtggg ggaaatgggc ggcggagatc cggaccccca agaaggcggc gcgggtgtgg      600
ctcggcacct tcgacacggc ggaggacgcc gccatcgcct acgacgaggc ggcgctccgg      660
ttcaagggca ccaaggccaa gctcaacttc ccggagcgcg tccagggccg caccgacatg      720
ggattcctcg tcacccgcgg catccccgac cggcaccacc accaaggagg ggcggcggtg      780
acgctggcgg caatgccgcc cccgcaccgg caacaccacc agaccgtcgt gccgtacccg      840
gacctcatgc agtacgcgca gctgctgcag ggcggcggcc ggggcggcgg cggcgccgga      900
gaccaccacg ccgaggcggc ggcccagcag gcgcaggcgc ggctcatgat gatggcccgc      960
ggcggcgtca gcctgccgtt cggcgccgcg tcgttctcgt cgtcctcctc gtcggcgccg     1020
cagatactgg acttctccac gcagcagctc atccggcccg gccgccgtc gccggcagcc     1080 gcggcgccat ccacgccgtc atccacgacc acggcgtcgt cgcccggcgg cagtgcatgg     1140
ccgtacggtg gggagcacca caggaataaa aagacgcgt ga                         1182
```

<210> SEQ ID NO 69
<211> LENGTH: 885
<212> TYPE: DNA
<213> ORGANISM: Sorghum bicolor

<400> SEQUENCE: 69

```
atgaccaaga agctcatctc cgccatggcc gggaagcaag gtttcaagga gcagcagttc       60
aatgatcaga ggagacagca ggcttcgatt caaggagacg acatcgccaa gagcctggtg      120
gggttcggcg gcggcggcgg caggctgatc tcccatgagc aggaggacgc catcatcgtg      180
gcggcgctgc ggcacgtggt gtccgggtac agcacgccgc cgccggaggt cgtcacggtg      240
gcgggcggcg agccgtgcgg ggtctgcggc atcgacggat gcctcggctg cgacttcttc      300
ggggcggcgc cggagctgac gcaacaggaa gcagtgaact tcggcacagg gcagatggta      360
gcgacagctg cggcagcggc ggccggaggg gagcacgggg agaggacgcg gcggcgtcgg      420
aagaagaaca tgtaccgcgg cgtgcggcag cggccgtggg ggaagtgggc ggcggagatc      480
cgcgacccgc ggcgcgcggc gcgcgtgtgg ctgggcacgt tcgacaccgc ggaggaggcc      540
gccagggcct acgactgcgc cgccatcgag ttccgcggcg cgcgcgccaa gctcaatttc      600
ccgggccacg aggcgttgct gccgttccag ggccatggcc atggcggcga cgcttgcgcc      660
accgcggcgg cgaacgccga dacgcagacg acaccgatgc tgatgacgcc gtcgccgtgc      720
agtgcagacg ccgcggcggc ggcgccggga gactggcagc tgggcggcgg cgtggacggc      780
ggagagggag acgaggtgtg ggaaggtctg ctacaggacc tgatgaagca ggacgaggcg      840
gacctctggt tcttgccatt ttccggcgct gcatctagtt tttga                      885
```

<210> SEQ ID NO 70
<211> LENGTH: 711
<212> TYPE: DNA

<213> ORGANISM: Theobroma cacao

<400> SEQUENCE: 70

| | | | | | |
|---|---|---|---|---|---|
| atgacagcca | tggttacagc | tcttactcat | gtgatgggaa | ccggcgggag | cgatgagcag | 60 |
| cttagtttca | caccatcgtc | ggtgccctta | tcacaatctg | cggtgaaaga | agagcctgac | 120 |
| cctcctcaac | ctgttcaaga | tcaagaaaat | acaaggagaa | gacattacag | aggagtgagg | 180 |
| caaaggccat | ggggcaaatg | gcagctgaa | atacgcgacc | ccaagaaagc | agcccgagtc | 240 |
| tggcttggca | cttttgacac | agctgaggat | gcagcccttg | catatgatag | agctgctctt | 300 |
| aagttcaaag | gaaccaaggc | aaaactaaat | tttcctgaac | gagttcaagg | gaatacggag | 360 |
| gtaagctatt | tcacgggtca | tggagattca | agtactgtcc | gtcctgacca | aaatcctacg | 420 |
| ccagcagcta | ctcctccatc | atggtcgcag | gattcatatc | cccacttgtt | tcaatacgca | 480 |
| caactacttt | caagtagtaa | tgatgctgat | atctcttatt | acacttcaaa | tctcttcaat | 540 |
| caagaacctc | tatctccaca | gtttccgtca | atggcggcgt | cacccaacat | ctcatcacaa | 600 |
| taccaccatc | aagaccagac | aagattttca | accaagtatg | agagctcttc | tggttctgat | 660 |
| tatccggagc | aatatgggaa | ggactctgat | ccaagtaacc | gaagcgagta | g | 711 |

<210> SEQ ID NO 71
<211> LENGTH: 699
<212> TYPE: DNA
<213> ORGANISM: Elaeis guineensis

<400> SEQUENCE: 71

| | | | | | |
|---|---|---|---|---|---|
| atggtgtcgg | ctctcgcgca | tgtgatcagc | tcgagcttgt | cggggtgg | agtgggagtg | 60 |
| ggaaggagcg | agtctgtggt | gattcagtcc | gagttgaacc | cagccatggc | cggaccggag | 120 |
| tcgggaagca | tggagagaga | gctcagccag | ccttcagaag | agcaagggaa | tgtgaggagg | 180 |
| agacactaca | ggggagtgag | gcaaaggcca | tgggggaaat | gggccgcaga | gataagggac | 240 |
| cccaggaagg | cagcgcgagt | atggctaggg | acctacaaca | cggccgaaga | agccgccata | 300 |
| gcctacgatg | aggcagccct | gaggttcaaa | ggcaccaagg | ccaagctcaa | ttttcccgag | 360 |
| agagtccaag | gccggactga | cctcggcttc | ttagtcagca | gggggatccc | agagcgaccg | 420 |
| ccccagccca | tcaccccacc | gccgacagca | tcatacccctg | acctccttca | gtatgctcag | 480 |
| ctcctccaaa | gtagagatga | ggacctgcac | agtgtggcat | cggggctctt | cgttacagac | 540 |
| tctttcacct | cggggtcttc | tcaagtgtca | tatcattcca | cgtcaggctc | ctcgcaagag | 600 |
| ttttggatt | tcttttcgca | gatgaggagc | tcttcttcct | ctagctcaag | gcagcctcgt | 660 |
| ggagaccaga | aggataaaga | cagcaaccag | cagcagtga | | | 699 |

<210> SEQ ID NO 72
<211> LENGTH: 705
<212> TYPE: DNA
<213> ORGANISM: Elaeis guineensis

<400> SEQUENCE: 72

| | | | | | |
|---|---|---|---|---|---|
| atggtatcgg | cccttgctca | tgtgatcagc | tcgagctcac | cggggtgg | agtgggagtg | 60 |
| ggagtgggag | gggcgagac | tagggagatc | cagccggagt | tgagcccggc | catgccgggg | 120 |
| acgggctcgg | gaagcatgga | gatcagggag | ctcagccaac | cttcacaaga | gcaagggaat | 180 |
| gtgaggagaa | ggcactacag | ggggagtgagg | caaagaccat | ggggaaatg | ggcagcagaa | 240 |
| ataagggacc | ccaagaaggc | agcaagagta | tggttaggga | cctttgacac | ggccgaacaa | 300 |
| gccgccatag | cctacgatga | ggcggccctg | aggttcaaag | gcaccaaggc | caagctcaat | 360 |

```
ttccctgaga gagtccaagg ccggactgac cttggcttct tacttagtag gggaatccca    420
gagcgacaac cagagcccat caccccatcg gcggcagcta catacccgga cctacttcag    480
tatgcccagc tcctccaaag tagagacgaa gacttccaca atgtggcatc agggctctac    540
atcggaggct ccttcgcgtc gggatcttct caaatgtcac cggcatctat gtcgggttct    600
tcgcaagagt ttttggattt ctcttcgcag tttggtacct cttcttcctc tacctcatgg    660
cctcatggag accagaagga taaagacagc agccagcatc cgtga                   705
```

<210> SEQ ID NO 73
<211> LENGTH: 735
<212> TYPE: DNA
<213> ORGANISM: Malus domestica

<400> SEQUENCE: 73

```
atgtcagcca tggtttctgc tctcactcaa gttattggaa ccaccgatga tcatgctgcc    60
gtgcaaccaa accctacatc catctcagac tcatccctcc tagtcaaaca agaacccgac    120
cgctctcaac cggttcaaga tcaagagccc gtaaggaggc gacactatag aggagtgaga    180
caaagacctt ggggaaaatg ggcagctgaa atacgtgacc caagaaaagc agccagagtt    240
tggcttggga ctttcgagac cgccgaagat gccgccattg catatgataa cgcagctctc    300
aagttcaaag gcacaaaagc caagctcaac ttccccgaac gagttcaagg caagaccgat    360
ttgggcatcc taatgggcag ttctggtagt ggtgctgcct cgactcaacg aacacaaaat    420
ctcatgacac cagctggcca tattgttaat cctcagccag ctcctgctcc attaatgatg    480
tcgcagcagc cagaaacttt ccctgatctt tatcagtacg cgcggcttct ttccggcaat    540
gatgctgatt tctacaatta ttcttcctat ccatttaatc aagatccaag atttacttca    600 cggttttgc catcatcgac gcattttca tcttccactg catcacaaga ttcacaacca     660
ccgcaacaag gacaacaaga tcatgaggaa gatgggggga atgaggaccg gaattggagt    720
aatccaaggg agtag                                                    735
```

<210> SEQ ID NO 74
<211> LENGTH: 807
<212> TYPE: DNA
<213> ORGANISM: Malus domestica

<400> SEQUENCE: 74

```
atgatcttcg atccgttttg ctcatctgct cgatctcaac atgagatgtc tgccatggtc    60
tcagctctag ctcaagttct tggaagcaat aacagccaga ccccggctgt tcaagagccg    120
gtggagccgc cactgatcac gccccagtcc agcgccatgg aattgcatga tggtcaatct    180
cctcaacagg ctcaagatca agggaatgtg aggagaaggc actatagagg agtgaggcag    240
cgaccatggg gaaagtgggc agctgagatt cgtgacccca gaaggcagc tcgagtgtgg     300 ctcggcacct ttgaaaccgc agaggccgca gcgatttctt atgatgaagc agctctcagg    360
tttaaaggaa gcaaagctaa gctcaacttt cccgaaagag ttcagggaag aattactgaa    420
ttaggttacc tcactacaac tagtactcaa caaaacttgc cagctgaggc tcaaagtatt    480
acggaccacc accagcctct tcctgatcat caatatcaac tgcaggcatt ccctaataat    540
gttgctactc ctcatgatca atatgcacca tattttctga gtggtaacga gggtgtaaat    600
tatgatgatt taccaactaa tcttagtgaa agagaaagat ttgcttttcca gacttcagaa    660 actacttcat catctttgtt accttcttta ccatctcatc aacaagaaga tcaacaacat    720
```

```
ccccttaaact attctatgcc ggcattcggt tcttcttctt cttcgagttc aaatcctccc    780
cctaggaata ggaaccgtcg accttga                                        807
```

<210> SEQ ID NO 75
<211> LENGTH: 819
<212> TYPE: DNA
<213> ORGANISM: Malus domestica

<400> SEQUENCE: 75

```
atgatcttcg agccgttttg ctcatcagct cgatctcaac atgagatgtc tgccatggtc     60
tcagctctat ctcaagttct tggaagcact aacaaccaga ccccagctgt tcaagtgccg    120
atggagccac caatgattgc tccccagtcc agcgccatgg agtcgcatga tgatcaatcy    180
cctcaacacg ctcgagatca agggactgcg aggagaaggc actatagagg agtgaggcag    240
agaccatggg ggaagtgggc ggctgagatt cgtgacccga agaaggcagc tcgggtgtgg    300
ctcggcacct ttgaaaccga cgaggcagcg gcacttgctt atgatgaagc agctctcagg    360
tttaaaggaa gcaaagctaa gctcaacttt cccgaaaagg ttcaaggaag aattactgaa    420
ttaggttccc tcactgccac tagtactcaa caaaacttgc cagctgggac atctcaagga    480
gtaattactg accaccatca ccctctttct gatyatcaat atcaactgca ggcattccct    540
aataatgttg ttactcctcc tcatgatcaa tatgcacaat attttcggag tggtcacgag    600
tgcataagtt atgatttacc agctactctt tatgaaagag atatttgc tamccagaca      660 tcagaaacta ctacatcgtc atcatcttta ttacctttct taccatctca tcaacaagaa    720
gatcaacaac atcccttaag ctattctatg ccggggttcg ggtcttcttc ttcttcgagt    780
tcaaatcctc ctcctaggaa taggaaccgt cgaccttga                           819
```

<210> SEQ ID NO 76
<211> LENGTH: 795
<212> TYPE: DNA
<213> ORGANISM: Malus domestica

<400> SEQUENCE: 76

```
atgtatgaca ttgcaacgaa ttcgcaattt gatgttcata agtggatcg aaaacatggg      60 aagaggctgc tggcttcggt tgaatcggag gagaaagagg aggatcaaat ctttcctgtt    120
tactcgactc gatctcagca agacacttct gccatggttt cagctctagc tcaggtgatt    180
ggaaaaaata gtgaccaaat taataaccca cttgatcaag tgcaaggaat aaatccatta    240
atcacctcac agtccagccc tacagagact caatctcaaa cagtacttca agatcaagga    300
aatttgagga gacaacatta cagaggagtg aggcggagac catsgggaaa gtgggctgct    360
gagattcgtg acccggtgaa ggcagcccga gtgtggctgg gcacttttga cacagctgag    420
gctgcagcac tagcttatga taaagcagca ctcaagttca arggaagcaa agctaagcta    480
aacttcccyg agagagttca agggatctct gagtcaggtt gcctcgcatt aataactact    540
gatcaacaag acagcttgaa cattaatcct cctcagccta atattactcg accaacttct    600
tccagtgttt tcgattgtac acaatataat aatgtcacat cttctacatc cttgttgtcg    660
tcgtcctcca tgccatctca acaagcggca gagctcccaa gcttttcgat gcagttcggt    720
tcttcttttt cgagttcaag ttcaggtcct cctcataagt ataggaaaga ctttgacagc    780
agtcactcaa gatga                                                     795
```

<210> SEQ ID NO 77
<211> LENGTH: 645

```
<212> TYPE: DNA
<213> ORGANISM: Malus domestica

<400> SEQUENCE: 77
atggtttcag ctctagctca ggtgatcgga aaaatagtg accaaattaa taacccactt      60
ggtcaagtgc aaggaataaa tccattaacc acctcacagt ccagccctac ggagactcaa    120
tctcaaccgg tgctacttca agatcaagga aatttgagga acaacatta cagaggagtg     180 aggcggagac catcgggaaa gtgggctgct gagattcgtg acccggtgaa ggcagcccga    240
gtgtggctgg gcacttttga cacagctgag gctgcagcac tagcttatga taaagcagca   300
ctcaagttca aaggaagcaa agctaagttw aacttccccg agagagttca agggagctct    360
gagtcaggtt gcctcacatt aataactact gatcaacaag acagcttgaa cattaatcct    420
cctcagccta atattactcg accaacttct tccagtgttt tcgattgtac acaacataat    480
aatgtcatat attgtacatc cttgttgtcg tcgtcctcca tgccatctca acaagcggca    540
gagctcccaa gcttttcgat gcagttcggt tcttcttttt cgagttcaag ttcgggccct    600
cctcataagt ataggaaaga ctttgacagc cgtcactcaa gatga                    645

<210> SEQ ID NO 78
<211> LENGTH: 915
<212> TYPE: DNA
<213> ORGANISM: Malus domestica

<400> SEQUENCE: 78 atgttttttcc ggtatacttt tctacttggt atcagagcag tttcatccgt cgtcttccgc    60
tcatccgtag tcgaagccat tcttgtcacc accaccgcac tacaatatgt ccagacaacc   120
cgcaccacca tctccgctgc tacatccacc tgttcacggg ttaagctaga caaagtggat    180
ctaaaacatg ggaagaggcc actggcttcg gttgaatcgg aggagaaaga ggaagatcaa    240
atatttcctg tttactcagc tcgatctcag caagacactt ctgccatggt ttcagctcta   300
gctcaggtga tcggaaataa tagtgaccaa attaataacc cacttgatca agtgcaagga    360
ataagttcgt taatcacctc acagtctagc cctaccgaga ctcaatctca accagtacta    420
cttcaagatc aagggaattt gaggagacaa cactatagag gagtgaggcg gagaccatgg    480
ggaaagtggg cggcggagat tcgtgatccg attaaggcag cccgagtgtg gctcggcact    540
ttcaacacag ccgaggctgc agctctagct tatgatggag ctgctctcag gttcaaagga    600
agcaaagcta agctcaactt ccccgaaaga gtagttcaag ggagctctga gtcaggttgt    660
ctcacaataa ctactcaatt acaacacagc ttgaacaata ttcctcctga ggctaatatt    720
tctcgaccaa catattccaa tgttttcgat tatgcacgat ataataatgt cacatctaca    780
tcgtcgtcct ccatgccatc tcaacaagcc gcagagctcc gaagcttttc gatgcagttt    840
ggttcttctt caagttcgag ttcgggtcct ccttataagt ataggaaaga ctttgacaga    900
agtcactcaa gatga                                                     915

<210> SEQ ID NO 79
<211> LENGTH: 732
<212> TYPE: DNA
<213> ORGANISM: Fragaria vesca

<400> SEQUENCE: 79
atgtcagcca tggtttctgc tctcactcaa gttatcggaa accccgaaga agataacaag     60
caggtgcaat caaaccctgc ttcagtgaaa gatgaaccgg accgctcaca accggttcaa    120
```

```
gatcaagaga gtactgtgag aagaaggcac tatagaggag tgaggcaaag gccttggggc    180
aaatgggcag ccgaaatccg agaccctaag aaagcagctc gagtttggct aggaactttt    240
gagacagctg aggatgcagc cattgcatat gataatgcag ctctcaaatt taaaggcaca    300
aaagccaagc tcaactttcc tgaacgagtt caaggtaact ccagcatcct tattcagggt    360
tcatccggca cgacaagtag cggcagcagt gtctccactg aacgaaatcg gagccgacca    420
gccttaaccg ttcctcatca tgatgcttcc tatgttgcac cgtcccagcc gcagcaggaa    480
agtagtagct tccctgatct atatcaatat gcgcagcttc ttcaaagcaa tgatattgat    540
ttcagctcga attatcagta ccctccaaat aatccattca atcaagatta tcatccgcag    600
tattctactc cgcagtttcc accatcaaca tattatcctt cgcatcagca acaaggacag    660
caagacgatc atgttcagga agatcatcag aatgagaaca agaactggaa taggcgtaat    720
ccgagcgagt ag                                                        732

<210> SEQ ID NO 80
<211> LENGTH: 723
<212> TYPE: DNA
<213> ORGANISM: Fragaria vesca

<400> SEQUENCE: 80
atgtctgcca tggtctcagt tctatctcga gtgattagtg gagacagtag cactgatact     60
gacccaaacc ctgcactgct tcaacttccc aacagtcca gcaccgccac accggaactt    120
gatcaatccc atcaacaagc ggcgccagat caagcaggaa gcgtgaggag gagacattat    180
agaggagtga ggcagagacc atgggggaaa tgggcagccg agattcgtga tccaaagaag    240
gcagcccgag tgtggctcgg aacttttgaa acggcggagg ctgctgcact tgcttatgat    300
gaagcagctc tcagattcaa aggaagcaaa gctaagctta acttcccgga aagagttcaa    360
gggacaagtg aatcaggcgg ttacctcaca actcaaacag ttgctcatca gcctctcatt    420
tctgattatc atcagcaaca actggtatac cgaataata tcactactac tgatcaatat    480
tatccacaat tttatgggaa cttaaactat ggtcagccag atccgagatt ttataaccag    540
cctgctacat cttcatatcc acctttcata ccaatatctc aagcacaaga agaagatcga    600
caacaacagc cggccttaag ctctcctatg ccggatttcg gttcaccgtc ttcaagtttg    660
catcctgaat atccacagta tgatactaca agaaattttg acaatagtca ttggagagga    720
tag                                                                  723

<210> SEQ ID NO 81
<211> LENGTH: 675
<212> TYPE: DNA
<213> ORGANISM: Fragaria vesca

<400> SEQUENCE: 81
atggccaagg agcaggagca cgccatcatg gtctccgccc tcgaacaggt catcggcggc     60
ggcattgcca ccagaaccag tggaacctct cagaaccact gccagtatgc cacgtcagcg    120
gctgaagcgg gaacaaataa gaaggttgtg atattagttt cggatggcga cacctgtcag    180
gtatgcaaga tcgatggctg cctcggctgc gagttcttcc cgccaagcaa taagcatggc    240
aaagggaaga gggtcaagaa gagcaagtac aggggagtga ggcagaggcc gtggggaaa     300 tgggcggcga agattcgtga cccgcggcgg gcggtgaggg tgtggctcgg acgttccag    360 acggcggagg aagcggcgag ggcttacgac aaggcggcgg tcgagttccg aggagagaaa    420
gccaagctca acttcccacg aataagcagt gaagctggta ccagtactgc agcattgacc    480
```

| | |
|---|---|
| aagcaaagca tggagactga tgatgaggtc cataatcaag tcaatccaag taatgagaag | 540 |
| tcagcgaatc aggaattggg acagggcagt gatgttaaag acgacgagat tgatcgtttc | 600 |
| atctggaaaa tgcttaaaga tgacgacggc gatgaagatt taagcacaat ggtcaactca | 660 |
| aatatgttga attga | 675 |

<210> SEQ ID NO 82
<211> LENGTH: 768
<212> TYPE: DNA
<213> ORGANISM: Fragaria vesca

<400> SEQUENCE: 82

| | |
|---|---|
| atggtatcgg ctctaactca ggtgattgga aacactactc atgaacaaaa tccgcttcaa | 60 |
| gttattgatc atcaagttct tggaaacccc caagtctttt ctgcagaaaa ccctgttgag | 120 |
| caatctcaac ctgcagtagt tcttcaagct caaggaaatg tgagacaaca ctataggga | 180 |
| gtgaggcgga ggccatgggg gaagtgggca gccgagattc gtgatccaca taaagcagcc | 240 |
| agagtgtggc tcgggacttt tgaaaccgcg gaggctgctg cccttgctta tgatgaagca | 300 |
| gctctcagat ttaaaggaag caaggctaag cttaacttcc ccgaaagagt tcaagggatc | 360 |
| agccctagta cttctagtgg tctctacctt gcaataagta ctagtaccgg tcatgatcat | 420 |
| cgactagcca attcagctcc tccagctgct ccaatttctc gaccaacaac atatagtatt | 480 |
| aatccaaata atgttaatat tgattatgat gcacttgtat catcgtctca aaaccacgga | 540 |
| caagaaagaa ctatgccgca gattaatgta caaacgacgt tgtcttctac atcctcggcc | 600 |
| tcttccatgc catctcatca tcaacaagaa cgagtacagc agcaagaaga tcagcagcag | 660 |
| cttttaaagt ttcccattat gccatttggc ggttcgtctt cgagttcatc agatcctcct | 720 |
| actaagtaca ggagagactc ctctgggagc ggtgacttta gaagatga | 768 |

<210> SEQ ID NO 83
<211> LENGTH: 720
<212> TYPE: DNA
<213> ORGANISM: Eucalyptus grandis

<400> SEQUENCE: 83

| | |
|---|---|
| atggtctcgg ctctgagccg ggtcatctcg accagcgacg acgcgccgag ctcggccgac | 60 |
| gacccggcag cgccggtgca agaggagcat ggggaccctc cgcagcaggc tccagatcaa | 120 |
| gagagtgtta gaaaaaaaca ctataggga gtaagacaaa ggccatgggg aaaatgggcg | 180 |
| gcggaaatac gcgaccccaa gaaagcagcc cgtgtttggc ttggcacttt cgagactgcc | 240 |
| gaggatgcgg ccttggcata tgatagggca gctctcaagt tcaaaggcac caaggctaag | 300 |
| ctcaatttcc ctgaacgagt tcaaggcaaa cccgagtatg ccgcatactc caatccaagt | 360 |
| caccaaaact caggtgtcaa tgttttgcct gaacaaatca atcctcagcc ggcacctttt | 420 |
| gttccatatc cacacgcggc ttttccagac ctggctcagt atgcacagct tctatcaagt | 480 |
| aatgatgctg aatttcctta ttatgtttcg aatctctatg gtcaggaacc ttttggttcg | 540 |
| caacaatctt catcaacgtc gtcctcatca attagctcat cgtcctatca ctacaaccag | 600 |
| caacaacagc aacaggagcc gcaaaatgag ccatcaagaa cttcttttgg atggtcccca | 660 |
| tctaattatg attttcaagg atatggagat ggatttgatc caagaaatca agggcaatag | 720 |

<210> SEQ ID NO 84
<211> LENGTH: 804
<212> TYPE: DNA

<213> ORGANISM: Eucalyptus grandis

<400> SEQUENCE: 84

| | | | | | |
|---|---|---|---|---|---|
| atggagggga | gaaattggaa | gagatccaag | tcccaggcag | gccatgtatc | ggaggagaca | 60 |
| gaggatggtg | atcggaagag | aaacaattat | gcatatccct | caagcttgat | ggaaacggcc | 120 |
| cgatctcaac | aagacacatc | cgccatcgta | tccgccctcg | ctcaagtcat | tgcaaaccct | 180 |
| gctgccgccg | catctcatca | tgcatccctc | agttcatccg | catctttatc | tcaaagttcg | 240 |
| cttcatgatc | atcaggctcc | agatgcacaa | gtagggaaga | acaagaagct | ggaggtgagt | 300 |
| aggaactata | gaggggtgag | gcaaaggccg | tggggtaagt | atgcagctga | gattcgggat | 360 |
| ccgaagaagg | cagctcgagt | gtggctcgga | acattcgaca | ctgcggaggg | agccgcgctg | 420 |
| gcttacgatg | aggccgccct | caggttcaaa | ggcaacaaag | ccaagctcaa | cttccctgaa | 480 |
| agagttcact | ctttgcctcc | acctatggt | cccgcttgca | atgcttctca | gcctcaatct | 540 |
| cagctgctcc | ctccagcttt | cagctcatgt | gacaatcatg | ttggggctca | actgatggat | 600 |
| ggttgtgcca | tgccacctcc | acgtcccagc | tatgtccgcg | gacaaggccc | tacttcttca | 660 |
| gcttccgcca | gtgattattt | tcagtcactc | cagcctactc | cttcgttgtc | gtcgtcttct | 720 |
| tccatgccgt | ccccttttcca | tcaacacgat | ccccaacata | gcttcgatgg | cttttcttct | 780 |
| tcttggagat | cctcccatga | atag | | | | 804 |

<210> SEQ ID NO 85
<211> LENGTH: 804
<212> TYPE: DNA
<213> ORGANISM: Eucalyptus grandis

<400> SEQUENCE: 85

| | | | | | |
|---|---|---|---|---|---|
| atggagggga | gaaattggaa | gagatccaag | tcccaggcag | gccatgtatc | ggcggagaga | 60 |
| gaggatggtg | ataagaagag | aaacaattat | gcatatccct | caagcttgat | ggaaacgggc | 120 |
| cgatctcaac | aagacacatc | cgccatcgta | tccgccctcg | ctcaagtcat | tgcaaaccct | 180 |
| gctgccgccg | aatctcatca | tgcatccctc | agttcatccg | catctttatc | tcaaagttcg | 240 |
| cttcatgatc | atcaggctcc | agatgcacaa | gtagggaaga | acaagaagct | ggaggtgagt | 300 |
| aggaactata | gaggggtgag | gcaaaggcca | tggggtaagt | atgcagctga | gattcgggat | 360 |
| ccgaagaagg | cagctcgagt | gtggctcgga | acattcgaca | ctgcggaggg | agccgcgctg | 420 |
| gcttacgatg | aggccgccct | caggttcaaa | ggcaacaaag | ccaagctcaa | cttccctgaa | 480 |
| agagttcact | ctttgcctcc | acctatggt | cccgctagca | atgcttctca | gcctcaatct | 540 |
| cagcagctcc | ctccagcttt | cagctcatgt | gacaatcatg | ttggggctca | actgatggat | 600 |
| ggttgtgcca | tgccacctcc | atgtcccagc | tttgtccgcg | gacaaggccc | tacttcttca | 660 |
| gcttccgcca | gtgattattt | tcagtctctc | cagcctactc | cttcatcgtc | gtcgtcttct | 720 |
| tccacgacat | cccctttcca | tcaacacgat | ccccaacata | gcttcgatgg | cttttcttct | 780 |
| tcttggagat | cctcccaaga | atag | | | | 804 |

<210> SEQ ID NO 86
<211> LENGTH: 849
<212> TYPE: DNA
<213> ORGANISM: Eucalyptus grandis

<400> SEQUENCE: 86

| | | | | | |
|---|---|---|---|---|---|
| atgtcggggc | tgaaggtggc | tgatcggggt | gacaaagcgc | cgatcctcta | tcccgggctg | 60 |
| gacagggaaa | gagagacgtc | agccatggtg | ctggctctgg | cgcgagtggt | ggccggggaa | 120 |

```
gtccccggcg atgccgagga gtcgtgtcct tttccttttc cctccggagt cctgaggctg    180
aagagaggcc atggagatct gtcggccgag ccatcggcgg aggcgcagct tcggagagcc    240
cctggaagag agtcgtccgt tgatgatgct gcgagaggca tcatggaagg tcccagcatg    300
aagacaacaa accatgcaac tccaacttat gagtacagca acagtacagc tgcgatgtcg    360
atgtccaacg acgaacacca accgagaaga aaatacagag gagtgagaca gaggccgtgg    420
gggaagtggg cagccgagat ccgagaccca gtcaaggccg cgagggtttg gctaggcacg    480
tttgagacgg ctgaaggggc ggcccaggcg tatgacgtcg cagccttgaa ataccgaggc    540
aacaaggcca agctcaactt cccggagaac gtcgtggccc gcctgtcgct ggcggctcct    600
cccgcgaccc agatgacggt tccagacgcc gcgaggaccc atgtgaccgt tccagcagac    660
acggagcatc agttggcctc gggtccggat catggctgcg gtgaatggtg ctcttggttg    720
tctcctgatc ctgacctcgc gcattctaat ctgttgccat catcttcttc gccgtcttct    780
tcttcatctt cagtttcaaa agcagcatct tttgctttcc ccactcgatc tggttcctgg    840
ccattttag                                                           849

<210> SEQ ID NO 87
<211> LENGTH: 1164
<212> TYPE: DNA
<213> ORGANISM: Eucalyptus grandis

<400> SEQUENCE: 87
atggaagagg cggtcatgcc gatgtactcg ccatactgtc cgcccggaga gacgtcggcg     60
atagtgtcgg ctctaacgca cgttgtcacg gggaccagag gcggtcagca tggaggagcg    120
taccaatcga cattggctcc ttcattcgct tacgattcgg cgtcggccgg cagctcatca    180
cagcttccat ggacttatat tgggcaaaag agagagcgtg acgaagcagg gagttcatca    240
caatttttgg ccgagcctcc tttaagtcag agggattact atgggatcta tggtggcagt    300
tttgcattaa gagaaacctc tgctatttcc gcttccttac ctggactcca ggcaaggact    360
gtcgccgcca cctccaacgt cccgccgcca ccttctggag cgggcccgcc gcccatatgag   420 ggcggagaga ggaggaggag atacagggga gtgaggcaga ggccgtgggg gaaatgggcg    480
gcggagatcc gcgacccccca aaaagccgca agggtctggc taggaacctt cgacacggcg   540
gaggccgccg cccgggcgta cgacgaggcc gccctccggt tcgtggcaa ccgtgccaag    600 ctcaacttcc ctgaaaacgt cagagtcatc ccgcccaacg tcccgactta cggttcccct    660
gccgccgccc ccgcgaccct cgccgccggc tccgctcctc cggcgatagc ggcgggtcag    720
ctagctcctc cgtatgcggg ggcggtcccg ctatatccta gaggatctga aggcttcaat    780
ttgggggact actgggagta ctctcagctt cttcaagggc atcatcatca tcaacctgcg    840
agcttgatgg agcaaatgat gtattcttcg cagatggctt cttcacactc gtcgttatca    900
ttgccttctt catctccgcc gcagccgccg ccgccgcctc cttctttttcc ttcatcagat    960 ttatacgggt cttcgtcatc atctggtttt ggcggcgctt cttcgttttc ttcttcagtt    1020
cctctgtttt tccctcagca gcccccgtta ggatacttcc ggcctccgcc gccgcggccc    1080
ccgcacgacc agggaagcgg cggggaagac tctgagccgc cgccgtcatc ggattcaagt    1140
cattaccatt catcaaccag ttga                                          1164

<210> SEQ ID NO 88
<211> LENGTH: 1047
<212> TYPE: DNA
```

<213> ORGANISM: Eucalyptus grandis

<400> SEQUENCE: 88

| | | | | | |
|---|---|---|---|---|---|
| atgtccataa | tggtttctgc | tctacgccgc | gtcgtgtctg | gagaagtgtt | gtcgggcgat | 60 |
| gatcagcaac | agcagttcaa | tttgagcgga | gggtacgagc | cggcagcgtt | acttggccgg | 120 |
| tccagctctt | tggattccgt | cggtgtcgga | caaaagagag | gaaggggaga | ttcgacctcg | 180 |
| tcatctgagt | tcttggtatc | tcaggattcg | gtagcttttg | gcggttttcc | gcaggcaggc | 240 |
| tcatcgtcat | cttctgatgc | cagaggtcat | gcaggctcaa | caactgttga | gacagcaaaa | 300 |
| gcagatacag | cagatggtac | tgctccaaaa | tatgaataca | actatgaggc | ccgacgacg | 360 |
| atggcagcat | caaggttgga | cccgactgtg | aggaggaaat | acagaggagt | gagacagagg | 420 |
| ccgtgggga | agtgggcggc | cgagatccga | gacccttca | aggcctcgag | ggtgtggctc | 480 |
| ggcacgtttg | acacggctga | ggggcggct | cgtgcctacg | accgggctgc | cctccagttc | 540 |
| agaggcagca | aggccaaact | caacttcccc | gagaatgtcc | ggctccggca | acaacctgct | 600 |
| cctgtggcct | ctgcagcctt | tccgtcggca | acccacttca | ccatttcccg | agagttgccg | 660 |
| gcttctggca | atttcgatgc | cactggctac | gacgggcagg | ctcctatgca | gcagtttcct | 720 |
| gaaaatgatt | ttcgcgaata | tcaccgcgat | gttgctgctc | atcaggaacg | actgcaggga | 780 |
| cgaaccatga | gtttgtacga | gcagatgctg | ttttccaact | cttcgttcgg | gagtcagttt | 840 |
| cagccagctt | tctcgctctc | tccttcttct | tcatcatcat | cgagttcagt | gctcgcgcgg | 900 |
| tctccaaact | cctctctttt | catgccttct | ccgccgaacg | tgacctcgag | gtcccaagag | 960 |
| agtcggagag | gcagcggcga | cggggcggcc | gtcttttctc | agcatccctg | gacagattcc | 1020 |
| agccattaca | gttcttcttc | aggatag | | | | 1047 |

<210> SEQ ID NO 89
<211> LENGTH: 771
<212> TYPE: DNA
<213> ORGANISM: Eucalyptus grandis

<400> SEQUENCE: 89

| | | | | | |
|---|---|---|---|---|---|
| atgcagcaat | tgcacgacct | cggcatgacc | cgagacgacg | aacacggcat | catggttaac | 60 |
| gctctccagc | acgtgatatc | cgggagcagc | tccacgcggc | ccgagccgat | cccggccttc | 120 |
| cggtcgtcca | cgccgtcgca | cctctccgcc | gacgggaccg | ccgcggagca | gcgggccccg | 180 |
| ggcctcctct | cgcttcccga | cgtggccact | tgccaggtgt | gcaggatcga | cgggtgcctc | 240 |
| gggtgcaact | tcttcgcacc | gggcagagtc | gccatggcgg | tgcagggcgg | cggggacccc | 300 |
| gccaaggctg | cccaggcgct | cggtgtgggc | cagagcaaca | agagcgccgg | caggaagagg | 360 |
| aagggcttct | acaggggagt | gcggcagagg | ccgtggggga | agtgggcggc | ggagatccgg | 420 |
| gacccgcgga | gggcggcgcg | ggtgtggctc | gggacgttcg | acacggcgga | gcaggcggcc | 480 |
| cgcgcctacg | acagggcggc | gctcgagttc | cgcggtgcgc | gggccaagct | gaacttccca | 540 |
| ctgctgccga | atgactgcac | gagcaccggt | gccggcaaga | gcaggacat | gatggaggac | 600 |
| ggcgaggctg | aagaaacgat | caaagcgagg | gcggaagggg | gagagagtaa | cgatgtccgt | 660 |
| gaaaaagctc | cgtctttcga | gcgtgatgac | gagagaggag | cgagcgagtt | ctgggagaag | 720 |
| cttgagaagg | aggagctgga | gcagtggccg | gtcatgcact | tgcctccatg | a | 771 |

<210> SEQ ID NO 90
<211> LENGTH: 741
<212> TYPE: DNA
<213> ORGANISM: Citrus sinensis

```
<400> SEQUENCE: 90
atgtacggta cagcagtggt ttcagcccett tctcaagtta ttgggaatac ccaaaatagc      60
ccaactagtc ttcaactctc tcaaaaccct aatttcacca cttcttctcc caacacatct     120
gaacgagacc tatctcaacg cgtcgaagat caagggaatg tgaggagaag acactacaga     180
ggagtgaggc aaaggccatg gggcaaatgg gcagctgaga ttcgtgatcc taagaaggca     240
gcacgggtat ggctaggaac ttttgacaca gctgaagcag cagcacttgc ttacgatgaa     300
gcagctctta ggttcaaagg aagcaaagcc aagctgaact cccagaaag agttcaagct      360 aatctcacga ctcaccgtta tcaagatcat tattatcatg ctgcggccgc tacaacttca     420
cagcaagttt ctaatcctcc tcctcctcct cctcctcgtc tctaccact aactcaagag      480 gtaatgtatt cgaatctttt tcagtatcag caagcaaact atggcatccc gtccggtttc     540
tacggcgagt ataggtatct accggtgact ttaccgacca cttcttcatc ttcatcttcg     600
tcttctgcga cgtcgtctca gcaaccgcag cagcatgagt tattaagata tggcatgcag     660
cttgaaagct cttcatcatc agcttctgat cctcatgaga gtacaaggag aaattctgat     720
acaagtcacc caggtgatta g                                                741

<210> SEQ ID NO 91
<211> LENGTH: 702
<212> TYPE: DNA
<213> ORGANISM: Citrus sinensis

<400> SEQUENCE: 91
atgtctgcca tggtttccgc tcttacacaa gtaattggca ccactaccac cgacgccgac      60
gccgacccct cgccggcagc cgttaaagaa gaatcctccg ataacccact tcaacaaact     120
caaactcaaa ctcaagatca agatcaaggt acaaggagga gacattacag aggagtaaga     180
caaagacctt ggggcaaatg gcagccgaa attagagacc ctaaaaaggc agcacgagta      240
tggctaggta catttgagac tgctgaagat gcagccatgg cttatgataa agctgccctc     300
aaattcaaag gcaccaaagc taagcttaat ttccctgaaa gagttcaggg tactactgag     360
tttgtgtatt tagattcatc atcatcaagc tctgccttc atcatcatca tgagtcggtg      420
atgcctgctc ctcctcctag gcctacatca atgcaccatg gtgcataccc ggacttgctt     480
caatatgctc aaattctatc ttctgatgat gctacttta attactatac gtccaatctc      540
tttaatccac aatcatcatc ttcttcttct tctactcctt cgacgttttc atcatctacc     600
acctcattgg aacaacaaca ggagatgacg agattttcgt caaattatga aagcttgtct     660
ggttctgatt ttcaagatca tagtaacaac ccaaatgggt ag                         702

<210> SEQ ID NO 92
<211> LENGTH: 705
<212> TYPE: DNA
<213> ORGANISM: Citrus sinensis

<400> SEQUENCE: 92
atgtctgcca tggtttccgc tcttacacaa gtaattggca ccactaccac cgacgccgac      60
gccgacccct cgccggcagc cgttaaagaa gaatcctccg ataacccact tcaacaaact     120
caaactcaaa ctcaagatca agatcaagaa ggtacaagga ggagacatta cagaggagta     180
agacaaagac cttggggcaa atgggcagcc gaaattagag accctaaaaa ggcagcacga     240
gtatggctag gtacatttga gactgctgaa gatgcagcca tggcttatga taaagctgcc     300
```

```
ctcaaattca aaggcaccaa agctaagctt aatttccctg aaagagttca gggtactact    360
gagtttgtgt atttagattc atcatcatca agctctgcct ttcatcatca tcatgagtcg    420
gtgatgcctg ctcctcctcc taggcctaca tcaatgcacc atggtgcata cccggacttg    480
cttcaatatg ctcaaattct atcttctgat gatgctactt ttaattacta tacgtccaat    540
ctctttaatc cacaatcatc atcttcttct tcttctactc cttcgacgtt ttcatcatct    600
accacctcat tggaacaaca acaggagatg acgagatttt cgtcaaatta tgaaagcttg    660
tctggttctg attttcaaga tcatagtaac aacccaaatg ggtag                    705

<210> SEQ ID NO 93
<211> LENGTH: 1188
<212> TYPE: DNA
<213> ORGANISM: Carica papaya

<400> SEQUENCE: 93
atgtgtggag gtgctataat ctccgatttc atacccaccg ctactactcg gtcgtgcaag     60
ttgaccgccg actacttatg gcccgatctg aacaggaata ggaagtctaa gaagagctcc    120
aagaggtctg aggttgtcga cttggacgat gacttcgagg ctgatttcca gggcttcaag    180
gacgacgaat ccgatattga cgtcgacgaa gatctcgacg atattgatgc tgtcttctct    240
gatattaagc cctttgcctt ctctgcaact cctcttcccc gcaaaaccac agcctctgct    300
ctctccaatg gatcaaagcc tgtgaaagct gtggaattca atgggctggc agagaaatct    360
gcaaaaagaa agaggaagaa ccaatacagg ggaatcaggc aacgcccttg ggcaaatgg     420 gctgctgaaa tccgtgaccg aaggaagggg gtcagggtct ggttaggtac ttttaacact    480
gctgaagaag ctgcaagagc ttatgatgct gaggcacgga gaattcgtgg caagaaagcc    540
aaggtgaact tcccagatga atctccacgt gcgtctccaa agcgtgccgt gaactcaatg    600
aaaccagttg ccaaggcaat cctgaattca gcacagccaa atctgagtca gaatgttaat    660
tacttcaaca accttggtca ggattactac aatacaatgg ttttttgttga tgagaaacca    720 caaatgaatc agtttgcatc aatgaattca tttcctccac gtcgaaatgc tggagttaaa    780 cccttttgtcc ctagtgacaa cacccatatg tacttcagtt ctgacccagg gagtaactcg    840
tttgggtgtt ctgaatttgg ctggggagat caggccacaa agactcctga atctcctct    900 gttcttttgg atcaacctca gtttgtggag gattgtaacc cagagaagaa gttgaagtgt    960
agttctgaaa ctatggtgcc tgttcaaggc aatgccaaca agtctctgtc tgaggagctg   1020
ctagcttttg acaatcaaat gaagtactta caagtgcctc atcttgactc gaactgggat   1080
tcatctcttg atgctttcct taacggcgat gcgcctcagg atgctgggaa ctcaatggac   1140
ctttgggcct tgatgacctt ccttctctg gttgggggag tctttttga               1188

<210> SEQ ID NO 94
<211> LENGTH: 1215
<212> TYPE: DNA
<213> ORGANISM: Musa acuminata subsp. malaccensis

<400> SEQUENCE: 94
atggcggcct gtagctcggg aactgcgaaa tggaagctcc gagaaggaaa gaggaagagg     60
gcgagggggt gggaaaaggc caaatcaaag caagaatgta gagctcatca aagccgtcgc    120
ccagcccaat catcagagcg tctgttctta tcacaatccc gaatcatcca ctctttatct    180
ttccttctgc tgcgactgct cctcgatcgg ctgcctctct ctcctctctc tgctgtaaat    240
atctccgtct ctctctctcg ctgctgtata tatctccgtc tatctgtagt cttttctttgt   300
```

```
cgtcgacgtc gctgtcacca ccaacgtata tcaccggatc ctttgtcggg gcgacggaag      360
gaagaggaaa ggtcaagaaa cgataaggtg gatcgaaggc ctgggaagag gccccttcct      420
cctgatgagc tggagaagaa ggaaggagac cagcagcagg cggtctcacg cttcgcctcg      480
tcacgcgccg accacgacgc atcggccatg gtgtccgctc tcgcgcacgt catcagctcg      540
agctcatcgg ttgtcgacac ccgaggaggg gagccagcgt cgacccaaca gggcataaaa      600
ctggaggagg ctgcaggtcg cggcgacacg gaagccgcac aggtctcgga agagcaaggg      660
aatgtgagga gaagacacta caggggagtg aggcaaaggc cgtggggcaa atgggcagcg      720
gagataaggg accccaggaa ggcggctcgt gtgtggctcg ggaccttcga cacggccgag      780
gacgcggccg tcgcctacga cgaggcagcg ttgcggttca aaggcaccaa agccaagctc      840
aactttcccg agagagtcca aggccggacc gacctcggct tcctcgtcag cccaggggtc      900
cccgagaggc agccaccccg agtaccgcta cagctgcctg cgacctcgta ccccgacctg      960
ctgcagtacg ctcaactcct ccagagtagg gatgaagact tgcagaatgt agcttcgggg     1020
ctctacgtcg gcggcacctt cacgccggtg tcctctcaga cgccaacaac ttctgcttta     1080
gggtcttcac agcacttctt ggacttctca tctcagtctc agtatacgaa cttttcttcg     1140
tcttcttctt cttcgtcttc tagctcatgg gttcatggag aacagaagga caaagacggc     1200
agtcgacctc catga                                                      1215
```

<210> SEQ ID NO 95
<211> LENGTH: 684
<212> TYPE: DNA
<213> ORGANISM: Musa acuminata subsp. malaccensis

<400> SEQUENCE: 95

```
atggtctctg ctctctctcg cgtgatcagc tcgagctcgt cggtcatcga cgcctcagcc       60
ggggagccga cggtgaacca acaagggatt aaactggagg gcgctgatcc tggggagaaa      120
caagccatcc agatctcaga agagcaaggg actgtgagaa gacactacag ggggtgagg       180 caaaggccat gggcaaatg gcagcagaa ataagggatc caagaaggc tgcacgtgtg         240 tggctgggga ccttcgacac cgccgaggac gcggccgtcg cttacgatga ggcagcattg      300
aggttcaaag gcagcaaggc caagctcaac ttccccagc gagtccaagg ccgggcggag      360
ctcagcttcc tcgccagccc ggggatcccc agaaggcaac cacagccacc gacgcggccg      420
ccggcgtctt catatccaga cttgtttcga tacgctcagc tcctccagag tggagacgac      480
aacctgcaga gcgtagcctc gggcctctac gtcggaagcg ccttcacgtc ggcgccctct      540
caggccccgc catcttctac gtcgggatct ctaccgcagt tcttgggctt ctcgtctcac      600
tcgccgtaca gttcttcttc ttcttcttct ggttcatggg tttatggaga tcacaaggat      660
aaagacagca gtcgacctcc ctga                                            684
```

<210> SEQ ID NO 96
<211> LENGTH: 771
<212> TYPE: DNA
<213> ORGANISM: Musa acuminata subsp. malaccensis

<400> SEQUENCE: 96

```
atggatcgaa gacatggaaa gaggcctctt cctcctgacg aggcggcacc ggaggagaaa       60 gcggagagc tctcgtgctc gccactggcc cgggccgatc aggatgcgtc ggccatcgtg      120
tcggccctcg cccacgtgat cggctcttgc tcgccggtgg ccggcgtcgg aggggggtgag      180
```

| | |
|---|---|
| atgcgacaag atgttagtgg atcaggaaca ggctcggtgg agaacaggac tcagccctcc | 240 |
| gaagagcaag gaaatgcggg acgaaggcat tataggggag tgaggcaaag gccatggggg | 300 |
| aaatgggcag cggagataag ggatccccag aaggctgctc gtgtatggct tgggaccttc | 360 |
| gacacggcgg tggatgcggc catcgcctac gacgaggccg ccctcaggtt caaaggctgc | 420 |
| aaagccaagc tcaacttccc cgagagagtc caaggccgct ctgacctcgg cttcttgaca | 480 |
| catcgatggc aagctcagcc gccggtgcaa ctcccggcga cttcgtaccc ggacttgctt | 540 |
| cggtacgctc gactcctcca gagtagggac gacgacctgc acaaccgggc tgtcgggctc | 600 |
| caccccgcgg gaagctcctt catgtcaacc tcctcgcaca caacgccgac ttcttctttg | 660 |
| tctgggtctt cgcaggagct ggtgggtttc tcacaccatt ggcagttgag gagctcttct | 720 |
| tcttcgagct cgtggcctca ggttgacctg caggacgagg acgaagacta g | 771 |

<210> SEQ ID NO 97
<211> LENGTH: 690
<212> TYPE: DNA
<213> ORGANISM: Musa acuminata subsp. malaccensis

<400> SEQUENCE: 97

| | |
|---|---|
| atggtctcgg ccctctctca cgtgatcagc tcccgctcgc cgcccgtcgg cgccggagga | 60 |
| ggcgagccag tcatggtcca gcatgatgga aaactcagcg gatctgggtc tggctcggcg | 120 |
| gagatcagga cgcagccctc cggtgagcaa ggcagaagac attacagggg agtgaggcag | 180 |
| aggccatggg ggaaatgggc agcggagata agggatccca ggaaagcagc tcgtgtatgg | 240 |
| ctggggacgt tcgacacggc ggaggacgcc gccattgcct acgatgaagc cgccctgcgg | 300 |
| ttcaaaggca ccaaagccaa gctcaacttc cccgagcgag tacagggccg caccgacctc | 360 |
| ggcttcttgg tgagcggcgg aggctcggaa cggcaacccc agccaccgac gcagcggctg | 420 |
| ccggcggcta attcgtaccc gaacctgctc cagtacgcgc aactcctcca gagcagggac | 480 |
| caagacctgc accaggcggc cttcggcctc tacgctggga gcaccttcac gtccacgtcc | 540 |
| tcccagacat cgccgacttc catgtccgcg gcgtcttcgc aagagatgct ggacttcacc | 600 |
| tgccaatcgc atttcaagag ctcctcttct tcgagttcgt ggcctcatgg cggccacaag | 660 |
| cacgaagacc agcagccacc aggcatgtaa | 690 |

<210> SEQ ID NO 98
<211> LENGTH: 642
<212> TYPE: DNA
<213> ORGANISM: Musa acuminata subsp. malaccensis

<400> SEQUENCE: 98

| | |
|---|---|
| atggtgtctg ccctcaccca cgtgatcagc tctgtctccc cggtcgtcgg tgccggagga | 60 |
| gatgagctgg tggcggaacc ggatgctagt tgtggatcag ggccaggttc catggagatc | 120 |
| ggaacacagg cttccgaaga gcaaggtagg aggcactaca ggggagtgag gcaaaggccg | 180 |
| tgggggaaat gggcagcaga gatcagagac ccgaagaagg ccgctcgtgt atggctgggg | 240 |
| accttcgaca gggccgagga cgccgccatg gcctacgacg aggccgccct aaggttcaag | 300 |
| ggcactaaag ccaagctcaa cttccccgag agagtccaag gccgcaccga cctcggcttc | 360 |
| ctggtgactc gagcagcacc cgaacggcaa ccccaaccgc cggcgacttc atatccggac | 420 |
| ctgcgtcagt acgctcagct cctccagagc ggggacgcag acgtgcacaa cgcggccctc | 480 |
| ggcctctacg ccggaagcac catcacgtcg acgtccttgt ctggctcttc gcaagagacg | 540 |
| caggatttat cttctcgatc gcagttcacg agctcttccg cttccagctc gtggcctcag | 600 |

| | |
|---|---|
| agtggccaga aggagaaaga tcagcggcca ccaaccatgt aa | 642 |

<210> SEQ ID NO 99
<211> LENGTH: 1107
<212> TYPE: DNA
<213> ORGANISM: Musa acuminata subsp. malaccensis

<400> SEQUENCE: 99

| | |
|---|---|
| atgtgtcaca acgtggcgaa cccacaccag ctgcccgacg acagcttcgc cgccgagggg | 60 |
| agtgatggcg caccgctctc gagttaccat cgggcgcagg agatatccac catagtgtca | 120 |
| gcgctggcgc atgtcatggc ttccgagcgg aggccgcggc cggttgggat ggcagtggac | 180 |
| tccgtgtcgg tcgtctcttc ctcgtcttcc tcctcctcct cctcatcatc ttcgctgtcc | 240 |
| tgcatctctt cttcgtactc gtccccgtct ctgggcggtc aaggtggcgg cgcaagaagt | 300 |
| cagaacagga cgagacgggt gccgtcgccg cctgacttgg cgttgaggca ccatcaaggc | 360 |
| cttggcgagt tcgcacgcta ccgaggcgac gcatcaccag acgttgcagc aacagagcag | 420 |
| tatccacaag gaggccctct gccgatacta ggatacgctg ttcctgcagc agccatggaa | 480 |
| gagccctccc ctgcttcctc caacccggaa gaggcggaga gaagcgagcc gagaaggaag | 540 |
| taccgcggcg tccgccagcg gccgtgggga aaatggcgg cggagatccg ggatccccac | 600 |
| aaggcggcgc gggtgtggct gggcacgttc gagactgccg aggaggcagc gcgggcgtac | 660 |
| gacgcggccg cctccgcttc cgtggcaga agagccaaac tcaacttccc ggagaacgtc | 720 |
| cgactgcagc cgtcgctctc cgtcccgctt gcgacgtcca attccctgc caccacgtcg | 780 |
| gataccataa ccgattactt ggcgtacacg aggctgttgc aggggggcga ggagcacccg | 840 |
| cggatccctc cgacgagtct cttggatcag tacatgtact ccaattacgc ttcgcccatg | 900 |
| tgttcgactg tgaacgacgg cagttcttta cctgctccct ccatccctac ctactcctcc | 960 |
| gttgtatctt catcatcaac tccgtactct ccattctatg cttcgagcac gacggagcag | 1020 |
| cagacgaact ggagtggagt gtcggatatt ccggagacat catggatggg ttccagccag | 1080 |
| tttcctccat cttcttcggg cagctga | 1107 |

<210> SEQ ID NO 100
<211> LENGTH: 1164
<212> TYPE: DNA
<213> ORGANISM: Musa acuminata subsp. malaccensis

<400> SEQUENCE: 100

| | |
|---|---|
| atgtgtctaa aagtggcgaa cccacaccag tcgtcggacg gcagcttcgc tgcggcgggg | 60 |
| agcgatgaga tggaagagga cgcggcggcg gcggcgggga tgatgtattc ttcggtgacg | 120 |
| gcccaggcgg cgttgctttc gggtcatcgc cgctctcggg agacatccac catggtctcg | 180 |
| gccctgacac gcgtcatggc cggcgagcag aggccgaggc cagttccgat ggctgtggac | 240 |
| tccatgtcgg ccgtctcttc ttcctcgtcg ttctcttaca tcttttctcc tcctccgtcg | 300 |
| tattcctcgc catcgaccgg tggtcaaagt ggcggcgcaa gtagtcagac gagaacgaga | 360 |
| ccggagctgc cgtctcacct ggcactgagg tactaccgat gtcttggcga gttcgggagc | 420 |
| tactacggcg gagcatcacc cgatgttgca gcagtggagc agtatccaca agcatttctg | 480 |
| ccgatgctgc aatcccctgc tcctgcagca gcagccgtgg aggaggcctc ccctgcttcc | 540 |
| tcgaaccaag aggaagggga aagggcggcg ccgaaaagga agtatcgcgg cgtccgccag | 600 |
| cggccgtggg gcaaatgggc ggccgagatc cgcgaccct acaaggctgc tcgggtatgg | 660 |

```
ctggggacct tcgagacggc cgaggaggcg gcgcggcgt acgacgaggc cgccctccgc    720
ttccgtggca gcagagccaa gctcaacttc cccgagaacg tccgccttca gccgtcccac    780
tccgtcgctc tggcggcgca ggtgccgccg tccaactccc ccgctacctc ttccggcgcc    840
gtgagcgact acttggcgta ctcgaggctc ctgcagggcg cctcggagta ccagaggctc    900
cctccggcga gcctgttgga cccgttcgtg cactctggcg tgaacgacag cagttctctg    960
cctgcctcgt cctttcacgc caactccgtt ccatcttcga ctgttatctc tccttcttcc   1020
tcctcctcct cctcttatcc tccatcctac gcttcgagca caccaacgga gcggcagatg   1080
atctggggcg gggcgtcggg gtttcctgag acatcatgga ctcattcaag ccagtttcct   1140
ccgtcatctt ctggggacag ctga                                          1164

<210> SEQ ID NO 101
<211> LENGTH: 490
<212> TYPE: PRT
<213> ORGANISM: Arabidopsis thaliana

<400> SEQUENCE: 101

Met Tyr Lys Gln Pro Arg Gln Glu Leu Glu Ala Tyr Tyr Phe Glu Pro
1               5                   10                  15

Asn Ser Val Glu Lys Leu Arg Tyr Leu Pro Val Asn Asn Ser Arg Lys
                20                  25                  30

Arg Phe Cys Thr Leu Glu Pro Phe Pro Asp Ser Pro Pro Tyr Asn Ala
            35                  40                  45

Leu Ser Thr Ala Thr Tyr Asp Asp Thr Cys Gly Ser Cys Val Thr Asp
        50                  55                  60

Glu Leu Asn Asp Phe Lys His Lys Ile Arg Glu Ile Glu Thr Val Met
65                  70                  75                  80

Met Gly Pro Asp Ser Leu Asp Leu Leu Val Asp Cys Thr Asp Ser Phe
                85                  90                  95

Asp Ser Thr Ala Ser Gln Glu Ile Asn Gly Trp Arg Ser Thr Leu Glu
            100                 105                 110

Ala Ile Ser Arg Arg Asp Leu Arg Ala Asp Leu Val Ser Cys Ala Lys
        115                 120                 125

Ala Met Ser Glu Asn Asp Leu Met Met Ala His Ser Met Met Glu Lys
130                 135                 140

Leu Arg Gln Met Val Ser Val Ser Gly Glu Pro Ile Gln Arg Leu Gly
145                 150                 155                 160

Ala Tyr Leu Leu Glu Gly Leu Val Ala Gln Leu Ala Ser Ser Gly Ser
                165                 170                 175

Ser Ile Tyr Lys Ala Leu Asn Arg Cys Pro Glu Pro Ala Ser Thr Glu
            180                 185                 190

Leu Leu Ser Tyr Met His Ile Leu Tyr Glu Val Cys Pro Tyr Phe Lys
        195                 200                 205

Phe Gly Tyr Met Ser Ala Asn Gly Ala Ile Ala Glu Ala Met Lys Glu
210                 215                 220

Glu Asn Arg Val His Ile Ile Asp Phe Gln Ile Gly Gln Gly Ser Gln
225                 230                 235                 240

Trp Val Thr Leu Ile Gln Ala Phe Ala Ala Arg Pro Gly Gly Pro Pro
                245                 250                 255

Arg Ile Arg Ile Thr Gly Ile Asp Asp Met Thr Ser Ala Tyr Ala Arg
            260                 265                 270

Gly Gly Gly Leu Ser Ile Val Gly Asn Arg Leu Ala Lys Leu Ala Lys
        275                 280                 285
```

```
Gln Phe Asn Val Pro Phe Glu Phe Asn Ser Val Ser Val Ser
    290                 295                 300

Glu Val Lys Pro Lys Asn Leu Gly Val Arg Pro Gly Glu Ala Leu Ala
305                 310                 315                 320

Val Asn Phe Ala Phe Val Leu His His Met Pro Asp Glu Ser Val Ser
                325                 330                 335

Thr Glu Asn His Arg Asp Arg Leu Leu Arg Met Val Lys Ser Leu Ser
                340                 345                 350

Pro Lys Val Val Thr Leu Val Glu Gln Glu Ser Asn Thr Asn Thr Ala
                355                 360                 365

Ala Phe Phe Pro Arg Phe Met Glu Thr Met Asn Tyr Tyr Ala Ala Met
                370                 375                 380

Phe Glu Ser Ile Asp Val Thr Leu Pro Arg Asp His Lys Gln Arg Ile
385                 390                 395                 400

Asn Val Glu Gln His Cys Leu Ala Arg Asp Val Val Asn Ile Ile Ala
                405                 410                 415

Cys Glu Gly Ala Asp Arg Val Glu Arg His Glu Leu Leu Gly Lys Trp
                420                 425                 430

Arg Ser Arg Phe Gly Met Ala Gly Phe Thr Pro Tyr Pro Leu Ser Pro
                435                 440                 445

Leu Val Asn Ser Thr Ile Lys Ser Leu Leu Arg Asn Tyr Ser Asp Lys
                450                 455                 460

Tyr Arg Leu Glu Glu Arg Asp Gly Ala Leu Tyr Leu Gly Trp Met His
465                 470                 475                 480

Arg Asp Leu Val Ala Ser Cys Ala Trp Lys
                485                 490

<210> SEQ ID NO 102
<211> LENGTH: 542
<212> TYPE: PRT
<213> ORGANISM: Zea mays

<400> SEQUENCE: 102

Met Ser Ala Arg Asp Ser Asn His Ser Tyr Lys Cys Ser Asp Asp Ser
1               5                   10                  15

Gln Met Pro Tyr Tyr Asn Asn Ser Ala Pro Val Gly Glu Asn Gly Arg
                20                  25                  30

Ile His Met Ala Glu Asn Ser Leu Gly His His Tyr Ser Ser Ser Asp
                35                  40                  45

Ile Gly Ser Gln Arg Ile Asn Asn Ser Asn Pro Gln Val Phe Glu Ala
    50                  55                  60

Gln Tyr Cys Thr Leu Glu Ser Ser Ala Asn Gly Val Tyr Pro Ala
65                  70                  75                  80

Gln Ser Ser Thr Ser Ser His Ser Ile Ser Pro Leu Ser Gly Ser Pro
                85                  90                  95

Leu Ser Gln His Asp Ser His Ser Asp His Thr Tyr Ser Ser Pro Pro
                100                 105                 110

Ser Ala Ser Cys Leu Thr Glu Val Ala Asp Leu Leu Ile Lys Gln Lys
                115                 120                 125

Glu Leu Glu Asn Ser Ile Val Gly Pro Gly Leu Asp Ile Ser Ser Asp
                130                 135                 140

Cys Ser Arg Ser Leu Leu Gln Ala His Val Pro Val Arg Pro Asp Asn
145                 150                 155                 160

Trp Arg Gln Leu Leu Gly Ile Asn Gly Gly Asp Leu Met Gln Val Val
```

```
                165                 170                 175
Ile Ala Cys Gly Lys Ala Val Ala Glu Asn Asp Val Phe Ala Thr Glu
            180                 185                 190
Leu Leu Ile Ser Glu Leu Gly His Leu Val Ser Val Ser Gly Asp Pro
        195                 200                 205
Met Gln Arg Leu Gly Ala Tyr Met Leu Glu Gly Ile Val Ala Arg Leu
    210                 215                 220
Ser Ser Ser Gly Ser Met Leu Tyr Lys Ser Leu Lys Cys Lys Glu Pro
225                 230                 235                 240
Thr Ser Ser Glu Leu Met Ser Tyr Met His Leu Leu Tyr Glu Ile Cys
                245                 250                 255
Pro Phe Tyr Lys Phe Gly Tyr Met Ser Ala Asn Gly Ala Ile Ala Glu
            260                 265                 270
Ala Ile Lys Gly Glu Asn Phe Val His Ile Ile Asp Phe Gln Ile Ala
        275                 280                 285
Gln Gly Ser Gln Trp Val Thr Leu Leu Gln Ala Leu Ala Ala Arg Pro
    290                 295                 300
Gly Gly Pro Pro Tyr Ile Arg Ile Thr Gly Ile Asp Asp Ser Asn Ser
305                 310                 315                 320
Ala Tyr Ala Arg Gly Gly Gly Leu Asp Ile Val Gly Arg Thr Leu Cys
                325                 330                 335
Asp Val Ala Asn Ser Cys Gly Leu Pro Phe Glu Phe Asn Ala Val Pro
            340                 345                 350
Ala Ala Ser His Glu Val Glu Leu Gln His Leu Ala Ile Arg His Gly
        355                 360                 365
Glu Ile Ile Ala Val Asn Phe Ala Tyr Gln Leu His His Val Pro Asp
    370                 375                 380
Glu Ser Val Ser Thr Glu Asn His Arg Asp Arg Ile Ile Arg Met Ile
385                 390                 395                 400
Lys Ser Ile Asn Pro Arg Val Val Thr Leu Val Glu Gln Glu Ser Asn
                405                 410                 415
Thr Asn Thr Ala Pro Phe Phe Pro Arg Tyr Met Glu Thr Leu Asn Tyr
            420                 425                 430
Tyr Thr Ala Met Phe Glu Ser Ile Asp Val Ala Leu Pro Arg Asp Asp
        435                 440                 445
Arg Arg Arg Met Ser Ala Glu Gln His Cys Val Ala Arg Asp Ile Val
    450                 455                 460
Asn Leu Ile Ala Cys Glu Gly Ala Glu Arg Val Glu Arg His Glu Leu
465                 470                 475                 480
Phe Gly Lys Trp Lys Ser Arg Phe Ala Met Ala Gly Phe Arg Pro Tyr
                485                 490                 495
Pro Leu Ser Ser Val Val Asn Asn Thr Ile Asn Thr Leu Leu His Thr
            500                 505                 510
Tyr Asn Ser Tyr Arg Leu Glu Glu Arg Asp Gly Val Leu Tyr Leu
        515                 520                 525
Gly Trp Lys Asn Arg Val Leu Val Ser Ser Ala Trp Cys
    530                 535                 540

<210> SEQ ID NO 103
<211> LENGTH: 554
<212> TYPE: PRT
<213> ORGANISM: Zea mays

<400> SEQUENCE: 103
```

```
Met Ala Asp Thr Pro Thr Ser Arg Met Val His Pro Phe Gly Asp Ala
1               5                   10                  15

Pro Arg Gln Thr Pro Lys Gln Phe Leu Tyr Ser Gly Asn Pro Gln His
            20                  25                  30

Leu Cys His Pro Tyr Gln Ser Ala Pro Asp Thr His Val Val Leu Gln
            35                  40                  45

Arg Arg Tyr Thr Val Arg Ser Gln Ser His Ser Pro Asn Asn Ala Gly
50                  55                  60

Ser Glu Asp His Glu Thr His Lys Gln Tyr Thr Leu Glu Ser Ser Ala
65                  70                  75                  80

Ala Ser Gly Cys Ser Arg His Gly Ser Pro Ser Gln Ser Val His
                85                  90                  95

Ala Gly Ser Gly Ser Pro Val Ser His Asp Ser His Ser Gly Ser
                100                 105                 110

Thr Asn Gly His Gly Ser Pro Val Ser Ala Ser Cys Val Thr Gly Glu
            115                 120                 125

Asp Pro Thr Asp Leu Lys Gln Lys Leu Lys Asp Leu Glu Ala Val Met
    130                 135                 140

Leu Gly Thr Ser Glu Thr Asp Pro Glu Ile Val Asn Ser Leu Glu Ile
145                 150                 155                 160

Ser Ala Ala Asn Gln Leu Ser Leu Glu Pro Glu Glu Trp Glu His Met
                165                 170                 175

Val Ser Met Pro Arg Gly Asn Leu Lys Glu Leu Leu Ile Ala Cys Ala
            180                 185                 190

Arg Ala Val Glu Arg Asn Asn Ser Tyr Ala Ile Asp Leu Met Ile Thr
            195                 200                 205

Glu Leu Arg Lys Met Val Ser Val Ser Gly Glu Pro Leu Glu Arg Leu
    210                 215                 220

Gly Ala Tyr Met Val Glu Gly Leu Val Ala Arg Leu Ala Ala Ser Gly
225                 230                 235                 240

Ser Ser Ile Tyr Lys Ala Leu Lys Cys Lys Glu Pro Arg Ser Ser Asp
            245                 250                 255

Leu Leu Ser Tyr Met His Phe Leu Tyr Glu Ala Cys Pro Tyr Phe Lys
            260                 265                 270

Phe Gly Tyr Met Ser Ala Asn Gly Ala Ile Ala Glu Ala Ile Lys Gly
            275                 280                 285

Glu Asp Arg Ile His Ile Ile Asp Phe His Ile Ala Gln Gly Ala Gln
    290                 295                 300

Trp Val Ser Leu Leu Gln Ala Leu Ala Ala Arg Pro Gly Gly Pro Pro
305                 310                 315                 320

Phe Val Arg Val Thr Gly Ile Asp Asp Ser Val Ser Ala Tyr Ala Arg
            325                 330                 335

Gly Gly Gly Leu Glu Leu Val Gly Arg Arg Leu Thr His Ile Ala Gly
            340                 345                 350

Leu Tyr Lys Val Pro Phe Gln Phe Asp Ala Val Ala Ile Ser Gly Ser
    355                 360                 365

Glu Val Glu Glu Glu His Leu Gly Val Val Pro Gly Glu Ala Val Ala
    370                 375                 380

Val Asn Phe Thr Leu Glu Leu His His Ile Pro Asp Glu Thr Val Ser
385                 390                 395                 400

Thr Ala Asn His Arg Asp Arg Ile Leu Arg Leu Val Lys Gly Leu Ser
            405                 410                 415

Pro Lys Val Leu Thr Leu Val Glu Gln Glu Ser Asn Thr Asn Thr Ala
```

```
               420                 425                 430
Pro Phe Ala Gln Arg Phe Ala Glu Thr Leu Asp Tyr Tyr Thr Ala Ile
            435                 440                 445

Phe Glu Ser Ile Asp Leu Ala Leu Pro Arg Asp Asp Arg Glu Arg Ile
450                 455                 460

Asn Ile Glu Gln His Cys Leu Ala Arg Glu Ile Val Asn Leu Val Ala
465                 470                 475                 480

Cys Glu Gly Glu Arg Val Glu Arg His Glu Val Phe Gly Lys Trp
                485                 490                 495

Lys Ala Arg Leu Met Met Ala Gly Phe Ser Pro Ser Pro Leu Ser Ala
                500                 505                 510

Leu Val Asn Ala Thr Ile Lys Thr Leu Leu Gln Ser Tyr Ser Pro Asp
                515                 520                 525

Tyr Lys Leu Ala Glu Arg Asp Gly Val Leu Tyr Leu Gly Trp Lys Asn
                530                 535                 540

Arg Pro Leu Ile Val Ser Ser Ala Trp His
545                 550

<210> SEQ ID NO 104
<211> LENGTH: 558
<212> TYPE: PRT
<213> ORGANISM: Zea mays

<400> SEQUENCE: 104

Met Ala Asp Pro Pro Thr Ser Arg Met Val Gln His Pro Phe Gly Asp
1               5                   10                  15

Ile Pro Ser Gln Thr Pro Lys Gln Phe Leu Tyr Ser Gly Ser Ser Gln
                20                  25                  30

His Leu Cys His Pro Tyr Gln Ser Ala Ser Asp Ala His Val Ala Pro
            35                  40                  45

Gln Arg His Tyr Thr Val Arg Ser Gln Ser Gln Ser Gln Ser Pro Asp
        50                  55                  60

Ala Gly Ser Glu Asp Phe Glu Thr His Ser Arg Gln Tyr Thr Leu Asp
65                  70                  75                  80

Ser Ser Ser Ala Ser Gly Cys Ser Gly His Gly Ser Pro Ser Cys Gln
                85                  90                  95

Ser Val His Ala Gly Ser Arg Ser Pro Val Ser His Ser His Asp Asp
                100                 105                 110

Ser His Ser Gly Ser Thr Asn Gly Asn Gly Ser Pro Ala Ser Ala Ser
            115                 120                 125

Cys Val Thr Glu Asp Pro Thr Asp Leu Lys Gln Lys Leu Lys Asp Leu
130                 135                 140

Glu Ala Val Met Leu Gly Thr Asp Thr Asp Pro Glu Thr Val Asp Ser
145                 150                 155                 160

Leu Glu Ile Ala Ile Ala Asp Arg Leu Ser Val Glu Pro Glu Glu Trp
                165                 170                 175

Lys Asn Asn Met Val Ser Val Pro Arg Gly Asp Leu Lys Glu Leu Leu
                180                 185                 190

Ile Ala Cys Ala Arg Ala Val Glu Gln Asn Asn Gly Tyr Ser Ile Asp
            195                 200                 205

Leu Met Val Pro Glu Leu Arg Lys Met Val Ser Val Ser Gly Glu Pro
        210                 215                 220

Leu Glu Arg Leu Gly Ala Tyr Met Val Glu Gly Leu Val Ala Arg Leu
225                 230                 235                 240
```

```
Ala Ala Ser Gly Ser Ser Ile Tyr Lys Ala Leu Arg Cys Lys Glu Pro
            245                 250                 255

Arg Ser Ser Asp Leu Leu Ser Tyr Met His Phe Leu Tyr Glu Ala Cys
        260                 265                 270

Pro Tyr Phe Lys Phe Gly Tyr Met Ser Ala Asn Gly Ala Ile Ala Glu
        275                 280                 285

Ala Val Lys Gly Glu Asp Arg Ile His Ile Ile Asp Phe His Ile Ala
        290                 295                 300

Gln Gly Ala Gln Trp Val Ser Leu Leu Gln Ala Leu Ala Ala Arg Pro
305                 310                 315                 320

Gly Gly Pro Pro Phe Val Arg Val Thr Gly Ile Asp Asp Pro Val Ser
                325                 330                 335

Ala Tyr Ala Arg Gly Gly Gly Leu Glu Leu Val Gly Lys Arg Leu Ser
        340                 345                 350

His Ile Ala Gly Leu Tyr Lys Val Pro Phe Gln Phe Asp Ala Val Ala
        355                 360                 365

Ile Ser Gly Ser Glu Val Glu Glu Gly His Leu Gly Val Val Pro Gly
        370                 375                 380

Glu Ala Val Ala Val Asn Phe Thr Leu Glu Leu His His Ile Pro Asp
385                 390                 395                 400

Glu Thr Val Ser Thr Ala Asn His Arg Asp Arg Val Leu Arg Leu Val
                405                 410                 415

Lys Gly Leu Ser Pro Arg Val Leu Thr Leu Val Glu Gln Glu Ser Asn
                420                 425                 430

Thr Asn Thr Ala Pro Phe Ala Gln Arg Phe Ala Glu Thr Leu Asp Tyr
        435                 440                 445

Tyr Ala Ala Ile Phe Glu Ser Ile Asp Leu Ala Leu Pro Arg Gly Asp
450                 455                 460

Arg Glu Arg Ile Asn Ile Glu Gln His Cys Leu Ala Arg Glu Ile Val
465                 470                 475                 480

Asn Leu Val Ala Cys Glu Gly Glu Glu Arg Val Glu Arg His Glu Val
                485                 490                 495

Phe Gly Lys Trp Lys Ala Arg Leu Met Met Ala Gly Phe Arg Pro Ser
                500                 505                 510

Pro Leu Ser Ala Leu Val Asn Ala Thr Ile Lys Thr Leu Leu Gln Ser
        515                 520                 525

Tyr Ser Pro Asp Tyr Lys Leu Ala Glu Arg Glu Gly Val Leu Tyr Leu
        530                 535                 540

Gly Trp Lys Asn Arg Pro Leu Ile Val Ser Ser Ala Trp His
545                 550                 555

<210> SEQ ID NO 105
<211> LENGTH: 484
<212> TYPE: PRT
<213> ORGANISM: Vitis vinifera

<400> SEQUENCE: 105

Met Gln Ala Ser Gln Gln His Arg Ser Ser Gly Met Ser Asn Arg Leu
1               5                   10                  15

Tyr Tyr Leu Pro Pro Gln Glu Ala Glu Ala His Cys Leu Pro Gln Phe
                20                  25                  30

Gln Ser Phe Asp His Gln Leu Cys Tyr Asn Asp Gly Ser Gln Gly Thr
            35                  40                  45

Asn Phe Ser Phe Gln Gly Ser Ser Glu Arg Tyr Cys Thr Leu Glu Ser
        50                  55                  60
```

```
Ser Pro Asn Ser Gln Gln Asp Ser Gln Ser Tyr Pro Ser Asp Pro His
 65                  70                  75                  80

His Ser Pro Asp Asn Thr Tyr Gly Ser Pro Met Ser Ala Ser Cys Ile
                 85                  90                  95

Thr Asp Asp Val Ser Asp Leu Lys His Lys Leu Arg Glu Leu Glu Thr
            100                 105                 110

Val Met Leu Gly Pro Asp Ser Asp Ile Ile Asn Ser Tyr Asp Asn Asn
            115                 120                 125

Asp Leu Leu Met Ala Gln Trp Leu Met Asp Glu Leu Arg Gln Met Val
            130                 135                 140

Ser Val Ser Gly Glu Pro Ile Gln Arg Leu Gly Ala Tyr Met Leu Glu
145                 150                 155                 160

Gly Leu Val Ala Arg Leu Ala Ser Ser Gly Ser Ser Ile Tyr Lys Ala
                165                 170                 175

Leu Arg Cys Lys Glu Pro Ala Ser Ala Asp Leu Leu Ser Tyr Met His
                180                 185                 190

Ile Leu Tyr Glu Val Cys Pro Tyr Phe Lys Phe Gly Tyr Met Ser Ala
            195                 200                 205

Asn Gly Ala Ile Ala Glu Ala Met Lys Asp Glu Asn Arg Val His Ile
210                 215                 220

Ile Asp Phe Gln Ile Gly Gln Gly Ser Gln Trp Ile Thr Leu Ile Gln
225                 230                 235                 240

Ala Phe Ser Ala Arg Pro Gly Gly Pro Pro His Ile Arg Ile Thr Gly
                245                 250                 255

Ile Asp Asp Ser Thr Ser Ala Tyr Ala Arg Gly Gly Gly Leu Asn Ile
                260                 265                 270

Val Gly Gln Arg Leu Ser Arg Leu Ala Glu Ser Val Lys Val Pro Phe
            275                 280                 285

Glu Phe His Ala Ala Asp Met Ser Gly Cys Glu Val Gln Leu Glu Asn
            290                 295                 300

Leu Gly Ala Arg Pro Gly Glu Ala Leu Ala Val Asn Phe Ala Phe Met
305                 310                 315                 320

Leu His His Met Pro Asp Glu Ser Val Ser Thr Gln Asn His Arg Asp
                325                 330                 335

Arg Leu Leu Arg Leu Val Lys Ser Leu Ser Pro Lys Val Val Thr Leu
                340                 345                 350

Val Glu Gln Glu Ser Asn Thr Asn Thr Ala Ala Phe Phe Pro Arg Phe
            355                 360                 365

Leu Glu Thr Leu Asn Tyr Tyr Thr Ala Met Phe Glu Ser Ile Asp Val
            370                 375                 380

Thr Leu Pro Arg Glu His Lys Lys Arg Ile Ser Val Glu Gln His Cys
385                 390                 395                 400

Leu Ala Arg Asp Val Val Asn Ile Ile Ala Cys Glu Gly Val Glu Arg
                405                 410                 415

Val Glu Arg His Glu Leu Leu Gly Lys Trp Arg Leu Arg Phe Ala Met
                420                 425                 430

Ala Gly Phe Thr Pro Tyr Pro Leu Ser Ser Leu Val Asn Ala Thr Ile
                435                 440                 445

Lys Arg Leu Leu Glu Asn Tyr Ser Asp Lys Tyr Arg Leu Glu Glu Arg
            450                 455                 460

Glu Gly Ala Leu Tyr Leu Gly Trp Met Asp Arg Asp Leu Val Ala Ser
465                 470                 475                 480
```

Cys Ala Trp Lys

<210> SEQ ID NO 106
<211> LENGTH: 533
<212> TYPE: PRT
<213> ORGANISM: Populus trichocarpa

<400> SEQUENCE: 106

Met Gln Thr Ser Gln Lys Lys Thr Ile Ser Asp Gly Ser Arg Arg Tyr
1               5                   10                  15

Gly Asp Gln Pro Met Gln Tyr Gln Glu Ser Tyr Cys Trp Pro Pro Ile
            20                  25                  30

Gln Asn Ile Asp Ala Gly Ser Gly Thr His Leu Ser Pro Met Thr
        35                  40                  45

Ser Asp Gln Tyr Cys Thr Leu Glu Ser Ser Glu Thr Ser Ala Tyr
    50                  55                  60

Pro Val Gln Asn Ser Pro Ser Thr Ala Ser Phe Ser Pro Asn Glu Ser
65                  70                  75                  80

Val Val Ser Gln Pro Asn Ser Arg Ser Tyr Pro Ser Asp Leu Gln Asp
                85                  90                  95

Ser Ser Glu Asn Ala Cys Gly Ser Pro Thr Ser Glu Ser Tyr Val Thr
            100                 105                 110

His Lys Leu Arg Glu Leu Glu Thr Ala Met Leu Gly Pro Asp Ser Asp
        115                 120                 125

Asn Leu Asp Met His Ser Met Thr Ala Met Pro Gly Pro Asn Gln Ile
    130                 135                 140

Val Ser Glu Ala Glu Lys Trp Lys Phe Leu Val Glu Met Met Ser Arg
145                 150                 155                 160

Gly Asp Leu Lys Glu Ala Leu Cys Thr Cys Ala Leu Ala Ile Ala Asn
                165                 170                 175

Gly Asp Met Phe Thr Val Glu Trp Leu Met Ser Glu Leu Arg Gln Met
            180                 185                 190

Val Ser Val Thr Gly Glu Pro Ile Gln Arg Leu Gly Ala Tyr Met Leu
        195                 200                 205

Glu Gly Leu Val Ala Arg Leu Ala Ser Ser Gly Ser Ser Ile Tyr Asn
    210                 215                 220

Ala Leu Arg Cys Lys Glu Pro Ala Gly Ala Asp Leu Leu Ser Tyr Met
225                 230                 235                 240

Leu Leu Leu Tyr Glu Ala Cys Pro Tyr Phe Lys Phe Gly Tyr Met Ser
                245                 250                 255

Ala Asn Gly Ala Ile Ala Asp Ala Met Lys Asp Glu Ile Ser Val His
            260                 265                 270

Ile Ile Asp Phe Gln Ile Ala Gln Gly Ser Gln Trp Val Thr Leu Ile
        275                 280                 285

Gln Ala Leu Ala Ala Arg Pro Gly Gly Pro Pro Arg Ile Arg Ile Thr
    290                 295                 300

Gly Ile Asp Asp Ser Thr Ser Ala Tyr Ala Arg Gly Gly Gly Leu Asp
305                 310                 315                 320

Ile Val Gly Lys Arg Leu Leu Lys Leu Ala Glu Ser Tyr Lys Val Pro
                325                 330                 335

Phe Glu Phe His Thr Ala Gly Val Ser Ala Ser Glu Ile Gln Ile Glu
            340                 345                 350

Asn Leu Gly Ile Gln Pro Gly Glu Ala Val Ala Val Asn Phe Ala Leu
        355                 360                 365

```
Thr Leu His His Leu Pro Asp Glu Ser Val Gly Thr Gln Asn His Arg
    370                 375                 380

Asp Arg Leu Leu Arg Leu Val Lys Ser Leu Ser Pro Lys Val Val Thr
385                 390                 395                 400

Leu Val Glu His Glu Ser Asn Thr Asn Thr Val Pro Phe Phe Ala Arg
                405                 410                 415

Phe Val Glu Thr Leu Asn Tyr Tyr Leu Ala Ile Phe Glu Ser Ile Asp
            420                 425                 430

Val Thr Leu Pro Arg Glu Asn Lys Lys Arg Ile Ser Val Glu Gln His
        435                 440                 445

Cys Leu Ala Arg Glu Val Val Asn Ile Val Ala Cys Glu Gly Ala Glu
450                 455                 460

Arg Val Glu Arg His Glu Pro Leu Gly Lys Trp Arg Ser Arg Phe Glu
465                 470                 475                 480

Met Ala Gly Phe Thr Pro Tyr Pro Leu Ser Ser Phe Val Asn Ser Thr
                485                 490                 495

Ile Lys Ile Leu Leu Glu Asn Tyr Ser Glu Lys Tyr Thr Leu Glu Glu
            500                 505                 510

Arg Asp Gly Ala Leu Phe Leu Gly Trp Met Asn Arg Pro Leu Val Ala
        515                 520                 525

Ser Cys Ala Trp Arg
    530

<210> SEQ ID NO 107
<211> LENGTH: 553
<212> TYPE: PRT
<213> ORGANISM: Solanum lycopersicum

<400> SEQUENCE: 107

Met Gln Ala Ser Gln Gly Pro Gln Arg Ser Cys Ser Val His Lys Leu
1               5                   10                  15

Tyr Asn Lys Pro Met Gln Gln Val Gln Gln Asn Tyr Thr Pro Cys Arg
            20                  25                  30

Ala Ser Asp Asn Ser Asn Tyr Asn Asp Gly Ser Asn Ser Gln Ala Gln
        35                  40                  45

Val Ser Leu Thr Thr Glu Asn Glu Lys Phe Phe Thr Val Asp Thr Phe
    50                  55                  60

Pro Ala Thr Asp Cys Ala Ile Tyr Asp Gly Asp Pro Ser Val Ser Val
65                  70                  75                  80

Ser Ser Asn Arg Ser Pro Phe Ser Ser Gln Cys Ser Gln Ser Asn Met
                85                  90                  95

Phe Glu Gln Arg Arg Ser Tyr Glu Lys Thr Ala Gly Ser Pro Val Ser
            100                 105                 110

Leu Cys Ser Gly Val Asp Asp Ser Asn Gly Lys Lys His Glu Leu Arg
        115                 120                 125

Glu Leu Asn Asn Lys Leu Leu Arg Pro Glu Ser Asp Ile Asp Asp Ser
    130                 135                 140

Cys Ser Cys Ser Leu Asn Gly Val Val Ser Lys His Phe Ser Leu Thr
145                 150                 155                 160

Arg Arg Asn Gln Val Leu Asp Val Ala Ser Arg Leu Asp Leu Lys Glu
                165                 170                 175

Leu Leu Val Ala Cys Ala Glu Ala Val Asp Glu Ala Asp Thr Ser Thr
            180                 185                 190

Ala Glu Val Leu Met Asp Ala Leu Glu Lys Arg Val Ser Val Tyr Gly
        195                 200                 205
```

Glu Pro Met Gln Arg Leu Ser Ala Tyr Met Leu Glu Gly Leu Arg Ala
    210                 215                 220

Arg Leu Leu Ser Ser Gly Ser Asn Ile Tyr Lys Leu Lys Cys Asn
225                 230                 235                 240

Glu Pro Thr Ser Ser Glu Leu Leu Ser Tyr Met Gln Val Leu Tyr His
                    245                 250                 255

Ile Thr Pro Tyr Phe Lys Phe Ala Tyr Met Ser Ala Asn Val Val Ile
                260                 265                 270

Ser Glu Ala Met Lys Asn Glu Asn Arg Ile His Ile Ile Asp Phe Gln
            275                 280                 285

Ile Ala Gln Gly Ser Gln Trp Val Phe Leu Ile His Tyr Leu Ala Arg
        290                 295                 300

Arg Pro Gly Gly Pro Pro Phe Leu Arg Ile Thr Gly Ile Asp Asp Ser
305                 310                 315                 320

Gln Ser Ala His Ala Arg Gly Gly Leu Gln Leu Val Gly Glu Arg
                325                 330                 335

Leu Ala Ser Ile Ala Lys Ser Cys Gly Val Pro Phe Glu Phe His Thr
                340                 345                 350

Ala Ala Leu Ser Gly Cys Met Val Lys Leu Glu Asn Leu Arg Val Arg
                355                 360                 365

His Gly Glu Ser Leu Ala Val Asn Phe Pro Tyr Met Leu His His Met
370                 375                 380

Pro Asp Glu Ser Val Ser Thr Met Asn His Arg Asp Arg Leu Leu Arg
385                 390                 395                 400

Leu Val Lys Ser Leu Ser Pro Lys Ile Val Ala Leu Val Glu Gln Glu
                405                 410                 415

Met Asn Thr Asn Thr Ala Pro Phe Leu Pro Arg Phe Arg Glu Thr Leu
                420                 425                 430

Asp Tyr His Lys Ala Ile Phe Glu Ser Val Asp Val Thr Arg Pro Arg
            435                 440                 445

Asn Asp Met Gln Arg Ile Arg Ser Glu Glu His Cys Ile Ala Arg Asp
        450                 455                 460

Val Val Asn Leu Ile Ala Cys Glu Gly Ala Asp Arg Val Glu Arg His
465                 470                 475                 480

Glu Val Phe Gly Lys Trp Arg Ser Arg Leu Leu Met Ala Gly Phe Thr
                485                 490                 495

Pro Cys Pro Leu Ser Pro Ser Val Ala Glu Ala Ile Lys Val Met Leu
                500                 505                 510

Lys Glu Tyr Ser Ser Asn Tyr Lys Leu Ala Glu Ser Gln Gly Ala Leu
            515                 520                 525

Tyr Ile Gly Trp Asn Asn Arg Ala Leu Ala Thr Ser Ser Ala Trp Gln
        530                 535                 540

Leu Pro His Ser Leu Pro Leu Gly Ser
545                 550

<210> SEQ ID NO 108
<211> LENGTH: 544
<212> TYPE: PRT
<213> ORGANISM: Solanum tuberosum

<400> SEQUENCE: 108

Met Gln Ala Ser Gln Gly Pro Gln Arg Pro Cys Ser Val His Lys Leu
1               5                   10                  15

Cys Asn Gln Pro Met Gln Gln Val Gln Gln Tyr Tyr Thr Pro Cys His

-continued

```
                20                  25                  30
Ala Ser Asp Asn Ser Ser Tyr Asn Asp Gly Ser Asn Ser Gly Thr Glu
                35                  40                  45
Val Ser Leu Lys Thr Gln Asn Glu Lys Phe Phe Thr Met Asp Ser Phe
            50                  55                  60
Pro Ala Thr Asp Cys Ala Ile Tyr Asp Ala Asp Pro Ser Ile Ser Val
 65                 70                  75                  80
Ser Ser Asn Arg Ser Pro Phe Ser Pro Gln Cys Ser Gln Ser Asn Met
                85                  90                  95
Phe Glu Lys Arg Arg Ser Ser Glu Asn Thr Ser Gly Ser Pro Val Ser
                100                 105                 110
Leu Cys Ser Gly Val Asp Asp Ser Asn Gly Lys Lys His Glu Leu Trp
            115                 120                 125
Glu Leu Asn Asn Lys Leu Leu Arg Pro Glu Ser Asp Ile Asp Asp Ser
            130                 135                 140
Cys Ser Cys Ser Leu Asn Gly Val Val Ser Lys His Phe Ser Leu Thr
145                 150                 155                 160
Arg Arg Asn Gln Val Leu Asp Val Ala Ser Arg Leu Asp Leu Lys Glu
                165                 170                 175
Leu Leu Val Ala Cys Ala Glu Ala Val Asp Glu Ala Asp Thr Ser Thr
                180                 185                 190
Ala Glu Val Leu Met Asp Ala Leu Glu Lys Arg Val Ser Val Ser Gly
                195                 200                 205
Glu Pro Met Gln Arg Leu Ser Ala Tyr Met Leu Glu Gly Leu Arg Ala
            210                 215                 220
Arg Leu Leu Ser Ser Gly Ser Asn Ile Tyr Lys Lys Leu Lys Cys Asn
225                 230                 235                 240
Glu Pro Thr Ser Ser Glu Leu Leu Ser Tyr Met Gln Val Leu Tyr Asn
                245                 250                 255
Ile Thr Pro Tyr Phe Lys Phe Ala Tyr Met Ser Ala Asn Val Val Ile
            260                 265                 270
Ser Glu Ala Met Lys Asn Glu Asn Arg Ile His Ile Ile Asp Phe Gln
            275                 280                 285
Ile Ala Gln Gly Ser Gln Trp Met Phe Leu Ile His Tyr Leu Ala Arg
            290                 295                 300
Arg Pro Gly Gly Pro Phe Leu Arg Ile Thr Gly Val Asp Asp Ser
305                 310                 315                 320
Gln Ser Ala His Ala Arg Gly Gly Leu Gln Leu Val Gly Glu Arg
                325                 330                 335
Leu Ala Ser Ile Ala Lys Ser Cys Gly Val Pro Phe Glu Phe His Asn
                340                 345                 350
Ala Ala Leu Ser Gly Cys Met Val Lys Leu Glu Asn Leu Arg Val Arg
            355                 360                 365
His Gly Glu Ser Leu Ala Val Asn Phe Pro Tyr Met Leu His His Met
            370                 375                 380
Pro Asp Glu Ser Val Ser Thr Met Asn His Arg Asp Arg Leu Leu Arg
385                 390                 395                 400
Leu Val Lys Ser Leu Ser Pro Lys Ile Val Ala Leu Val Glu Gln Glu
                405                 410                 415
Met Asn Thr Asn Thr Ala Pro Phe Leu Pro Arg Phe Arg Glu Thr Leu
                420                 425                 430
Asp Tyr His Lys Ala Met Phe Glu Ser Val Asp Val Thr Arg Pro Arg
            435                 440                 445
```

Asn Asp Met Gln Arg Ile Arg Ser Glu Glu His Cys Ile Ala Arg Asp
            450                 455                 460

Val Val Asn Leu Ile Ala Cys Glu Gly Ala Asp Arg Val Glu Arg His
465                 470                 475                 480

Glu Val Phe Gly Lys Trp Arg Ser Arg Leu Leu Met Ala Gly Phe Thr
            485                 490                 495

Pro Cys Pro Leu Ser Pro Ser Val Ala Glu Thr Ile Lys Val Met Leu
            500                 505                 510

Lys Glu Tyr Ser Ser Asn Tyr Lys Leu Ala Glu Ser Gln Gly Ala Leu
            515                 520                 525

Tyr Ile Gly Trp Asn Asn Arg Ala Leu Ala Thr Ser Ser Ala Trp Gln
            530                 535                 540

<210> SEQ ID NO 109
<211> LENGTH: 545
<212> TYPE: PRT
<213> ORGANISM: Glycine max

<400> SEQUENCE: 109

Met Gln Met Ser Gln Lys His Lys Met Ser Tyr Asp Ser Ser Arg Phe
1               5                   10                  15

Thr Ser Glu Pro Val Gln Asn Leu Gly Ser Cys Cys Phe Leu Gln Ser
            20                  25                  30

Gly Asn Leu Asp Tyr Tyr Ser Ser Asp Asn Ser Ser His Ala Thr
            35                  40                  45

Tyr Pro Ser Val Cys Thr Phe Glu Gln Tyr Cys Thr Leu Glu Ser Ser
    50                  55                  60

Thr Asn Asn Asn Leu Pro Ser Leu Asn Ser Ser Thr Val Ser Phe
65                  70                  75                  80

Ser Pro Asn Asn Ser Pro Val Ser Lys Leu Gln Ser Lys Ser Asn Val
                85                  90                  95

Leu Ser Ser Gln Asn Ser Leu Glu Leu Val Asn Asp Ser Leu Glu Asn
            100                 105                 110

Glu Ser Cys Leu Thr Leu Asn Asn Asp Glu Leu Arg His Lys Ile Arg
            115                 120                 125

Glu Leu Glu Ser Ala Leu Leu Gly His Asp Thr Tyr Ile Leu Asp Thr
            130                 135                 140

Tyr Asp Thr Ile Ile Pro Glu Glu Ser Asp Ser Phe Met Leu Glu Ala
145                 150                 155                 160

Glu Arg Trp Lys Arg Met Met Glu Met Ile Ser Arg Gly Asp Leu Lys
            165                 170                 175

Glu Met Leu Cys Thr Cys Ala Lys Thr Val Ala Val Asn Asp Met Glu
            180                 185                 190

Thr Thr Glu Trp Leu Met Ser Glu Leu Arg Lys Met Val Ser Val Ser
            195                 200                 205

Gly Asp Pro Ile Gln Arg Leu Gly Ala Tyr Met Leu Glu Ala Leu Val
            210                 215                 220

Ala Arg Leu Ala Ser Ser Gly Ser Thr Ile Tyr Lys Val Leu Lys Cys
225                 230                 235                 240

Lys Glu Pro Thr Gly Ser Glu Leu Leu Ser His Met His Leu Leu Tyr
            245                 250                 255

Glu Ile Cys Pro Tyr Leu Lys Phe Gly Tyr Met Ser Ala Asn Gly Ala
            260                 265                 270

Ile Ala Glu Ala Met Lys Glu Glu Ser Glu Val His Ile Ile Asp Phe

```
            275                 280                 285
Gln Ile Asn Gln Gly Ile Gln Trp Val Ser Leu Ile Gln Ala Leu Ala
    290                 295                 300
Gly Arg Pro Gly Gly Pro Lys Ile Arg Ile Thr Gly Phe Asp Asp
305                 310                 315                 320
Ser Thr Ser Ala Tyr Ala Arg Glu Gly Leu Glu Ile Val Gly Ala
                325                 330                 335
Arg Leu Ser Thr Leu Ala Gln Ser Tyr Asn Val Pro Phe Glu Phe His
                340                 345                 350
Ala Ile Arg Ala Ser Pro Thr Glu Val Glu Leu Lys Asp Leu Ala Leu
            355                 360                 365
Gln Pro Gly Glu Ala Ile Ala Val Asn Phe Ala Met Met Leu His His
    370                 375                 380
Val Pro Asp Glu Ser Val Asp Ser Gly Asn His Arg Asp Arg Leu Val
385                 390                 395                 400
Arg Leu Ala Lys Cys Leu Ser Pro Lys Ile Val Thr Leu Val Glu Gln
                405                 410                 415
Glu Ser His Thr Asn Asn Leu Pro Phe Phe Pro Arg Phe Val Glu Thr
                420                 425                 430
Met Asn Tyr Tyr Leu Ala Ile Phe Glu Ser Ile Asp Val Ala Leu Pro
            435                 440                 445
Arg Glu His Lys Glu Arg Ile Asn Val Glu Gln His Cys Leu Ala Arg
    450                 455                 460
Glu Val Val Asn Leu Ile Ala Cys Glu Gly Glu Arg Val Glu Arg
465                 470                 475                 480
His Glu Leu Leu Lys Lys Trp Arg Ser Arg Phe Thr Met Ala Gly Phe
                485                 490                 495
Ala Pro Tyr Pro Leu Asn Ser Phe Ile Thr Cys Ser Ile Lys Asn Leu
                500                 505                 510
Gln Arg Ser Tyr Arg Gly His Tyr Thr Leu Glu Glu Arg Asp Gly Ala
            515                 520                 525
Leu Cys Leu Gly Trp Met Asn Gln Val Leu Ile Thr Ser Cys Ala Trp
    530                 535                 540
Arg
545

<210> SEQ ID NO 110
<211> LENGTH: 584
<212> TYPE: PRT
<213> ORGANISM: Gossypium raimondii

<400> SEQUENCE: 110

Met Asp Ser His Gln Leu Phe Gly Tyr Gly Val Thr Gly Ala Gly Leu
1               5                   10                  15
Ser Tyr Ser Thr Phe Pro Ser Ile Pro Asn Arg Leu Phe Ser Ser Leu
                20                  25                  30
Lys Ser Asp Ile Gly Asn Ser Pro Asn Ser Phe Phe Thr Pro Phe
            35                  40                  45
Asp Cys Asp Thr Asn Thr Thr Leu Ser Asp Ser Gln Glu Gln His Ser
        50                  55                  60
Ser Thr Glu Asn Leu Ser Gly Leu Ser Pro Ser Cys Asn Ser Ser Leu
65              70                  75                  80
Glu Ser Asn Thr Cys Phe His Arg Leu Ser Pro Ser Leu Gly Cys Arg
                85                  90                  95
```

```
Ser Glu Ser Leu Leu Phe Ser Ser Gly Thr Ser Tyr Thr Gln Asp
             100                 105                 110

Ala Asn Ser Gly His Lys Val Ile Tyr Thr Leu Gln Glu Leu Glu Thr
            115                 120                 125

Ala Leu Met Ala Pro Asp Glu Asn Glu Asp Leu Thr Thr Pro Ser Val
        130                 135                 140

Ser His Gly Glu Ser Ser Arg Pro Gln Thr Ala Gly Gln Arg Ser Arg
145                 150                 155                 160

Ala Trp Ser Gln Glu Arg Gln Gly Ser Leu Ala Leu Leu Pro Gln Thr
                165                 170                 175

Ser Phe Val Ser Lys His Arg Gln Ser Thr Glu Val Ser His Val Glu
            180                 185                 190

Lys Arg Gln Lys Ser Ile Glu Asp Phe Ser Trp Leu Gly Ile Pro Pro
                195                 200                 205

Gly Asn Leu Lys Gln Leu Leu Ile Ala Cys Ala Lys Val Leu Ser Glu
210                 215                 220

Asn Asn Met Asp Glu Phe Asp Lys Leu Ile Ala Lys Ala Arg Gly Ala
225                 230                 235                 240

Val Ser Ile Ser Gly Glu Pro Val Gln Arg Leu Gly Ala Tyr Met Val
            245                 250                 255

Glu Gly Leu Val Ala Arg Lys Glu Ala Ser Gly Ser Ser Ile Tyr Arg
            260                 265                 270

Ala Leu His Cys Arg Glu Pro Glu Gly Lys Asp Leu Leu Ser Tyr Met
            275                 280                 285

Gln Val Leu Tyr Glu Ile Cys Pro Tyr Leu Lys Phe Gly His Met Ala
290                 295                 300

Ala Asn Gly Ala Ile Ala Glu Ala Cys Arg Thr Glu Asp Arg Ile His
305                 310                 315                 320

Ile Ile Asp Phe Gln Ile Ala Gln Gly Thr Gln Trp Met Thr Leu Leu
            325                 330                 335

Gln Ala Leu Ala Ala Arg Pro Gly Gly Ala Pro His Val Arg Ile Thr
            340                 345                 350

Gly Ile Asp Asp Pro Ile Ser Lys Tyr Ala Arg Gly Gly Gly Leu Glu
            355                 360                 365

Ala Val Lys Arg Arg Leu Glu Ala Leu Ser Glu Lys Phe Asn Ile Pro
370                 375                 380

Val Glu Phe Gln Gly Met Pro Val Phe Ala Pro Asp Ile Thr Arg Asp
385                 390                 395                 400

Met Leu Asp Val Arg Pro Gly Glu Ala Leu Ala Val Asn Phe Pro Leu
            405                 410                 415

Gln Leu His His Thr Pro Asp Glu Ser Val Asp Val Asn Asn Pro Arg
            420                 425                 430

Asp Gly Leu Leu Arg Met Val Lys Ser Leu Ser Pro Lys Val Thr Thr
            435                 440                 445

Leu Val Glu Gln Glu Ser Asn Thr Asn Thr Ala Pro Phe Leu Pro Arg
            450                 455                 460

Phe Ile Glu Thr Leu Glu Tyr Tyr Leu Ala Met Phe Glu Ser Ile Asp
465                 470                 475                 480

Glu Thr Leu Pro Arg Asp Arg Lys Glu Arg Val Asn Val Glu Glu His
                485                 490                 495

Cys Leu Ala Arg Asp Ile Val Asn Ile Ile Ala Cys Glu Gly Lys Glu
            500                 505                 510

Arg Val Glu Arg His Glu Leu Phe Gly Lys Trp Lys Ser Arg Leu Thr
```

-continued

```
                515                 520                 525
Met Ala Gly Phe Arg Gln Tyr Pro Leu Ser Ser Tyr Val Asn Ser Val
            530                 535                 540

Ile Arg Gly Leu Leu Arg Cys Tyr Ser Lys His Tyr Lys Leu Val Glu
545                 550                 555                 560

Lys Asp Gly Ala Met Leu Leu Gly Trp Lys Asp Arg Asn Leu Ile Ser
            565                 570                 575

Ala Ser Ala Trp His Cys Asp Ser
            580

<210> SEQ ID NO 111
<211> LENGTH: 535
<212> TYPE: PRT
<213> ORGANISM: Brassica rapa

<400> SEQUENCE: 111

Met Gln Thr Ser Gln Lys His His Ser Ala Ala Gly Leu His Met Leu
1               5                   10                  15

Tyr Pro Gln Val His Cys Ser Pro Gln Phe Gln Val Ile Asp Lys Lys
            20                  25                  30

Asn Lys Lys Ser Ala Phe Ser Asp Thr Thr Pro Ser Lys Glu Ser Phe
        35                  40                  45

Phe Thr Leu Glu Ser Ser Thr Ala Ser Gly Pro Leu Pro Ser Tyr Glu
50                  55                  60

Ser Pro Ser Val Ser Ile Thr Ser Gly Arg Ser Pro Phe Ser Pro Gln
65                  70                  75                  80

Ala Ser Cys Ile Ser Asp Leu His Pro Ser Pro Glu Asn Ile Tyr Glu
            85                  90                  95

Ser Pro Leu Ser Gly Ala Ser Ser His Val Tyr Asp Glu Ala His Val
        100                 105                 110

Lys Asn Lys Ile Arg Glu Leu Glu Val Ser Leu Leu Ser Val Asp Pro
    115                 120                 125

Lys Val Glu Glu Tyr Ser Gly Phe Ser Pro Ala Ala Gly Lys Ser Trp
130                 135                 140

Asn Trp Asp Glu Leu Leu Ala Leu Thr Pro Gln Leu Asp Leu Lys Glu
145                 150                 155                 160

Val Leu Val Glu Ala Ala Gln Ala Val Ala Glu Gly Asp Phe Ala Ala
            165                 170                 175

Ala Cys Gly Phe Ile Asp Val Leu Glu Gln Met Val Ser Val Ser Gly
        180                 185                 190

Thr Pro Ile Gln Arg Leu Gly Thr Tyr Met Ala Glu Gly Leu Arg Ala
    195                 200                 205

Arg Leu Gln Gly Thr Gly Gly Asn Ile Tyr Arg Ala Leu Lys Cys Asn
210                 215                 220

Glu Pro Thr Gly Arg Glu Leu Met Ser Tyr Met Gly Val Leu Tyr Glu
225                 230                 235                 240

Ile Cys Pro Tyr Trp Lys Phe Ala Tyr Asn Ala Ala Asn Ala Ala Ile
            245                 250                 255

Leu Glu Ala Val Ala Gly Glu Lys Arg Val His Ile Ile Asp Phe Gln
        260                 265                 270

Ile Ala Gln Gly Thr Gln Tyr Met Phe Leu Ile Asn Glu Leu Ala Lys
    275                 280                 285

Leu Pro Gly Gly Pro Pro Leu Leu Arg Val Thr Gly Val Asp Asp Ser
290                 295                 300
```

```
Gln Ser Arg Phe Ala Arg Gly Gly Gly Leu Asn Leu Val Gly Glu Lys
305                 310                 315                 320

Leu Ala Asn Lys Ala Gln Ser Cys Gly Val Pro Phe Glu Phe His Asp
                325                 330                 335

Ala Ile Met Ser Gly Cys Lys Val His Arg Glu His Leu Gly Val Glu
            340                 345                 350

Pro Gly Phe Ala Val Val Asn Phe Pro Tyr Val Leu His His Met
        355                 360                 365

Pro Asp Glu Ser Val Ser Val Glu Asn His Arg Asp Arg Leu Leu Arg
    370                 375                 380

Leu Ile Lys Ser Leu Gly Pro Lys Leu Val Thr Leu Val Glu Gln Glu
385                 390                 395                 400

Ser Asn Thr Asn Thr Ser Pro Phe Leu Ser Arg Phe Val Glu Thr Leu
                405                 410                 415

Asp Tyr Tyr Thr Ala Met Phe Glu Ser Ile Asp Ala Ala Arg Pro Arg
            420                 425                 430

Asp Asp Lys Gln Arg Ile Ser Ala Glu Gln His Cys Ala Ala Arg Asp
        435                 440                 445

Ile Val Asn Met Ile Ala Cys Glu Gln Arg Glu Arg Val Glu Arg His
    450                 455                 460

Glu Val Leu Gly Lys Trp Arg Val Arg Met Met Met Ala Gly Phe Met
465                 470                 475                 480

Gly Trp Pro Val Ser Ser Ala Ala Phe Ala Ala Ser Glu Met Leu
            485                 490                 495

Lys Gly Tyr Asp Lys Asn Tyr Lys Leu Gly Glu Asn Glu Gly Ala Leu
        500                 505                 510

Tyr Leu Phe Trp Lys Arg Arg Pro Met Ala Thr Cys Ser Ala Trp Lys
    515                 520                 525

Pro Asn Pro Asn Gln Ile Val
        530                 535

<210> SEQ ID NO 112
<211> LENGTH: 557
<212> TYPE: PRT
<213> ORGANISM: Hordeum vulgare

<400> SEQUENCE: 112

Met Ala Asp Thr Pro Thr Ser Arg Met Ile His Pro Phe Ser Asn Met
1               5                   10                  15

Gln Arg Gln Asn Pro Lys Gln Phe Gln Phe Gln Tyr Pro Asp Asn Pro
                20                  25                  30

Gln His Pro Cys His Pro Tyr Gln Pro Ser Pro Asp Thr His Val Val
            35                  40                  45

Pro Gln His His Tyr Ser Leu Lys Ser His Ser Ser Asp Ala Ser Tyr
        50                  55                  60

Glu Asn His Val Ala Gln Met Lys His Thr Leu Val Asp Ser Ser Ala
65                  70                  75                  80

Ala Ala Gly Cys Met Arg His Asp Ser Pro Ser Ser His Ser Phe Thr
                85                  90                  95

Pro Pro Ser Ile Arg Ser Gly Gly Ser Pro Ser Ser His Asp Asp
            100                 105                 110

Ser His Ser Asp Ser Thr Asp Gly Ser Pro Val Ser Ala Ser Cys Val
        115                 120                 125

Thr Val Thr Glu Asp Pro Asn Asp Leu Lys Gln Lys Leu Lys Asp
    130                 135                 140
```

```
Leu Glu Ala Glu Met Leu Gly Pro Asp Ala Ala Glu Ile Val Asn Ser
145                 150                 155                 160

Leu Glu Ser Ser Val Ala Lys Gln Leu Ser Leu Glu Pro Glu Lys Trp
            165                 170                 175

Ala Gln Met Met Asp Phe Pro Arg Gly Asn Leu Lys Glu Leu Leu Leu
        180                 185                 190

Ala Cys Ala Arg Ala Val Glu Glu Lys Asn Met Tyr Ala Val Asp Val
    195                 200                 205

Met Val Pro Glu Leu Arg Lys Met Val Ser Val Ser Gly Thr Pro Leu
210                 215                 220

Glu Arg Leu Gly Ala Tyr Met Val Glu Gly Leu Val Ala Arg Leu Ala
225                 230                 235                 240

Ser Ser Gly His Ser Ile Tyr Lys Ala Leu Arg Cys Lys Glu Pro Lys
                245                 250                 255

Ser Ser Asp Leu Leu Ser Tyr Met His Phe Leu Tyr Glu Ala Cys Pro
            260                 265                 270

Tyr Phe Lys Phe Gly Tyr Met Ser Ala Asn Gly Ala Ile Ala Glu Ala
        275                 280                 285

Val Lys Gly Glu Asp Arg Ile His Ile Ile Asp Phe His Ile Ala Gln
    290                 295                 300

Gly Ala Gln Trp Ile Ser Leu Leu Gln Ala Leu Ala Ala Arg Pro Gly
305                 310                 315                 320

Gly Pro Pro Thr Val Arg Ile Thr Gly Ile Asp Asp Ser Val Ser Ala
                325                 330                 335

Tyr Ala Arg Gly Gly Gly Leu Asp Leu Val Gly Arg Arg Leu Ser His
            340                 345                 350

Ile Ala Gly Leu Cys Lys Val Pro Phe Glu Phe Arg Ser Val Ala Met
        355                 360                 365

Ala Gly Glu Glu Val Glu Glu Gly His Leu Gly Val Val Pro Gly Glu
    370                 375                 380

Ala Leu Ala Val Asn Phe Thr Leu Glu Leu His His Ile Pro Asp Glu
385                 390                 395                 400

Thr Val Ser Thr Ala Asn His Arg Asp Arg Ile Leu Arg Leu Val Lys
                405                 410                 415

Gly Leu Arg Pro Lys Val Leu Thr Leu Val Glu Gln Glu Ser Asn Thr
            420                 425                 430

Asn Thr Ala Pro Phe Pro Gln Arg Phe Ala Glu Thr Leu Asp Tyr Tyr
        435                 440                 445

Thr Ala Ile Phe Glu Ser Ile Asp Leu Thr Leu Pro Arg Asp Asp Arg
    450                 455                 460

Glu Arg Val Asn Met Glu Gln His Cys Leu Ala Arg Glu Val Val Asn
465                 470                 475                 480

Leu Ile Ala Cys Glu Gly Ala Glu Arg Val Glu Arg His Glu Val Phe
                485                 490                 495

Gly Lys Trp Lys Ala Arg Leu Thr Met Ala Gly Phe Arg Pro Ser Pro
            500                 505                 510

Leu Ser Ser Leu Val Asn Ala Thr Ile Ser Lys Leu Leu Gln Ser Tyr
        515                 520                 525

Ser Asp Asn Tyr Lys Leu Ala Glu Arg Asp Gly Ala Leu Tyr Leu Gly
    530                 535                 540

Trp Lys Lys Arg Pro Leu Val Val Ser Ser Ala Trp His
545                 550                 555
```

-continued

```
<210> SEQ ID NO 113
<211> LENGTH: 524
<212> TYPE: PRT
<213> ORGANISM: Oryza sativa ssp. Indica

<400> SEQUENCE: 113

Met Pro Tyr Tyr Asn Asn Ser Val Pro Ser Gly Gly Asn Gly Arg Phe
1               5                   10                  15

Tyr Ile Thr Gln Asn His Gln Asp Ala His Tyr Ala Ser Ser Asp Asp
            20                  25                  30

Gly Ser Gln Lys Ile Gly Ser Ser Pro Gln Ala Phe Glu Ala Pro Tyr
        35                  40                  45

Cys Thr Leu Glu Ser Ser Ala Asn Gly Ala His Pro Ala His Ser
    50                  55                  60

Ser Ala Ser Ser His Ser Ile Ser Pro Ile Ser Gly Ser Pro Leu Ser
65                  70                  75                  80

His His Asp Ser His Ser Asp His Thr Tyr Asn Ser Pro Pro Ser Ala
                85                  90                  95

Ser Cys Val Thr Glu Ile Thr Asp Leu Gln Ile Lys Leu Arg Glu Leu
            100                 105                 110

Glu Asn Ala Ile Leu Gly Pro Glu Leu Asp Ile Ala Tyr Asp Ser Pro
        115                 120                 125

Glu Ser Ala Leu Gln Pro Asn Ile Met Ala Thr Pro Glu Asn Trp Arg
    130                 135                 140

Gln Leu Leu Gly Ile Asn Thr Gly Asp Leu Lys Gln Val Ile Ala
145                 150                 155                 160

Cys Gly Lys Ala Val Ala Glu Asn Asp Val Arg Leu Thr Glu Leu Leu
                165                 170                 175

Ile Ser Glu Leu Gly Gln Met Val Ser Val Ser Gly Asp Pro Leu Gln
            180                 185                 190

Arg Leu Gly Ala Tyr Met Leu Glu Gly Leu Val Ala Arg Leu Ser Ser
        195                 200                 205

Ser Gly Ser Lys Ile Tyr Lys Ser Leu Lys Cys Lys Glu Pro Thr Ser
    210                 215                 220

Ser Glu Leu Met Ser Tyr Met His Leu Leu Tyr Glu Ile Cys Pro Phe
225                 230                 235                 240

Phe Lys Phe Gly Tyr Met Ser Ala Asn Gly Ala Ile Ala Glu Ala Ile
                245                 250                 255

Lys Gly Glu Asn Phe Val His Ile Ile Asp Phe Gln Ile Ala Gln Gly
            260                 265                 270

Ser Gln Trp Met Thr Leu Ile Gln Ala Leu Ala Ala Arg Pro Gly Gly
        275                 280                 285

Pro Pro Phe Leu Arg Ile Thr Gly Ile Asp Asp Ser Asn Ser Ala Tyr
    290                 295                 300

Ala Arg Gly Gly Gly Leu Asp Val Val Gly Met Arg Leu Tyr Lys Val
305                 310                 315                 320

Ala Gln Ser Phe Gly Leu Pro Phe Glu Phe Asn Ala Val Pro Ala Ala
                325                 330                 335

Ser His Glu Val Tyr Leu Glu Leu Asp Ile Arg Val Gly Glu Val
            340                 345                 350

Ile Val Val Asn Phe Ala Tyr Gln Leu His His Thr Pro Asp Glu Ser
        355                 360                 365

Val Ser Thr Glu Asn His Arg Asp Arg Ile Leu Arg Met Val Lys Ser
    370                 375                 380
```

-continued

Leu Ser Pro Arg Leu Val Thr Leu Val Glu Gln Glu Ser Asn Thr Asn
385                 390                 395                 400

Thr Arg Pro Phe Phe Pro Arg Tyr Leu Glu Thr Leu Asp Tyr Tyr Thr
            405                 410                 415

Ala Met Phe Glu Ser Ile Asp Val Ala Leu Pro Arg Asp Asp Lys Arg
        420                 425                 430

Arg Met Ser Ala Glu Gln His Cys Val Ala Arg Asp Ile Val Asn Leu
    435                 440                 445

Ile Ala Cys Glu Gly Ala Glu Arg Val Glu Arg His Glu Val Phe Gly
450                 455                 460

Lys Trp Lys Ala Arg Leu Thr Met Ala Gly Phe Arg Pro Tyr Pro Leu
465                 470                 475                 480

Ser Ser Val Val Asn Ser Thr Ile Lys Thr Leu Leu His Thr Tyr Asn
                485                 490                 495

Ser Phe Tyr Arg Leu Glu Glu Arg Asp Gly Val Leu Tyr Leu Gly Trp
            500                 505                 510

Lys Asn Arg Val Leu Val Val Ser Ala Trp Cys
            515                 520

<210> SEQ ID NO 114
<211> LENGTH: 541
<212> TYPE: PRT
<213> ORGANISM: Orysa sativa ssp. Japonica

<400> SEQUENCE: 114

Met Ser Ala Arg Ala Ser Asn His Ala Tyr Ile Cys Ser Asp Asp Ser
1               5                   10                  15

Gln Met Pro Tyr Tyr Asn Asn Ser Val Pro Ser Gly Gly Asn Gly Arg
            20                  25                  30

Phe Tyr Ile Thr Gln Asn His Gln Asp Ala His Tyr Ala Ser Ser Asp
        35                  40                  45

Asp Gly Ser Gln Lys Ile Gly Ser Ser Pro Gln Ala Phe Glu Ala Pro
    50                  55                  60

Tyr Cys Thr Leu Glu Ser Ser Ser Ala Asn Gly Ala His Pro Ala His
65                  70                  75                  80

Ser Ser Ala Ser Ser His Ser Ile Ser Pro Ile Ser Gly Ser Pro Leu
                85                  90                  95

Ser His His Asp Ser His Ser Asp His Thr Tyr Asn Ser Pro Pro Ser
            100                 105                 110

Ala Ser Cys Val Thr Glu Ile Thr Asp Leu Gln Ile Lys Leu Arg Glu
        115                 120                 125

Leu Glu Asn Ala Ile Leu Gly Pro Glu Leu Asp Ile Ala Tyr Asp Ser
    130                 135                 140

Pro Glu Ser Ala Leu Gln Pro Asn Ile Met Ala Thr Pro Glu Asn Trp
145                 150                 155                 160

Arg Gln Leu Leu Gly Ile Asn Thr Gly Asp Leu Lys Gln Val Ile Ile
                165                 170                 175

Ala Cys Gly Lys Ala Val Ala Glu Asn Asp Val Arg Leu Thr Glu Leu
            180                 185                 190

Leu Ile Ser Glu Leu Gly Gln Met Val Ser Val Ser Gly Asp Pro Leu
        195                 200                 205

Gln Arg Leu Gly Ala Tyr Met Leu Glu Gly Leu Val Ala Arg Leu Ser
    210                 215                 220

Ser Ser Gly Ser Lys Ile Tyr Lys Ser Leu Lys Cys Lys Glu Pro Thr

```
              225             230             235             240
Ser Ser Glu Leu Met Ser Tyr Met His Leu Leu Tyr Glu Ile Cys Pro
                245                 250                 255

Phe Phe Lys Phe Gly Tyr Met Ser Ala Asn Gly Ala Ile Ala Glu Ala
            260                 265                 270

Ile Lys Gly Glu Asn Phe Val His Ile Ile Asp Phe Gln Ile Ala Gln
            275                 280                 285

Gly Ser Gln Trp Met Thr Leu Ile Gln Ala Leu Ala Ala Arg Pro Gly
    290                 295                 300

Gly Pro Pro Phe Leu Arg Ile Thr Gly Ile Asp Asp Ser Asn Ser Ala
305                 310                 315                 320

Tyr Ala Arg Gly Gly Leu Asp Ile Val Gly Met Arg Leu Tyr Lys
                325                 330                 335

Val Ala Gln Ser Phe Gly Leu Pro Phe Glu Phe Asn Ala Val Pro Ala
                340                 345                 350

Ala Ser His Glu Val Tyr Leu Glu His Leu Asp Ile Arg Val Gly Glu
                355                 360                 365

Val Ile Val Val Asn Phe Ala Tyr Gln Leu His His Thr Pro Asp Glu
    370                 375                 380

Ser Val Ser Thr Glu Asn His Arg Asp Arg Ile Leu Arg Met Val Lys
385                 390                 395                 400

Ser Leu Ser Pro Arg Leu Val Thr Leu Val Glu Gln Glu Ser Asn Thr
                405                 410                 415

Asn Thr Arg Pro Phe Phe Pro Arg Tyr Leu Glu Thr Leu Asp Tyr Tyr
                420                 425                 430

Thr Ala Met Phe Glu Ser Ile Asp Val Ala Leu Pro Arg Asp Asp Lys
            435                 440                 445

Arg Arg Met Ser Ala Glu Gln His Cys Val Ala Arg Asp Ile Val Asn
            450                 455                 460

Leu Ile Ala Cys Glu Gly Ala Glu Arg Val Arg His Glu Val Phe
465                 470                 475                 480

Gly Lys Trp Lys Ala Arg Leu Thr Met Ala Gly Phe Arg Pro Tyr Pro
                485                 490                 495

Leu Ser Ser Val Val Asn Ser Thr Ile Lys Thr Leu Leu His Thr Tyr
            500                 505                 510

Asn Ser Phe Tyr Arg Leu Glu Glu Arg Asp Gly Val Leu Tyr Leu Gly
            515                 520                 525

Trp Lys Asn Arg Val Leu Val Val Ser Ser Ala Trp Cys
    530                 535                 540

<210> SEQ ID NO 115
<211> LENGTH: 542
<212> TYPE: PRT
<213> ORGANISM: Setaria italica

<400> SEQUENCE: 115

Met Ser Ala Arg Ala Ser Asn His Pro Tyr Lys Ile Ser Asn Asp Ser
1               5                   10                  15

Gln Met Pro Tyr Tyr Ser Asp Ser Ala Pro Val Gly Glu Asn Gly Arg
            20                  25                  30

Phe His Ala Met Gln Asn Asn Leu Asp His His Tyr Ser Ser Pro Asp
        35                  40                  45

Asp Gly Ser Gln Arg Ile Asn Ser Ser Asn Thr Gln Val Phe Glu Ala
    50                  55                  60
```

```
Gln Tyr Cys Thr Leu Glu Ser Ser Ala Asn Gly Ile Tyr Pro Ala
 65                  70                  75                  80

Gln Ser Ser Thr Ser Ser His Ser Ile Ser Pro Leu Ser Gly Ser Pro
                 85                  90                  95

Leu Ser Gln His Asp Gly His Ser Asp His Thr Tyr Ser Ser Pro Pro
                100                 105                 110

Ser Ala Ser Cys Leu Thr Glu Val Ala Asp Leu Gln Ile Lys Leu Lys
            115                 120                 125

Glu Leu Glu Asn Val Ile Leu Gly Pro Glu Leu Asp Ile Thr Ser Asp
130                 135                 140

Ser Pro Glu Ser Phe Leu Gln Ala Asn Val Gln Leu Arg Pro Asp Asn
145                 150                 155                 160

Trp Arg Gln Leu Leu Gly Ile Asp Ala Gly Asp Leu Lys Gln Val Ile
                165                 170                 175

Ile Ala Cys Gly Lys Ala Val Ala Glu Asn Asp Val Phe Ala Thr Glu
                180                 185                 190

Leu Leu Ile Ser Glu Leu Gly Gln Leu Val Ser Val Ser Gly Asp Pro
            195                 200                 205

Met Gln Arg Leu Gly Ala Tyr Met Leu Glu Gly Ile Val Ala Arg Leu
210                 215                 220

Ser Ser Ser Gly Ser Met Leu Tyr Lys Ser Leu Lys Cys Lys Glu Pro
225                 230                 235                 240

Thr Gly Ser Glu Leu Met Ser Tyr Met His Leu Leu Tyr Glu Ile Cys
                245                 250                 255

Pro Phe Tyr Lys Phe Gly Tyr Met Ser Ala Asn Gly Ala Ile Ala Glu
                260                 265                 270

Ala Ile Lys Gly Glu Asn Phe Val His Ile Ile Asp Phe Gln Ile Ala
            275                 280                 285

Gln Gly Ser Gln Trp Ile Thr Leu Ile Gln Ala Leu Ala Ala Arg Pro
290                 295                 300

Gly Gly Pro Pro Tyr Ile Arg Ile Thr Gly Ile Asp Asp Ser Asn Ser
305                 310                 315                 320

Ala Tyr Ala Arg Gly Gly Gly Leu Asp Ile Val Gly Arg Arg Leu His
                325                 330                 335

Ser Val Ala Gln Ser Cys Gly Leu Pro Phe Glu Phe Asn Ala Val Pro
                340                 345                 350

Ala Ala Ser His Glu Val Gln Leu Glu His Leu Ala Val Arg Pro Gly
            355                 360                 365

Glu Ile Ile Val Val Asn Phe Ala Tyr Gln Leu His His Val Pro Asp
370                 375                 380

Glu Ser Val Ser Ile Glu Asn His Arg Asp Arg Ile Ile Arg Met Ile
385                 390                 395                 400

Lys Ser Ile Asn Pro Arg Val Val Thr Leu Val Glu Gln Glu Ser Asn
                405                 410                 415

Thr Asn Thr Ala Pro Phe Phe Pro Arg Tyr Met Glu Thr Leu Asn Tyr
                420                 425                 430

Tyr Thr Ala Met Phe Glu Ser Ile Asp Val Ala Leu Pro Arg Asp Asp
            435                 440                 445

Arg Arg Arg Met Ser Ala Glu Gln His Cys Val Ala Arg Asp Ile Val
450                 455                 460

Asn Leu Ile Ala Cys Glu Gly Pro Glu Arg Val Glu Arg His Glu Leu
465                 470                 475                 480

Phe Gly Lys Trp Lys Ala Arg Phe Ala Met Ala Gly Phe Arg Pro Tyr
```

```
                    485                 490                 495
Pro Leu Ser Ser Val Val Asn Asn Thr Ile Asn Thr Leu Leu Arg Ser
            500                 505                 510

Tyr Asn Ser Cys Tyr Asn Leu Glu Glu Arg Asp Gly Val Leu Tyr Leu
            515                 520                 525

Gly Trp Lys Asn Arg Val Leu Val Val Ser Ser Ala Trp Cys
            530                 535                 540

<210> SEQ ID NO 116
<211> LENGTH: 547
<212> TYPE: PRT
<213> ORGANISM: Sorghum bicolor

<400> SEQUENCE: 116

Met Ala Asp Thr Pro Thr Ser Arg Met Val His Pro Phe Gly Asp Val
1               5                   10                  15

Pro Arg Gln Thr Pro Lys Gln Phe Leu Tyr Ser Gly Asn Ser Gln His
            20                  25                  30

Leu Cys Tyr Pro Tyr Gln Ser Ala Ser Asp Thr His Val Val Pro Gln
        35                  40                  45

Arg His Cys Thr Met Arg Ser His Ser Pro Asp Ala Gly Ser Glu Asp
    50                  55                  60

His Asp Asn His Lys Gln Tyr Thr Leu Asp Ser Ser Ala Thr Ser Gly
65                  70                  75                  80

Cys Ser Arg His Asp Ser Pro Ser Ser Gln Ser Val His Ala Gly Ser
                85                  90                  95

Gly Ser Pro Val Ser Leu Glu Asp Ser His Ser Gly Ser Thr Asn Gly
            100                 105                 110

Asn Gly Ser Pro Val Ser Ala Ser Cys Val Thr Glu Asp Pro Thr Asp
        115                 120                 125

Leu Lys Gln Lys Leu Lys Asp Leu Glu Ala Ala Met Leu Gly Thr Asp
    130                 135                 140

Pro Glu Ile Val Asn Ser Leu Glu Ile Ser Ile Ala Asp Gln Leu Ser
145                 150                 155                 160

Leu Glu Pro Glu Glu Trp Lys His Met Met Ser Met Pro Gly Gly Asn
                165                 170                 175

Leu Lys Glu Leu Leu Ile Ala Cys Ala Arg Ala Val Glu Tyr Asn Asn
            180                 185                 190

Ser Tyr Ala Ile Asp Leu Met Ile Pro Glu Leu Arg Lys Lys Val Ser
        195                 200                 205

Val Ser Gly Glu Pro Leu Glu Arg Leu Gly Ala Tyr Met Val Glu Gly
    210                 215                 220

Leu Val Ala Arg Leu Ala Ala Ser Gly Ser Ser Ile Tyr Lys Ala Leu
225                 230                 235                 240

Lys Cys Lys Glu Pro Arg Ser Ser Asp Leu Leu Ser Tyr Met His Phe
                245                 250                 255

Leu Tyr Glu Ala Cys Pro Tyr Phe Lys Phe Gly Tyr Met Ser Ala Asn
            260                 265                 270

Gly Ala Ile Ala Glu Ala Val Lys Gly Glu Asp Arg Ile His Ile Ile
        275                 280                 285

Asp Phe His Ile Ala Gln Gly Ala Gln Trp Ile Ser Leu Leu Gln Ala
    290                 295                 300

Leu Ala Ala Arg Pro Gly Gly Pro Pro Phe Val Arg Ile Thr Gly Ile
305                 310                 315                 320
```

```
Asp Asp Ser Val Ser Ala Tyr Ala Arg Gly Gly Leu Glu Leu Val
            325                 330                 335

Gly Arg Arg Leu Ser His Ile Ala Gly Leu Tyr Lys Val Pro Phe Gln
        340                 345                 350

Phe Asp Ala Val Ala Ile Ser Ser Glu Val Glu Glu Gly His Leu
        355                 360                 365

Gly Ile Val Pro Gly Glu Ala Val Ala Val Asn Phe Thr Leu Glu Leu
    370                 375                 380

His His Ile Pro Asp Glu Thr Val Ser Thr Ala Asn His Arg Asp Arg
385                 390                 395                 400

Ile Leu Arg Leu Val Lys Gly Leu Ser Pro Lys Val Leu Thr Leu Val
                405                 410                 415

Glu Gln Glu Ser Asn Thr Asn Thr Ala Pro Phe Ala Gln Arg Phe Ala
            420                 425                 430

Glu Thr Leu Asp Tyr Tyr Thr Ala Ile Phe Glu Ser Ile Asp Leu Ala
        435                 440                 445

Leu Pro Arg Asp Asp Arg Glu Arg Ile Asn Ile Glu Gln His Cys Leu
    450                 455                 460

Ala Arg Glu Ile Val Asn Leu Val Ala Cys Glu Gly Glu Arg Val
465                 470                 475                 480

Glu Arg His Glu Val Phe Gly Lys Trp Lys Ala Arg Leu Met Met Ala
                485                 490                 495

Gly Phe Arg Pro Ser Pro Leu Ser Ala Leu Val Asn Ala Thr Ile Lys
            500                 505                 510

Thr Leu Leu Gln Ser Tyr Ser Pro Asp Tyr Lys Leu Ala Glu Arg Asp
        515                 520                 525

Gly Val Leu Tyr Leu Gly Trp Lys Asn Arg Pro Leu Ile Val Ser Ser
    530                 535                 540

Ala Trp His
545

<210> SEQ ID NO 117
<211> LENGTH: 596
<212> TYPE: PRT
<213> ORGANISM: Theobroma cacao

<400> SEQUENCE: 117

Met Asp Ala His Gln Leu Phe Ser Tyr Gly Val Thr Gly Ala Ser Leu
1               5                   10                  15

Ser Tyr Ser Thr Ser Tyr Ser Thr Val Pro Ser Ile Pro Asn Arg Leu
            20                  25                  30

Phe Ser Ser Leu Lys Ser Asp Ile Gly Asn Ser Pro Asn Ser Pro Phe
        35                  40                  45

Ser Ser Gln Phe Asp Ser Pro Phe Ser Thr Gln Phe Asp Cys Asp Thr
    50                  55                  60

Asn Thr Thr Leu Ser Asp Ser Gln Glu Gln His Ser Ser Thr Glu Asn
65                  70                  75                  80

Leu Ser Gly Leu Ser Pro Ser Cys Asn Ser Ser Phe Glu Ser Asn Thr
                85                  90                  95

Tyr Cys His Lys Leu Ser Pro Ser Leu Asp Cys Lys Arg Glu Ile Leu
            100                 105                 110

Pro Leu Cys Ser Gly Gly Thr Ser Tyr Ile Gln Asp Ala Asn Ser Ser
        115                 120                 125

His Lys Ile Ile Tyr Thr Leu Gln Glu Leu Glu Thr Ala Leu Met Ala
    130                 135                 140
```

```
Pro Asp Ala Asp Glu Val Thr Thr Pro Asn Val Ser Cys Gly Glu
145                 150                 155                 160

Ser Ser Arg Pro Gln Thr Thr Gly Gln Arg Ser Arg Ala Trp Ser Gln
            165                 170                 175

Glu His Gln Gly Ser Leu Val Leu Gln Pro Gln Thr Ser Phe Val Ser
                180                 185                 190

Arg His Arg Gln Ser Thr Glu Val Ser His Ala Glu Lys Arg Gln Lys
            195                 200                 205

Ala Ile Gly Asp Leu Ser Leu Gln Asp Ile Pro Pro Gly Asn Leu Lys
                210                 215                 220

Gln Leu Leu Ile Val Cys Ala Gln Ala Leu Ser Glu Asn Asn Met Asp
225                 230                 235                 240

Asp Phe Asp Lys Leu Ile Ala Lys Ala Arg Asn Ala Val Ser Ile Cys
                245                 250                 255

Gly Glu Pro Ile Gln Arg Leu Gly Ala Tyr Met Val Glu Ala Leu Val
                260                 265                 270

Ala Arg Lys Glu Ala Ser Gly Ser Asn Ile Tyr Arg Ala Arg Arg Cys
            275                 280                 285

Arg Glu Pro Glu Gly Lys Asp Leu Leu Ser Tyr Met Gln Ile Leu Tyr
            290                 295                 300

Glu Ile Cys Pro Tyr Leu Lys Phe Gly Tyr Met Ala Ala Asn Gly Ala
305                 310                 315                 320

Ile Ala Glu Ala Cys Arg Thr Glu Asp Arg Ile His Ile Asp Phe
                325                 330                 335

His Ile Gly Gln Gly Thr Gln Trp Val Thr Leu Leu Gln Ala Leu Ala
                340                 345                 350

Ala Arg Pro Gly Gly Ala Pro His Val Arg Ile Thr Gly Ile Asp Asp
            355                 360                 365

Pro Leu Ser Lys Tyr Ala Arg Gly Gly Gly Leu Glu Ala Val Gly Arg
                370                 375                 380

Arg Leu Ala Ala Leu Ser Glu Lys Phe Asn Ile Pro Val Glu Phe His
385                 390                 395                 400

Gly Val Pro Val Phe Ala Pro Asp Ile Thr Arg Gly Met Leu Asp Val
                405                 410                 415

Arg Pro Gly Glu Ala Leu Ala Val Asn Phe Pro Leu Gln Leu His His
            420                 425                 430

Thr Pro Asp Glu Ser Val Asp Val Asn Asn Pro Arg Asp Gly Leu Leu
            435                 440                 445

Arg Met Val Lys Ser Leu Ser Pro Lys Val Thr Thr Leu Val Glu Gln
            450                 455                 460

Glu Ser Asn Thr Asn Thr Ala Pro Phe Leu Pro Arg Phe Ile Glu Thr
465                 470                 475                 480

Leu Asp Tyr Tyr Leu Ala Met Phe Glu Ser Ile Asp Glu Thr Leu Pro
                485                 490                 495

Arg Asp Arg Lys Glu Arg Ile Asn Val Glu Gln His Cys Leu Ala Arg
            500                 505                 510

Asp Ile Val Asn Val Ile Ala Cys Glu Gly Lys Glu Arg Val Glu Arg
            515                 520                 525

His Glu Leu Phe Gly Lys Trp Lys Ser Arg Leu Thr Met Ala Gly Phe
            530                 535                 540

Arg Gln Tyr Pro Leu Ser Ser Tyr Val Asn Ser Val Ile Arg Ser Leu
545                 550                 555                 560
```

Leu Arg Cys Tyr Ser Lys His Tyr Lys Leu Val Glu Lys Asp Gly Ala
                565                 570                 575

Met Leu Leu Gly Trp Lys Asp Arg Asn Leu Ile Ser Ala Ser Ala Trp
            580                 585                 590

His Cys Asp Ser
        595

<210> SEQ ID NO 118
<211> LENGTH: 538
<212> TYPE: PRT
<213> ORGANISM: Elaeis guineensis

<400> SEQUENCE: 118

Met Gln Ala Ser Glu Arg Asp Lys His Ser Asn Lys Ser Gln Lys Pro
1               5                   10                  15

Tyr His Pro His Asn Ser Met Pro Val Arg Glu Ala Glu Ser His Phe
            20                  25                  30

Leu Ser Gln Asn His Gln Ser Leu Asn Tyr Val Ser Ser Asp Asp Gly
        35                  40                  45

Ser Ser Gln Arg Asn Val His Pro His Thr Ser Gly Gln Phe Cys Thr
    50                  55                  60

Leu Glu Ser Ser Leu Ala Thr Pro Gly Tyr Ala Thr His Asn Ser Pro
65                  70                  75                  80

Ser Ser Leu Ala Phe Ser Pro Asn Ser Gly Ser Pro Leu Ser Gln Gln
                85                  90                  95

Glu Cys Gln Ser Asp Asn Thr Tyr Gly Ser Pro Ile Ser Val Ser Cys
            100                 105                 110

Ile Thr Glu Asp Pro Asn Asp Leu Lys Leu Lys Leu Arg Glu Leu Glu
        115                 120                 125

Thr Ala Met Leu Gly Pro Asp Pro Asp Ile Val Glu Ser Phe Glu Thr
    130                 135                 140

Thr Tyr Pro Ser Asn Thr Ser Met Asp Pro Glu Lys Trp Arg Gln Val
145                 150                 155                 160

Met Gly Ile Pro Arg Gly Asp Leu Lys Gln Met Leu Ile Ala Cys Ala
                165                 170                 175

Arg Ala Val Ala Glu Asn Asp Ile Leu Val Val Glu Trp Leu Ile Ser
            180                 185                 190

Glu Leu Arg Gln Met Val Ser Val Ser Gly Glu Pro Ile Gln Arg Leu
        195                 200                 205

Gly Ala Tyr Met Leu Glu Gly Leu Val Ala Lys Leu Ser Ser Ser Gly
    210                 215                 220

Ser Ala Ile Tyr Lys Ala Leu Arg Cys Lys Glu Pro Thr Ser Ser Glu
225                 230                 235                 240

Leu Leu Ser Tyr Met His Ile Leu Tyr Glu Val Cys Pro Tyr Phe Lys
                245                 250                 255

Phe Gly Tyr Met Ser Ala Asn Gly Ala Ile Ala Glu Ala Val Lys Gly
            260                 265                 270

Glu Asn Met Val His Ile Ile Asp Phe Gln Ile Ala Gln Gly Ser Gln
        275                 280                 285

Trp Met Thr Leu Ile Gln Ala Leu Ala Ala Arg Pro Gly Gly Pro Pro
    290                 295                 300

Cys Leu Arg Ile Thr Gly Ile Asp Asp Ser Val Ser Ala Tyr Ala Arg
305                 310                 315                 320

Gly Gly Gly Leu His Leu Val Gly Gln Arg Leu Ser Arg Leu Ala Gln
                325                 330                 335

Ala Cys Asn Val Pro Phe Glu Phe His Ala Ala Ile Ser Gly Cys
            340                 345                 350

Asp Val Glu Leu Glu His Leu Gly Val Arg Pro Gly Glu Ala Leu Ala
        355                 360                 365

Val Asn Phe Ala Phe Gln Leu His His Met Pro Asp Glu Ser Val Ser
370                 375                 380

Thr Arg Asn His Arg Asp Arg Leu Leu Arg Met Val Lys Ser Leu Ser
385                 390                 395                 400

Pro Lys Val Val Thr Leu Val Glu Gln Glu Ala Asn Thr Asn Thr Ala
                405                 410                 415

Pro Phe Phe Pro Arg Phe Leu Glu Thr Leu Asp Tyr Tyr Ser Ala Met
                420                 425                 430

Phe Glu Ser Ile Asp Val Thr Leu Pro Arg Glu Asn Lys Glu Arg Ile
            435                 440                 445

Ser Val Glu Gln His Cys Leu Ala Arg Asp Ile Val Asn Ile Ile Ala
        450                 455                 460

Cys Glu Gly Ala Glu Arg Val Glu Arg His Glu Leu Phe Gly Lys Trp
465                 470                 475                 480

Arg Ser Arg Phe Thr Met Ala Gly Phe Lys Pro His Pro Leu Ser Pro
                485                 490                 495

Leu Val Asn Ala Thr Ile Lys Thr Leu Leu Glu Asn Tyr Cys Glu His
                500                 505                 510

Tyr Arg Leu Glu Glu Arg Asp Gly Val Leu Tyr Leu Gly Trp Lys Asn
            515                 520                 525

Arg Ala Leu Val Val Ser Cys Ala Trp Arg
        530                 535

<210> SEQ ID NO 119
<211> LENGTH: 539
<212> TYPE: PRT
<213> ORGANISM: Elaeis guineensis

<400> SEQUENCE: 119

Met Gln Ala Ser Asn Lys Cys Gly Ser Ser Asp Glu Ser Pro Glu Leu
1               5                   10                  15

Tyr Leu Gln His Asn Ser Met Pro Arg Arg Glu Glu Glu Phe Arg Leu
            20                  25                  30

Arg Pro Gln Asn Tyr Gln Ser Phe Asp Gln Leu Phe Ser Asp Asn Gly
        35                  40                  45

Ser Leu Ser Gln Ser Cys Pro Leu Gln Ala Ser His Val Gln Tyr Cys
    50                  55                  60

Thr Arg Asp Ser Ala Leu Thr Thr Ala Cys Tyr Ala Leu Arg Asp Ser
65                  70                  75                  80

Pro Ser Thr Leu Ser Phe Ser Pro Ser Phe Gly Ser Pro Val Ser Gln
                85                  90                  95

Gln Asp Tyr His Ser Asp Asn Ile Asn Gly Ser Pro Leu Asn Val Ser
            100                 105                 110

Cys Leu Thr Glu Asp Pro Ala Asp Leu Lys His Lys Leu Arg Glu Leu
        115                 120                 125

Glu Val Ala Met Leu Gly Pro Asp Phe Asp Thr Ile Asp Ser Ser Glu
    130                 135                 140

Ser Ser Phe Arg Ser Tyr Leu Met Ser Lys Pro Glu Met Trp Lys Gln
145                 150                 155                 160

Met Met Gly Ile Pro Glu Gly Asp Leu Lys Glu Thr Leu Ile Ala Cys

```
            165                 170                 175
Ala Arg Ala Val Ala Asp Asn Asp Ala Gln Val Met Asp Trp Leu Ile
            180                 185                 190

Pro Glu Leu Arg Gln Met Val Ser Val Ser Gly Pro Ile Gln Arg
        195                 200                 205

Val Gly Ala Tyr Met Leu Glu Gly Leu Ile Ala Arg Leu Ser Ser Ser
    210                 215                 220

Gly Ser Ser Ile Tyr Lys Ala Leu Lys Cys Lys Glu Pro Thr Ser Ser
225                 230                 235                 240

Asp Leu Leu Ser Tyr Met His Ile Leu Tyr Asp Val Cys Pro Tyr Phe
                245                 250                 255

Lys Phe Ala Tyr Leu Ser Ala Asn Gly Ala Ile Ala Glu Ala Leu Lys
            260                 265                 270

Asn Glu Asp Lys Val His Ile Ile Asp Phe Gln Ile Ala Gln Gly Ser
        275                 280                 285

Gln Trp Met Thr Leu Leu Gln Ala Leu Ala Ala Arg Pro Gly Gly Pro
    290                 295                 300

Pro His Val Arg Ile Thr Gly Ile Asp Asp Ser Met Ser Ala Tyr Ala
305                 310                 315                 320

Arg Gly Gly Gly Leu His Ile Val Gly Gln Arg Leu Phe Arg Phe Ala
                325                 330                 335

Glu Ser Cys Ser Val Pro Phe Glu Phe His Ala Ala Asp Val Ser Cys
            340                 345                 350

Cys Asp Leu Glu Val Lys Asp Leu Gly Val His Pro Gly Glu Ala Leu
        355                 360                 365

Ala Val Asn Phe Pro Phe Gln Leu His His Val Pro Asp Glu Ser Val
    370                 375                 380

Ser Thr Glu Asn His Arg Asp Arg Ile Leu Arg Met Val Lys Ser Leu
385                 390                 395                 400

Ser Pro Gln Val Val Thr Leu Val Glu Gln Glu Ser Asn Thr Asn Thr
                405                 410                 415

Ala Pro Leu Phe Gln Arg Phe Val Glu Thr Leu Asn Tyr Tyr Thr Ala
            420                 425                 430

Ile Phe Glu Ser Ile Asp Val Thr Leu Pro Arg Asp Ser Lys Glu Arg
        435                 440                 445

Ile Asn Val Glu Gln His Cys Leu Ala Arg Asp Ile Val Asn Ile Ile
    450                 455                 460

Ala Cys Glu Gly Ala Glu Arg Val Glu Arg His Glu Leu Phe Gly Lys
465                 470                 475                 480

Trp Lys Ser Arg Phe Thr Met Ala Gly Phe Gly Pro Tyr Pro Leu Ser
                485                 490                 495

Pro Leu Val Asn Ala Thr Ile Lys Ser Leu Leu Ala Lys Tyr Cys Glu
            500                 505                 510

Asn Tyr Thr Leu Glu Glu Arg Asp Gly Val Leu Tyr Leu Gly Trp Lys
        515                 520                 525

Asn Arg Arg Leu Ser Val Ser Ser Ala Trp Arg
    530                 535

<210> SEQ ID NO 120
<211> LENGTH: 553
<212> TYPE: PRT
<213> ORGANISM: Malus domestica
<220> FEATURE:
<221> NAME/KEY: misc_feature
<222> LOCATION: (143)..(143)
```

<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid

<400> SEQUENCE: 120

```
Met Gln Ala Ser Lys Glu Gln Arg Ile Ser Gly Met Ser Asn Gln Leu
1               5                   10                  15

Tyr Tyr Gln Pro Ile Gln Glu Val Ala Tyr Cys Leu Pro Arg Phe
            20                  25                  30

Gln Thr Leu Asp Pro Arg Leu His Tyr Asn Glu Ser Ser Gln Ser Thr
        35                  40                  45

His Leu Pro Leu Gln Ser Phe His Glu His Tyr Cys Thr Leu Glu Ser
 50                  55                  60

Ser Trp Ser Asn Gly Ser Tyr Thr Val Tyr Asn Thr Pro Ser Asn Val
 65                  70                  75                  80

Ser Phe Ser Pro Ser Gly Ser Pro Met Ser Gln Gln Asp Ser His Ser
                85                  90                  95

Tyr Leu Ser Asp Gln Tyr His Ser Pro Asp Gln Thr Tyr Ser Ser Pro
            100                 105                 110

Met Ser Gly Ser Cys Ile Thr Asp Asp Ala Thr Asp Leu Lys Tyr Lys
        115                 120                 125

Leu Lys Gln Leu Glu Thr Val Met Leu Gly Pro Asp Ser Asn Xaa Leu
130                 135                 140

Asp Asn Tyr Cys Xaa Thr Phe Pro Asn Gly Ala Ser Asn Ser Leu Pro
145                 150                 155                 160

Asp Glu Asp Ser Trp Gly Gln Ile Met Glu Ser Ile Ser Lys Lys Asp
                165                 170                 175

Leu Lys Gln Val Leu Ile Phe Cys Ala Lys Ala Val Ala Asp Asn Asp
            180                 185                 190

Leu Leu Met Ala Gln Trp Met Met Asp Glu Leu Arg Gln Met Val Ser
        195                 200                 205

Val Ser Gly Glu Pro Ile Gln Arg Leu Gly Ala Tyr Leu Leu Glu Gly
210                 215                 220

Leu Val Ala Arg Lys Ala Ser Ser Gly Ser Asn Ile Tyr Lys Ala Leu
225                 230                 235                 240

Arg Cys Lys Glu Pro Ala Ser Cys Glu Leu Leu Ser Tyr Met His Ile
                245                 250                 255

Leu Tyr Glu Val Cys Pro Tyr Phe Lys Phe Gly Tyr Met Ser Ala Asn
            260                 265                 270

Gly Ala Ile Ala Glu Ala Met Lys Asp Glu Ser Val His Ile Ile
        275                 280                 285

Asp Phe Gln Ile Gly Gln Gly Ser Gln Trp Val Thr Leu Ile Gln Ala
290                 295                 300

Phe Ala Ser Arg Pro Gly Gly Pro Pro His Ile Arg Ile Thr Gly Ile
305                 310                 315                 320

Asp Asp Ser Met Ser Ala Tyr Ala Arg Gly Gly Leu Asn Ile Val
                325                 330                 335

Gly Lys Arg Leu Ser Lys Leu Ala Glu Leu Val Lys Val Pro Phe Glu
            340                 345                 350

Phe His Ala Thr Ser Met Ser Gly Cys Asp Val Gln Leu Glu His Leu
        355                 360                 365

Cys Val Arg Pro Gly Glu Ala Leu Ala Ile Asn Phe Ala Phe Met Leu
370                 375                 380
```

His His Met Pro Asp Glu Ser Val Ser Thr Gln Asn His Arg Asp Arg
385                 390                 395                 400

Leu Leu Arg Leu Val Lys Ser Leu Ser Pro Lys Val Val Thr Leu Val
            405                 410                 415

Glu Gln Glu Ser Asn Thr Asn Thr Ala Ala Phe Tyr Pro Arg Phe Val
            420                 425                 430

Glu Thr Leu Asn Tyr Tyr Thr Ala Met Phe Glu Ser Ile Asp Val Thr
            435                 440                 445

Leu Pro Arg Asp His Lys Glu Arg Ile Asn Val Glu Gln His Cys Leu
            450                 455                 460

Ala Arg Glu Val Val Asn Ile Ile Ala Cys Glu Gly Val Glu Arg Val
465                 470                 475                 480

Glu Arg His Glu Leu Leu Gly Lys Trp Arg Leu Arg Phe Ala Met Ala
            485                 490                 495

Gly Phe Thr Pro Tyr Pro Leu Ser Ser Leu Val Asn Ala Thr Ile Lys
            500                 505                 510

Thr Leu Leu Asp Asn Tyr Ser Asp Lys Tyr Arg Leu Glu Glu Arg Asp
            515                 520                 525

Gly Ala Leu Tyr Leu Gly Trp Lys Asn Arg Asp Leu Val Ala Ser Cys
530                 535                 540

Ala Trp Arg Cys Lys Pro Ser Thr Asn
545                 550

<210> SEQ ID NO 121
<211> LENGTH: 551
<212> TYPE: PRT
<213> ORGANISM: Fragaria vesca subsp. Vesca

<400> SEQUENCE: 121

Met Gln Ala Ser Lys Gln His Arg Ser Ser Gly Met Ser Lys Arg Leu
1               5                   10                  15

His Tyr Gln Pro Lys Gln Glu Val Glu Ala Tyr Cys Leu Pro Pro Phe
            20                  25                  30

Arg Ile Leu Asp His Gln Pro Ala Tyr Asn Glu Ser Ser Gln Ser Thr
            35                  40                  45

His Ser Thr Ala Gln Ser Phe His Glu Arg Tyr Cys Thr Leu Glu Ser
        50                  55                  60

Ser Ser Thr Asn Gly Ser Tyr Asn Thr Leu Tyr Thr Ser Ser Ser Thr
65                  70                  75                  80

Val Ser Phe Ser Pro Ser Gly Ser Pro Met Ser Gln His Glu Gln Asp
            85                  90                  95

Ser His Tyr Gln His His Ser Pro Asp His Met Tyr Gly Ser Pro Ile
            100                 105                 110

Ser Gly Ser Cys Ile Thr Asp Asp Ala Thr Asp Phe Lys Tyr Lys Leu
            115                 120                 125

Lys Glu Leu Glu Thr Ala Met Leu Gly Asp Ser Asn Ile Phe Asp Asn
            130                 135                 140

Tyr Cys Ser Ser Leu Gln Asn Gly Ala Arg Asn Thr Arg Pro Glu Val
145                 150                 155                 160

Asp Ser Trp Gly Gln Ile Met Asp Ser Ile Ser Lys Lys Asp Leu Asn
            165                 170                 175

Gln Val Leu Ile Phe Cys Ala Lys Ala Val Ala Asp Asn Asp Leu Leu
            180                 185                 190

Met Ala Gln Trp Met Met Asp Glu Leu Arg Gln Met Val Ser Val Ser

```
                195                 200                 205
Gly Glu Pro Ile Gln Arg Leu Gly Ala Tyr Met Leu Glu Gly Leu Val
210                 215                 220

Ala Arg Arg Ala Ser Ser Gly Ser Ser Ile Cys Lys Ala Leu Arg Cys
225                 230                 235                 240

Lys Glu Pro Ala Ser Ser Glu Leu Leu Ser Tyr Met His Ile Leu Tyr
                245                 250                 255

Glu Val Cys Pro Tyr Phe Lys Phe Gly Tyr Met Ser Ala Asn Gly Ala
                260                 265                 270

Ile Ala Glu Ala Met Lys Asp Glu Asp Lys Val His Ile Ile Asp Phe
                275                 280                 285

Gln Ile Gly Gln Gly Ser Gln Trp Leu Thr Leu Ile Gln Ala Phe Ala
290                 295                 300

Ala Arg Pro Gly Gly Pro Pro His Ile Arg Ile Thr Gly Ile Asp Asp
305                 310                 315                 320

Ser Thr Ser Ala Tyr Ala Arg Gly Gly Gly Leu Asn Ile Val Gly Lys
                325                 330                 335

Arg Leu Ser Lys Leu Ala Glu Met Phe Lys Val Pro Phe Glu Phe His
                340                 345                 350

Ala Ala Ala Ile Ser Gly Cys Asp Val Gln Leu Glu Asn Leu Gly Val
                355                 360                 365

Arg Pro Gly Glu Ala Leu Ala Met Asn Phe Ala Phe Met Leu His His
370                 375                 380

Met Pro Asp Glu Ser Val Ser Thr Gln Asn His Arg Asp Arg Leu Leu
385                 390                 395                 400

Arg Leu Val Lys Ser Leu Ser Pro Lys Val Val Thr Leu Val Glu Gln
                405                 410                 415

Glu Ser Asn Thr Asn Thr Ala Ala Phe Phe Pro Arg Phe Val Glu Thr
                420                 425                 430

Leu Asn Tyr Tyr Thr Ala Met Phe Glu Ser Ile Asp Val Thr Leu Pro
                435                 440                 445

Arg Asp His Lys Glu Arg Ile Asn Val Glu Gln His Cys Leu Ala Lys
                450                 455                 460

Glu Val Val Asn Ile Ile Ala Cys Glu Gly Ile Glu Arg Val Glu Arg
465                 470                 475                 480

His Glu Leu Leu Gly Lys Trp Arg Ser Arg Phe Ala Met Ala Gly Phe
                485                 490                 495

Thr Pro Tyr Pro Leu Ser Ser Leu Val Asn Ala Thr Ile Lys Thr Leu
                500                 505                 510

Leu Lys Asn Tyr Ser Asp Lys Tyr Arg Leu Gln Glu Arg Asp Gly Ala
                515                 520                 525

Leu Tyr Leu Gly Trp Lys Asn Arg Asp Leu Val Ala Ser Cys Ala Trp
                530                 535                 540

Lys Cys Lys Pro Gly Thr Asn
545                 550

<210> SEQ ID NO 122
<211> LENGTH: 466
<212> TYPE: PRT
<213> ORGANISM: Beta vulgaris subsp. vulgaris

<400> SEQUENCE: 122

Met Gln Asn Pro Arg Asn Thr Gln Gly Phe Ser Cys Thr Phe Asp Ser
1               5                   10                  15
```

-continued

```
Ser Leu Leu Ile Gly Ala Asp Asn Phe Cys Gly Ser Pro Thr Glu
            20                  25                  30

Ser Ile Ser Gly Asn Gly Ser Thr Val Ser Leu Ile Asp Pro Glu Tyr
        35                  40                  45

Ser Ser Ser Asp Ser His Asp Ile Asp Asn Leu Arg Asn Gln Leu Arg
    50                  55                  60

Glu Leu Glu Asn Val Met Met Gly Thr Thr Ser Gly Ser Phe Glu Thr
65                  70                  75                  80

Glu Asn Trp Gln Arg Leu Val Glu Met Ile Lys Arg Gly Glu Leu Lys
                85                  90                  95

Glu Val Leu Ile Ala Cys Ala Lys Ala Val Ser Asp Asp Leu Leu
            100                 105                 110

Thr Ala Glu Trp Leu Ile Ser Glu Leu Gln His Met Val Ser Val Ser
        115                 120                 125

Gly Glu Pro Ile Gln Arg Leu Gly Ala Tyr Met Leu Glu Gly Leu Ile
    130                 135                 140

Ala Arg Phe Ser Ser Ser Gly Ile Ser Ile Tyr Lys Thr Leu Asn Cys
145                 150                 155                 160

Asn Glu Pro Thr Ser Gly Glu Leu Leu Ser His Met Gln Leu Leu Tyr
                165                 170                 175

Glu Val Cys Pro Tyr Phe Lys Phe Gly Tyr Met Ser Ala Asn Gly Ala
            180                 185                 190

Ile Ala Asp Ala Leu Lys Asn Glu Asp Arg Ile His Ile Ile Asp Phe
        195                 200                 205

Gln Ile Ala Gln Gly Ser Gln Trp Val Ser Leu Ile Gln Ala Leu Ala
    210                 215                 220

Ala Arg Pro Gly Gly Pro Pro Gln Val Arg Ile Thr Gly Ile Asp Asp
225                 230                 235                 240

Ser Thr Ser Glu Tyr Ala Arg Gly Gly Gly Leu Asn Ile Val Gly Glu
                245                 250                 255

Arg Leu Ser Lys Leu Ala Lys Ala Cys Asn Leu Pro Phe Glu Phe Gln
            260                 265                 270

Ala Ala Ala Leu Arg Cys Gly Thr Glu Val Lys Leu Glu Asn Phe Val
        275                 280                 285

Leu Arg Pro Glu Glu Ala Leu Ala Val Asn Phe Pro Phe Arg Leu His
    290                 295                 300

His Ile Pro Asp Glu Ser Val Gly Pro Glu Asn His Arg Asp Thr Leu
305                 310                 315                 320

Leu Arg Leu Val Lys Ser Trp Ser Pro Lys Val Val Thr Leu Val Glu
                325                 330                 335

Tyr Glu Leu Asn Thr Asn Thr Ala Pro Phe Phe Pro Arg Phe Leu Glu
            340                 345                 350

Thr Leu Asp Tyr Tyr Ser Ala Ile Phe Glu Ser Ile Asn Val Thr Leu
        355                 360                 365

Pro Thr Asp His Lys Glu Arg Ile Asn Val Gln His Cys Leu Ala
    370                 375                 380

Lys Glu Val Val Asn Ile Ile Ala Cys Glu Gly Ala Glu Arg Ile Glu
385                 390                 395                 400

Arg His Glu Leu His Gly Lys Trp Lys Ser Arg Phe Leu Met Ala Gly
                405                 410                 415

Phe Asn Pro Tyr Pro Leu Ser Pro Leu Val Asn Gly Thr Ile Arg Thr
            420                 425                 430

Leu Leu Gln Lys Tyr Ser Arg Ser Tyr Gly Leu Glu Glu Arg Asn Gly
```

```
            435                 440                 445
Ala Leu Tyr Leu Gly Trp Met Asn Arg Val Leu Val Thr Ala Cys Ala
    450                 455                 460

Trp Gln
465

<210> SEQ ID NO 123
<211> LENGTH: 525
<212> TYPE: PRT
<213> ORGANISM: Eucalyptus grandis

<400> SEQUENCE: 123

Met Gln Thr Ser Gln Lys Lys Ser His Leu Ser Met Ser Asn Lys Ile
1               5                   10                  15

Cys Tyr Gln Ser Ala Leu Glu Ile Gly Thr Tyr Cys Leu Pro Gln Phe
            20                  25                  30

His Thr Leu Asp Cys Tyr Pro Ser Tyr Cys Thr Leu Glu Ser Ser Ser
        35                  40                  45

Ala Ser Gly Gly Tyr Ala Ile Tyr Asn Pro Pro Ser Thr Ile Ser Phe
    50                  55                  60

Ser Ser Asp Gly Ser Pro Val Ser Leu Gln Asp Ser Val Ser Tyr Pro
65                  70                  75                  80

Pro Asp Ala Leu His Ser Pro Asp Asn Thr Tyr Ala Ser Ser Ile Ser
                85                  90                  95

Gly Ser Cys Val Thr Asp Asp Ala Asn Asp Phe Leu His Lys Leu Arg
            100                 105                 110

Glu Leu Glu Asn Val Met Leu Gly Pro Asp Ser Asp Ile Ser Ile Asn
        115                 120                 125

Asn Asp Arg Ser Phe Gln Lys Gly Ile His Val Ala Ser Pro Gly Ser
    130                 135                 140

Lys Leu Lys Asp Ala Ile Glu Arg Lys Asp Leu Lys Arg Val Leu Ile
145                 150                 155                 160

Ala Ser Ala Lys Ala Val Ser Glu Asn Asp Leu Trp Thr Ala Asn Trp
                165                 170                 175

Leu Met Asp Glu Leu Arg Gly Met Val Ser Val Ser Gly Glu Pro Ile
            180                 185                 190

Gln Arg Leu Gly Ala Tyr Met Leu Glu Gly Leu Val Ala Arg Leu Ala
        195                 200                 205

Ser Ser Gly Ser Ser Ile Tyr Lys Ala Leu Arg Cys Lys Glu Pro Glu
    210                 215                 220

Ser Ser Glu Leu Leu Ser Tyr Met His Ile Leu Tyr Glu Val Cys Pro
225                 230                 235                 240

Tyr Phe Lys Phe Gly Tyr Met Ser Ala Asn Gly Ala Ile Ala Asp Ala
                245                 250                 255

Met Lys Asn Glu Asn Arg Val His Ile Ile Asp Phe Gln Ile Gly Gln
            260                 265                 270

Gly Ser Gln Trp Ile Thr Leu Ile Gln Ala Phe Ala Ala Arg Pro Gly
        275                 280                 285

Gly Pro Pro His Ile Arg Ile Thr Gly Phe Asp Asp Ser Thr Ser Ala
    290                 295                 300

Tyr Ala Arg Gly Gly Gly Leu Glu Ile Val Gly Lys Arg Leu Thr Lys
305                 310                 315                 320

Leu Ala Gln Leu Tyr Lys Val Pro Phe Glu Phe His Ala Leu Ile
                325                 330                 335
```

```
Pro Gly Ser Asp Leu Leu His His Leu Asp Val Arg Arg Gly Glu
            340                 345                 350

Ala Leu Ala Val Asn Phe Ala Phe Met Leu His His Met Ala Asp Glu
        355                 360                 365

Ser Val Ser Ile Gln Asn His Arg Asp Arg Leu Leu Arg Leu Val Lys
    370                 375                 380

Ser Leu Ser Pro Lys Val Val Thr Leu Val Glu Gln Glu Ser Asn Thr
385                 390                 395                 400

Asn Thr Ala Ala Phe Leu Pro Arg Phe Ile Glu Ala Met Asp Tyr Tyr
                405                 410                 415

Ala Ala Met Phe Glu Ser Ile Asp Val Thr Leu His Arg Glu His Lys
            420                 425                 430

Glu Arg Ile Asn Val Glu Gln His Cys Leu Ala Arg Asp Val Val Asn
        435                 440                 445

Ile Ile Ala Cys Glu Gly Ala Glu Arg Val Glu Arg His Glu Leu Leu
    450                 455                 460

Gly Lys Trp Arg Leu Arg Phe Ala Met Ala Gly Phe Thr Pro Phe Pro
465                 470                 475                 480

Leu Ser Ser Leu Val Asn Gly Thr Ile Lys Thr Leu Leu Glu Asn Tyr
                485                 490                 495

Ser His Arg Tyr Arg Leu Glu Glu Arg Asp Gly Ala Leu Tyr Leu Gly
            500                 505                 510

Trp Met Asn Arg Asp Leu Val Ala Ser Cys Ala Trp Lys
        515                 520                 525

<210> SEQ ID NO 124
<211> LENGTH: 545
<212> TYPE: PRT
<213> ORGANISM: Citrus sinensis

<400> SEQUENCE: 124

Met Gln Phe Ser Arg Met His Lys Met Ser Asp Gly Thr Gln Lys Phe
1               5                   10                  15

Tyr Asp Gln Pro Val Gln Lys Leu Ala Ser Lys Asn Trp Pro Pro His
            20                  25                  30

Gln Asn Ile Asp His Gln Pro Ser Ser Asp Asp Ser Asn Glu Arg Ala
        35                  40                  45

Arg Leu Ser Val Asp Thr Phe Glu Gln Tyr Cys Thr Leu Glu Ser Ser
    50                  55                  60

Ser Gly Thr Gly Ser His Gly Ala Pro Asn Ser Pro Ser Thr Ala Ser
65                  70                  75                  80

Phe Ser Pro Glu Lys Thr Gln Val Ser Trp Pro Asn Gln Gln Ser Tyr
                85                  90                  95

Ser Ser Glu Leu Tyr Gln Ser Pro Asp Arg Thr Cys Gly Ser Pro Val
            100                 105                 110

Ser Gly Ser Cys Ile Thr Gln Asn Glu Asn Asp Leu Arg His Lys Leu
        115                 120                 125

Arg Glu Leu Glu Thr Val Met Leu Gly Pro Asp Leu Asp Thr Pro Ala
    130                 135                 140

Met Tyr Asn Val Thr Ser Pro Lys Glu Asp Gln Ile Ser Glu Ser Ser
145                 150                 155                 160

Glu Arg Trp Lys Cys Leu Val Glu Ile Ile Ser Arg Gly Asp Leu Lys
                165                 170                 175

Glu Leu Leu Cys Ala Cys Ala Lys Ala Ile Glu Asn Asn Asp Met Tyr
            180                 185                 190
```

```
Ala Ala Glu Ser Leu Met Ala Glu Ser Arg Gln Met Val Ser Val Ser
            195                 200                 205
Gly Asp Pro Ile Gln Arg Leu Gly Ala Tyr Met Leu Glu Gly Leu Ile
        210                 215                 220
Ala Arg Leu Ala Ser Ser Gly Ser Ser Ile Tyr Lys Ala Leu Arg Cys
225                 230                 235                 240
Lys Glu Pro Ala Ser Ala Glu Leu Leu Ser Tyr Met His Leu Leu Tyr
                245                 250                 255
Glu Ile Cys Pro Tyr Phe Lys Phe Gly Tyr Met Ser Ala Asn Gly Ala
            260                 265                 270
Ile Ala Glu Ala Met Lys Asp Glu Asn Lys Ile His Ile Ile Asp Phe
        275                 280                 285
Leu Ile Ala Gln Gly Ser Gln Trp Ile Ile Leu Ile Met Ala Leu Ala
    290                 295                 300
Ser Arg Pro Gly Gly Pro Pro His Ile Arg Ile Thr Gly Ile Asp Asp
305                 310                 315                 320
Ser Thr Ala Ala Tyr Ala Arg Gly Gly Gly Leu Glu Ile Val Gly Gln
                325                 330                 335
Arg Leu Ser Lys Leu Ala Asp Leu Tyr Lys Val Pro Phe Glu Phe Asn
            340                 345                 350
Ala Ala Ala Ile Ser Gly Ser Glu Val Gln Leu Glu Asn Leu Glu Val
        355                 360                 365
Arg Pro Gly Glu Ala Leu Ala Val Asn Phe Ser Met Met Leu His His
    370                 375                 380
Met Pro Asp Glu Ser Val Ser Ile Gln Asn His Arg Asp Arg Leu Leu
385                 390                 395                 400
Arg Leu Val Lys Gly Leu Ser Pro Lys Val Val Thr Leu Val Glu Gln
                405                 410                 415
Glu Ala Asn Thr Asn Thr Ala Pro Phe Phe His Arg Phe Leu Glu Thr
            420                 425                 430
Met Asn His Tyr Gly Ala Ile Phe Asp Ser Ile Asp Val Ala Leu Pro
        435                 440                 445
Arg Asp Ser Lys Asp Arg Ile Asn Val Glu Gln His Cys Leu Ala Arg
    450                 455                 460
Glu Ile Val Asn Leu Ile Ala Cys Glu Gly Ala Glu Arg Val Glu Arg
465                 470                 475                 480
His Glu Pro Phe Gly Lys Trp Arg Ser Arg Phe Ile Met Ala Gly Phe
                485                 490                 495
Thr Pro Tyr Pro Leu Ser Pro Phe Val Asn Ala Thr Ile Lys Thr Leu
            500                 505                 510
Leu Glu Asn Tyr Asn Asp Asn Tyr Thr Leu Glu Glu Arg Asp Gly Ala
        515                 520                 525
Leu Phe Leu Gly Trp Lys Asn Gln Ala Ile Ile Val Ser Ser Ala Trp
    530                 535                 540
Arg
545

<210> SEQ ID NO 125
<211> LENGTH: 536
<212> TYPE: PRT
<213> ORGANISM: Musa acuminata subsp. Malaccensis

<400> SEQUENCE: 125

Met Gln Ala Ser Thr Asn Tyr Lys Val Leu Ser Lys Gln His Gln Ser
```

-continued

```
1               5                   10                  15
Tyr Asn Gln Asn Leu Gly Arg Asp Pro Glu Ser Arg Phe Met Pro Gln
                20                  25                  30
Asn Tyr Leu Thr Ser His Cys Asp Ser Ser Ala Asp Gly Phe Gln Gln
                35                  40                  45
Gly Asn Ser His His Gln Thr Ile His Asp Gln Phe Tyr Thr Leu Glu
                50                  55                  60
Ser Ser Ser Glu Ala Ala Asn Phe Thr Thr His Asn Ser Pro Ser Ser
65                  70                  75                  80
Pro Ser Tyr Ser Pro Ile Ser Arg Ser Pro Ala Ser His Gln Asp Ser
                85                  90                  95
Gln Ser Asp Asn Asn Tyr Asp Ser Pro Ile Ser Tyr Ser Cys Ile Thr
                100                 105                 110
Glu Asp Ser Asn Asp Leu Lys His Lys Leu Arg Glu Ile Glu Ala Ala
                115                 120                 125
Met Leu Gly Pro Asp Ser Asp Ser Ile Asp Ser Phe Glu Asn Ala Tyr
                130                 135                 140
Ser Ser Tyr Ile Ser Leu Glu Gln Glu Lys Trp Gln Gln Val Met Gly
145                 150                 155                 160
Thr Pro Arg Gly Asp Leu Lys Gln Ile Leu Ile Ala Cys Ala Arg Ala
                165                 170                 175
Val Glu Asn Asn Asp Ile Leu Val Val Glu Trp Leu Ile Pro Lys Leu
                180                 185                 190
Arg Gln Met Val Ser Val Ser Gly Glu Pro Ile Gln Arg Leu Gly Ala
                195                 200                 205
Tyr Leu Leu Glu Gly Leu Val Ala Lys Leu Ala Ser Ser Gly Ser Ser
                210                 215                 220
Ile Tyr Lys Ala Leu Lys Cys Lys Glu Pro Thr Ser Ser Asp Leu Leu
225                 230                 235                 240
Ser Tyr Met His Ile Leu Tyr Asp Val Cys Pro Tyr Phe Lys Phe Gly
                245                 250                 255
Tyr Met Ser Ala Asn Gly Ala Ile Ala Glu Ala Leu Lys Gly Glu Asn
                260                 265                 270
Met Val His Ile Ile Asp Phe Gln Ile Ala Gln Gly Ser Gln Trp Val
                275                 280                 285
Thr Leu Ile Gln Ala Leu Ala Ala Arg Pro Gly Gly Pro Pro Arg Val
                290                 295                 300
Arg Ile Thr Gly Ile Asp Asp Ser Val Ser Ala Tyr Ala Arg Gly Gly
305                 310                 315                 320
Gly Leu His Ile Val Gly Gln Arg Leu Ser Arg Leu Ala Lys Ser Cys
                325                 330                 335
Asn Val Pro Phe Glu Phe His Gly Ala Ala Leu Ser Gly Cys Asp Leu
                340                 345                 350
Glu Leu Glu His Leu Asp Ile Arg Pro Gly Glu Ala Leu Ala Val Asn
                355                 360                 365
Phe Ala Phe Gln Leu His His Met Pro Asp Glu Ser Val Ser Thr Arg
                370                 375                 380
Asn Tyr Arg Asp Arg Leu Leu Gln Met Ile Lys Ser Leu Ser Pro Thr
385                 390                 395                 400
Val Val Thr Leu Val Glu Gln Glu Ser Asn Thr Asn Thr Ala Pro Phe
                405                 410                 415
Phe Pro Arg Phe Leu Glu Thr Val Asp Tyr Tyr Ala Ala Ile Phe Glu
                420                 425                 430
```

```
Ser Ile Asp Val Thr Leu Pro Arg Glu Asn Lys Glu Arg Ile Asn Val
    435                 440                 445
Glu Gln His Cys Leu Ala Arg Asp Ile Val Asn Ile Ile Ala Cys Glu
    450                 455                 460
Gly Asp Glu Arg Val Arg His Glu Leu Phe Gly Lys Trp Arg Ser
465                 470                 475                 480
Arg Phe Met Met Ala Gly Phe Arg Pro Tyr Pro Leu Ser Pro Leu Val
                485                 490                 495
Asn Ala Thr Ile Lys Met Leu Leu Glu Asn Tyr Cys Glu Asn Tyr Arg
            500                 505                 510
Leu Glu Arg Asp Gly Val Leu Tyr Leu Gly Trp Lys Asn Arg Ala
    515                 520                 525
Leu Val Val Ser Cys Ala Trp Lys
    530                 535

<210> SEQ ID NO 126
<211> LENGTH: 1473
<212> TYPE: DNA
<213> ORGANISM: Arabidopsis thaliana

<400> SEQUENCE: 126
atgtacaagc agcctagaca agagcttgag gcttattatt ttgagcctaa ctctgttgag     60
aagcttaggt acttaccggt taacaactct cgtaaacggt tttgtacgct cgagccattt    120
cctgactctc ctccttataa tgctctatct actgctacat atgatgatac atgtggctct    180
tgtgtaacgg atgagttgaa tgacttcaaa cacaagatta gggaaatcga acggtgatg    240
atggggccgg actcgttgga cttacttgtc gattgcacgg actcatttga ttccacggcg    300
agtcaagaga ttaatggttg gagatcaact ctagaggcta tctcgaggcg ggatttaaga    360
gctgatcttg tttcatgtgc caaagctatg tcggaaaatg atcttatgat ggctcattca    420
atgatggaga agttgcggca gatggtttcg gtttctggtg agcctattca acggttggga    480
gcttacttat tggaaggtct agtggcgcag ctagcttcgt cgggcagttc tatatacaaa    540
gcacttaata ggtgtcctga accggctagc acagagcttc tctcttacat gcacattctc    600
tatgaggttt gtccttactt caagtttgga tacatgtcag caaatggtgc tattgctgag    660
gcaatgaagg aagaaaacag agttcacatt attgatttcc aaatcggtca agggagtcaa    720
tgggtcactc ttatccaggc ttttgcagct aggcctggtg ggcctccgcg gattcggata    780
acgggtatcg atgatatgac ttcagcgtat gctcgtggag gtggcctaag cattgttgga    840
aatagactcg ctaagcttgc taagcagttc aacgttccat tcgagtttaa ctcggtatcg    900
gtgtcagttt ccgaggttaa acctaaaaac ctcggggttc gacctgggga agctctagcc    960
gtaaactttg cctttgtgct tcatcatatg ccagacgaaa gcgtgagcac cgagaatcac   1020
cgcgaccggt tattgagaat ggtgaagagc ttatctccca aggtggtgac tcttgtggaa   1080
caagagtcaa acacaaacac agccgctttc ttcccgaggt tcatggagac aatgaactac   1140
tatgccgcga tgtttgagtc aattgatgtg actctaccaa gagatcacaa acagaggatt   1200
aatgtggagc aacattgtct agcaagagat gtcgtgaaca tcatcgcatg tgaaggagct   1260
gatcgggtgg agcgacacga gctcctagga aaatggaggt cacggtttgg gatggcgggt   1320
ttcactcctt acccgttgag tcccttggtg aattcaacca ttaaaagtct gcttaggaac   1380
tactcagaca gtacaggct agaagaaaga gatggagctt gtatcttgg ttggatgcat   1440
cgagatttgg ttgcctcgtg tgcttggaaa tga                                1473
```

<210> SEQ ID NO 127
<211> LENGTH: 1629
<212> TYPE: DNA
<213> ORGANISM: Zea mays

<400> SEQUENCE: 127

```
atgtcagcta gggattctaa tcattcatat aaatgttcgg atgattctca aatgccgtac      60
tacaataact cagcacctgt aggagaaaat ggtaggatcc atatggcaga aaacagtcta     120
ggacatcatt actcatcctc cgatattgga tcacaaagga tcaacaattc caaccctcaa     180
gtatttgaag cacagtactg cactctggaa tcatcctcag caaatggtgt ttatcctgca     240
caaagctcca catcttctca tagcatctcc cctttaagtg ggagccccct gtctcagcat     300
gacagccact cagaccacac atatagttct cctccaagtg cttcctgtct aactgaggtt     360
gcagatctcc tgattaaaca aaaagaatta gagaattcca ttgttggacc tggactggac     420
attagttctg actgctctcg gagcttgttg caagcccatg ttccagtgag accagacaac     480
tggagacaac ttctgggaat aatggagga gacttgatgc aagtagtcat agcatgtggt     540
aaggctgttg cagagaatga tgtctttgca acagaactgt taatatctga gcttggtcac     600
ctggtatctg tatctggaga tccaatgcaa cgacttggag cctatatgct tgaaggaatt     660
gttgctagac tttcttcctc cggcagtatg ctatataaat ctttgaaatg taagaaacct     720
acaagctctg agctcatgtc atatatgcat ctcctttacg agatctgccc attctacaag     780
tttggttaca tgtcagcaaa tggtgccatt gccgaggcta ttaagggcga gaactttgtt     840
cacataattg atttccaaat tgctcagggg agccagtggg ttactctgct acaggccctt     900
gctgcaagac ctgggggggcc accatacatt agaatcactg gtatagatga ctcaaattct     960
gcttatgcca gaggaggcgg gcttgatata gttgggagga cgttgtgtga tgttgctaat    1020
tcatgtggtc ttcctttga gttcaatgcc gttccagctg ctagccatga ggttgagctt    1080
cagcatcttg ctataagaca tggggagatt attgctgtga attttgccta tcagctacat    1140
catgttcctg acgaaagtgt aagtacagaa aatcatcggg ataggattat aagaatgatc    1200
aagagcatca atcctagggt tgttactctc gttgaacagg agtcaaatac aaacacagct    1260
ccattcttcc caaggtacat ggaaactctc aactactata cagccatgtt tgagtcgata    1320
gatgttgctc tcccaaggga tgataggagg cggatgagcg cagaacaaca ctgtgttgca    1380
agggatattg ttaatttaat cgcatgcgag ggtgctgaaa gggttgagag cacgagctg    1440
tttgaaaat ggaagtcaag atttgcaatg gctggattta ccgtacccc actgagttca    1500
gttgtgaaca acactatcaa cacattgttg catacctaca acagctacta caggcttgag    1560
gagagagatg gtgtccttta ccttggatgg aaaaacagag tattggttgt atcttcggca    1620
tggtgttga                                                            1629
```

<210> SEQ ID NO 128
<211> LENGTH: 1665
<212> TYPE: DNA
<213> ORGANISM: Zea mays

<400> SEQUENCE: 128

```
atggctgaca ctccaacgtc ccgcatggtg cacccctttg gcgacgcccc aaggcagact      60
cccaagcaat tcctgtattc tggtaacccg cagcacctct gccatccgta ccagtcagct     120
ccggacaccc atgtcgtgct ccagcgccgt tacaccgtga ggtctcagtc tcactcacca     180
```

```
aataatgctg gttctgaaga ccatgagact cacaagcagt acacgctgga gtcctcagcg    240
gcttctggtt gttcaaggca tggttctccc tccagccaaa gcgtccatgc cgggagtggc    300
agccctgtgt ctcacgacga cagccactcc ggctccacga atggccatgg atcacctgtg    360
agcgcgtcgt gtgtcaccgg cgaggaccct actgatctca agcagaaact gaaggatctt    420
gaggctgtaa tgctggggac gtctgagact gaccccgaga tagtcaacag tctcgagatc    480
tccgcggcaa accaactctc gttggagccc gaggagtggg agcacatggt gagcatgccc    540
agagggaacc tgaaggagct gctgattgcc tgcgctaggg cagtggaacg taacaacagc    600
tacgccattg atctgatgat cacagagctg aggaagatgg tttcggtgtc cggcgagccg    660
cttgagaggc tgggagccta catggtggaa ggtcttgttg ccaggctcgc ggcctccggc    720
agctcaatct acaaggcttt gaagtgtaag gagcccagga gctctgatct cctctcctac    780
atgcacttcc tgtatgaggc ctgcccctac ttcaagttcg gctacatgtc agccaacggc    840
gcgatcgcgg aggccatcaa gggagaggac aggatcccta tcatcgactt ccacatcgcg    900 caagggctc agtgggtctc tctcctccaa gcccttgcag ccaggcctgg cgggccaccg     960
ttcgtgaggg tcaccggcat tgatgattca gtctcagctt acgctcgagg cggcggtctg   1020
gagttggttg gcaggaggtt gacacatatt gctggcctct acaaggtgcc ctttcagttc   1080
gacgcagtcg ctatctcagg cagtgaggtg gaggaggagc atctgggcgt cgtcccaggc   1140
gaagccgtcg ccgtcaactt caccctttgag ctgcaccaca tccccgacga gaccgtgagc   1200
acggcgaacc accgggaccg gatcctgagg ctggtgaagg gcctgtcgcc caaggtgctc   1260
acgctggtgg agcaggagtc caacaccaac acggccccct tcgcgcagcg gttcgcagag   1320
acgctggact actacacggc catcttcgag tccatcgacc tggcgctgcc gagggacgac   1380
agggagcgga tcaacatcga gcagcactgc ctggcccggg agatcgtgaa cctggtggcc   1440
tgcgagggcg aggagcgggt ggagcggcac gaggtgttcg gcaagtggaa ggcgcggctg   1500
atgatggccg ggttcagccc gtccccgctc agcgcgctgg tgaacgccac catcaagacg   1560
ctgctgcaga gctactcgcc ggactacaag ctcgccgaga gggacggcgt gctctacctc   1620
ggctggaaga acaggcccct gatcgtctca tcggcatggc actag                   1665
```

<210> SEQ ID NO 129
<211> LENGTH: 1677
<212> TYPE: DNA
<213> ORGANISM: Zea mays

<400> SEQUENCE: 129

```
atggccgacc ctccaacttc ccgcatggtg cagcacccct tcggcgacat cccaagccag     60
actcccaagc aattcctata ctctggtagc tcacagcacc tctgccatcc ataccagtca    120
gcttcggacg cccacgtcgc gccgcagcgt cactacaccg tgaggtctca gtctcagtct    180
cagtcaccgg atgctgggtc tgaagacttt gagacgcaca gcaggcagta cacgctggac    240
tcctcttcgg cttccggttg ctcagggcac ggttctccct cctgtcagag tgtccatgcc    300
gggagtcgca gccctgtgtc tcactctcat gacgacagcc actccggctc caccaatggc    360
aacggatcgc ctgcgagcgc gtcgtgtgtc accgaggacc ctactgacct caagcagaaa    420
ctgaaggatc ttgaggctgt gatgctgggg acggacacgg acccagagac cgtggacagt    480
ctcgagatcg ccatagcgga ccggctttcg gtggagcccg aggagtggaa gaacaacatg    540
gtgagcgtgc ctagagggga cctgaaggag ctgctgatcg cctgcgccag gcagtggag     600 caaaacaacg gctactccat cgacctgatg gtcccagagc tgaggaagat ggtgtcggtg    660
```

```
tccggcgagc cgctcgagag gctgggagcc tacatggtgg aaggtctcgt cgccaggctc      720
gccgcctctg gcagctccat ctacaaggct ctgaggtgta aggagcccag gagctccgac      780
ctcctctcct acatgcactt cctgtacgag gcctgcccct acttcaagtt cggctacatg      840
tcggccaacg gcgcgatcgc ggaggccgtc aagggagaag acaggatcca tatcatcgac      900
ttccacatcg ctcaggggc gcagtgggtc tctctcctcc aagcccttgc ggcccggcct      960
ggcgggccac cgttcgtgag ggtcaccggc attgatgatc ccgtttcagc ttacgcccga     1020
ggcggcggct tagagttggt cggcaagagg ctgtcacaca tcgctggcct ctacaaggtg     1080
ccctttcagt tcgacgcggt cgccatctcc ggcagcgagg tggaggaggg gcatctgggc     1140
gtcgtccctg gcgaagccgt cgccgtcaac tttactctag agctgcacca tatccccgac     1200
gagaccgtga gcacggcgaa ccacagggac cgggtcctga gctggtcaa gggcctgtcg      1260 cccagggtgc tcacgctggt ggagcaggag tccaacacca acacggcccc cttcgcgcag     1320
cggttcgcgg agacgctgga ctactacgcg gccatcttcg agtccatcga cctggcgctg     1380
cccaggggcg acagggagcg gatcaacatc gagcagcact gcctggctcg ggagatcgtc     1440
aacctggtgg cctgcgaggg cgaggagcgg gtggagcggc acgaggtgtt cggcaagtgg     1500
aaggcgcgcc tcatgatggc cgggttcagg ccgtccccgc tcagcgcgct ggtcaacgcc     1560
accatcaaga cgctgctgca gagctactcg ccggactaca agctcgccga gagggaaggc     1620
gtgctctacc tcggctggaa gaacaggccc ctcattgttt catcggcatg gcactag      1677
```

<210> SEQ ID NO 130
<211> LENGTH: 1455
<212> TYPE: DNA
<213> ORGANISM: Vitis vinifera

<400> SEQUENCE: 130

```
atgcaagcat ctcagcagca tagaagttca ggcatgtcta acaggttgta ttacctacct       60
ccgcaagagg ctgaggccca ttgcttgcct cagttccaga gttttgacca ccagctgtgc      120
tacaacgatg gcagccaagg aaccaacttc tcctttcagg gttccagtga gcgttactgt      180
actctggagt catctcccaa ctcccagcaa gattctcagt cgtatccgtc tgatcctcac      240
cattcccccg acaacaccta cggctctcct atgagtgcat cctgtattac tgatgatgta      300
agcgacctga agcacaagct gagagaattg gagactgtaa tgctggggcc tgattctgat      360
atcatcaata gctatgacaa taatgatctg ctgatggccc aatggctgat ggatgagttg      420
cggcagatgg tgtcggtctc tggtgaaccg atccaaaggc tgggagctta catgttggaa      480
gggcttgtag cacggctggc ctcctccggg agttccatct acaaagctct gagatgcaaa      540
gaaccggcca gcgctgacct tctctcgtat atgcacattc tgtatgaggt ctgcccctac      600
ttcaagttcg gatacatgtc tgcgaatggt gccattgcag aagccatgaa ggatgaaaac      660
agggttcata ttatcgactt ccagattggt caggggagcc aatggattac tctaatccag      720
gccttttcag ctcggcctgg ggggccaccc cacatccgca taacaggtat cgacgattca      780
acatctgctt atgcccgtgg cggggactc aacattgtgg acaaaggct atccaggctt      840 gctgagtcag tcaaagttcc attcgagttc catgcagcag acatgtccgg ctgtgaagtc      900
cagctggaaa atctcggggc tcgaccaggt gaagcgttgg cggtgaattt tgccttcatg      960
ctgcatcaca tgccggatga gagtgtcagc acccagaatc accgggacag gctactgagg     1020
ctggtcaaga gcttatctcc caaggtggtc accctcgttg agcaagaatc aaacacaaat     1080
```

| | |
|---|---|
| accgctgcat tcttccccag gttccttgag acattgaatt attatacagc catgttcgaa | 1140 |
| tcaattgacg tgactcttcc aagggagcat aagaagcgga taagcgtcga gcaacactgc | 1200 |
| ctggcaaggg atgttgttaa cataatcgca tgcgaggggg ttgagagggt ggagcgccat | 1260 |
| gaacttctcg gaaatggag gttgaggttt gcaatggcgg ggtttactcc atacccatta | 1320 |
| agctccctgg tgaacgccac cattaaaaga cttctagaaa actacagtga caagtatagg | 1380 |
| ctcgaggaga gggaaggagc gctctatctt ggctggatgg acagagattt ggttgcgtcg | 1440 |
| tgtgcgtgga agtag | 1455 |

```
<210> SEQ ID NO 131
<211> LENGTH: 1602
<212> TYPE: DNA
<213> ORGANISM: Populus trichocarpa

<400> SEQUENCE: 131
```

| | |
|---|---|
| atgcaaacat cccagaagaa aacaatttca gatgggtctc gtaggtatgg tgaccaacct | 60 |
| atgcaatatc aggagtccta ttgttggccg cccatccaga atattgatgc aggaagtcaa | 120 |
| gggacgcacc tttcacctat gacttctgat caatactgta ccctagaatc atcctctgaa | 180 |
| actagtgctt acccagttca gaattctcca tccacagcta gtttctcgcc aaatgaaagt | 240 |
| gtggtttcac agccaaattc tcggtcatat ccttcagatc tgcaggattc ctctgagaat | 300 |
| gcttgtggtt caccaacaag tgagtcttat gtcacccaca agttaagaga actggaaact | 360 |
| gctatgctgg ggcctgattc agataatctt gacatgcaca gcatgactgc aatgcctgga | 420 |
| cccaaccaga ttgtatctga ggcagagaaa tggaagtttt tggttgagat gatgtccaga | 480 |
| ggagacttga agaagcact ttgcacttgt gctctagcca ttgcaaatgg tgatatgttc | 540 |
| acggttgaat ggttaatgtc agagttacgc cagatggtgt cagttactgg tgagcctatc | 600 |
| caacgtttgg gagcttacat gctggaaggc cttgttgcaa ggttggcatc atcaggaagt | 660 |
| tctatctaca atgccctgag gtgtaaggag cctgctggtg ctgatctcct ttcctacatg | 720 |
| cttttactct atgaagcctg cccatacttc aagtttgggt atatgtcagc aaatggagca | 780 |
| attgctgatg caatgaagga tgaaattagt gtccatataa ttgattttca aattgcgcaa | 840 |
| ggcagccagt gggtcacctt aatccaggct cttgcagctc ggcctggagg accccacgt | 900 |
| attcggatta caggaattga tgattccaca tcagcttatg cccggggagg aggacttgat | 960 |
| atagtgggga agagactgtt gaagctcgct gagtcataca aggtaccatt tgagttccat | 1020 |
| actgctggag tttctgcttc tgaaattcaa attgaaaatc ttggaattca acccggggaa | 1080 |
| gctgtggcag ttaattttgc attaacgctc caccacttgc cagatgaaag tgtgggcact | 1140 |
| caaaatcatc gggacaggtt attgaggttg gttaaatcct tgtctcccaa ggtggtaact | 1200 |
| cttgttgaac acgaatctaa tactaataca gtcccttct ttgcccgttt tgttgagaca | 1260 |
| ctaaactatt atctagctat ctttgaatca attgatgtta cattaccaag agaaaacaag | 1320 |
| aaacgaatca gtgttgaaca gcactgtctt gctcggagg ttgttaatat tgtagcatgt | 1380 |
| gagggtgctg agagagttga acgccatgaa cctcttggca agtggagatc tcggtttgag | 1440 |
| atggctggat ttacacctta tccactaagc tcttttgtca attctactat caagattctg | 1500 |
| ctggagaact actctgaaaa gtatactctt gaagagagag atggagctct ctttcttggc | 1560 |
| tggatgaacc gacctttggt tgcctcttgt gcatggagat ga | 1602 |

```
<210> SEQ ID NO 132
<211> LENGTH: 1662
```

<212> TYPE: DNA
<213> ORGANISM: Solanum lycopersicum

<400> SEQUENCE: 132

```
atgcaagcat ctcagggacc tcaaaggtcg tgtagtgtac ataaattgta caataagcca      60
atgcagcaag ttcagcaaaa ctacacccct gccgtgctt  ctgacaacag caattataat     120
gatggtagca actcccaggc acaggtttct ttaacgacag agaatgagaa gttcttcact     180
gtggacacat ttccggctac tgactgtgcc atctacgatg gagatccttc cgtaagcgtc     240
tcttccaaca ggagtccttt ctcttctcaa tgttctcagt cgaacatgtt tgagcaacgt     300
cgttcttacg agaaaactgc tggttcacct gtaagtttgt gttcaggagt tgatgacagc     360
aacgggaaga agcatgagct gcgggaactg aataataagt tgctaaggcc tgaatccgat     420
attgatgaca gctgcagttg ctcattaaat ggtgtagtct caaacatttt ttccttgaca     480
aggcggaatc aagtattgga cgtagcctca agattggact tgaaagagtt gcttgttgcc     540
tgtgctgaag cagtagatga agctgatacc tcgactgcag aagttctgat ggatgctttg     600
gagaaaaggg tatcggttta tggggaacct atgcaacgac tgagtgcata catgttggaa     660
ggtctaagag cacgattatt gtcctccggg agtaacatat acaaaaaact gaagtgcaat     720
gaaccaacta gctcagaatt gttgtcctac atgcaagtcc tgtatcacat caccccttac     780
ttcaagttcg cttatatgtc cgccaatgtt gtcataagcg aagccatgaa gaatgagaat     840
agaatccata tcattgattt tcaaattgca cagggaagtc aatgggtgtt cctcatccac     900
tatctggctc gtcggcctgg tggtccgcca tttcttcgca tcacaggcat tgatgattcc     960
caatcagctc atgcacgcgg tggtggactt cagctagttg gcgaaaggtt agcgagcatt    1020
gccaagtcct gcggagtgcc tttcgaattc catactgctg cattgtcagg ctgtatggtc    1080
aaactagaga acctaagagt tagacatgga gaaagcctgg cagttaactt ccccttacatg   1140
ttgcaccaca tgccagacga gagcgtaagc actatgaacc atcgggaccg cctattaaga    1200
ctagtcaaga gcttgtctcc caaaatcgtg gccttagttg aacaagaaat gaacaccaat    1260
accgccccctt tccttccaag gttccgtgaa actctagatt accacaaagc aatattcgaa   1320
tcagtcgatg taactcgccc gaggaatgac atgcaacgga tcagatcaga ggagcattgt    1380
attgcacggg atgttgtcaa tctcatagca tgtgaagggg ctgatagagt ggaaaggcat    1440
gaagttttg  gcaagtggag gtcaagactt ttgatggctg gatttactcc atgcccgctg   1500
agtccatcgg ttgctgaggc cattaaggtc atgttgaagg agtatagctc aaattataag    1560
cttgctgaaa gccaggggggc gctttatatt ggatggaaca acagagcttt agcaacttct    1620
tctgcttggc aattaccctca ttcgctgcct ttgggatctt ga                      1662
```

<210> SEQ ID NO 133
<211> LENGTH: 1635
<212> TYPE: DNA
<213> ORGANISM: Solanum tuberosum

<400> SEQUENCE: 133

```
atgcaagcat ctcagggacc tcaaaggcca tgtagtgtac ataaattgtg caatcagcca      60
atgcagcaag ttcagcaata ctacacccct gccatgctt  ctgataacag cagttataat     120
gatggtagca actccggaac agaggtttct ttaaagacac agaatgaaaa gttcttcact     180
atggactcat ttccggctac tgactgtgcc atctacgatg cagatccttc cataagcgtc     240
tcttccaaca ggagtccttt ctctcctcaa tgttctcagt caaacatgtt tgagaaacgt     300
```

| | |
|---|---|
| cgttcctctg agaacacttc tggttcacct gtaagtttgt gttcaggagt tgatgacagc | 360 |
| aacggaaaga agcatgagct gtgggaactg aataataagt tgctaaggcc tgaatccgat | 420 |
| attgatgaca gctgcagttg ctcgttaaat ggtgtagtct caaaacattt ttccttgaca | 480 |
| aggcggaatc aagtattgga cgtagcctca agattggact tgaaagagtt gctcgttgcc | 540 |
| tgtgctgaag cagtagatga agctgatacc tcgactgcag aagttctgat ggatgctttg | 600 |
| gagaaaaggg tatcggtttc tggggaacct atgcaacgac tgagtgcata catgttggaa | 660 |
| ggtctaagag cacgattatt gtcctccggg agtaacatat acaaaaaact gaagtgcaac | 720 |
| gaaccaacta gctcagaatt gttgtcctac atgcaagtcc tctataacat cacccccttac | 780 |
| ttcaagttcg cttatatgtc cgccaatgtt gtcataagcg aagccatgaa gaacgagaat | 840 |
| agaatccata tcattgattt tcaaattgca cagggaagtc aatggatgtt cctcatccac | 900 |
| tatctggctc gtcggcctgg tggtccgcca tttctccgca tcacaggcgt tgatgattcc | 960 |
| caatcagctc atgcacgcgg tggtggactt cagctagtcg gcgaaaggtt agcgagcatt | 1020 |
| gccaagtcct gcggagtgcc tttcgaattc cataatgctg cattgtcagg ctgtatggtc | 1080 |
| aaactagaga acctacgagt tagacatgga gaaagcctgg cagttaactt cccttacatg | 1140 |
| ttgcaccaca tgccagacga gagcgtaagc actatgaacc atcgagaccg cctattaaga | 1200 |
| ctagtcaaga gcttgtctcc caaaatcgtg gccctagttg aacaagaaat gaacaccaat | 1260 |
| actgccccctt tccttccaag gttccgtgaa actctagatt accacaaagc aatgttcgaa | 1320 |
| tcagtcgatg taactcgccc gaggaatgac atgcagcgga tcagatcaga ggagcattgt | 1380 |
| attgcacggg atgttgtcaa tctcatagca tgtgaagggg ctgatagagt ggaaaggcat | 1440 |
| gaagttttg gcaagtggag gtcaagactt ttgatggctg gatttacacc atgcccactg | 1500 |
| agtccatcgg ttgctgagac catcaaggtc atgctgaagg agtatagctc aaattataag | 1560 |
| cttgctgaaa gccaggggc gctttatatt ggatggaaca acagagcttt agcaacttct | 1620 |
| tctgcttggc aataa | 1635 |

<210> SEQ ID NO 134
<211> LENGTH: 1638
<212> TYPE: DNA
<213> ORGANISM: Glycine max

<400> SEQUENCE: 134

| | |
|---|---|
| atgcaaatgt ctcagaaaca taaaatgtcc tatgactcta gcaggttcac cagtgagcct | 60 |
| gtgcaaaatc tggggtcatg ttgcttcctg caaagtggga acctagacta ctactcatcc | 120 |
| tctgataaca gtagccatgc aacctaccct tctgtttgta ctttcgaaca atattgcacc | 180 |
| ctggaatctt ctacaaacaa caatttacct tccctaaatt cttcatctac tgtcagtttc | 240 |
| tcacctaaca atagcccagt ctcaaagctg caatcaaaat caaacgtgtt gagttcgcag | 300 |
| aattctcttg aacttgttaa tgattcgcta gaaaacgaat cttgtttgac acttaacaat | 360 |
| gacgagctga ggcacaagat aagagagctt gaaagtgctt tgttgggaca tgatacatat | 420 |
| attctggata cttatgatac cataattcca gaagaatctg attcatttat gttagaggca | 480 |
| gaaagatgga agagaatgat ggaaatgata tctagagggg atttgaaaga gatgctctgt | 540 |
| acatgtgcaa aaacagtggc agtaaatgat atggagacaa ctgaatggtt gatgtcggag | 600 |
| ttgcgtaaaa tggtctccgt gtctggtgat ccaatccaac gactgggagc atacatgttg | 660 |
| gaggctcttt tgcaaggct ggcctcttca ggaagcacaa tctacaaagt cttgaaatgt | 720 |
| aaagagccta ctggtagtga actcctttca cacatgcatc tactttatga aatctgtcca | 780 |

```
tatctcaaat tgggtacat gtccgcaaat ggagctattg ctgaagccat gaaggaggaa       840
agtgaagtcc acattattga ttttcagatt aaccagggaa ttcagtgggt aagcctaatc       900
caagctcttg ctggcagacc tggaggaccc cccaagatta gaataacagg ttttgatgac       960
tccacttcag cttatgccag ggaagggggc cttgaaattg ttggagcgag gttatcaacg      1020
cttgcacaat catataatgt acccttgag ttccatgcta tacgagcttc tcccactgag      1080
gttgaactca aagaccttgc acttcaacct ggtgaagcta ttgctgtgaa ctttgccatg      1140
atgttgcacc atgttccaga tgaaagtgtg gatagtggga accatcgtga ccggttggtg      1200
agattggcaa agtgcttgtc tcctaagatt gtgacactag ttgagcaaga atcacatacc      1260
aacaacctcc cattcttccc ccgtttcgtt gagacgatga actactactt ggctattttt      1320
gaatcaattg atgttgctct gccgagggag cacaaagaaa ggattaatgt ggagcagcat      1380
tgtttggctc gagaagttgt caacttaata gcatgtgaag gggaggaaag agtggaacgt      1440
cacgagcttc tgaagaagtg gagatcgcgt tttactatgg ctggattcgc accatatcca      1500
ctgaactcgt ttattacttg ttcaataaaa aatcttcagc gaagctaccg aggacattac      1560
actctagagg agagagatgg ggctctgtgt cttggttgga tgaatcaagt tcttattacc      1620
tcttgtgctt ggaggtga                                                   1638

<210> SEQ ID NO 135
<211> LENGTH: 1755
<212> TYPE: DNA
<213> ORGANISM: Gossypium raimondii

<400> SEQUENCE: 135
atggactcac accagctttt cggatacggt gtgactggtg caggcctatc ctactcaact        60
tttccttcaa tacctaatag gctgtttagt tctttgaaat ctgatatagg aaactcaccc       120
aactcacctt tttttactcc atttgattgt gataccaaca ctacgttgag tgacagtcag       180
gagcagcata gctctactga gaatctctca ggacttagcc cttcttgcaa ctcttcgctt       240
gaatctaaca cttgtttcca tcggttgagt ccctctctgg gctgcaggag tgaaagctta       300
ttgttcagtt ctggtggaac ttcttatacg caagatgcaa attctggcca caagtaata        360 tacactttgc aggaattgga gaccgcactt atggcacctg atgagaatga agacttaacc       420 accccctagtg tttcccacgg agaaagtagt agaccacaga ctgcaggcca gcgatctagg       480
gcatggagtc aggagcgcca aggatctttg gcacttctgc ctcagacatc ctttgtctct       540
aagcataggc aatcgactga agtttctcat gttgaaaaac gccagaaatc aatagaggat       600
ttctcttggc tgggtattcc acccggcaat ctgaagcagt tgctgattgc ttgtgctaaa       660
gttctctctg aaaacaatat ggatgaattt gataagttga ttgcgaaggc cagggggtgct       720 gtctctatca gtggggaacc ggtccagcgt cttggtgctt acatggtgga agggttggtg       780
gcaaggaagg aagcatcagg gtctagcata tatcgtgccc ttcattgcag agagcctgaa       840
ggcaaggact tgctgtccta catgcaagtc ctgtatgaaa tctgccctta cttaaagttc       900
gggcacatgg cagccaatgg agccattgct gaagcatgcc gaaccgaaga tcgcattcac       960
attattgatt tccagattgc tcagggaaca caatggatga ctctcttgca ggcacttgca      1020
gctagaccag gtggagctcc tcatgtccgg attacaggaa ttgatgatcc tatttctaaa      1080
tatgctcgtg gtggtggatt ggaagcagtt aaaagacgtt tggaagcact atctgagaag      1140
ttcaatattc cagttgagtt tcagggaatg ccagttttg caccagatat cacaagggac      1200
```

| | |
|---|---|
| atgcttgatg tcaggcctgg ggaggctctg gctgtcaact tccctctgca gctccatcac | 1260 |
| acccctgacg agagcgttga tgtgaacaat cctagggatg ggcttctacg tatggtaaag | 1320 |
| tcactgtctc ccaaggttac acattggta gagcaagaat caaacacgaa cacggcccct | 1380 |
| ttcctcccca ggttcataga gactctggag tactacttgg caatgtttga gtccatagat | 1440 |
| gaaacactgc caagggacag aaaggaacga gttaacgtgg aagaacattg cctggccagg | 1500 |
| gatattgtga atatcattgc ttgtgaggga aaggagaggg ttgagcgtca tgaactcttt | 1560 |
| ggtaagtgga agtctagatt aacaatggca ggatttcgac aataccctt aagctcttat | 1620 |
| gtcaattccg tgatacgagg cttgctgagg tgttactcta acattataa gctggtagag | 1680 |
| aaggatggcg ctatgttgtt ggggtggaag gataggaacc ttatatcagc ttctgcttgg | 1740 |
| cactgtgaca gctga | 1755 |

<210> SEQ ID NO 136
<211> LENGTH: 1608
<212> TYPE: DNA
<213> ORGANISM: Brassica rapa

<400> SEQUENCE: 136

| | |
|---|---|
| atgcaaacgt ctcagaaaca tcacagtgcg gctggactgc acatgctgta ccctcaagtc | 60 |
| cactgttcac ctcagttcca agtcatagac aagaagaata agaagagcgc cttctctgat | 120 |
| accaccccat ctaaagaaag cttcttcacc ctcgaatcct ccactgcttc tggtcctctt | 180 |
| ccttcctacg agtccccttc cgtgagcatc acatctggcc gcagcccgtt ttctcctcag | 240 |
| gcctcatgca tctccgacct ccatccttcc cctgaaaaca tctacgaatc tcccttgagt | 300 |
| ggtgcgtctt ctcacgttta tgatgaagct cacgtcaaga acaagatccg agagcttgag | 360 |
| gtctcgctgc tgagtgttga ccccaaagtt gaagagtact caggcttcag ccccgctgct | 420 |
| gggaagtcat ggaactggga tgagctcttg gcgttgactc cacagctgga cttgaaagag | 480 |
| gtgctggttg aggcagcgca ggcggttgcc aaggggact tcgctgcagc gtgtgggttc | 540 |
| atcgatgtct ggaacagat ggtgtcggtc tcgggcactc cgatccaaag gctaggtact | 600 |
| tacatggcgg aagggcttag ggcgaggctt caaggtacag gtggcaatat ctacagagcg | 660 |
| ttgaagtgca atgaaccaac ggggagagag ctcatgtctt acatgggagt tctctatgag | 720 |
| atctgcccctt actggaaatt cgcgtacaat gctgcaaacg ctgctatctt ggaagcagtg | 780 |
| gctggggaga agagtccca catcatcgat ttccagattg ctcagggaac acagtacatg | 840 |
| tttctcatca cgagcttgc taaactcccc ggtgggccac cgttgcttcg tgttactggt | 900 |
| gtggatgatt cccagtccag gtttgcccgt gggggagggc ttaacttggt aggtgagaag | 960 |
| ctcgcgaaca aggcgcagtc gtgcggtgta ccgtttgagt tccacgatgc gatcatgtcc | 1020 |
| gggtgcaagg tccaccggga gcatctcggt gtggagcctg gctttgccgt cgttgtgaac | 1080 |
| ttcccttacg tgctgcacca catgcctgat gagagcgtga gcgttgagaa tcacagagac | 1140 |
| aggctgctcc gtctgatcaa gagcctcgga ccgaaactgg tgacgctagt ggagcaagag | 1200 |
| tccaacacca acacttctcc cttttttgtca aggtttgtgg agacgcttga ttactacaca | 1260 |
| gcgatgttcg agtcaataga tgcggctcgg ccacgggatg ataagcagag gatcagcgcg | 1320 |
| gagcagcact gcgcggcgag ggatatagtg aacatgatag cgtgcgagga gagggagaga | 1380 |
| gttgagagac acgaggtgct tgggaagtgg agggtgagga tgatgatggc cggcttcatg | 1440 |
| ggctggcctg tcagctcatc cgcagcgttt cagcgagttg agatgcttaa aggttatgac | 1500 |
| aaaaactaca agctaggaga aaatgaagga gcgctctatc tcttctggaa gaggagaccc | 1560 |

```
atggctacat gttccgcttg gaaaccaaac ccaaaccaga ttgtgtga                  1608
```

<210> SEQ ID NO 137
<211> LENGTH: 1674
<212> TYPE: DNA
<213> ORGANISM: Hordeum vulgare

<400> SEQUENCE: 137

```
atggccgata ctccgacttc ccggatgatc caccccttca gcaacatgca gaggcagaac      60
ccgaagcagt tccagttcca gtacccggac aacccacagc atccctgcca cccttaccag     120
ccatctccag acacccacgt cgtgccacag catcactaca gcctcaagtc tcactcgtca     180
gatgctagct acgagaacca tgttgctcag atgaagcaca ctctggtgga ctcctcggcc     240
gcggccggct gcatgaggca cgactcgccc tccagccata gcttcactcc tcgtccatc     300
aggagcggca gtggcagccc ttcgtctcac gacgacagcc actccgactc cacggacggg     360
tctcctgtca gtgcttcatg cgtcactgtg acgaccgagg atcctaacga tctgaagcag     420
aagctcaagg acctcgaggc tgagatgctt gggccagacg ccgctgagat agttaacagc     480
ctcgagagct cggtggcgaa gcagctctcg ctggagccgg agaagtgggc gcagatgatg     540
gactttccca ggggcaacct caaggagctg ctgcttgctt gtgccagagc tgtggaagag     600
aagaacatgt acgcggtcga cgtgatggtg ccggagctga ggaagatggt ttcggtctcc     660
ggtacgccgc tcgagaggct gggagcctac atggtggaag ggctcgtcgc caggctcgcc     720
tcctccggcc actccatcta caaggccttg aggtgcaagg agcccaagag ctccgacctg     780
ctgtcctaca tgcatttcct gtacgaggcc tgccctact tcaagttcgg ctacatgtcg      840
gccaacggcg ccatcgcgga ggccgtcaag ggggaggaca ggatccacat aatcgacttc     900
catatcgctc aaggagctca gtggatctcc ctcctccagg cccttgcggc caggcccggc     960
ggaccgccga ccgtgaggat caccggcatt gatgactcgg tgtcagccta cgcgcgaggc    1020
ggcgggctgg acctcgttgg aggagactg tcgcacatcg ccggcctctg caaggttccc     1080
tttgagttcc gctcggtcgc catggccggc gaggaggtgg aggagggca cctcggggtg     1140
gtccccgggg aggcactggc ggtgaacttc accctggagc tgcaccacat cccggacgag    1200
acggtgagca cggcgaacca ccgggaccgg atcctgcggc tggtgaaggg gctgaggccc    1260
aaggtgctga ccctggtgga gcaggagtcc aacaccaaca cggcccccgtt cccgcagagg    1320
ttcgccgaga cgctggacta ctacacggcc atcttcgagt ccatcgacct cacgctgccc    1380
agggacgaca gggagcgggt caacatggag cagcactgcc tggcgaggga ggtggtgaac    1440
ctgatcgcgt gcgagggcgc ggagcgggtg agcgacacg aggtgttcgg caagtggaag    1500
gcgcgcctca ccatggccgg cttcaggccc tcgccgctca gctcgctggt caacgccacc    1560
atcagcaagc tgctgcagag ctactccgac aactacaagc tcgccgagag ggacggggcg    1620
ctctacctcg gctggaagaa gaggcccctc gtggtctcgt ccgcctggca ctag          1674
```

<210> SEQ ID NO 138
<211> LENGTH: 1575
<212> TYPE: DNA
<213> ORGANISM: Oryza sativa ssp. Indica

<400> SEQUENCE: 138

```
atgccgtact ataataactc agtgccttca gggggaaatg gtaggttcta tataacacaa      60
aatcatcagg atgctcacta cgcttcttct gatgatgggt cacagaagat tggttcgagc     120
```

| | |
|---|---|
| cctcaagcat tgaagcgcc gtactgcact ctagaatcat cctcagcaaa tggtgctcat | 180 |
| cctgcccata gctctgcatc ttctcacagc atctctccta ttagcgggag cccctgtct | 240 |
| catcatgata gccactcaga ccacacgtac aattcccctc caagtgcatc ctgtgtcaca | 300 |
| gagattacag atctccagat taaactgagg gagctggaga atgcaattct tgggcctgag | 360 |
| ctagacatag cttatgacag ccctgagagc gccttgcaac caaacataat ggcaacacca | 420 |
| gaaaattgga gacagcttct gggaattaat acaggagatt tgaagcaagt aatcatagca | 480 |
| tgtggcaagg ctgttgccga gaatgatgtt cggctgacag aactactgat atctgagtta | 540 |
| ggtcagatgt gtctgtctc tggtgatcca ttgcaacgat tgggggctta tatgttggaa | 600 |
| ggccttgttg ccagactttc ttcctctggc agtaagatat ataaatcctt gaagtgtaag | 660 |
| gagcctacaa gctctgagct catgtcatac atgcatcttc tttacgagat atgcccattc | 720 |
| ttcaaatttg gttatatgtc agctaatggc gccatcgctg aagctattaa gggagagaac | 780 |
| tttgttcaca taattgactt ccaaattgca caagggagtc aatggatgac attaatacag | 840 |
| gcccttgcag cgaggcctgg aggaccacca tttctacgaa tcactggtat agatgactcg | 900 |
| aattctgctt acgccagagg tggtggactg gatgtagttg gtatgagatt gtataaagtt | 960 |
| gctcagtctt ttggtctgcc ctttgagttc aatgctgttc cagctgctag ccatgaggtt | 1020 |
| tatcttgagc atcttgatat aagagttggt gaagttattg ttgtgaattt tgcctatcag | 1080 |
| ctgcatcaca ctccagatga aagtgtaagc acagaaaacc atcgggatag gattttaaga | 1140 |
| atggtcaaga gcctctcccc taggttggtg actcttgttg agcaggagtc aaatacaaac | 1200 |
| acacggccat tcttcccaag atacttggag actctcgact actacacagc catgtttgag | 1260 |
| tcgatagatg tcgctctccc aagggatgat aagagacgga tgagcgcaga gcaacactgt | 1320 |
| gtggcgcggg acattgtcaa tttaatcgca tgtgagggtg ctgagagggt agagaggcat | 1380 |
| gaggtctttg gaaaatggaa ggcaagatta acgatggcag ggtttcggcc ataccgctg | 1440 |
| agttcagtgg tgaacagtac catcaaaacg ctgttgcata cttacaatag cttctacagg | 1500 |
| cttgaggagc gagatggtgt cctttacctt ggatggaaga acagagtatt ggttgtatct | 1560 |
| tctgcatggt gttga | 1575 |

<210> SEQ ID NO 139
<211> LENGTH: 1626
<212> TYPE: DNA
<213> ORGANISM: Orysa sativa ssp. Japonica

<400> SEQUENCE: 139

| | |
|---|---|
| atgtcagcta gggcttcaaa ccatgcatat atatgttcag atgattctca aatgccgtac | 60 |
| tataataact cagtgccttc aggggaaat ggtaggttct atataacaca aaatcatcag | 120 |
| gatgctcact acgcttcttc tgatgatggg tcacagaaga ttggttcgag ccctcaagca | 180 |
| tttgaagcgc cgtactgcac tctagaatca tcctcagcaa atggtgctca tcctgcccat | 240 |
| agctctgcat cttctcacag catctctcct attagcggga gcccctgtc tcatcatgat | 300 |
| agccactcag accacacgta caattcccct ccaagtgcat cctgtgtcac agagattaca | 360 |
| gatctccaga ttaaactgag ggagctggag aatgcaattc ttgggcctga gctagacata | 420 |
| gcttatgaca gccctgagag cgccttgcaa ccaaacataa tggcaacacc agaaaattgg | 480 |
| agacagcttc tgggaattaa tacaggagat ttgaagcaag taatcatagc atgtggcaag | 540 |
| gctgttgccg agaatgatgt tcggctgaca gaactactga tatctgagtt aggtcagatg | 600 |
| tgtctgtctc tggtgatcca ttgcaacga ttgggggctt atatgttgga aggccttgtt | 660 |

```
gccagacttt cttcctctgg cagtaagata tataaatcct tgaagtgtaa ggagcctaca    720
agctctgagc tcatgtcata catgcatctt ctttacgaga tatgcccatt cttcaaattt    780
ggttatatgt cagctaatgg cgccatcgct gaagctatta agggagagaa ctttgttcac    840
ataattgact tccaaattgc acagggagt caatggatga cattaataca ggcccttgca     900
gcgaggcctg gaggaccacc atttctacga atcactggta tagatgactc gaattctgct    960
tacgccagag tggtggact ggatatagtt ggtatgagat tgtataaagt tgctcagtct    1020
tttggtctgc cctttgagtt caatgctgtt ccagctgcta gccatgaggt ttatcttgag   1080
catcttgata taagagttgg tgaagttatt gttgtgaatt ttgcctatca gctgcatcac   1140
actccagatg aaagtgtaag cacagaaaac catcgggata ggattttaag aatggtcaag   1200
agcctctccc ctaggttggt gactcttgtt gagcaggagt caaatacaaa cacacggcca   1260
ttcttcccaa gatacttgga gactcttgac tactacacag ccatgtttga gtcgatagat   1320
gtcgctctcc caaggatga taagagacg atgagcgcag agcaacactg tgtggcgcgg     1380
gacattgtca atttaatcgc atgtgagggt gctgagaggg tagagaggca tgaggtcttt   1440
ggaaaatgga aggcaagatt aacgatggca gggtttcggc catacccgct gagttcagtg   1500
gtgaacagta ccatcaaaac gctgttgcat acttacaata gcttctacag gcttgaggag   1560
cgagatggtg ttctttacct tggatggaag aacagagtat tggttgtatc ttctgcatgg   1620
tgttga                                                              1626

<210> SEQ ID NO 140
<211> LENGTH: 1629
<212> TYPE: DNA
<213> ORGANISM: Setaria italica

<400> SEQUENCE: 140
atgtcagcta gggcttctaa ccatccgtac aaaatttcaa atgattctca aatgccatac     60
tacagtgact cagcacctgt aggagaaaat ggtaggtttc atgcgatgca aaataatcta    120
gatcatcact actcttctcc tgatgatgga tcacagagga ttaatagttc taacacccaa    180
gtatttgaag cacagtactg cactctggaa tcgtcgtcag caaatggtat ttatcctgca    240
caaagctcca catcttctca cagcatttcc cctttaagtg ggagccccct gtctcagcat    300
gatggccact cagatcacac atatagttct cccccaagtg cttcctgtct aactgaagtt    360
gcagatctcc agattaaatt aaaagagtta gagaatgtta ttcttggacc tgaattggac    420
attacttctg acagccctga gagcttctta caagccaatg ttcaattgag accagacaac    480
tggagacaac ttctgggaat tgatgcagga gacttgaagc aagttatcat agcatgtggt    540
aaggctgttg cggagaatga tgtctttgca acagaactgc tgatatctga gctaggtcag    600
ctcgtatctg tatccggaga tccaatgcaa agactcggag catatatgtt ggaaggaatt    660
gttgcaagac tttcttcctc tggcagtatg ctatataaat ctttgaaatg taagaaccct    720
acaggctctg agctcatgtc atacatgcat ctcctttacg agatctgccc attctacaag    780
tttggttata tgtcagcaaa tggtgctatt gccgaggcta ttaagggtga gactttgtt    840
cacatcattg atttccaaat tgctcagggg agccaatgga ttactctgat acaggccctt    900
gctgcaaggc ctgggggtcc accatacatt agaatcactg gtattgatga ctcaaattct   960
gcttatgcca gaggggtgg gcttgatata gttgggagga gattgcatag tgttgctcag   1020
tcatgtggtc ttccctttga gttcaatgcc gttccagctg ctagccatga ggttcagctt  1080
```

```
gagcatcttg ctgtaagacc cggggagatt attgttgtga attttgccta tcagctgcat      1140
catgttcctg atgaaagcgt aagcattgaa aatcatcggg ataggattat aagaatgatc      1200
aagagcatca atcctagggt tgttactctt gttgagcagg agtcaaatac aaacacagct      1260
ccattcttcc cgagatacat ggaaactctc aactactata cagccatgtt tgagtcgata      1320
gatgttgctc tcccaaggga tgacaggagg cggatgagcg cagaacaaca ctgtgttgca      1380
agggatattg ttaatttaat cgcatgtgag ggtcctgaaa gagttgagag catgagctg       1440 tttggaaaat ggaaggcaag atttgcaatg gctggattta ggccttaccc actgagttca      1500
gtggtgaaca acaccatcaa cactctgttg cgtagttaca acagctgtta caatcttgag      1560
gaaagagatg gtgtccttta ccttggatgg aagaacagag tattagtcgt atcttcagca      1620
tggtgttga                                                              1629

<210> SEQ ID NO 141
<211> LENGTH: 1644
<212> TYPE: DNA
<213> ORGANISM: Sorghum bicolor

<400> SEQUENCE: 141
atggctgaca ctccaacttc ccgcatggtg caccccttg gcgacgtccc aaggcagact        60
cccaagcagt tcctgtattc tggtaactca cagcacctct gttatccata ccagtcagct      120
tcggacaccc atgtcgtgcc gcagcgtcat tgcaccatga ggtctcattc accagatgct      180
ggctctgaag accatgataa tcacaagcag tacacactgg actcctcagc aacttctggt      240
tgttcaaggc atgattctcc ctccagtcaa agtgtccatg ctgggagtgg cagccctgta      300
tctcttgaag acagccactc tggctctaca aatggcaatg gatcacctgt gagtgcatcg      360
tgtgtcactg aggaccctac tgatctcaag cagaaactga aggatcttga ggctgcaatg      420
ctgggtacag accagagat cgtcaacagt ctcgagatct ccatagcaga ccaactttcg      480
ttggagcccg aggagtggaa gcacatgatg agcatgcccg agggaaacct gaaggagctg      540
ctgattgcct gcgctagagc ggtggaatat aacaacagct acgccattga tctgatgatc      600
ccagagctga ggaagaaggt ttcagtgtct ggtgaaccac ttgagaggct gggagcctac      660
atggtggaag gtcttgttgc caggctcgcc gcctctggca gctcaatcta caaagctttg      720
aagtgtaagg agcccaggag ttctgatctc ctctcctaca tgcacttcct gtatgaggcc      780 tgccctact tcaagttcgg ctacatgtca gcgaacggcg caatcgcaga ggctgtcaag      840
ggagaagaca ggatccatat cattgacttc cacatcgctc aagggctcca gtggatctct      900
ctccttcaag cccttgcagc caggcctggc gggccaccgt tcgtgaggat caccggcatt      960
gatgattcag tctcagctta cgcccgaggc ggtggtctgg agttggttgg caggaggctg     1020
tcacacattg ctggcctcta caaggtgcca tttcagttcg acgcagtcgc tatctccagc     1080
agcgaagtgg aggagggca tctcggcatc gtccctggcg aagccgtcgc tgtcaacttc      1140
accctggagc tgcaccacat ccccgacgag accgtgagca cggcgaacca ccgagatcgg      1200
atcctgaggc tggtgaaggg cctgtcgccc aaggtgctca cgctggtgga gcaggagtcc      1260
aacaccaaca cggcccccctt cgcgcagcgg ttcgcggaga cgctggacta ctatactgcc      1320
atcttcgagt ccatcgacct ggcgctgccg agggacgaca gggagcggat caacatcgag      1380
cagcactgct tggctcggga gatcgtgaac ctggtggcct gcgagggcga ggaacgggtg      1440
gaacggcacg aggtgttcgg caagtggaag gcgcggctga tgatggccgg gttcaggccg      1500
tccccgctca gcgcgctggt caacgccacc atcaagacgc tgctgcagag ctactcgccg      1560
```

```
gactacaagc tcgccgagag ggacggcgtg ctctacctcg gtggaagaa caggcccctg    1620 attgtctcgt cggcatggca ctag                                          1644
```

<210> SEQ ID NO 142
<211> LENGTH: 1791
<212> TYPE: DNA
<213> ORGANISM: Theobroma cacao

<400> SEQUENCE: 142

```
atggacgcac accagctttt cagttacggt gtgactggtg cgagcctatc ctactcaacc     60
tcttattcaa ctgttccttc tatacctaat cggctgttta gttctttgaa atctgacata    120
ggaaactcac ccaactcgcc cttttcgtct caatttgatt cgccttttc gactcaattt     180
gattgtgata ccaacaccac gttgagtgac agccaggagc agcatagctc cacggagaat    240
ctctcgggac ttagcccttc ttgtaactct tcatttgaat ctaacactta ttgccataaa    300
ttgagtccct ctctggactg caagcgtgaa atcctaccac tctgttctgg tggaacttct    360
tatatacagg atgcaaattc tagccacaaa ataatataca ctttgcagga attagagact    420
gcactaatgg cacctgatgc ggatgaagaa gtaaccaccc cgaatgtttc ctgtggagaa    480
agtagtagac cacagacaac aggccagcga tctagggcat ggagtcagga gcaccaagga    540
tctttggtgc ttcagcctca gacatccttt gtttctaggc ataggcagtc aactgaagtt    600
tctcatgctg agaaacgtca gaaagcaata ggggatttgt ctttgcagga tattccacct    660
ggcaatctta agcaattatt gattgtgtgt gctcaagctc tctctgaaaa caatatggat    720
gattttgata agttgattgc gaaggccagg aatgctgtgt ctatctgtgg agaaccaatc    780
cagcgccttg gtgcttacat ggtggaagcg ttggtggcaa ggaaggaggc atcagggtcg    840
aacatatatc gtgcccgtcg ttgcagagag cctgaaggca aggacttact ttcctacatg    900
cagatcctgt atgaaatttg cccctatttg aagtttggct acatggcagc caatggggcc    960
attgctgaag catgcagaac tgaagatcgc attcacatta tcgatttcca cattggtcag   1020
ggaacacaat gggtgacccct cttgcaggcg cttgcagcca gacctggtgg agctcctcat   1080
gtccgcatta caggaattga tgatcctctt tctaaatatg ctcgtggtgg tggattggaa   1140
gctgttggca gacgtttggc tgcactatct gaaaagttca atattccagt tgagtttcat   1200
ggagtgccag ttttttgcacc ggatatcacg aggggggatgc ttgatgtcag gcctggggag   1260
gctctggctg tcaacttccc tctgcagctc catcacaccc ctgatgagag cgttgatgtg   1320
aacaacccta gggatgggct tctgcgaatg gtaaaatcac tttctcccaa agttaccaca   1380
ttggtagagc aagaatcaaa cacaaacaca gccccttcc tcccccaggtt catagagact   1440
ctggattact acttggcaat gtttgagtcc atcgatgaga cactgccaag ggacagaaag   1500
gagcgaatta atgtggagca gcactgcctg gccagagata ttgtgaatgt cattgcttgt   1560
gagggaaagg agagggtgga gcgccatgag ctctttggta agtggaagtc taggctaaca   1620
atggcaggat tccggcaata ccctttaagc tcttatgtga attctgtgat aagaagcctg   1680
ctgaggtgtt actcaaagca ttataaactg gtgagaaagg atggcgcaat gttgctgggc   1740
tggaaggata ggaaccttat atcggcttct gcttggcact gtgacagctg a            1791
```

<210> SEQ ID NO 143
<211> LENGTH: 1617
<212> TYPE: DNA
<213> ORGANISM: Elaeis guineensis

<400> SEQUENCE: 143

```
atgcaagctt ccgagaggga caaacattca aataagtctc agaaaccata ccatcctcac      60
aattccatgc ctgttagaga agcagaatct cattttcttt ctcagaacca ccaatcctta     120
aactatgtat catctgatga tgggtccagt cagaggaatg ttcaccctca tacaagtgga     180
caattttgca ccctagaatc ctccttggca actcctgggt atgctactca caactctcca     240
tcttctcttg ctttctcccc taacagtggg agcccgctat cacagcaaga atgccagtca     300
gacaacacct atgggtcccc aataagtgtt tcatgtatta ctgaagaccc aaacgatctc     360
aaactcaagt tgagggaatt agagactgct atgctgggc ctgacccaga tatagttgaa      420
agctttgaga caacctaccc aagtaacacc tcaatggatc cggaaaaatg agacaagtg      480
atgggaattc ccagaggaga cttgaaacag atgctcatag cttgtgctag agctgtggct     540
gagaatgata ttcttgtggt ggaatggcta atttcagagt taaggcagat ggtttcggtt     600
tctggggagc caattcaacg gctgggtgcc tacatgttgg aaggccttgt tgctaagctg     660
tcatcctcag ggagtgctat ctataaagct ttgaggtgta agaacctac aagctctgaa      720
ctcctgtcct acatgcacat cctctatgag gtctgtccat attttaagtt tgggtacatg     780
tccgcaaatg tgccattgc tgaagctgtt aaggggaaa atatggttca tattattgat       840
ttccagatag cacagggaag tcaatggatg actctaattc aggcccttgc agcgaggcct     900
ggtgggccac catgcttaag aattactggc attgatgact ctgtttcagc ctatgcgaga     960
ggtggtggac ttcatcttgt ggggcagaga ttatctcggc ttgctcaggc atgcaatgtg    1020
ccctttgaat ccatgcagc agccatatca ggctgtgatg tagaacttga gcatcttggt     1080
gttcgacctg gggaagcctt ggctgtgaac tttgctttcc agttgcatca catgccggat    1140
gaaagcgtga gcacaaggaa tcaccgtgac aggctcttga aatggttaa gagcctgtct     1200
ccaaaggtgg tgactctcgt ggagcaagaa gccaacacca acactgctcc tttctttcca    1260
agattcttgg agactctgga ttactattct gccatgtttg aatcgattga tgtgactctt    1320
ccgagggaga acaaggaacg tatcagtgtg aacagcact gcttggcaag ggacatagtt     1380
aatatcattg cttgtgaagg agctgaaagg gtggaaagac atgagctttt tgggaaatgg    1440
aggtcaaggt tcacaatggc tggatttaag ccacacccat tgagtccatt ggtgaatgcc    1500
actattaaga cactgttaga gaactactgt gaacactata ggcttgagga gagagatggt    1560
gtactatacc ttggttggaa gaacagagca ttggtcgtct cttgcgcatg gagatga       1617
```

<210> SEQ ID NO 144
<211> LENGTH: 1620
<212> TYPE: DNA
<213> ORGANISM: Elaeis guineensis

<400> SEQUENCE: 144

```
atgcaagctt ctaataaatg tggaagttcc gatgagtctc cagagttgta ccttcagcac      60
aattcgatgc ctagaagaga agaggaattt cggcttaggc cacagaacta ccagtctttt     120
gaccaacttt tctctgataa tggatcccta tcccaaagtt gccccttca agcatctcac      180
gtgcaatatt gcacgcgtga ctctgccttg acaacagctt gttatgcact tcgtgactct     240
ccatcaactc ttagcttctc cccttctttt gggagccctg tctcacagca agattatcac     300
tcagacaaca tcaatggatc tccattaaat gtttcatgtt taactgaaga tcccgctgat     360
ttgaaacaca agctaaggga attggaggtt gcaatgcttg gtcctgactt cgataccatt     420
gacagctcgg aaagtagctt caggagctac ttaatgtcca aaccagagat gtggaaacaa     480
```

```
atgatgggca tccctgaagg agacctgaag gaaacactca ttgcttgtgc gcgagctgtg    540
gccgacaatg atgctcaggt aatggattgg ctaataccgg agttaaggca gatggtttct    600
gtttctggag aacccatcca acgggtagga gcttacatgc tggaaggcct tattgctagg    660
ctgtcttctt caggcagttc tatctacaaa gctttgaagt gtaaagaacc tacgagctct    720
gacctcctct cttacatgca cattctctat gatgtgtgcc cttacttcaa atttgcatac    780
ttgtctgcaa atggtgccat tgctgaagct ttgaagaatg aagataaggt tcacattatt    840
gatttccaga ttgcacaggg aagccaatgg atgactctgc tgcaggccct gctgcaagg    900 cctggtgggc caccacatgt gagaatcact ggcatcgatg actccatgtc tgcatatgcc    960
cgaggcgggg gactacacat tgtggggcag cggttgtttc gcttcgctga atcatgtagt    1020
gtgccgtttg aattccatgc tgctgatgtg tcttgttgtg acttagaggt caaggatcta    1080
ggcgttcatc ctggcgaagc cttggctgta aactttccct ccaactgca tcatgtgcca    1140 gatgagagtg tgagcaccga aaatcaccgt gaccgaattt tgagaatggt caagagcttg    1200
tccccccagg tggttactct tgtggagcaa gaatctaata caaatactgc tcctttgttc    1260
caacggtttg tggagactct caattactat actgcaatat ttgaatcaat agatgtgact    1320
cttcctaggg acagcaaaga gaggatcaat gtggaacagc actgcttggc aagagacata    1380
gtgaacataa ttgcctgtga gggtgcagaa agggtggagc ggcatgagct ttttgggaaa    1440
tggaagtcga ggtttacaat ggctggattt ggtccttacc cattgagtcc attggtaaat    1500
gccactataa agtcacttct ggcaaagtac tgcgagaatt atacactcga agagagagat    1560
ggtgtccttt atcttggatg gaagaatagg cgtttgtctg tctccagtgc atggagatga    1620
```

<210> SEQ ID NO 145
<211> LENGTH: 1662
<212> TYPE: DNA
<213> ORGANISM: Malus domestica

<400> SEQUENCE: 145

```
atgcaagcat caaaggagca gagaatttca gggatgtcaa accagttata ttatcagcca     60
atccaagaag tagaggccta ctgcttgcct cgtttccaaa ctttggaccc gcggctacat    120
tacaatgaga gcagccaaag tacccacctc ccattgcaga gtttccatga acactactgc    180
actttggagt cttcctggtc taatggtagc tacaccgttt ataacacccc atcaaatgtc    240
agtttctcac ctagtggaag cccgatgtca cagcaagact ctcattcgta tctgtctgat    300
cagtaccatt cccctgacca gacctacagc tctccgatga gtggatcctg cataaccgat    360
gatgcaactg acttaaagta caagctgaaa caattagaaa ctgtaatgct gggtcctgat    420
tccaatrttc ttgataacta ttgcaytact ttcccgaatg gggcgagcaa ttccctgcca    480
gacgaggaca gctggggaca gattatggaa tcaatctcta aaaaggattt gaagcaagtc    540
ctcatcttct gtgcaaaagc agtagcagat aatgatctgt taatggcaca atggatgatg    600
gatgagttac gccagatggt ttcagtttcg ggtgaaccaa ttcagaggtt gggtgcatac    660
ttgctggaag gactagttgc gcggaaggca tcttcgggga gtaacatcta caaagcactg    720
agatgcaaag aaccagcgag ttgcgaactc ctttcttaca tgcatattct ctatgaggtt    780
tgcccttact tcaaattcgg gtacatgtct gcaaatggag ccattgcaga agccatgaag    840
gatgaggaca gtgttcacat cattgatttc caaatmggtc aggggagtca gtgggtcact    900
ctaatccaag cttttgcatc caggcctggt ggaccacccc acatccgtat aacaggtatt    960
```

```
gacgattcca tgtcagctta tgcccgtgga ggaggactaa acattgtggg aaagaggttg    1020
tctaagcttg cagagttggt caaggttcca ttcgagttcc atgccacttc catgtctggt    1080
tgtgacgtac agctggagca tctttgtgtt cgacctgggg aggctttggc tatcaacttt    1140
gcgttcatgc tgcaccacat gcccgatgag agcgtcagca ctcagaatca ccgggatagg    1200
ctgttgaggt tggttaagag cttgtctccr aaagtrgtga ccctcgttga gcaagaatct    1260
aacacaaaca ctgctgcatt ctatccacgc tttgtagaaa cactaaatta ctacacagct    1320
atgttcgagt caattgatgt gactcttccg agagatcaca aggagcggat caatgtggag    1380
caacactgct tggctaggga ggttgttaac ataatagcat gcgagggcgt tgagagggtg    1440
gaaagacacg agcttcttgg aaagtggagg ttgcggtttg caatggctgg atttacaccg    1500
taccctttaa gctccttggt aaatgccacc atcaagacgc tgctggataa ctactctgac    1560
aaatatcggc ttgaagagcg agatggggca ctctatcttg gctggaagaa cagagacttg    1620
gttgcttctt gtgcatggag gtgcaaaccg agcacgaatt ga                       1662
```

<210> SEQ ID NO 146
<211> LENGTH: 1656
<212> TYPE: DNA
<213> ORGANISM: Fragaria vesca subsp. Vesca

<400> SEQUENCE: 146

```
atgcaagcat caaagcagca cagaagttca ggtatgtcga acggttgca ctatcaaccg      60 aagcaagaag tagaagccta ttgcttgcct ccattccgga tcttggacca ccaaccagca    120
tacaatgaga gcagccaaag tacccactcc acggctcaga gtttccatga gaggtactgc    180
acattggagt catcctcaac aaatggcagc tacaacactc tttataccte ctcatcaact    240 gtcagtttct cacccagcgg aagcccgatg tcacagcatg agcaagattc tcattaccag    300
caccattctc ctgatcatat gtacggctct ccaataagtg gctcctgcat tactgatgat    360
gcaaccgact tcaagtacaa gctaaaagaa ctagaaactg caatgcttgg cgattccaat    420
atctttgaca actattgcag ttcccttcag aatggggcaa gaaataccag gccagaagtg    480
gacagctggg gacagattat ggactcaata tctaagaagg attaaaatca agtcctgatc    540
ttctgtgcaa aagcagtagc ggataatgat ctgttgatgg cacaatggat gatggatgaa    600
ttacgccaga tggtttcggt ttctggggaa ccaattcaaa ggttgggagc atacatgttg    660
gaaggactag ttgcgcgtcg agcatcctca gggagcagca tctgtaaagc attgagatgc    720
aaagaaccag caagttctga actcctgtct tacatgcata ttctttacga ggtctgtccc    780
tacttcaagt ttgggtatat gtctgcaaat ggagccattg cggaagccat gaaggatgaa    840
gataaagtcc acatcattga ttttcaaatt ggtcagggga gtcagtggtt gactttaatc    900
caggcttttg cagcaagacc tggaggacca cccatattc gaataaccgg gattgatgat    960
tcgacgtcag cttatgcacg aggtggagga ctcaatattg gggaaagag gctatctaag   1020 cttgcagaga tgtttaaggt gccatttgag ttccatgctg ctgctatctc tggttgtgat   1080
gttcagctgg agaatcttgg ggttagacca ggggaggctt tggctatgaa ctttgcattc   1140
atgctgcatc acatgccaga tgagagcgtc agcactcaga tcaccgtga tcggctactg   1200 aggttggtta agagcttgtc tccaaaagtt gtgaccctgg ttgagcaaga atcaaacaca   1260
aacactgctg catttttttcc gaggtttgta gaaacactaa attactacac ggctatgttt   1320
gagtcaatag atgtaactct tccgagggat cacaaggaga ggatcaatgt tgagcaacat   1380
tgcttggcca aggaagttgt gaacataata gcatgcgagg gaattgagag ggtggaaaga   1440
```

| | |
|---|---|
| catgagcttc tcgggaagtg gaggtcgcgg tttgcaatgg caggatttac tccatacccct | 1500 |
| ttaagttcct tggtaaatgc aaccatcaag acactgctca agaactactc agacaagtat | 1560 |
| aggcttcaag agagagatgg tgcgctctat ctcggctgga agaacagaga tttggttgct | 1620 |
| tcttgtgcat ggaagtgcaa acctggcacc aattag | 1656 |

<210> SEQ ID NO 147
<211> LENGTH: 1401
<212> TYPE: DNA
<213> ORGANISM: Beta vulgaris subsp. vulgaris

<400> SEQUENCE: 147

| | |
|---|---|
| atgcagaatc caagaaatac tcaagggttt tcttgcactt ttgattcttc gttgttaatt | 60 |
| ggtgccgata acttttgtgg atctccatcg acagaaagca tctctggtaa cgggagcaca | 120 |
| gtttcactta ttgatcccga atattcttca agtgactcac atgatattga taatctaagg | 180 |
| aatcagctca gagagctcga gaacgtcatg atgggaacca cttcaggtag ctttgaaacc | 240 |
| gagaattggc aacgtttggt ggaaatgata aagagagggg aacttaagga ggtgctaatt | 300 |
| gcgtgcgcaa aagcagtatc tgatgatgac ttgctgacag ctgagtggtt gatttctgag | 360 |
| ctacaacata tggtttcagt ttctggtgaa ccaattcaaa ggttgggagc ctacatgtta | 420 |
| gaagggttaa ttgcaagatt ttcttcttca ggaatttcca tttacaaaac cctgaattgt | 480 |
| aacgaaccta caagtggtga actcctctca catatgcagt tgctctatga agtctgtccg | 540 |
| tatttcaagt ttgggtatat gtcagctaac ggggcaattg ccgatgccct gaaaaacgag | 600 |
| gaccgcattc acataattga ttttcagatt gctcaaggga gtcaatgggt tagtcttatc | 660 |
| caagctttgg ctgcccggcc gggtgggccc ccacaagttc gtataacagg catcgacgat | 720 |
| tccacatctg agtatgctcg tggaggagga cttaacattg taggggaaag actgtctaag | 780 |
| cttgcaaagg cttgcaacct accattcgag ttccaagctg cagccctcag gtgtgggact | 840 |
| gaggttaagc ttgagaactt tgtactgcga cccgaagaag cattagccgt aaattttcct | 900 |
| ttcagattgc accatatacc agatgagagt gtgggacctg agaatcaccg agacacgtta | 960 |
| ttgaggctcg ttaagagctg gtcacccaag gtggtaaccc tcgttgagta tgaattgaac | 1020 |
| acaaatacag ctccatttttt tcctcgttttt ctcgagacac tggattatta ttctgccatt | 1080 |
| ttcgagtcaa tcaatgttac actccctaca gatcacaagg agaggatcaa tgtggagcag | 1140 |
| cattgtttag ctaaggaggt tgttaacatt atagcatgtg aaggcgctga gagaatagaa | 1200 |
| cggcatgagc tgcacgggaa gtggaaatcc cggttcctaa tggctggttt taacccatat | 1260 |
| cctctgagcc cactcgtaaa tggtaccatc aggactttat tgcagaagta cagtaggagt | 1320 |
| tatggacttg aagagagaaa tggagctctt tacctcggat ggatgaaccg agttttggtt | 1380 |
| acagcttgtg catggcagta a | 1401 |

<210> SEQ ID NO 148
<211> LENGTH: 1578
<212> TYPE: DNA
<213> ORGANISM: Eucalyptus grandis

<400> SEQUENCE: 148

| | |
|---|---|
| atgcaaacat cccagaagaa gagtcattta agcatgtcga acaaaatttg ttatcagtct | 60 |
| gctcttgaga tcggcaccta ttgcttgcct cagtttcata cattagattg ttacccttcc | 120 |
| tactgcaccc ttgagtcatc ctccgctagt ggaggttatg ctatatacaa cccaccatca | 180 |

```
accatcagct tctcatccga tgggagtccc gtatccttgc aagattctgt gtcttatcca      240
cctgatgcgc tacactcccc agataatacc tacgcctcct ccataagtgg atcttgtgtc      300
actgacgatg caaatgattt tttgcacaag ctgagagaat tggagaacgt aatgcttgga      360
cctgattcgg atatttccat taacaatgac aggagtttcc agaaggggat ccatgtagct      420
tcaccaggga gcaaactaaa agatgcaata gaacggaagg atttgaaacg agttctcatt      480
gcctctgcga aggcagtttc agaaaatgat ctatggacag cgaactggtt gatggatgag      540
ttgcgtggaa tggtctcagt ttctggggaa ccgatccagc ggctgggagc atatatgttg      600
gaaggtctcg ttgcacgttt ggcctcctca ggaagctcca tctataaagc tctgcgatgc      660
aaagaacctg aaagctcaga gctcctctcc tacatgcaca tttatatga ggtctgtcca       720 tacttcaaat ttggatacat gtcagcaaat ggggcgatag ccgacgcaat gaagaatgag      780
aatagagtcc acatcattga cttccaaatt ggtcagggca gccagtggat cactttaatc      840
caggcatttg cagcaaggcc tggcgggcca ccccacataa gaataactgg ttttgatgat      900
tccacgtcag cttatgcccg tggaggagga ttggaaattg tggggaagag gcttactaag      960
cttgctcagt tgtacaaagt cccattcgag ttccatgctg cattgatacc aggttcggat     1020
ttactgcttc accatcttga tgttaggcgc ggggaggctt tggccgtaaa tttcgcgttt     1080
atgcttcacc acatggctga tgagagtgtg agcattcaga accatcggga ccggctcctg     1140
aggctggtca gagcctgtc accgaaggtg gtgaccctag tggagcaaga atctaacacg      1200
aatactgctg cctttttgcc acggttcatt gaggcgatgg actattatgc agccatgttt     1260
gagtcgattg atgtgactct tcacagagag cacaaggaga ggattaatgt agagcagcac     1320
tgcctggcaa gagatgttgt caatataatc gcatgcgagg gggctgagag agtcgaaagg     1380
cacgagcttc tggggaagtg gaggttgcgt tttgcgatgg caggatttac accattccct     1440
ttgagttccc tagtgaacgg caccatcaag acgctgttgg agaattactc tcacagatat     1500
aggcttgagg agagagatgg agctctttat ttgggatgga tgaaccggga cttggtagcg     1560
tcctgtgcat ggaagtga                                                   1578
```

<210> SEQ ID NO 149
<211> LENGTH: 1638
<212> TYPE: DNA
<213> ORGANISM: Citrus sinensis

<400> SEQUENCE: 149

```
atgcagtttt cgcggatgca taagatgtca gatggaactc agaagttcta tgaccagcct       60
gtgcaaaagc tggcctccaa aaattggcct ccccatcaga acatagacca ccagccatcc      120
tctgatgaca gcaacgaacg agcacgccta tcagtagata cttttgaaca atactgcacc      180
cttgagtcat cctctggtac aggcagtcac ggtgctccta attctccatc cactgccagt      240
ttctcacctg aaaaaaccca gtttcttgg ccaaaccagc agtcatattc ctcagaactg       300
tatcagtcgc ctgatcgtac ctgtggctca cctgtaagtg ggtcttgtat aacacaaaat      360
gaaaatgatc tgaggcacaa actgcgagaa ttggaaaccg ttatgctggg acctgatttg      420
gatacccctg ccatgtacaa tgttaccagc ccaaaggaag accaaatctc atcagaatca      480
gagaggtgga agtgtttggt agagataatc tccagagggg atctgaaaga gttactttgc      540
gcttgtgcaa aggctataga gaataatgat atgtacgcag ctgaaagttt gatggcagaa      600
tcacgacaga tggtgtcagt ttctggtgat cctatccaac gtttaggagc ctacatgttg      660
gaagggctca ttgcaaggtt ggcctcgtca ggaagttcta tctacaaagc cctgagatgc      720
```

```
aaagagcctg ccagtgctga gctcctatct tacatgcatt tactgtatga gatctgtcca      780
tacttcaagt ttggatatat gtcagcaaat ggggcaattg ctgaagccat gaaggacgaa      840
aataaaatcc acataatcga ttttctaatt gctcaaggca gccagtggat catacttatt      900
atggctctcg cttctcgtcc tggagggccc ccacacattc gaattacagg cattgatgat      960
tctacagcag cttatgctcg cgggggagga cttgaaattg tgggtcagag actatcaaag     1020
ctcgcagact tatataaggt gccttttgag ttcaatgctg ctgcaatttc tggttctgag     1080
gttcaacttg aaaaccttga agttcgacct ggtgaagccc ttgccgtgaa tttttccatg     1140
atgctccatc acatgccgga tgaaagtgtg agcatccaga atcatcgaga caggctcctg     1200
aggctggtaa aaggcttgtc tcctaaggtg gtgacacttg ttgagcagga agccaacact     1260
aatactgccc cattttttca ccgtttcctt gaaacgatga atcactatgg cgctatcttt     1320
gattcaattg atgttgctct gccaagagat agcaaggacc gaatcaatgt ggagcagcac     1380
tgcttggcac gtgagattgt caaccttata gcatgcgaag gagctgagag agtggaacgc     1440
catgagcctt ttggcaagtg gagatcgcgt tttataatgg ccgggtttac accctatcca     1500
ttgagcccctt tgtgaatgc aaccatcaaa actctgctgg aaaactacaa tgacaactac     1560
acacttgaag agagggatgg agcgctcttt cttggctgga aaaatcaagc tataattgtt     1620
tcctctgcat ggaggtga                                                    1638

<210> SEQ ID NO 150
<211> LENGTH: 1611
<212> TYPE: DNA
<213> ORGANISM: Musa acuminata subsp. Malaccensis

<400> SEQUENCE: 150
atgcaagctt caacaaacta caaagtatta agtaaacagc atcagtcata caatcaaaac       60
cttgggagag atccggaatc ccgttttatg cctcaaaatt acctaacttc acattgtgac      120
tcctctgctg atggattcca acaagggaac tcccatcatc agacaattca tgaccaattc      180
tacactctgg agtcctcctc ggaagctgcg aattttacca ctcataactc tccatcttct      240
cctagttact ccccgatcag caggagcccc gcatctcatc aagattctca gtcagataac      300
aactatgact ctcccataag ctattcatgt attaccgaag actcaaatga tcttaagcat      360
aagttacggg agatagaggc tgcaatgctt gggcctgatt cagatagcat tgacagcttt      420
gagaatgctt actccagcta tatctccttg gagcaagaga gtggcaaca agtgatggga      480
accccctagag gagacttgaa acagatccta atagcctgtg ctcgagctgt agaaaacaat      540
gatattcttg tggttgagtg gctaattcca aagttaaggc agatggtatc agtctctggg      600
gaaccaattc aacgtctggg agcatacttg ttggaaggcc tcgtagctaa gctggcttcc      660
tcgggaagtt ccatatacaa ggctttgaag tgtaaagaac ccactagttc agacctcctc      720
tcatacatgc acattcttta tgatgtatgc ccatacttca agtttgggta tatgtctgca      780
aatggagcaa tagctgaggc tcttaagggt gagaacatgg ttcatattat cgatttccag      840
attgcccagg gaagtcaatg ggtaactctc attcaagctc ttgcagcacg acctggtggg      900
cctccacgtg taagaataac agggattgat gactctgttt ctgcctacgc ccgtggtggt      960
gggctacata ttgtggggca gaggttatct cggcttgcca agtcatgcaa tgtgcccttc     1020
gaattccatg gcgcagctct ctcagggtgt gatttagaac ttgagcatct tgacattcga     1080
cctggggagg cattggccgt taactttgct ttccaactgc atcacatgcc agatgagagt     1140
```

```
gtgagcacaa ggaactaccg agatagactt ctacagatga ttaagagctt gtctccaaca   1200
gttgttactc ttgtggagca ggaatcaaac acaaacactg ctccattctt tccaagattt   1260
ttagaaactg tagactacta tgctgccatc tttgagtcga tagatgtgac tcttccaagg   1320
gagaacaagg aaaggatcaa cgtggagcag cattgcctag cacgagacat agttaacatc   1380
attgcatgtg agggagatga aagggtggag cgccatgagc ttttcgggaa atggaggtcg   1440
aggtttatga tggctggatt caggccatat cctctgagtc ctttagtgaa tgcaacaatc   1500
aagatgcttt tagagaacta ctgtgagaac tatcgtcttg aagagagaga cggtgtgctt   1560
tatcttggat ggaagaatag agctttggtt gtctcttgtg catggaaata a            1611
```

<210> SEQ ID NO 151
<211> LENGTH: 243
<212> TYPE: PRT
<213> ORGANISM: Arabidopsis thaliana

<400> SEQUENCE: 151

```
Met Tyr Gly Gln Cys Asn Ile Glu Ser Asp Tyr Ala Leu Leu Glu Ser
1               5                   10                  15

Ile Thr Arg His Leu Gly Gly Gly Glu Asn Glu Leu Arg Leu
            20                  25                  30

Asn Glu Ser Thr Pro Ser Ser Cys Phe Thr Glu Ser Trp Gly Gly Leu
        35                  40                  45

Pro Leu Lys Glu Asn Asp Ser Glu Asp Met Leu Val Tyr Gly Leu Leu
    50                  55                  60

Lys Asp Ala Phe His Phe Asp Thr Ser Ser Ser Asp Leu Ser Cys Leu
65                  70                  75                  80

Phe Asp Phe Pro Ala Val Lys Val Glu Pro Thr Glu Asn Phe Thr Ala
                85                  90                  95

Met Glu Glu Lys Pro Lys Lys Ala Ile Pro Val Thr Glu Thr Ala Val
            100                 105                 110

Lys Ala Lys His Tyr Arg Gly Val Arg Gln Arg Pro Trp Gly Lys Phe
        115                 120                 125

Ala Ala Glu Ile Arg Asp Pro Ala Lys Asn Gly Ala Arg Val Trp Leu
    130                 135                 140

Gly Thr Phe Glu Thr Ala Glu Asp Ala Ala Leu Ala Tyr Asp Ile Ala
145                 150                 155                 160

Ala Phe Arg Met Arg Gly Ser Arg Ala Leu Leu Asn Phe Pro Leu Arg
                165                 170                 175

Val Asn Ser Gly Glu Pro Asp Pro Val Arg Ile Thr Ser Lys Arg Ser
            180                 185                 190

Ser Ser Ser Ser Ser Ser Ser Ser Thr Ser Ser Ser Glu Asn
        195                 200                 205

Gly Lys Leu Lys Arg Arg Arg Lys Ala Glu Asn Leu Thr Ser Glu Val
    210                 215                 220

Val Gln Val Lys Cys Glu Val Gly Asp Glu Thr Arg Val Asp Glu Leu
225                 230                 235                 240

Leu Val Ser
```

<210> SEQ ID NO 152
<211> LENGTH: 282
<212> TYPE: PRT
<213> ORGANISM: Arabidopsis thaliana

<400> SEQUENCE: 152

```
Met Ala Thr Pro Asn Glu Val Ser Ala Leu Phe Leu Ile Lys Lys Tyr
1               5                   10                  15

Leu Leu Asp Glu Leu Ser Pro Leu Pro Thr Thr Ala Thr Thr Asn Arg
            20                  25                  30

Trp Met Asn Asp Phe Thr Ser Phe Asp Gln Thr Gly Phe Glu Phe Ser
        35                  40                  45

Glu Phe Glu Thr Lys Pro Glu Ile Ile Asp Leu Val Thr Pro Lys Pro
    50                  55                  60

Glu Ile Phe Asp Phe Asp Val Lys Ser Glu Ile Pro Ser Glu Ser Asn
65                  70                  75                  80

Asp Ser Phe Thr Phe Gln Ser Asn Pro Pro Arg Val Thr Val Gln Ser
                85                  90                  95

Asn Arg Lys Pro Pro Leu Lys Ile Ala Pro Pro Asn Arg Thr Lys Trp
            100                 105                 110

Ile Gln Phe Ala Thr Gly Asn Pro Lys Pro Glu Leu Pro Val Pro Val
        115                 120                 125

Val Ala Ala Glu Glu Lys Arg His Tyr Arg Gly Val Arg Met Arg Pro
    130                 135                 140

Trp Gly Lys Phe Ala Ala Glu Ile Arg Asp Pro Thr Arg Arg Gly Thr
145                 150                 155                 160

Arg Val Trp Leu Gly Thr Phe Glu Thr Ala Ile Glu Ala Ala Arg Ala
                165                 170                 175

Tyr Asp Lys Glu Ala Phe Arg Leu Arg Gly Ser Lys Ala Ile Leu Asn
            180                 185                 190

Phe Pro Leu Glu Val Asp Lys Trp Asn Pro Arg Ala Glu Asp Gly Arg
        195                 200                 205

Gly Leu Tyr Asn Lys Arg Lys Arg Asp Gly Glu Glu Glu Glu Val Thr
    210                 215                 220

Val Val Glu Lys Val Leu Lys Thr Glu Glu Ser Tyr Asp Val Ser Gly
225                 230                 235                 240

Gly Glu Asn Val Glu Ser Gly Leu Thr Ala Ile Asp Asp Trp Asp Leu
                245                 250                 255

Thr Glu Phe Leu Ser Met Pro Leu Leu Ser Pro Leu Ser Pro His Pro
            260                 265                 270

Pro Phe Gly Tyr Pro Gln Leu Thr Val Val
        275                 280

<210> SEQ ID NO 153
<211> LENGTH: 192
<212> TYPE: PRT
<213> ORGANISM: Arabidopsis thaliana

<400> SEQUENCE: 153

Met Val Ser Met Leu Thr Asn Val Val Ser Gly Glu Thr Glu Pro Ser
1               5                   10                  15

Ala Ser Ala Thr Trp Thr Met Gly His Lys Arg Glu Arg Glu Glu Phe
            20                  25                  30

Ser Leu Pro Pro Gln Pro Leu Ile Thr Gly Ser Ala Val Thr Lys Glu
        35                  40                  45

Cys Glu Ser Ser Met Ser Leu Glu Arg Pro Lys Lys Tyr Arg Gly Val
    50                  55                  60

Arg Gln Arg Pro Trp Gly Lys Trp Ala Ala Glu Ile Arg Asp Pro His
65                  70                  75                  80

Lys Ala Thr Arg Val Trp Leu Gly Thr Phe Glu Thr Ala Glu Ala Ala
                85                  90                  95
```

Ala Arg Ala Tyr Asp Ala Ala Leu Arg Phe Arg Gly Ser Lys Ala
            100                 105                 110

Lys Leu Asn Phe Pro Glu Asn Val Gly Thr Gln Thr Ile Gln Arg Asn
            115                 120                 125

Ser His Phe Leu Gln Asn Ser Met Gln Pro Ser Leu Thr Tyr Ile Asp
            130                 135                 140

Gln Cys Pro Thr Leu Leu Ser Tyr Ser Arg Cys Met Glu Gln Gln
145                 150                 155                 160

Pro Leu Val Gly Met Leu Gln Pro Thr Glu Glu Asn His Phe Phe
            165                 170                 175

Glu Lys Pro Trp Thr Glu Tyr Asp Gln Tyr Asn Tyr Ser Ser Phe Gly
            180                 185                 190

<210> SEQ ID NO 154
<211> LENGTH: 268
<212> TYPE: PRT
<213> ORGANISM: Arabidopsis thaliana

<400> SEQUENCE: 154

Met His Tyr Pro Asn Asn Arg Thr Glu Phe Val Gly Ala Pro Ala Pro
1               5                   10                  15

Thr Arg Tyr Gln Lys Glu Gln Leu Ser Pro Glu Gln Glu Leu Ser Val
            20                  25                  30

Ile Val Ser Ala Leu Gln His Val Ile Ser Gly Glu Asn Glu Thr Ala
            35                  40                  45

Pro Cys Gln Gly Phe Ser Ser Asp Ser Thr Val Ile Ser Ala Gly Met
            50                  55                  60

Pro Arg Leu Asp Ser Asp Thr Cys Gln Val Cys Arg Ile Glu Gly Cys
65                  70                  75                  80

Leu Gly Cys Asn Tyr Phe Phe Ala Pro Asn Gln Arg Ile Glu Lys Asn
            85                  90                  95

His Gln Gln Glu Glu Ile Thr Ser Ser Ser Asn Arg Arg Arg Glu
            100                 105                 110

Ser Ser Pro Val Ala Lys Lys Ala Glu Gly Gly Gly Lys Ile Arg Lys
            115                 120                 125

Arg Lys Asn Lys Lys Asn Gly Tyr Arg Gly Val Arg Gln Arg Pro Trp
            130                 135                 140

Gly Lys Phe Ala Ala Glu Ile Arg Asp Pro Lys Arg Ala Thr Arg Val
145                 150                 155                 160

Trp Leu Gly Thr Phe Glu Thr Ala Glu Asp Ala Ala Arg Ala Tyr Asp
            165                 170                 175

Arg Ala Ala Ile Gly Phe Arg Gly Pro Arg Ala Lys Leu Asn Phe Pro
            180                 185                 190

Phe Val Asp Tyr Thr Ser Ser Val Ser Ser Pro Val Ala Ala Asp Asp
            195                 200                 205

Ile Gly Ala Lys Ala Ser Ala Ser Ala Ser Val Ser Ala Thr Asp Ser
            210                 215                 220

Val Glu Ala Glu Gln Trp Asn Gly Gly Gly Asp Cys Asn Met Glu
225                 230                 235                 240

Glu Trp Met Asn Met Met Met Met Asp Phe Gly Asn Gly Asp Ser
            245                 250                 255

Ser Asp Ser Gly Asn Thr Ile Ala Asp Met Phe Gln
            260                 265

```
<210> SEQ ID NO 155
<211> LENGTH: 220
<212> TYPE: PRT
<213> ORGANISM: Arabidopsis thaliana

<400> SEQUENCE: 155

Met Ser Ala Met Val Ser Ala Leu Thr Gln Val Val Ser Ala Arg Ser
1               5                   10                  15

Gln Thr Glu Ala Glu Gly Ala His Ser Ser Ser Ser Ala Gly His
                20                  25                  30

Lys Arg Gly Trp Leu Gly Ile Asp Ser Ala Pro Ile Pro Ser Ser Phe
            35                  40                  45

Ala Arg Val Asp Ser Ser His Asn Pro Ile Glu Glu Ser Met Ser Lys
        50                  55                  60

Ala Phe Pro Glu Glu Ala Arg Glu Lys Lys Arg Arg Tyr Arg Gly Val
65                  70                  75                  80

Arg Gln Arg Pro Trp Gly Lys Trp Ala Ala Glu Ile Arg Asp Pro His
                85                  90                  95

Arg Ala Ala Arg Val Trp Leu Gly Thr Phe Asp Thr Ala Glu Ala Ala
                100                 105                 110

Ala Arg Ala Tyr Asp Glu Ala Ala Leu Arg Phe Arg Gly Asn Lys Ala
            115                 120                 125

Lys Leu Asn Phe Pro Glu Asp Val Arg Ile Leu Pro Pro Pro Pro
130                 135                 140

Leu Leu Arg Ser Pro Ala Asp Thr Val Ala Asn Lys Ala Glu Glu Asp
145                 150                 155                 160

Leu Ile Asn Tyr Trp Ser Tyr Thr Lys Leu Leu Gln Ser Ser Gly Gln
                165                 170                 175

Arg Ser Phe Leu Glu Arg Gly Gln Glu Glu Ser Ser Asn Ile Phe Glu
            180                 185                 190

His Ser Pro Met Glu Gln Pro Leu Pro Pro Ser Ser Ser Gly Pro Ser
        195                 200                 205

Ser Ser Asn Phe Pro Ala Pro Ser Leu Pro Asn Thr
    210                 215                 220

<210> SEQ ID NO 156
<211> LENGTH: 391
<212> TYPE: PRT
<213> ORGANISM: Arabidopsis thaliana

<400> SEQUENCE: 156

Met Cys Val Leu Lys Val Ala Asn Gln Glu Asp Asn Val Gly Lys Lys
1               5                   10                  15

Ala Glu Ser Ile Arg Asp Asp His Arg Thr Leu Ser Glu Ile Asp
                20                  25                  30

Gln Trp Leu Tyr Leu Phe Ala Ala Glu Asp Asp His His Arg His Ser
            35                  40                  45

Phe Pro Thr Gln Gln Pro Pro Ser Ser Ser Ser Ser Leu Ile
        50                  55                  60

Ser Gly Phe Ser Arg Glu Met Glu Met Ser Ala Ile Val Ser Ala Leu
65                  70                  75                  80

Thr His Val Val Ala Gly Asn Val Pro Gln His Gln Gln Gly Gly Gly
                85                  90                  95

Glu Gly Ser Gly Glu Gly Thr Ser Asn Ser Ser Ser Ser Gly Gln
            100                 105                 110

Lys Arg Arg Arg Glu Val Glu Glu Gly Gly Ala Lys Ala Val Lys Ala
```

```
              115                 120                 125
Ala Asn Thr Leu Thr Val Asp Gln Tyr Phe Ser Gly Gly Ser Ser Thr
            130                 135                 140

Ser Lys Val Arg Glu Ala Ser Ser Asn Met Ser Gly Pro Gly Pro Thr
145                 150                 155                 160

Tyr Glu Tyr Thr Thr Thr Ala Thr Ala Ser Ser Glu Thr Ser Ser Phe
                165                 170                 175

Ser Gly Asp Gln Pro Arg Arg Arg Tyr Arg Gly Val Arg Gln Arg Pro
            180                 185                 190

Trp Gly Lys Trp Ala Ala Glu Ile Arg Asp Pro Phe Lys Ala Ala Arg
        195                 200                 205

Val Trp Leu Gly Thr Phe Asp Asn Ala Glu Ser Ala Ala Arg Ala Tyr
    210                 215                 220

Asp Glu Ala Ala Leu Arg Phe Arg Gly Asn Lys Ala Lys Leu Asn Phe
225                 230                 235                 240

Pro Glu Asn Val Lys Leu Val Arg Pro Ala Ser Thr Glu Ala Gln Pro
                245                 250                 255

Val His Gln Thr Ala Ala Gln Arg Pro Thr Gln Ser Arg Asn Ser Gly
            260                 265                 270

Ser Thr Thr Thr Leu Leu Pro Ile Arg Pro Ala Ser Asn Gln Ser Val
        275                 280                 285

His Ser Gln Pro Leu Met Gln Ser Tyr Asn Leu Ser Tyr Ser Glu Met
    290                 295                 300

Ala Arg Gln Gln Gln Gln Phe Gln Gln His His Gln Gln Ser Leu Asp
305                 310                 315                 320

Leu Tyr Asp Gln Met Ser Phe Pro Leu Arg Phe Gly His Thr Gly Gly
                325                 330                 335

Ser Met Met Gln Ser Thr Ser Ser Ser Ser His Ser Arg Pro Leu
            340                 345                 350

Phe Ser Pro Ala Ala Val Gln Pro Pro Glu Ser Ala Ser Glu Thr
        355                 360                 365

Gly Tyr Leu Gln Asp Ile Gln Trp Pro Ser Asp Lys Thr Ser Asn Asn
    370                 375                 380

Tyr Asn Asn Ser Pro Ser Ser
385                 390

<210> SEQ ID NO 157
<211> LENGTH: 231
<212> TYPE: PRT
<213> ORGANISM: Arabidopsis thaliana

<400> SEQUENCE: 157

Met His Ser Gly Lys Arg Pro Leu Ser Pro Glu Ser Met Ala Gly Asn
1               5                   10                  15

Arg Glu Glu Lys Lys Glu Leu Cys Cys Cys Ser Thr Leu Ser Glu Ser
            20                  25                  30

Asp Val Ser Asp Phe Val Ser Glu Leu Thr Gly Gln Pro Ile Pro Ser
        35                  40                  45

Ser Ile Asp Asp Gln Ser Ser Ser Leu Thr Leu Gln Glu Lys Ser Asn
    50                  55                  60

Ser Arg Gln Arg Asn Tyr Arg Gly Val Arg Gln Arg Pro Trp Gly Lys
65                  70                  75                  80

Trp Ala Ala Glu Ile Arg Asp Pro Asn Lys Ala Ala Arg Val Trp Leu
                85                  90                  95
```

Gly Thr Phe Asp Thr Ala Glu Glu Ala Ala Leu Ala Tyr Asp Lys Ala
            100                 105                 110

Ala Phe Glu Phe Arg Gly His Lys Ala Lys Leu Asn Phe Pro Glu His
        115                 120                 125

Ile Arg Val Asn Pro Thr Gln Leu Tyr Pro Ser Pro Ala Thr Ser His
    130                 135                 140

Asp Arg Ile Ile Val Thr Pro Pro Ser Pro Pro Pro Ile Ala Pro
145                 150                 155                 160

Asp Ile Leu Leu Asp Gln Tyr Gly His Phe Gln Ser Arg Ser Ser Asp
                165                 170                 175

Ser Ser Ala Asn Leu Ser Met Asn Met Leu Ser Ser Ser Ser Ser Ser
            180                 185                 190

Leu Asn His Gln Gly Leu Arg Pro Asn Leu Glu Asp Gly Glu Asn Val
        195                 200                 205

Met Thr Thr Ile Ser Thr Glu Asp Asp Arg Arg Gln Gln His Ala
    210                 215                 220

Ser Pro Asp Arg Pro Ile Lys
225                 230

<210> SEQ ID NO 158
<211> LENGTH: 218
<212> TYPE: PRT
<213> ORGANISM: Arabidopsis thaliana

<400> SEQUENCE: 158

Met His Ser Gly Lys Arg Pro Leu Ser Pro Glu Ser Met Ala Gly Asn
1               5                   10                  15

Arg Glu Glu Lys Lys Glu Leu Cys Cys Cys Ser Thr Leu Ser Glu Ser
            20                  25                  30

Asp Val Ser Asp Phe Val Ser Glu Leu Thr Gly Gln Pro Ile Pro Ser
        35                  40                  45

Ser Ile Asp Asp Gln Ser Ser Ser Leu Thr Leu Gln Glu Lys Ser Asn
    50                  55                  60

Ser Arg Gln Arg Asn Tyr Arg Gly Val Arg Gln Arg Pro Trp Gly Lys
65                  70                  75                  80

Trp Ala Ala Glu Ile Arg Asp Pro Asn Lys Ala Ala Arg Val Trp Leu
                85                  90                  95

Gly Thr Phe Asp Thr Ala Glu Glu Ala Ala Leu Ala Tyr Asp Lys Ala
            100                 105                 110

Ala Phe Glu Phe Arg Gly His Lys Ala Lys Leu Asn Phe Pro Glu His
        115                 120                 125

Ile Arg Val Asn Pro Thr Gln Leu Tyr Pro Ser Pro Ala Thr Ser His
    130                 135                 140

Asp Arg Ile Ile Val Thr Pro Pro Ser Pro Pro Pro Ile Ala Pro
145                 150                 155                 160

Asp Ile Leu Leu Asp Gln Tyr Gly His Phe Gln Ser Arg Ser Ser Asp
                165                 170                 175

Ser Ser Ala Asn Leu Ser Met Asn Met Leu Ser Ser Ser Ser Ser Ser
            180                 185                 190

Leu Asn His Gln Gly Leu Arg Pro Asn Leu Glu Asp Gly Glu Asn Val
        195                 200                 205

Lys Asn Ile Ser Ile His Lys Arg Arg Lys
    210                 215

<210> SEQ ID NO 159

```
<211> LENGTH: 212
<212> TYPE: PRT
<213> ORGANISM: Arabidopsis thaliana

<400> SEQUENCE: 159

Met Val Ser Ala Leu Ser Arg Val Ile Glu Asn Pro Thr Asp Pro Pro
1               5                   10                  15

Val Lys Gln Glu Leu Asp Lys Ser Asp Gln His Gln Pro Asp Gln Asp
            20                  25                  30

Gln Pro Arg Arg His Tyr Arg Gly Val Arg Gln Arg Pro Trp Gly
        35                  40                  45

Lys Trp Ala Ala Glu Ile Arg Asp Pro Lys Lys Ala Ala Arg Val Trp
50                  55                  60

Leu Gly Thr Phe Glu Thr Ala Glu Glu Ala Ala Leu Ala Tyr Asp Arg
65                  70                  75                  80

Ala Ala Leu Lys Phe Lys Gly Thr Lys Ala Lys Leu Asn Phe Pro Glu
                85                  90                  95

Arg Val Gln Gly Pro Thr Thr Thr Thr Ile Ser His Ala Pro Arg
            100                 105                 110

Gly Val Ser Glu Ser Met Asn Ser Pro Pro Arg Pro Gly Pro Pro
        115                 120                 125

Ser Thr Thr Thr Thr Ser Trp Pro Met Thr Tyr Asn Gln Asp Ile Leu
130                 135                 140

Gln Tyr Ala Gln Leu Leu Thr Ser Asn Asn Glu Val Asp Leu Ser Tyr
145                 150                 155                 160

Tyr Thr Ser Thr Leu Phe Ser Gln Pro Phe Ser Thr Pro Ser Ser Ser
                165                 170                 175

Ser Ser Ser Ser Gln Gln Thr Gln Gln Gln Leu Gln Gln Gln Gln
            180                 185                 190

Gln Gln Arg Glu Glu Glu Lys Asn Tyr Gly Tyr Asn Tyr Tyr Asn
        195                 200                 205

Tyr Pro Arg Glu
            210

<210> SEQ ID NO 160
<211> LENGTH: 248
<212> TYPE: PRT
<213> ORGANISM: Arabidopsis thaliana

<400> SEQUENCE: 160

Met Tyr Gly Lys Arg Pro Phe Gly Gly Asp Glu Ser Glu Glu Arg Glu
1               5                   10                  15

Glu Asp Glu Asn Leu Phe Pro Val Phe Ser Ala Arg Ser Gln His Asp
            20                  25                  30

Met Arg Val Met Val Ser Ala Leu Thr Gln Val Ile Gly Asn Gln Gln
        35                  40                  45

Ser Lys Ser His Asp Asn Ile Ser Ser Ile Asp Asn Tyr Pro Ser
50                  55                  60

Val Tyr Asn Pro Gln Asp Pro Asn Gln Gln Val Ala Pro Thr His Gln
65                  70                  75                  80

Asp Gln Gly Asp Leu Arg Arg Arg His Tyr Arg Gly Val Arg Gln Arg
                85                  90                  95

Pro Trp Gly Lys Trp Ala Ala Glu Ile Arg Asp Pro Lys Lys Ala Ala
            100                 105                 110

Arg Val Trp Leu Gly Thr Phe Glu Thr Ala Glu Ser Ala Ala Leu Ala
        115                 120                 125
```

```
Tyr Asp Glu Ala Ala Leu Lys Phe Lys Gly Ser Lys Ala Lys Leu Asn
        130                 135                 140

Phe Pro Glu Arg Val Gln Leu Gly Ser Asn Ser Thr Tyr Tyr Ser Ser
145                 150                 155                 160

Asn Gln Ile Pro Gln Met Glu Pro Gln Ser Ile Pro Asn Tyr Asn Gln
                165                 170                 175

Tyr Tyr His Asp Ala Ser Ser Gly Asp Met Leu Ser Phe Asn Leu Gly
            180                 185                 190

Gly Gly Tyr Gly Ser Gly Thr Gly Tyr Ser Met Ser His Asp Asn Ser
        195                 200                 205

Thr Thr Thr Ala Ala Thr Thr Ser Ser Ser Gly Gly Ser Ser Arg
210                 215                 220

Gln Gln Glu Glu Gln Asp Tyr Ala Arg Phe Trp Arg Phe Gly Asp Ser
225                 230                 235                 240

Ser Ser Ser Pro His Ser Gly Tyr
                245

<210> SEQ ID NO 161
<211> LENGTH: 413
<212> TYPE: PRT
<213> ORGANISM: Arabidopsis thaliana

<400> SEQUENCE: 161

Met Asp Asn Val Arg Gly Ser Ile Met Leu Gln Pro Leu Pro Glu Ile
1               5                   10                  15

Ala Glu Ser Ile Asp Asp Ala Ile Cys His Glu Leu Ser Met Trp Pro
            20                  25                  30

Asp Asp Ala Lys Asp Leu Leu Leu Ile Val Glu Ala Ile Ser Arg Gly
        35                  40                  45

Asp Leu Lys Leu Val Leu Val Ala Cys Ala Lys Ala Val Ser Glu Asn
    50                  55                  60

Asn Leu Leu Met Ala Arg Trp Cys Met Gly Glu Leu Arg Gly Met Val
65                  70                  75                  80

Ser Ile Ser Gly Glu Pro Ile Gln Arg Leu Gly Ala Tyr Met Leu Glu
                85                  90                  95

Gly Leu Val Ala Arg Leu Ala Ala Ser Gly Ser Ser Ile Tyr Lys Ser
            100                 105                 110

Leu Gln Ser Arg Glu Pro Glu Ser Tyr Glu Phe Leu Ser Tyr Val Tyr
        115                 120                 125

Val Leu His Glu Val Cys Pro Tyr Phe Lys Phe Gly Tyr Met Ser Ala
    130                 135                 140

Asn Gly Ala Ile Ala Glu Ala Met Lys Asp Glu Glu Arg Ile His Ile
145                 150                 155                 160

Ile Asp Phe Gln Ile Gly Gln Gly Ser Gln Trp Ile Ala Leu Ile Gln
                165                 170                 175

Ala Phe Ala Ala Arg Pro Gly Gly Ala Pro Asn Ile Arg Ile Thr Gly
            180                 185                 190

Val Gly Asp Gly Ser Val Leu Val Thr Val Lys Lys Arg Leu Glu Lys
        195                 200                 205

Leu Ala Lys Lys Phe Asp Val Pro Phe Arg Phe Asn Ala Val Ser Arg
    210                 215                 220

Pro Ser Cys Glu Val Glu Val Glu Asn Leu Asp Val Arg Asp Gly Glu
225                 230                 235                 240

Ala Leu Gly Val Asn Phe Ala Tyr Met Leu His His Leu Pro Asp Glu
```

```
                    245                 250                 255
Ser Val Ser Met Glu Asn His Arg Asp Arg Leu Leu Arg Met Val Lys
            260                 265                 270

Ser Leu Ser Pro Lys Val Val Thr Leu Val Glu Gln Glu Cys Asn Thr
        275                 280                 285

Asn Thr Ser Pro Phe Leu Pro Arg Phe Leu Glu Thr Leu Ser Tyr Tyr
    290                 295                 300

Thr Ala Met Phe Glu Ser Ile Asp Val Met Leu Pro Arg Asn His Lys
305                 310                 315                 320

Glu Arg Ile Asn Ile Glu Gln His Cys Met Ala Arg Asp Val Val Asn
                325                 330                 335

Ile Ile Ala Cys Glu Gly Ala Glu Arg Ile Glu Arg His Glu Leu Leu
            340                 345                 350

Gly Lys Trp Lys Ser Arg Phe Ser Met Ala Gly Phe Glu Pro Tyr Pro
        355                 360                 365

Leu Ser Ser Ile Ile Ser Ala Thr Ile Arg Ala Leu Leu Arg Asp Tyr
    370                 375                 380

Ser Asn Gly Tyr Ala Ile Glu Glu Arg Asp Gly Ala Leu Tyr Leu Gly
385                 390                 395                 400

Trp Met Asp Arg Ile Leu Val Ser Ser Cys Ala Trp Lys
                405                 410

<210> SEQ ID NO 162
<211> LENGTH: 593
<212> TYPE: PRT
<213> ORGANISM: Arabidopsis thaliana

<400> SEQUENCE: 162

Met Val Glu Gln Thr Val Val Arg Glu His Ile Lys Ala Arg Val Met
1               5                   10                  15

Ser Leu Val Arg Ser Ala Glu Pro Ser Ser Tyr Arg Asn Pro Lys Leu
            20                  25                  30

Tyr Thr Leu Asn Glu Asn Gly Asn Asn Asn Gly Val Ser Ser Ala Gln
        35                  40                  45

Ile Phe Asp Pro Asp Arg Ser Lys Asn Pro Cys Leu Thr Asp Asp Ser
    50                  55                  60

Tyr Pro Ser Gln Ser Tyr Glu Lys Tyr Phe Leu Asp Ser Pro Thr Asp
65                  70                  75                  80

Glu Phe Val Gln His Pro Ile Gly Ser Gly Ala Ser Val Ser Ser Phe
                85                  90                  95

Gly Ser Leu Asp Ser Phe Pro Tyr Gln Ser Arg Pro Val Leu Gly Cys
            100                 105                 110

Ser Met Glu Phe Gln Leu Pro Leu Asp Ser Thr Ser Thr Ser Ser Thr
        115                 120                 125

Arg Leu Leu Gly Asp Tyr Gln Ala Val Ser Tyr Ser Pro Ser Met Asp
    130                 135                 140

Val Val Glu Glu Phe Asp Asp Glu Gln Met Arg Ser Lys Ile Gln Glu
145                 150                 155                 160

Leu Glu Arg Ala Leu Leu Gly Asp Glu Asp Asp Lys Met Val Gly Ile
                165                 170                 175

Asp Asn Leu Met Glu Ile Asp Ser Glu Trp Ser Tyr Gln Asn Glu Ser
            180                 185                 190

Glu Gln His Gln Asp Ser Pro Lys Glu Ser Ser Ser Ala Asp Ser Asn
        195                 200                 205
```

Ser His Val Ser Ser Lys Glu Val Val Ser Gln Ala Thr Pro Lys Gln
210                 215                 220

Ile Leu Ile Ser Cys Ala Arg Ala Leu Ser Glu Gly Lys Leu Glu Glu
225                 230                 235                 240

Ala Leu Ser Met Val Asn Glu Leu Arg Gln Ile Val Ser Ile Gln Gly
            245                 250                 255

Asp Pro Ser Gln Arg Ile Ala Ala Tyr Met Val Glu Gly Leu Ala Ala
        260                 265                 270

Arg Met Ala Ala Ser Gly Lys Phe Ile Tyr Arg Ala Leu Lys Cys Lys
    275                 280                 285

Glu Pro Pro Ser Asp Glu Arg Leu Ala Ala Met Gln Val Leu Phe Glu
290                 295                 300

Val Cys Pro Cys Phe Lys Phe Gly Phe Leu Ala Ala Asn Gly Ala Ile
305                 310                 315                 320

Leu Glu Ala Ile Lys Gly Glu Glu Val His Ile Ile Asp Phe Asp
            325                 330                 335

Ile Asn Gln Gly Asn Gln Tyr Met Thr Leu Ile Arg Ser Ile Ala Glu
        340                 345                 350

Leu Pro Gly Lys Arg Pro Arg Leu Arg Leu Thr Gly Ile Asp Asp Pro
    355                 360                 365

Glu Ser Val Gln Arg Ser Ile Gly Gly Leu Arg Ile Ile Gly Leu Arg
370                 375                 380

Leu Glu Gln Leu Ala Glu Asp Asn Gly Val Ser Phe Lys Phe Lys Ala
385                 390                 395                 400

Met Pro Ser Lys Thr Ser Ile Val Ser Pro Ser Thr Leu Gly Cys Lys
            405                 410                 415

Pro Gly Glu Thr Leu Ile Val Asn Phe Ala Phe Gln Leu His His Met
        420                 425                 430

Pro Asp Glu Ser Val Thr Thr Val Asn Gln Arg Asp Glu Leu Leu His
    435                 440                 445

Met Val Lys Ser Leu Asn Pro Lys Leu Val Thr Val Val Glu Gln Asp
450                 455                 460

Val Asn Thr Asn Thr Ser Pro Phe Phe Pro Arg Phe Ile Glu Ala Tyr
465                 470                 475                 480

Glu Tyr Tyr Ser Ala Val Phe Glu Ser Leu Asp Met Thr Leu Pro Arg
            485                 490                 495

Glu Ser Gln Glu Arg Met Asn Val Glu Arg Gln Cys Leu Ala Arg Asp
        500                 505                 510

Ile Val Asn Ile Val Ala Cys Glu Gly Glu Arg Ile Glu Arg Tyr
    515                 520                 525

Glu Ala Ala Gly Lys Trp Arg Ala Arg Met Met Ala Gly Phe Asn
530                 535                 540

Pro Lys Pro Met Ser Ala Lys Val Thr Asn Asn Ile Gln Asn Leu Ile
545                 550                 555                 560

Lys Gln Gln Tyr Cys Asn Lys Tyr Lys Leu Lys Glu Glu Met Gly Glu
            565                 570                 575

Leu His Phe Cys Trp Glu Glu Lys Ser Leu Ile Val Ala Ser Ala Trp
        580                 585                 590

Arg

<210> SEQ ID NO 163
<211> LENGTH: 529
<212> TYPE: PRT
<213> ORGANISM: Arabidopsis thaliana -continued

<400> SEQUENCE: 163

```
Met Gln Thr Ser Gln Lys His His Ser Ala Ala Gly Leu His Met Leu
1               5                   10                  15

Tyr Pro Gln Val Tyr Cys Ser Pro Gln Phe Gln Ala Lys Asp Asn Lys
            20                  25                  30

Gly Phe Ser Asp Ile Pro Ser Lys Glu Asn Phe Phe Thr Leu Glu Ser
        35                  40                  45

Ser Thr Ala Ser Gly Ser Leu Pro Ser Tyr Asp Ser Pro Ser Val Ser
    50                  55                  60

Ile Thr Ser Gly Arg Ser Pro Phe Ser Pro Gln Gly Ser Gln Ser Cys
65                  70                  75                  80

Ile Ser Asp Leu His His Ser Pro Asp Asn Val Tyr Gly Ser Pro Leu
                85                  90                  95

Ser Gly Val Ser Ser Leu Ala Tyr Asp Glu Ala Gly Val Lys Ser Lys
            100                 105                 110

Ile Arg Glu Leu Glu Val Ser Leu Leu Ser Gly Asp Thr Lys Val Glu
        115                 120                 125

Glu Phe Ser Gly Phe Ser Pro Ala Ala Gly Lys Ser Trp Asn Trp Asp
    130                 135                 140

Glu Leu Leu Ala Leu Thr Pro Gln Leu Asp Leu Lys Glu Val Leu Val
145                 150                 155                 160

Glu Ala Ala Arg Ala Val Ala Asp Gly Asp Phe Ala Thr Ala Tyr Gly
                165                 170                 175

Phe Leu Asp Val Leu Glu Gln Met Val Ser Val Ser Gly Ser Pro Ile
            180                 185                 190

Gln Arg Leu Gly Thr Tyr Met Ala Glu Gly Leu Arg Ala Arg Leu Glu
        195                 200                 205

Gly Ser Gly Ser Asn Ile Tyr Lys Ser Leu Lys Cys Asn Glu Pro Thr
    210                 215                 220

Gly Arg Glu Leu Met Ser Tyr Met Ser Val Leu Tyr Glu Ile Cys Pro
225                 230                 235                 240

Tyr Trp Lys Phe Ala Tyr Thr Thr Ala Asn Val Glu Ile Leu Glu Ala
                245                 250                 255

Ile Ala Gly Glu Thr Arg Val His Ile Ile Asp Phe Gln Ile Ala Gln
            260                 265                 270

Gly Ser Gln Tyr Met Phe Leu Ile Gln Glu Leu Ala Lys Arg Pro Gly
        275                 280                 285

Gly Pro Pro Leu Leu Arg Val Thr Gly Val Asp Asp Ser Gln Ser Thr
    290                 295                 300

Tyr Ala Arg Gly Gly Gly Leu Ser Leu Val Gly Glu Arg Leu Ala Thr
305                 310                 315                 320

Leu Ala Gln Ser Cys Gly Val Pro Phe Glu Phe His Asp Ala Ile Met
                325                 330                 335

Ser Gly Cys Lys Val Gln Arg Glu His Leu Gly Leu Glu Pro Gly Phe
            340                 345                 350

Ala Val Val Val Asn Phe Pro Tyr Val Leu His His Met Pro Asp Glu
        355                 360                 365

Ser Val Ser Val Glu Asn His Arg Asp Arg Leu Leu His Leu Ile Lys
    370                 375                 380

Ser Leu Ser Pro Lys Leu Val Thr Leu Val Glu Gln Glu Ser Asn Thr
385                 390                 395                 400

Asn Thr Ser Pro Phe Leu Ser Arg Phe Val Glu Thr Leu Asp Tyr Tyr
```

```
                    405                 410                 415
Thr Ala Met Phe Glu Ser Ile Asp Ala Ala Arg Pro Arg Asp Asp Lys
                420                 425                 430

Gln Arg Ile Ser Ala Glu Gln His Cys Val Ala Arg Asp Ile Val Asn
                435                 440                 445

Met Ile Ala Cys Glu Glu Ser Glu Arg Val Glu Arg His Glu Val Leu
            450                 455                 460

Gly Ile Trp Arg Val Arg Met Met Met Ala Gly Phe Thr Gly Trp Pro
465                 470                 475                 480

Val Ser Thr Ser Ala Ala Phe Ala Ala Ser Glu Met Leu Lys Ala Tyr
                485                 490                 495

Asp Lys Asn Tyr Lys Leu Gly Gly His Glu Gly Ala Leu Tyr Leu Phe
                500                 505                 510

Trp Lys Arg Arg Pro Met Ala Thr Cys Ser Val Trp Lys Pro Asn Pro
                515                 520                 525

Asn

<210> SEQ ID NO 164
<211> LENGTH: 526
<212> TYPE: PRT
<213> ORGANISM: Arabidopsis thaliana

<400> SEQUENCE: 164

Met Glu Ala Thr Gln Lys His Met Ile Gln Glu Gly Ser Ser Met Phe
1               5                   10                  15

Tyr His Gln Pro Ser Ser Val Lys Gln Met Asp Leu Ser Val Gln Thr
                20                  25                  30

Phe Asp Ser Tyr Cys Thr Leu Glu Ser Ser Gly Thr Lys Ser His
            35                  40                  45

Pro Cys Leu Asn Asn Lys Asn Asn Ser Ser Ser Thr Thr Ser Phe Ser
        50                  55                  60

Ser Asn Glu Ser Pro Ile Ser Gln Ala Asn Asn Asn Leu Ser Arg
65                  70                  75                  80

Phe Asn Asn His Ser Pro Glu Glu Asn Asn Asn Ser Pro Leu Ser Gly
                85                  90                  95

Ser Ser Ala Thr Asn Thr Asn Glu Thr Glu Leu Ser Leu Met Leu Lys
                100                 105                 110

Asp Leu Glu Thr Ala Met Met Glu Pro Asp Val Asp Asn Ser Tyr Asn
            115                 120                 125

Asn Gln Gly Gly Phe Gln Gln His Gly Val Val Ser Ser Ala Met
        130                 135                 140

Tyr Arg Ser Met Glu Met Ile Ser Arg Gly Asp Leu Lys Gly Val Leu
145                 150                 155                 160

Tyr Glu Cys Ala Lys Ala Val Glu Asn Tyr Asp Leu Glu Met Thr Asp
                165                 170                 175

Trp Leu Ile Ser Gln Leu Gln Gln Met Val Ser Val Ser Gly Glu Pro
            180                 185                 190

Val Gln Arg Leu Gly Ala Tyr Met Leu Glu Gly Leu Val Ala Arg Leu
                195                 200                 205

Ala Ser Ser Gly Ser Ser Ile Tyr Lys Ala Leu Arg Cys Lys Asp Pro
        210                 215                 220

Thr Gly Pro Glu Leu Leu Thr Tyr Met His Ile Leu Tyr Glu Ala Cys
225                 230                 235                 240

Pro Tyr Phe Lys Phe Gly Tyr Glu Ser Ala Asn Gly Ala Ile Ala Glu
```

```
                    245                 250                 255
Ala Val Lys Asn Glu Ser Phe Val His Ile Ile Asp Phe Gln Ile Ser
            260                 265                 270

Gln Gly Gly Gln Trp Val Ser Leu Ile Arg Ala Leu Gly Ala Arg Pro
        275                 280                 285

Gly Gly Pro Pro Asn Val Arg Ile Thr Gly Ile Asp Asp Pro Arg Ser
    290                 295                 300

Ser Phe Ala Arg Gln Gly Gly Leu Glu Leu Val Gly Gln Arg Leu Gly
305                 310                 315                 320

Lys Leu Ala Glu Met Cys Gly Val Pro Phe Glu Phe His Gly Ala Ala
                325                 330                 335

Leu Cys Cys Thr Glu Val Glu Ile Glu Lys Leu Gly Val Arg Asn Gly
            340                 345                 350

Glu Ala Leu Ala Val Asn Phe Pro Leu Val Leu His His Met Pro Asp
        355                 360                 365

Glu Ser Val Thr Val Glu Asn His Arg Asp Arg Leu Leu Arg Leu Val
    370                 375                 380

Lys His Leu Ser Pro Asn Val Val Thr Leu Val Glu Gln Glu Ala Asn
385                 390                 395                 400

Thr Asn Thr Ala Pro Phe Leu Pro Arg Phe Val Glu Thr Met Asn His
                405                 410                 415

Tyr Leu Ala Val Phe Glu Ser Ile Asp Val Lys Leu Ala Arg Asp His
            420                 425                 430

Lys Glu Arg Ile Asn Val Glu Gln His Cys Leu Ala Arg Glu Val Val
        435                 440                 445

Asn Leu Ile Ala Cys Glu Gly Val Glu Arg Glu Arg His Glu Pro
    450                 455                 460

Leu Gly Lys Trp Arg Ser Arg Phe His Met Ala Gly Phe Lys Pro Tyr
465                 470                 475                 480

Pro Leu Ser Ser Tyr Val Asn Ala Thr Ile Lys Gly Leu Leu Glu Ser
                485                 490                 495

Tyr Ser Glu Lys Tyr Thr Leu Glu Glu Arg Asp Gly Ala Leu Tyr Leu
            500                 505                 510

Gly Trp Lys Asn Gln Pro Leu Ile Thr Ser Cys Ala Trp Arg
        515                 520                 525

<210> SEQ ID NO 165
<211> LENGTH: 732
<212> TYPE: DNA
<213> ORGANISM: Arabidopsis thaliana

<400> SEQUENCE: 165
atgtacggac agtgcaatat agaatccgac tacgctttgt ggagtcgat aacacgtcac      60 ttgctaggag gaggaggaga gaacgagctg cgactcaatg agtcaacacc gagttcgtgt    120
ttcacagaga gttggggagg tttgccattg aaagagaatg attcagagga catgttggtg    180
tacggactcc tcaaagatgc cttccatttt gacacgtcat catcggactt gagctgtctt    240
tttgattttc cggcggttaa agtcgagcca actgagaact ttacggcgat ggaggagaaa    300
ccaaagaaag cgataccggt tacggagacg gcagtgaagg cgaagcatta cagaggagtg    360
aggcagagac cgtgggggaa attcgcggcg gagatacgtg atccggcgaa gaatggagct    420
agggtttggt tagggacgtt tgagacggcg gaagatgcgg cttagctta cgatatagct    480 gcttttagga tgcgtggttc ccgcgcttta ttgaattttc cgttgagggt taattccggt    540
```

```
gaacctgacc cggttcggat cacgtctaag agatcttctt cgtcgtcgtc gtcgtcgtcc    600
tcttctacgt cgtcgtctga aaacgggaag ttgaaacgaa ggagaaaagc agagaatctg    660
acgtcggagg tggtgcaggt gaagtgtgag gttggtgatg agacacgtgt tgatgagtta    720
ttggtttcat aa                                                        732
```

```
<210> SEQ ID NO 166
<211> LENGTH: 849
<212> TYPE: DNA
<213> ORGANISM: Arabidopsis thaliana

<400> SEQUENCE: 166
atggctacac caaacgaagt atcagctctt ttcctcatca agaagtatct cctcgacgaa     60
ttgtctccgt tgcctactac tgccaccacc aatcgatgga tgaacgattt cacgtcattt    120
gatcaaaccg gtttcgagtt ttctgaattt gaaaccaaac cggaaataat cgatctcgtc    180
actcccaaac cggagatttt tgatttcgat gtgaaatctg aaattccatc tgaatcgaac    240
gattccttca cgttccaatc gaatcctcct cgcgttactg ttcaatccaa tcgaaaaccg    300
ccgttgaaga tcgcaccacc gaaccgaacc aagtggattc aattcgcaac cggaaatcct    360
aaaccggaac ttcccgtacc ggttgtagca gcagaggaga gaggcatta cagaggagtg    420 aggatgaggc cgtgggggaa attcgcggcg gagattcgag acccgactcg tcgtggaact    480
cgtgtttggc tcgggacgtt tgagacgcg atcgaagcgg ctagagctta cgacaaagaa    540
gcgtttagac tacgaggatc aaaggcgatt ctgaatttcc cgcttgaagt tgacaagtgg    600
aatccacgcg ctgaagatgg tcgtggcctg tacaacaaac ggaagagaga cggcgaggag    660
gaggaagtga cggtggttga gaaagtgcta aagacggagg agagttacga cgttagcggc    720
ggcgagaatg ttgagtcagg tttgacggcg atagatgact gggatttgac ggagtttctg    780
agcatgccgc ttttatcgcc gttatctcca cacccaccgt ttggttatcc acaattgacc    840
gttgtttga                                                           849
```

```
<210> SEQ ID NO 167
<211> LENGTH: 579
<212> TYPE: DNA
<213> ORGANISM: Arabidopsis thaliana

<400> SEQUENCE: 167
atggtgtcta tgctgactaa tgttgtctct ggtgagaccg aaccctcggc atctgcgaca     60
tggacgatgg gtcataagag agaaagagaa gagttttctt tgcctcctca accattgatt    120
accggttcag ctgtgactaa agaatgtgaa agctcaatgt ccttggagag gccaaaaaaa    180
tatagaggag taaggcaacg accatgggga aaatgggcgg cggagattcg agacccacac    240
aaggcgacac gtgtatggct tgggacattc gagacagccg aggccgccgc aagagcctat    300
gatgcggcag cacttcgctt tagaggaagc aaagcaaagc ttaatttccc cgaaaatgtt    360
ggaactcaga cgattcaacg aaattctcat ttcttgcaaa actctatgca accttctctg    420
acatacatcg atcaatgtcc aactctatta tcttactctc gatgtatgga gcaacaacaa    480
ccattagtag gcatgttgca gccaacagaa gaggaaaatc acttttcga aaaaccatgg    540 accgaatatg atcaatacaa ttactcctct tttggttaa                          579
```

```
<210> SEQ ID NO 168
<211> LENGTH: 807
<212> TYPE: DNA
<213> ORGANISM: Arabidopsis thaliana
```

<400> SEQUENCE: 168

```
atgcattatc ctaacaacag aaccgaattc gtcggagctc cagccccaac ccggtatcaa      60
aaggagcagt tgtcaccgga gcaagagctt tcagttattg tctctgcttt gcaacacgtg     120
atctcagggg aaaacgaaac ggcgccgtgt cagggttttt ccagtgacag cacagtgata     180
agcgcgggaa tgcctcggtt ggattcagac acttgtcaag tctgtaggat cgaaggatgt     240
ctcggctgta actactttt cgcgccaaat cagagaattg aaaagaatca tcaacaagaa     300
gaagagatta ctagtagtag taacagaaga agagagagct ctcccgtggc gaagaaagcg     360
gaaggtggcg ggaaaatcag gaagaggaag aacaagaaga atggttacag aggagttagg     420
caaagacctt ggggaaaatt tgcagctgag atcagagatc ctaaaagagc cacacgtgtt     480
tggcttggta ctttcgaaac cgccgaagat gcggctcgag cttatgatcg agccgcgatt     540
ggattccgtg ggccaagggc taaactcaac ttccccttt tggattacac gtcttcagtt     600
tcatctcctg ttgctgctga tgatatagga gcaaaggcaa gtgcaagcgc cagtgtgagc     660
gccacagatt cagttgaagc agagcaatgg aacggaggag gaggggattg caatatggag     720
gagtggatga atatgatgat gatgatggat tttgggaatg gagattcttc agattcagga     780
aatacaattg ctgatatgtt ccagtga                                         807
```

<210> SEQ ID NO 169
<211> LENGTH: 663
<212> TYPE: DNA
<213> ORGANISM: Arabidopsis thaliana

<400> SEQUENCE: 169

```
atgtctgcca tggtctcggc cttgacacag gtggtttctg ctcgctctca gactgaggct      60
gaaggtgctc actcttcttc ctcttcggct ggacataaaa gaggatggct tggaatcgat     120
tctgctccta ttccctcatc atttgctcgt gtagactctt cacataatcc gatcgaagaa     180
tccatgagca aggcatttcc agaggaagca agggagaaaa aaggaggta cagaggagta     240
aggcagagac catggggcaa atgggcagct gagatacgtg atccacatag agccgctagg     300
gtttggctcg ggacgtttga tacagcggag gccgcggcta gagcctacga cgaggctgca     360
ctccggttcc gtggaaataa agcaaagcta aatttcccag aggatgtaag gattcttcct     420
cctccccctc ctcttcttcg ttcaccagct gacacggtgg cgaataaagc agaagaggat     480
ctgataaatt attggagtta tacaaagttg ttgcaaagtt caggccaacg gtcatttctc     540
gagcgaggac aagaagagag tagtaacata tttgaacatt caccaatgga acaacctctg     600
cctccttcaa gttctggtcc aagttcctct aatttcctg caccttctct acctaataca     660
tag                                                                   663
```

<210> SEQ ID NO 170
<211> LENGTH: 1176
<212> TYPE: DNA
<213> ORGANISM: Arabidopsis thaliana

<400> SEQUENCE: 170

```
atgtgtgtct taaaagtggc aaatcaggaa gataacgttg caaaaaagc cgagtctatt      60
agagacgatg atcatcggac gttatctgaa atcgatcaat ggctttactt attcgcagcc     120
gaagacgacc accaccgtca tagcttccct acgcagcagc cgcctccatc gtcgtcgtcc     180
tcatctctta tctcaggttt cagtagagag atggagatgt ctgctattgt ctctgctttg     240
```

| | |
|---|---|
| actcacgttg ttgctggaaa tgttcctcag catcaacaag gaggcggtga aggtagcgga | 300 |
| gaagggactt cgaattcgtc ttcttcctcg gggcagaaaa ggaggagaga ggtggaggaa | 360 |
| ggtggcgcca aagcggttaa ggcagctaat actttgacgg ttgatcaata tttctccggt | 420 |
| ggtagctcta cttctaaagt gagagaagct tcgagtaaca tgtcaggtcc gggcccaaca | 480 |
| tacgagtata caactacggc aactgctagt agcgaaacgt cgtcgtttag tggggaccaa | 540 |
| cctcggcgaa gatacagagg agttagacaa agaccatggg gaaagtgggc ggctgagatt | 600 |
| cgagatccat ttaaagcagc tagagtttgg ctcggtacgt tcgacaatgc tgaatcagca | 660 |
| gcaagagctt acgacgaagc tgcacttcgg tttagaggca acaaagccaa actcaacttc | 720 |
| cctgaaaacg tcaaactcgt tagacctgct tcaaccgaag cacaacctgt gcaccaaacc | 780 |
| gctgctcaaa gaccgaccca gtcaaggaac tcgggttcaa cgactaccct tttgcccata | 840 |
| agacctgctt cgaatcaaag cgttcattcg cagccgttga tgcaatcata caacttgagt | 900 |
| tactctgaaa tggctcgtca acaacaacag tttcagcaac atcatcaaca atctttggat | 960 |
| ttatacgatc aaatgtcgtt ccgttgcgt ttcggtcaca ctggaggttc aatgatgcaa | 1020 |
| tctacgtcgt catcatcatc tcattctcgt cctctgtttt ccccggctgc tgttcagccg | 1080 |
| ccaccagaat cagctagcga aaccggttat ctccaggata tacaatggcc atcagacaag | 1140 |
| actagtaata actacaataa tagtccatcc tcctga | 1176 |

<210> SEQ ID NO 171
<211> LENGTH: 696
<212> TYPE: DNA
<213> ORGANISM: Arabidopsis thaliana

<400> SEQUENCE: 171

| | |
|---|---|
| atgcatagcg ggaagagacc tctatcacca gaatcaatgg ccggaaatag agaagagaaa | 60 |
| aaagagttgt gttgttgctc aactttgtcg gaatctgatg tgtctgattt tgtctctgaa | 120 |
| ctcactggtc aacccatccc atcatccatt gatgatcaat cttcgtcgct tactcttcaa | 180 |
| gaaaaagta actcgaggca acgaaactac agaggcgtga ggcaaagacc gtgggaaaa | 240 |
| tgggcggctg agattcgtga cccgaacaag gcagctcgtg tgtggcttgg gacgttcgac | 300 |
| actgcagaag aagccgcctt agcgtatgat aaagctgcat ttgagtttag aggtcacaag | 360 |
| gccaagctta acttccccga gcatattcgt gtcaaccctt ctcaactcta tccatcgccc | 420 |
| gctacttccc atgatcgcat tatcgtgaca ccacctagtc cacctccacc aattgctcct | 480 |
| gacatacttc ttgatcaata tggccacttt caatctcgaa gtagtgattc cagtgccaac | 540 |
| ttgtccatga atatgctgtc ttcttcgtct tcatctttga atcatcaagg ctaagaccaa | 600 |
| aatttggagg atggtgaaaa cgtcatgacg actatatcca cagaagatga ccgacggaga | 660 |
| caacaacatg cctcacctga tcgaccgatc aaatga | 696 |

<210> SEQ ID NO 172
<211> LENGTH: 639
<212> TYPE: DNA
<213> ORGANISM: Arabidopsis thaliana

<400> SEQUENCE: 172

| | |
|---|---|
| atggtctccg ctctcagccg tgtcatagag aatccgacag acccgccggt caaacaagag | 60 |
| cttgataaat cggatcaaca tcaaccagac caagatcaac caagaagaag acactataga | 120 |
| ggcgtaaggc agagaccatg gggtaaatgg cggcagaaaa tccgcgatcc aaagaaagca | 180 |
| gcccgtgtct ggctcgggac tttcgagacg gcagaggaag ctgctttagc ctatgaccga | 240 |

```
gctgccctca aattcaaagg caccaaggct aaactgaact tccctgaacg ggtccaaggc    300
cctactacca ccacaaccat ttctcatgca ccaagaggag ttagtgaatc catgaactca    360
cctcctcctc gacctggtcc accttcaact actactactt cgtggccaat gacttataac    420
caggacatac ttcaatacgc tcagttgctt acgagtaaca atgaggttga tttatcatac    480
tacacgtcga ctctcttcag tcaaccttt tcaacgcctt cttcatcttc ttcttcctcc    540
caacagacgc agcaacagca gctacaacaa caacaacagc agcgtgaaga agaagagaag    600
aattatggtt acaattatta taactaccca agagaataa                           639

<210> SEQ ID NO 173
<211> LENGTH: 747
<212> TYPE: DNA
<213> ORGANISM: Arabidopsis thaliana

<400> SEQUENCE: 173
atgtatggga gaggcctttt tggaggtgat gaatctgaag aaagggaaga agatgagaac     60
ttgttcccgg tcttctcggc ccgatctcaa cacgacatgc gtgttatggt ctcggccttg    120
actcaagtaa tcggaaacca acaaagcaaa tctcatgata acatcagctc tattgatgat    180
aactatcctt ctgtgtataa tccacaagac cctaatcaac aagttgcgcc tactcatcaa    240
gaccaagggg acttgaggag gagacattat agaggtgtaa ggcaaaggcc atggggaaag    300
tgggcagctg aaatccgaga cccaaaaaag gcggcacgtg tgtggctcgg acatttgaa    360 accgctgaat ctgcggcctt agcttatgat gaagcagccc taagttcaa aggaagcaaa    420 gcaaaactca atttcccgga gagggttcag cttggaagta actctacata ttactcctcc    480
aaccaaattc cacaaatgga accacaaagt ataccgaact ataatcaata ctatcatgat    540
gcgagtagtg gtgatatgct aagttttaat ttgggcggtg ggtatgggag tggtaccgga    600
tattcaatgt ctcatgataa tagtactacg actgctgcta caacttcttc gtcttctggt    660
ggctcttcta ggcaacaaga agagcaagat tatgccagat tctggcgctt tggggattct    720
tcttcctctc ctcattcggg atattaa                                        747

<210> SEQ ID NO 174
<211> LENGTH: 1242
<212> TYPE: DNA
<213> ORGANISM: Arabidopsis thaliana

<400> SEQUENCE: 174
atggacaatg taagaggttc aataatgttg cagccactgc cagagatagc tgagagtatc     60
gatgatgcta tctgccatga actctccatg tggcctgatg atgctaaaga tttgttattg    120
atagtggagg caatatcaag gggagacttg aagttggtac ttgttgcttg tgcaaaagct    180
gtttctgaga ataatcttct aatggcacga tggtgtatgg gtgagttgcg cggtatggtt    240
tcgatttctg gtgagccaat ccagagattg ggagcttata tgttagaagg cttgttgct    300 aggcttgctg cttctggtag ttcgatatat aagtctctcc agtccagaga accagagagt    360
tatgaatttt tatcttatgt gtatgttctg catgaggttt gtccatattt caagtttgga    420
tacatgtcag cgaatggtgc gattgcagaa gcaatgaagg atgaagagag gattcacatt    480
attgacttcc aaattggaca agggagccag tggatagcac ttatccaggc ttttgcagct    540
aggcctggtg gggctccaaa tattcgaatt accggagttg gtgatggatc tgtcttggtt    600
acagtcaaga agagactaga gaaacttgca aagaagttg atgttccatt caggttcaat    660
```

```
gcggtttcaa ggccaagttg tgaagttgaa gtggaaaatc ttgatgtccg agatggcgaa      720
gcccttggag tgaactttgc ttacatgctg catcatttgc cagatgagag tgtaagcatg      780
gaaaaccaca gggaccggtt gctgaggatg gtgaagagtc tatcacctaa agtagtcact      840
cttgtggaac aagaatgcaa cacgaacact tcccctttcc ttcctaggtt ccttgagaca      900
ttaagttatt acacggcaat gttcgaatct atcgatgtta tgcttccgag aaatcacaag      960
gaaaggatca atatcgagca gcactgcatg gcaagggatg tcgtcaacat catagcttgt     1020
gaaggagccg agaggatcga agacacgag cttctcggga atggaagtc aaggttttcc      1080 atggcgggtt ttgagccata ccccttgagc tcaatcattt cagccaccat tagagccctc     1140
ttgagagatt acagcaacgg gtatgcgatt gaagaaagag atggtgctct gtaccttggt     1200
tggatggacc gaatcttggt ctcatcttgt gcatggaagt ga                        1242
```

<210> SEQ ID NO 175
<211> LENGTH: 1782
<212> TYPE: DNA
<213> ORGANISM: Arabidopsis thaliana

<400> SEQUENCE: 175

```
atggtggaac aaactgtggt tagagaacat atcaaagcga gagtcatgtc attagtgagg       60
tctgcagagc catcctcata taggaacccg aagctttaca cgttgaatga gaatggtaat      120
aacaatggtg tcagttctgc tcaaatcttt gatccagata ggtcaaagaa tccttgtctg      180
actgatgatt cttacccaag ccaaagttat gagaagtact ttcttgattc gccaactgat      240
gagtttgttc aacatcctat tggctctggt gcctcggtta gctcatttgg ctctttagac      300
tcatttcctt atcagtcaag accagttctt ggatgttcca tggaatttca gttaccgttg      360
gattcaacct ctacttcatc tacaaggctt ttgggagatt accagcggt tcttacagt       420 ccgagcatgg atgtagtgga ggagtttgat gatgagcaaa tgagatcaaa gattcaagag      480
cttgaaagag cgcttctcgg cgatgaagat gataaaatgg ttggaataga taacctcatg      540
gagattgaca gcgaatggtc gtaccaaaac gaaagcgaac agcatcaaga ctcgcccaaa      600
gaatcatcgt ctgcagattc caactctcat gtaagtagca agaagtggt gtctcaagcc      660 actccaaagc aaatcttgat atcttgtgct cgtgcgctat ctgaaggaaa attagaagaa      720
gctttgtcaa tggtaaatga gctgaggcag atagtttcta tccaaggaga cccttctcag      780
agaatcgcag cttacatggt ggaaggtcta gctgcaagaa tggccgcttc aggaaaattc      840
atctacagag cattgaaatg caaagagcct ccttcggatg agaggcttgc agctatgcaa      900
gtcctgtttg aagtctgccc ttgtttcaag ttcgggtttt tagcagctaa tggtgcgata      960
cttgaagcaa tcaaaggtga agaagaagtt cacataatcg atttcgatat aaaccaaggg     1020
aaccaataca tgacactgat acgaagcatt gctgagttgc ctggtaaacg acctcgcctg     1080
aggttaacag gaattgatga ccctgaatca gtccaacgct ccattggagg gctaagaatc     1140
atcggtctaa gactcgagca actcgcagag gataatggag tatccttcaa attcaaagca     1200
atgccttcaa agacttcgat tgtctctcca tcaacactcg gttgcaaacc aggagaaacc     1260
ttaatagtga actttgcatt ccaacttcac cacatgcctg acgagagtgt cacaacagta     1320
aaccagcggg acgagctact tcacatggtc aaaagcttaa acccaaagct tgtcacggtc     1380
gttgaacaag acgtgaacac aaacacttca ccgttctttc ccagattcat agaggcttac     1440
gaatactact cagcagtttt cgagtctcta gacatgacac ttccaagaga aagccaagag     1500
aggatgaatg tagaaagaca gtgtctcgct agagacatag tcaacattgt tgcttgcgaa     1560
```

| | |
|---|---|
| ggagaagaac ggatagagag atacgaggct gcgggaaaat ggagagcaag gatgatgatg | 1620 |
| gctggattca atccaaaacc aatgagtgct aaagtaacca acaatataca aaacctgata | 1680 |
| aagcaacaat attgcaataa gtacaagctt aaagaagaaa tgggtgagct ccattttgc | 1740 |
| tgggaggaga aaagcttaat cgttgcttca gcttggaggt aa | 1782 |

<210> SEQ ID NO 176
<211> LENGTH: 2453
<212> TYPE: DNA
<213> ORGANISM: Arabidopsis thaliana

<400> SEQUENCE: 176

| | |
|---|---|
| cactttatt atatctcaat ctccttcttc ttcctcaagc tgattcttga gtatgcaagg | 60 |
| aaaacttctc ttttgtcccc ttgtcaacaa aaatctccca ttcaacaaaa tttcttcagc | 120 |
| ttctctcctt caaaaggttt ttattctcct tggtttgaac aagttacact gtagagagtg | 180 |
| atttggctaa aagaagattg attcaggagc tgtgtagtgt attgctgggg ttttccaat | 240 |
| gcaaacgtct cagaaacatc acagtgcggc tggactgcac atgctgtatc ctcaagtcta | 300 |
| ctgttcacct cagtttcaag cgaaagacaa caaaggcttc tctgatatcc cgtccaaaga | 360 |
| aaacttttt accctcgaat cctccactgc ttctggtagt cttccttcgt atgactctcc | 420 |
| ttctgtgagc attacatctg gccggagccc gttttctcct cagggctctc agtcttgcat | 480 |
| ctcggatctc catcattccc ctgacaacgt ctatggatca cctttgagtg gggtgtcatc | 540 |
| tcttgcctat gatgaagctg gagtcaagag taagattcgg gaacttgagg tctcgctgct | 600 |
| gagtggtgat acaaaagttg aagaattctc aggttttagc cccgctgctg ggaagtcgtg | 660 |
| gaactgggat gaacttttgg ctttgactcc acagttggac ttgaaagagg tgctggtgga | 720 |
| ggctgctcgg gcagtcgctg atggggattt cgctacagcg tatggattcc ttgatgtctt | 780 |
| ggaacagatg gtgtcagtct caggcagtcc gatccaacgg ctaggcactt acatggcaga | 840 |
| agggcttaga gcgaggcttg aggggtctgg gagcaatata tacaaatcct tgaaatgcaa | 900 |
| tgaaccaacg ggaagggaac tgatgtctta catgagtgtt ctctatgaaa tctgcccta | 960 |
| ctggaaattc gcgtacacaa ctgcgaatgt tgagatcttg gaagcaatag ctggggaaac | 1020 |
| cagagtccac attatcgatt tcagattgc acagggatca caatacatgt ttttgattca | 1080 |
| ggagcttgcg aaacgcctg tgggccgcc gttgctgcgt gtgacgggtg tggatgattc | 1140 |
| acagtccacc tatgctcgtg ggggaggact cagcttggta ggtgagaggc ttgcaacttt | 1200 |
| ggcgcagtca tgtggtgtcc cgtttgagtt tcacgatgcc atcatgtctg ggtgcaaggt | 1260 |
| gcagcgggaa catctcgggt tggaacctgg ctttgctgtt gttgtgaact tcccatatgt | 1320 |
| attacaccac atgccagacg agagcgtaag tgttgaaaat cacagagaca ggctgctgca | 1380 |
| tctgatcaag agcctctccc caaaactggt tactctagta gagcaagaat ccaacacaaa | 1440 |
| cacctcgcca ttcctgtcac ggtttgtgga acactggat tactacacag cgatgtttga | 1500 |
| gtcgatagat gcagcacggc cacgggatga taagcagaga atcagcgcag aacaacactg | 1560 |
| tgtagcaaga gacatagtga acatgatagc atgtgaggag tcagagagag tagagagaca | 1620 |
| cgaggtactg gggatatgga gggtcagaat gatgatggct gggttcacgg gttggccggt | 1680 |
| cagcacatct gcagcgtttg cagcgagtga gatgctgaaa gcttatgaca aaactacaa | 1740 |
| actgggaggc catgaaggag cgctctacct cttctggaag agacgaccca tggctacatg | 1800 |
| ttccgtgtgg aagccaaacc caaactagat tgggtaagtt atagtgatga tggttacttg | 1860 |

```
agtggataaa gaagagcaca acaaaaacac atctgtcgct gtaaattttt taggatgtgc   1920
aatgatgttt taagttgtaa cacaacctaa gttatatatg tatacaaacc aaacctggtg   1980 gttgttttc tcttgtaaat tgtcatgtgg ttgtgggtgg gttgctagta atgaaatata   2040
accaaaacat tgattaggtc atttatgat cttcttctat atataccggt ataagtcaac    2100
tggcggctga acaaaggtcg tgaggtaaca aaatatgaga caaatctaca ggtcagattg   2160
ggttctgaat tctgataagg tcttaaaaag gagctcacca acccacaaaa ccatggattg   2220
aacaagtaca ggtcattgcc ttcattttat tctttacttt tctaaggctc aagcttcctt   2280
tattgccttt aataacaata tactaatgag tattttgcac tcagtaacaa aattcaggag   2340
agtaattttt tgccctaaca tgttactttt atgtgttaag agtttagaat tttggatcta   2400
tgattttagt ttttgttagg gaatcatatt catataaata aaatattgcc att          2453
```

<210> SEQ ID NO 177  
<211> LENGTH: 1581  
<212> TYPE: DNA  
<213> ORGANISM: Arabidopsis thaliana

<400> SEQUENCE: 177

```
atggaagcta ctcagaaaca tatgattcaa gaaggatctt caatgtttta ccatcaacca    60
tcttcagtca aacaaatgga cctttctgtt cagacatttg attcttactg cacacttgaa   120
tcctcttcag gcaccaagtc tcatccttgt cttaacaaca aaaacaactc ttcttcaacc   180
acaagctttt cctctaatga aagtcccatt tctcaagcca acaacaacaa cttatcaagg   240
tttaacaatc attcccctga agaaaacaat aactctccct tgagcggttc ttcagcgaca   300
aacaccaacg agacagagct tagtctcatg cttaaagatt tggagactgc aatgatggag   360
cctgatgtag acaacagcta taacaatcaa ggcgggtttg acagcagca tggagttgtt    420 tcttcagcta tgtatagatc tatggagatg atctctaggg gagatttaaa aggagtgctc   480
tatgaatgcg caaaagctgt tgaaaactat gatttggaaa tgactgattg gttgatctct   540
cagttacagc aaatggtttc tgtttctggt gagcctgttc agcgcttagg agcttatatg   600
cttgaaggtc tcgttgctag gttagcttct tcgggtagct ccatctataa agcattgaga   660
tgcaaagacc caacgggtcc tgagcttctt acttatatgc atatcttgta tgaagcctgc   720
ccttatttca aattcggtta tgaatctgct aatggagcta tagctgaagc tgtgaagaac   780
gaaagttttg tgcacattat cgatttccag atttctcaag gtggtcaatg ggtgagtttg   840
atccgtgctc ttggtgctag acctggtgga cctccgaacg ttaggataac gggaattgat   900
gatccgagat catcgtttgc tcgtcaagga ggacttgagt tagttggaca aagacttggg   960
aagctagctg aaatgtgcgg tgttccgttt gagttcatg gagctgcttt atgctgcacg   1020
gaagtcgaaa tcgagaagct aggagttaga atggagaag cgctcgcggt taacttcccg   1080
cttgttcttc accacatgcc tgatgagagt gtaactgtgg agaatcacag agatagattg   1140
ttgagattgg tcaaacactt gtcaccaaac gttgtgactc tggttgagca agaagcgaat   1200
acaaacactg cgccgtttct tccccggtt gtcgagacaa tgaaccatta cttggcagtt   1260
ttcgaatcaa tagatgtgaa actcgctaga gatcacaagg aaaggatcaa tgttgagcag   1320
cattgtttgg ctagagaggt tgtgaatctt atagcttgtg aaggtgttga agagaagag    1380 aggcacgagc cactagggaa atggaggtct cggtttcaca tggcgggatt taaaccgtat   1440
cctttgagct cgtatgtgaa cgcaacaatc aaaggattgc ttgagagtta ttcagagaag   1500
tatacacttg aagaaagaga tggagcattg tatttaggat ggaagaatca acctcttatc   1560
```

```
acttcttgtg cttggaggta a                                            1581
```

<210> SEQ ID NO 178
<211> LENGTH: 1266
<212> TYPE: DNA
<213> ORGANISM: Zea mays

<400> SEQUENCE: 178

```
atggaaaggg tgaagtactg cgattgcacc gtgtgctctg ttcagagaag cctgtgttct     60
actagaagaa gaaggcgcag gcggaggcag atcgataggc agcttactaa ggttgaccca    120
agacgcaggc atggcaagag gccacttcca gctgctgagg ttgaggagga agaagaggaa    180
gaggctttgc caccaggtcc accaccagct aagcacgagc aacttgagga accacaccac    240
gctgctgtgt ctcaacttca gggcgctact ttttctggcg gcggtggatc atctagcagc    300
tctgttattg gcggcccatc tccacctcaa gcctacgctc agtactacta ctctgccagg    360
gctgacaacg acgcttctgc agttgcttct gctctggctc atgtgatcag gcttctccca    420
gatcagcttc caccacaaca agctccagca ctttacggcg ctggtgttcc aggttctctt    480
aggcttggcg atcatccaca ggctagcgct catcattatc caggcccagg tggtcatgtg    540
gctgctgctg aagaggagca aggtagaagg cggcattaca ggggtgttag gcaaagacca    600
tggggcaagt gggcagctga gatcagggat ccaaagaagg ctgctagggt ttggctgggc    660
accttcgata cagctgagga tgctgctatc gcctacgatg aggctgctct taggttcaag    720
ggcaccaagg ccaagctgaa cttcccagaa agagtgcagg gcaggaccga tctgggcttc    780
cttgttacta ggggcatccc agatcacagg cacccaagtg ctgctgttac tctggctgct    840
atgccgccac cacatcatca gcatggccat cagactgtgg tgccataccc agaccttatg    900
cagtacgctc aactgcttca aggcggtaga ggtggtgggg gtcatgctga agcagctgtt    960
caacaggctc atcggcagca gcaacagcaa caactgatga ctatgatggg cggcaggcca   1020
ggcgttaacc tgccatctac attcagccca agctctagcg cctctgctcc acagatcctg   1080
gatttctcta cccagcagct tatcagacct ggcccaccct tctccatcac caagagct    1140
gccgctatgc catcttcatc tgcagccgct gctccaagca cccatcttc tacaactacc   1200
gctagctctc catctggtgg cgcttggcca tacggtggtg aaaggcatag gaacaagaag   1260
gacgcc                                                             1266
```

<210> SEQ ID NO 179
<211> LENGTH: 1332
<212> TYPE: DNA
<213> ORGANISM: Zea mays

<400> SEQUENCE: 179

```
atgcgcatct ctctccgcgt acttatcagt agcgagctcg gcacgtcatt gtgcactgct     60
gcaccgagcc tagcgcgagc ctccgtccga aagtccaaat cttcagctct ctccttgacg    120
catgcccgga tcgatcggtc cagctctacc caccggagga ggaggcagat caacgggcag    180
ctaactaagg tggatccaag gaggaggcat ggcaagaggc ccctaccccg cgacgaggag    240
gaagaagagg aggaggaact gccccctccg cctgcaaagt acgagcagct ggatcaggag    300
gagaagcatc acgttgtcgt ctcgcagctg caagcaggag ctacctttag cggtggccga    360
gggtcttcgt cgtcttcagt ggcaggtcct tcgcctgagg cgtacgcgca atactactac    420
tcggcacgtg ctgaccacga cgcttccgcc gtggcctccg cgttagctca tgtaatacgc    480
```

```
gcttctcccg accaacttcc acctcagcag gccgcatgct tgtacggtgc tgccggcgct        540
ccagtattaa ggcagggaga gggagatcat cctcaacctc aagcggctgc gcaccatcat        600
ccaggtggcc acgtcgccgc tgaggaagag caaggtctaa aaggcactaa cagaggggtg        660
aggcagaggc cgtggggtaa atgggcggct gagatacggg accctaaaaa ggcggcgcgg        720
gtgtggctag gcacattcga cacggctgag gatgctgcaa ttgcctatga cgaggcggcg        780
ctgaggttca agggcaccaa ggccaagctc aacttccctg agcgcgttca gggccgaacc        840
gacctcggct tcgtcgtcac acgaggaatt ccggaccatc atcgtcatcc acgggcggcg        900
gcagttaacc tggcagcaat gccgcaggct caggctcagc cgcacttgca acacggacga        960
ccaaccgtca tgccgtatcc gtacccatac cctgacctaa tgcagtacgc gcagctgctt       1020
cagggcggcc ggggaggtgg tgaccatgcg gctgcagttc agcaacagct catgatgatg       1080
ggaggacgag gaggcaacct gccattctcg ttctcgccgc catcgtcctg gagtgcgcct       1140
ccgcagatac tggacttctc ggcgaggcaa ctaattaccc aacccggacc accttcttct       1200
ccggctgctc caggtggcgc ggctccatcc acaccgtcat ctactactac tgcgtcatcg       1260
ccaagcgcca gcgcaagcgg aagtgcatgg ccatacggtg gggagcacca caggaataaa       1320
aaggacgcgt ga                                                          1332
```

<210> SEQ ID NO 180
<211> LENGTH: 1074
<212> TYPE: DNA
<213> ORGANISM: Zea mays

<400> SEQUENCE: 180

```
atgtgcttcg agctggctga tcagcgagga ccgcaggag gcggaggagc gggatggcct          60
gctaaaagga gagctggagg cgttcaagac gaaggtgctg ccgcggctgc aggaatggca         120
atggctgctg ctggccccgg ggaggtgatg tccgagtact accaggcgca ggagctgtcg         180
acgatggtgt ctgctctgac tcacgtcgtt gctggcgctc cgatgggaag cgcccctgct         240
cagaggccaa tgcacggcgc atcaggctac tacgcgcacg agatgggaag ttaccgcggt         300
gcaccatcgc ctgagctcgc aggttcggag ctgagttctg atacccagag tgcgggtgcg         360
gctgccatgg aggagcacca atcggcagct gcgctttcca gtcaagaagg tcccgagact         420
ccgaggagac gctaccgtgg ggtgcgccaa aggccgtggg gcaagtgggc cgctgaaatc         480
cgtgatcctc acaaggctgc gagagtatgg ctcggcacgt tcgagactgc tgaggccgcg         540
gcgcgcgcat atgacgaggc tgcgctacgc ttccgaggca gtcgtgccaa acttaacttc         600
cccgaggacg cgcgcttata tccggcgtca acggctggcg cggctgcacc tctcgctgct         660
gctgcttcga cttcaccacc tgtctactcc ggtggagtcc agggctcgtc ggactacctg         720
aggtaccacc agatgcttct gcaagcgtcc acgggcagcc agggtaccct gctcccattc         780
tatggcggcg gcatgagtaa tccatacggc ggcggtgctg ccatgaccgg ttcatacggt         840
ggagccggcg gcggcaacac gagtggttcc ttgggctcct actactcgtt cccggcctcc         900
tctgtttctg tcgccaccgt gccgtcctct acttcctctg cttcggggta ctactactcg         960
tctccgcacg actcgcaaca tagcgaggcg tctgcggctg ctgactggaa ttgggagagc        1020
gcgctggcat ggcctgactc gagccagtac ccgccaccac ctcacactca gtag             1074
```

<210> SEQ ID NO 181
<211> LENGTH: 1629
<212> TYPE: DNA
<213> ORGANISM: Zea mays

<400> SEQUENCE: 181

```
atgtcagcta gggattctaa tcattcatat aaatgttcgg atgattctca aatgccgtac      60
tacaataact cagcacctgt aggagaaaat ggtaggatcc atatggcaga aaacagtcta     120
ggacatcatt actcatcctc cgatattgga tcacaaagga tcaacaattc caaccctcaa     180
gtatttgaag cacagtactg cactctggaa tcatcctcag caaatggtgt ttatcctgca     240
caaagctcca catcttctca tagcatctcc cctttaagtg ggagccccct gtctcagcat     300
gacagccact cagaccacac atatagttct cctccaagtg cttcctgtct aactgaggtt     360
gcagatctcc tgattaaaca aaaagaatta gagaattcca ttgttggacc tggactggac     420
attagttctg actgctctcg gagcttgttg caagcccatg ttccagtcag accagacaac     480
tggagacaac ttctgggaat taatggagga acttgatgc aagtagtcat agcatgtggt      540
aaggctgttg cagagaatga tgtctttgca acagaactgt taatatctga gcttggtcac     600
ctggtatctg tatctggaga tccaatgcaa cgacttggag cctatatgct tgaaggaatt     660
gttgctagac tttcttcctc cggcagtatg ctatataaat ctttgaaatg taagaaccct     720
acaagctctg agctcatgtc atatatgcat ctcctttacg agatctgccc attctacaag     780
tttggttaca tgtcagcaaa tggtgccatt gccgaggcta ttaagggcga aactttgtt      840
cacataattg atttccaaat tgctcagggg agccagtggg ttactctgct acaggccctt     900
gctgcaagac ctgggggggcc accatacatt agaatcactg gtatagatga ctcaaattct     960
gcttatgcca gaggaggcgg gcttgatata gttggagga cgttgtgtga tgttgctaat     1020
tcatgtggtc ttccttttga gttcaatgcc gttccagctg ctagccatga ggttgagctt     1080
cagcatcttg ctataagaca tgggagatt ttgctgtga atttttgccta tcagctacat     1140
catgttcctg acgaaagtgt aagtacagaa aatcatcggg ataggattat aagaatgatc     1200
aagagcatca atcctagggt tgttactctc gttgaacagg agtcaaatac aaacacagct     1260
ccattcttcc caaggtacat ggaaactctc aactactata cagccatgtt tgagtcgata     1320
gatgttgctc tcccaaggga tgataggagg cggatgagcg cagaacaaca ctgtgttgca     1380
agggatattg ttaatttaat cgcatgcgag ggtgctgaaa gggttgagag gcacgagctg     1440
tttggaaaat ggaagtcaag atttgcaatg gctggattta accgtaccc actgagttca      1500
gttgtgaaca acactatcaa cacattgttg catacctaca acagctacta caggcttgag     1560
gagagagatg gtgtcctta ccttggatgg aaaaacagag tattggttgt atcttcggca     1620
tggtgttga                                                             1629
```

<210> SEQ ID NO 182
<211> LENGTH: 1665
<212> TYPE: DNA
<213> ORGANISM: Zea mays

<400> SEQUENCE: 182

```
atggctgaca ctccaacgtc ccgcatggtg cacccctttg gcgacgcccc aaggcagact      60
cccaagcaat tcctgtattc tggtaacccg cagcacctct gccatccgta ccagtcagct     120
ccggacaccc atgtcgtgct ccagcgccgt tacaccgtga ggtcacagtc tcactcacca     180
aataatgctg ttctgaaga ccatgagact cacaagcagt acacgctgga gtcctcagcg      240
gcttctggtt gttcaaggca tggttctccc tccagccaaa gcgtccatgc cgggagtggc     300
agccctgtgt ctcacgacga cagccactcc ggctccacga atggccatgg atcacctgtg     360
```

```
agcgcgtcgt gtgtcaccgg cgaggaccct actgatctca agcagaaact gaaggatctt    420
gaggctgtaa tgctggggac gtctgagact gaccccgaga tagtcaacag tctcgagatc    480
tccgcggcaa accaactctc gttggagccc gaggagtggg agcacatggt gagcatgccc    540
agagggaacc tgaaggagct gctgattgcc tgcgctaggg cagtggaacg taacaacagc    600
tacgccattg atctgatgat cacagagctg aggaagatgg tttcggtgtc cggcgagccg    660
cttgagaggc tgggagccta catggtggaa ggtcttgttg ccaggctcgc ggcctccggc    720
agctcaatct acaaggcttt gaagtgtaag gagcccagga gctctgatct cctctcctac    780
atgcacttcc tgtatgaggc ctgcccctac ttcaagttcg gctacatgtc agccaacggc    840
gcgatcgcgg aggccatcaa gggagaggac aggatccata tcatcgactt ccacatcgcg    900 caagggctc agtgggtgtc tctcctccaa gcccttgcag ccaggcctgg cgggccaccg    960
ttcgtgaggg tcaccggcat tgatgattca gtctcagctt acgctcgagg cggcggtctg   1020
gagttggttg gcaggaggtt gacacatatt gctggcctct acaaggtgcc ctttcagttc   1080
gacgcagtcg ctatctcagg cagtgaggtg gaggaggagc atctgggcgt cgtcccaggc   1140
gaagccgtcg ccgtcaactt cacccttgag ctgcaccaca tccccgacga gacggtgagc   1200
acggcgaacc accgggaccg gatcctgagg ctggtgaagg gcctgtcgcc caaggtgctc   1260
acgctggtgg agcaggagtc caacaccaac acggccccct tcgcgcagcg gttcgcagag   1320
acgctggact actacacggc catcttcgag tccatcgacc tggcgctgcc gagggacgac   1380
agggagcgga tcaacatcga gcagcactgc ctggcccggg agatcgtgaa cctggtggcc   1440
tgcgagggcg aggagcgggt ggagcggcac gaggtgttcg gcaagtggaa ggcgcggctg   1500
atgatggccg ggttcagccc gtccccgctc agcgcgctgg tgaacgccac catcaagacg   1560
ctgctgcaga gctactcgcc ggactacaag ctcgccgaga gggacggcgt gctctacctc   1620
ggctggaaga acaggcccct gatcgtctca tcggcatggc actag                   1665
```

<210> SEQ ID NO 183  
<211> LENGTH: 1677  
<212> TYPE: DNA  
<213> ORGANISM: Zea mays

<400> SEQUENCE: 183

```
atggccgacc ctccaacttc ccgcatggtg cagcacccct cggcgacat cccaagccag    60 actcccaagc aattcctata ctctggtagc tcacagcacc tctgccatcc ataccagtca   120
gcttcggacg cccacgtcgc gccgcagcgt cactacaccg tgaggtccca gtctcagtct   180
cagtcaccgg atgctgggtc tgaagacttt gagacgcaca gcaggcagta cacgctggac   240
tcctcttcgg cttccggttg ctcagggcac ggttctccct cctgtcagag tgtccatgcc   300
gggagtcgca gccctgtgtc tcactctcat gacgacagcc actccggctc caccaatggc   360
aacggatcgc ctgcgagcgc gtcgtgtgtc accgaggacc ctactgacct caagcagaaa   420
ctgaaggatc ttgaggctgt gatgctgggg acggacacgg acccagaaac cgtggacagt   480
ctcgagatcg ccatagcgga ccggcttttcg gtggagcccg aggagtggaa gaacaacatg   540
gtgagcgtgc ctagagggga cctgaaggag ctgctgatcg cctgcgccag gcagtggag    600 caaaacaacg gctactccat cgacctgatg gtcccagagc tgaggaagat ggtgtcggtg   660
tccggcgagc cgctcgagag gctgggagcc tacatggtgg aaggactcgt cgccaggctc   720
gccgcctctg gcagctccat ctacaaggct ctgaggtgta aggagcccag gagctccgac   780
ctcctctcct acatgcactt cctgtacgag gcctgcccct acttcaagtt cggctacatg   840
```

-continued

```
tcggccaacg gcgcgatcgc ggaggccgtc aagggagaag acaggatcca tatcatcgac    900
ttccacatcg ctcagggggc gcagtgggtg tctctcctcc aagcccttgc ggcccggcct    960
ggcgggccac cgttcgtgag ggtcaccggc attgatgatc ccgtttcagc ttacgcccga   1020
ggcggcggct tagagttggt cggcaagagg ctgtcacaca tcgctggcct ctacaaggtg   1080 cccttcagt cgacgcggt cgccatctcc ggcagcgagg tggaggaggg gcatctgggc    1140
gtcgtccctg gcgaagccgt cgccgtcaac tttactctag agctgcacca tatccccgac   1200
gaaaccgtga gcacggcgaa ccacagggac cgggtcctga ggctggtcaa gggcctgtcg   1260
cccagggtgc tcacgctggt ggagcaggag tccaacacca cacggcccc cttcgcgcag    1320 cggttcgcgg agacgctgga ctactacgcg gccatcttcg agtccatcga cctggcgctg   1380
cccaggggcg acagggagcg gatcaacatc gagcagcact gcctggctcg ggagatcgtc   1440
aacctggtgg cctgcgaggg cgaggagcgg gtggagcggc acgaggtgtt cggcaagtgg   1500
aaggcgcgcc tcatgatggc cgggttcagg ccgtccccgc tcagcgcgct ggtcaacgcc   1560
accatcaaga cgctgctgca gagctactcg ccggactaca agctcgccga gagggaaggc   1620
gtgctctacc tcggctggaa gaacaggccc ctcattgttt catcggcatg gcactag     1677
```

<210> SEQ ID NO 184
<211> LENGTH: 23
<212> TYPE: DNA
<213> ORGANISM: artificial sequence
<220> FEATURE:
<223> OTHER INFORMATION: Primer

<400> SEQUENCE: 184
atggcgaatt caggaaatta tgg                                              23

<210> SEQ ID NO 185
<211> LENGTH: 21
<212> TYPE: DNA
<213> ORGANISM: artificial sequence
<220> FEATURE:
<223> OTHER INFORMATION: Primer

<400> SEQUENCE: 185
tcacttcctc aatagcccttt g                                               21

<210> SEQ ID NO 186
<211> LENGTH: 23
<212> TYPE: DNA
<213> ORGANISM: artificial sequence
<220> FEATURE:
<223> OTHER INFORMATION: Primer

<400> SEQUENCE: 186
atgaggcact atagagggt aag                                               23

<210> SEQ ID NO 187
<211> LENGTH: 22
<212> TYPE: DNA
<213> ORGANISM: artificial sequence
<220> FEATURE:
<223> OTHER INFORMATION: Primer

<400> SEQUENCE: 187
tcaagctctc tcagggaaat tg                                               22

<210> SEQ ID NO 188

```
<211> LENGTH: 23
<212> TYPE: DNA
<213> ORGANISM: artificial sequence
<220> FEATURE:
<223> OTHER INFORMATION: Primer

<400> SEQUENCE: 188
atgcaactag caagtaacac tag                                             23

<210> SEQ ID NO 189
<211> LENGTH: 23
<212> TYPE: DNA
<213> ORGANISM: artificial sequence
<220> FEATURE:
<223> OTHER INFORMATION: Primer

<400> SEQUENCE: 189
tcaaaaacca gaattaggag gtg                                             23

<210> SEQ ID NO 190
<211> LENGTH: 55
<212> TYPE: DNA
<213> ORGANISM: artificial sequence
<220> FEATURE:
<223> OTHER INFORMATION: Primer

<400> SEQUENCE: 190
atggtctcag ccttgactca agtcattgga aacatgtacg gacagtgcaa tatag         55

<210> SEQ ID NO 191
<211> LENGTH: 31
<212> TYPE: DNA
<213> ORGANISM: artificial sequence
<220> FEATURE:
<223> OTHER INFORMATION: Primer

<400> SEQUENCE: 191
ggggacaagt ttgtacaaaa aagcaggctt g                                    31

<210> SEQ ID NO 192
<211> LENGTH: 56
<212> TYPE: DNA
<213> ORGANISM: artificial sequence
<220> FEATURE:
<223> OTHER INFORMATION: Primer

<400> SEQUENCE: 192
atggtctcag ccttgactca agtcattgga aacatggcta caccaaacga agtatc        56

<210> SEQ ID NO 193
<211> LENGTH: 31
<212> TYPE: DNA
<213> ORGANISM: artificial sequence
<220> FEATURE:
<223> OTHER INFORMATION: Primer

<400> SEQUENCE: 193
ggggacaagt ttgtacaaaa aagcaggctt g                                    31

<210> SEQ ID NO 194
<211> LENGTH: 24
<212> TYPE: DNA
<213> ORGANISM: artificial sequence
<220> FEATURE:
<223> OTHER INFORMATION: Primer

<400> SEQUENCE: 194
```

```
tcttatatct agtgtatttt cacc                                        24
```

<210> SEQ ID NO 195
<211> LENGTH: 25
<212> TYPE: DNA
<213> ORGANISM: artificial sequence
<220> FEATURE:
<223> OTHER INFORMATION: Primer

<400> SEQUENCE: 195

```
ctttgggaat aggttttttt ttttc                                       25
```

<210> SEQ ID NO 196
<211> LENGTH: 23
<212> TYPE: DNA
<213> ORGANISM: artificial sequence
<220> FEATURE:
<223> OTHER INFORMATION: Primer

<400> SEQUENCE: 196

```
gaccaataga tgatatacaa gtg                                         23
```

<210> SEQ ID NO 197
<211> LENGTH: 23
<212> TYPE: DNA
<213> ORGANISM: artificial sequence
<220> FEATURE:
<223> OTHER INFORMATION: Primer

<400> SEQUENCE: 197

```
ttctagtcac ttcaatgatc tgc                                         23
```

<210> SEQ ID NO 198
<211> LENGTH: 25
<212> TYPE: DNA
<213> ORGANISM: artificial sequence
<220> FEATURE:
<223> OTHER INFORMATION: Primer

<400> SEQUENCE: 198

```
atgtacaagc agcctagaca agagc                                       25
```

<210> SEQ ID NO 199
<211> LENGTH: 25
<212> TYPE: DNA
<213> ORGANISM: artificial sequence
<220> FEATURE:
<223> OTHER INFORMATION: Primer

<400> SEQUENCE: 199

```
tcatttccaa gcacacgagg caacc                                       25
```

<210> SEQ ID NO 200
<211> LENGTH: 27
<212> TYPE: DNA
<213> ORGANISM: artificial sequence
<220> FEATURE:
<223> OTHER INFORMATION: Primer

<400> SEQUENCE: 200

```
tttccaagca cacgaggcaa ccaaatc                                     27
```

<210> SEQ ID NO 201
<211> LENGTH: 20
<212> TYPE: DNA

```
<213> ORGANISM: artificial sequence
<220> FEATURE:
<223> OTHER INFORMATION: Primer

<400> SEQUENCE: 201
cctgagttgc agagtggaga                                            20

<210> SEQ ID NO 202
<211> LENGTH: 30
<212> TYPE: DNA
<213> ORGANISM: artificial sequence
<220> FEATURE:
<223> OTHER INFORMATION: Primer

<400> SEQUENCE: 202
tcttttatat gactacttat gatacaattc                                 30

<210> SEQ ID NO 203
<211> LENGTH: 24
<212> TYPE: DNA
<213> ORGANISM: artificial sequence
<220> FEATURE:
<223> OTHER INFORMATION: Primer

<400> SEQUENCE: 203
atggttaagt tcacaacttt cctc                                       24

<210> SEQ ID NO 204
<211> LENGTH: 22
<212> TYPE: DNA
<213> ORGANISM: artificial sequence
<220> FEATURE:
<223> OTHER INFORMATION: Primer

<400> SEQUENCE: 204
gggattgtgg ttttgagtgt ag                                         22

<210> SEQ ID NO 205
<211> LENGTH: 18
<212> TYPE: DNA
<213> ORGANISM: artificial sequence
<220> FEATURE:
<223> OTHER INFORMATION: Primer

<400> SEQUENCE: 205
taggtcacga ttcgtgcc                                              18

<210> SEQ ID NO 206
<211> LENGTH: 25
<212> TYPE: DNA
<213> ORGANISM: artificial sequence
<220> FEATURE:
<223> OTHER INFORMATION: Primer

<400> SEQUENCE: 206
cacaaataag caagtaagaa tcttt                                      25

<210> SEQ ID NO 207
<211> LENGTH: 25
<212> TYPE: DNA
<213> ORGANISM: artificial sequence
<220> FEATURE:
<223> OTHER INFORMATION: Primer

<400> SEQUENCE: 207
atggacaatg taagaggttc aataa                                      25
```

<210> SEQ ID NO 208
<211> LENGTH: 22
<212> TYPE: DNA
<213> ORGANISM: artificial sequence
<220> FEATURE:
<223> OTHER INFORMATION: Primer

<400> SEQUENCE: 208
tcacttccat gcacaagatg ag                                              22

<210> SEQ ID NO 209
<211> LENGTH: 21
<212> TYPE: DNA
<213> ORGANISM: artificial sequence
<220> FEATURE:
<223> OTHER INFORMATION: Primer

<400> SEQUENCE: 209
cttccatgca caagatgaga c                                               21

<210> SEQ ID NO 210
<211> LENGTH: 24
<212> TYPE: DNA
<213> ORGANISM: artificial sequence
<220> FEATURE:
<223> OTHER INFORMATION: Primer

<400> SEQUENCE: 210
agtagttaga gccaccatac ccaa                                            24

<210> SEQ ID NO 211
<211> LENGTH: 24
<212> TYPE: DNA
<213> ORGANISM: artificial sequence
<220> FEATURE:
<223> OTHER INFORMATION: Primer

<400> SEQUENCE: 211
gttcagatgt aaagtcctca actg                                            24

<210> SEQ ID NO 212
<211> LENGTH: 21
<212> TYPE: DNA
<213> ORGANISM: artificial sequence
<220> FEATURE:
<223> OTHER INFORMATION: Primer

<400> SEQUENCE: 212
ggctcctctt aacccaaagg c                                               21

<210> SEQ ID NO 213
<211> LENGTH: 22
<212> TYPE: DNA
<213> ORGANISM: artificial sequence
<220> FEATURE:
<223> OTHER INFORMATION: Primer

<400> SEQUENCE: 213
cacaccatca ccagaatcca gc                                              22

<210> SEQ ID NO 214
<211> LENGTH: 22
<212> TYPE: DNA
<213> ORGANISM: artificial sequence
<220> FEATURE:

-continued

```
<223> OTHER INFORMATION: Primer

<400> SEQUENCE: 214
accaccatta acgtgcgtca ac                                    22

<210> SEQ ID NO 215
<211> LENGTH: 24
<212> TYPE: DNA
<213> ORGANISM: artificial sequence
<220> FEATURE:
<223> OTHER INFORMATION: Primer

<400> SEQUENCE: 215
gatcttggcg agagaatcgg tatc                                  24

<210> SEQ ID NO 216
<211> LENGTH: 23
<212> TYPE: DNA
<213> ORGANISM: artificial sequence
<220> FEATURE:
<223> OTHER INFORMATION: Primer

<400> SEQUENCE: 216
ctctcgttcc agagctcgca aaa                                   23

<210> SEQ ID NO 217
<211> LENGTH: 23
<212> TYPE: DNA
<213> ORGANISM: artificial sequence
<220> FEATURE:
<223> OTHER INFORMATION: Primer

<400> SEQUENCE: 217
aagaacacgc atcctacgca tcc                                   23

<210> SEQ ID NO 218
<211> LENGTH: 20
<212> TYPE: DNA
<213> ORGANISM: artificial sequence
<220> FEATURE:
<223> OTHER INFORMATION: Primer

<400> SEQUENCE: 218
tttgcctttg tgcttcatca                                       20

<210> SEQ ID NO 219
<211> LENGTH: 20
<212> TYPE: DNA
<213> ORGANISM: artificial sequence
<220> FEATURE:
<223> OTHER INFORMATION: Primer

<400> SEQUENCE: 219
catcgcggca tagtagttca                                       20

<210> SEQ ID NO 220
<211> LENGTH: 20
<212> TYPE: DNA
<213> ORGANISM: artificial sequence
<220> FEATURE:
<223> OTHER INFORMATION: Primer

<400> SEQUENCE: 220
acgaaaacca atccaaccac                                       20
```

```
<210> SEQ ID NO 221
<211> LENGTH: 20
<212> TYPE: DNA
<213> ORGANISM: artificial sequence
<220> FEATURE:
<223> OTHER INFORMATION: Primer

<400> SEQUENCE: 221
attggacgct aggcatcaag                                               20

<210> SEQ ID NO 222
<211> LENGTH: 20
<212> TYPE: DNA
<213> ORGANISM: artificial sequence
<220> FEATURE:
<223> OTHER INFORMATION: Primer

<400> SEQUENCE: 222
gaggttccaa aagtggctga                                               20

<210> SEQ ID NO 223
<211> LENGTH: 20
<212> TYPE: DNA
<213> ORGANISM: artificial sequence
<220> FEATURE:
<223> OTHER INFORMATION: Primer

<400> SEQUENCE: 223
cgttggtttg atgaatgtcg                                               20

<210> SEQ ID NO 224
<211> LENGTH: 20
<212> TYPE: DNA
<213> ORGANISM: artificial sequence
<220> FEATURE:
<223> OTHER INFORMATION: Primer

<400> SEQUENCE: 224
ggacgggaag atatgaagca                                               20

<210> SEQ ID NO 225
<211> LENGTH: 20
<212> TYPE: DNA
<213> ORGANISM: artificial sequence
<220> FEATURE:
<223> OTHER INFORMATION: Primer

<400> SEQUENCE: 225
agggaaattg gtggtagcag                                               20

<210> SEQ ID NO 226
<211> LENGTH: 20
<212> TYPE: DNA
<213> ORGANISM: artificial sequence
<220> FEATURE:
<223> OTHER INFORMATION: Primer

<400> SEQUENCE: 226
caggcacgaa ttggaagagt                                               20

<210> SEQ ID NO 227
<211> LENGTH: 20
<212> TYPE: DNA
<213> ORGANISM: artificial sequence
<220> FEATURE:
<223> OTHER INFORMATION: Primer
```

<400> SEQUENCE: 227
aggcattagt ccacccacag								20

<210> SEQ ID NO 228
<211> LENGTH: 24
<212> TYPE: DNA
<213> ORGANISM: artificial sequence
<220> FEATURE:
<223> OTHER INFORMATION: Primer

<400> SEQUENCE: 228
ggatatgaca aggaagatag agca							24

<210> SEQ ID NO 229
<211> LENGTH: 22
<212> TYPE: DNA
<213> ORGANISM: artificial sequence
<220> FEATURE:
<223> OTHER INFORMATION: Primer

<400> SEQUENCE: 229
tgcaataaac tcttgcttgg tc							22

<210> SEQ ID NO 230
<211> LENGTH: 18
<212> TYPE: DNA
<213> ORGANISM: artificial sequence
<220> FEATURE:
<223> OTHER INFORMATION: Primer

<400> SEQUENCE: 230
gcatcagctc ggctcaat								18

<210> SEQ ID NO 231
<211> LENGTH: 21
<212> TYPE: DNA
<213> ORGANISM: artificial sequence
<220> FEATURE:
<223> OTHER INFORMATION: Primer

<400> SEQUENCE: 231
gcattcttct tctccaacac c								21

<210> SEQ ID NO 232
<211> LENGTH: 20
<212> TYPE: DNA
<213> ORGANISM: artificial sequence
<220> FEATURE:
<223> OTHER INFORMATION: Primer

<400> SEQUENCE: 232
cccggcttaa cttccctaac								20

<210> SEQ ID NO 233
<211> LENGTH: 20
<212> TYPE: DNA
<213> ORGANISM: artificial sequence
<220> FEATURE:
<223> OTHER INFORMATION: Primer

<400> SEQUENCE: 233
tagatctggc gacgaaacct								20

<210> SEQ ID NO 234
<211> LENGTH: 20

```
<212> TYPE: DNA
<213> ORGANISM: artificial sequence
<220> FEATURE:
<223> OTHER INFORMATION: Primer

<400> SEQUENCE: 234
ggctagggag aggcagaaac                                              20

<210> SEQ ID NO 235
<211> LENGTH: 20
<212> TYPE: DNA
<213> ORGANISM: artificial sequence
<220> FEATURE:
<223> OTHER INFORMATION: Primer

<400> SEQUENCE: 235
tccaccttgg agttggagtc                                              20

<210> SEQ ID NO 236
<211> LENGTH: 22
<212> TYPE: DNA
<213> ORGANISM: artificial sequence
<220> FEATURE:
<223> OTHER INFORMATION: Primer

<400> SEQUENCE: 236
aaagacgcgt gatcgagagc tg                                           22

<210> SEQ ID NO 237
<211> LENGTH: 24
<212> TYPE: DNA
<213> ORGANISM: artificial sequence
<220> FEATURE:
<223> OTHER INFORMATION: Primer

<400> SEQUENCE: 237
acgtgttgct caatcttgtc tcac                                         24

<210> SEQ ID NO 238
<211> LENGTH: 22
<212> TYPE: DNA
<213> ORGANISM: artificial sequence
<220> FEATURE:
<223> OTHER INFORMATION: Primer

<400> SEQUENCE: 238
aagtagctgt gcggaggaat gg                                           22

<210> SEQ ID NO 239
<211> LENGTH: 22
<212> TYPE: DNA
<213> ORGANISM: artificial sequence
<220> FEATURE:
<223> OTHER INFORMATION: Primer

<400> SEQUENCE: 239
gggtaagtgg cagcgacgat tt                                           22

<210> SEQ ID NO 240
<211> LENGTH: 23
<212> TYPE: DNA
<213> ORGANISM: artificial sequence
<220> FEATURE:
<223> OTHER INFORMATION: Primer

<400> SEQUENCE: 240
```

```
tgatgacacc cgagtggtct ttg                                              23

<210> SEQ ID NO 241
<211> LENGTH: 23
<212> TYPE: DNA
<213> ORGANISM: artificial sequence
<220> FEATURE:
<223> OTHER INFORMATION: Primer

<400> SEQUENCE: 241
acaccgatgg agtcttggag aac                                              23

<210> SEQ ID NO 242
<211> LENGTH: 23
<212> TYPE: DNA
<213> ORGANISM: artificial sequence
<220> FEATURE:
<223> OTHER INFORMATION: Primer

<400> SEQUENCE: 242
accttaccag cccttgacat atg                                              23

<210> SEQ ID NO 243
<211> LENGTH: 23
<212> TYPE: DNA
<213> ORGANISM: artificial sequence
<220> FEATURE:
<223> OTHER INFORMATION: Primer

<400> SEQUENCE: 243
gacttgacca aacatctcac gac                                              23

<210> SEQ ID NO 244
<211> LENGTH: 21
<212> TYPE: DNA
<213> ORGANISM: artificial sequence
<220> FEATURE:
<223> OTHER INFORMATION: Primer

<400> SEQUENCE: 244
agtccgttga gatgcaccat g                                                21

<210> SEQ ID NO 245
<211> LENGTH: 22
<212> TYPE: DNA
<213> ORGANISM: artificial sequence
<220> FEATURE:
<223> OTHER INFORMATION: Primer

<400> SEQUENCE: 245
cacataccca cgcttcagat cc                                               22
```

MEANS AND METHODS FOR IMPROVED REGENERATION

FIELD OF THE INVENTION

The present invention relates to the field of plant genetic engineering, particularly the modulation of gene expression in plant cells for improved regeneration competence. The invention discloses means and methods wherein the Ethylene Response Factor (ERF) and Phytochrome A Signal Transduction 1 (PAT1) transcription factor complex activity in plant cells grants increased regeneration.

BACKGROUND

Most plant cells are totipotent, which requires the acquisition of stem cell potential (dedifferentiation) in response to proper stimuli and expressing this potential during subsequent morphogenesis (regeneration).

During dedifferentiation, genome reprogramming occurs to establish a stem cell status, and subsequently, gene activity patterns change in a systematic manner while entering the regeneration phase[36,37]. Regeneration of a tissue damaged by injury represents a physiological response for organ recovery[1-3]. Although this regeneration process is conserved across multicellular taxa, plants appear to display extremely high regenerative capacities, a feature widely used in tissue culture for clonal propagation and grafting[4,5]. Regenerated cells arise predominantly from pre-existing populations of division-competent cells[6,7], however, the mechanisms by which these cells are triggered to divide in response to injury remain largely elusive[8]. In *Arabidopsis thaliana*, dividing root cells are mostly confined to specialized regions called meristems, of which the centre contains stem cells capable of self-renewal and differentiation into specific cell types. The stem cells' undifferentiated status is controlled by the quiescent centre (QC), containing a group of mitotically inactive cells, which are characterized by the expression of WUSCHEL RELATED HOMEOBOX5 (WOX5)[10-12]. Under DNA damage-inducing conditions, most stem cells are selectively killed[13]. Although this mechanism efficiently prevents deleterious mutations to be propagated through the organism, the dead stem cells need to be replaced to maintain a functional meristem and growth. Previously, the ETHYLENE RESPONSE FACTOR 115 (ERF115), a member of the ethylene response transcription factor family, has been found to be a rate-limiting factor for QC cell division and essential for the re-establishment of a functional stem cell niche (SCN) under DNA stress conditions[14,18].

Members of the APETALA2 (AP2) family of proteins play critical roles in a variety of important biological events including development, plant regeneration, cell division, etc. Accordingly, it is valuable to the field of agronomic development to identify and characterize novel AP2 family members and develop novel methods to modulate embryogenesis, transformation efficiencies, oil content, starch content and yield in a plant. The AP2/ERF transcription factor called EBE, or ERF114, is the closest homologue of ERF115, and is prominently expressed in proliferating cells and calli. Ectopic overexpression of ERF114 for cotyledons precultured on phytohormone-containing medium resulted in larger calli as a result from more pronounced cell proliferation leading to an increased cell number[38].

Furthermore, another member of the AP2 family that has been implicated in a variety of critical plant cellular functions is the Baby Boom protein (BBM). The BBM protein from *Arabidopsis* is preferentially expressed in seed and has been shown to play a central role in regulating embryo-specific pathways. Overexpression of BBM has been shown to induce spontaneous formation of somatic embryos and cotyledon-like structures on seedlings[39].

Current transformation technology provides an opportunity to engineer plants with desired traits. Major advances in plant transformation have occurred over the last few years. However, in many major crop plants, serious genotype limitations still exist. Transformation of some agronomically important crop plants continues to be both difficult and time consuming. Optimization of medium components and/or explant material and source has led to success in some genotypes, mostly model genotypes, whereas the process of introgressing transgenes into production inbreds is still laborious, expensive and time consuming. Accordingly, methods are needed in the art to increase transformation efficiencies of plants. Especially the regeneration step during plant transformation is often long and requires several hormone treatments to obtain transgenic plants.

It would be advantageous to find alternatives or generic solutions for improved regeneration capacities during transformation and regeneration of plants, in particular with reduced use of hormones. Further, it is often necessary to reduce the activity of a transgene because the transgene may negatively affect the growth or fertility of the plant. So in combination with generic regeneration capacity improvements, the further optimization of transient expression or recombination systems used to excise or limit the presence of the transgene are needed in the art.

SUMMARY OF THE INVENTION

The invention relates to the finding that the AP2 transcription factor Ethylene Response Factor 115 (ERF115) in complex with the Phytochrome A Signal Transduction 1 (PAT1) transcription factor revealed a function in sustaining the root meristem by promoting cell renewal after stem cell loss. Unexpectedly, ectopic expression of the ERF115-PAT1 complex lead to spontaneous callus formation thereby granting regeneration competence, even in the absence of phytohormone induction media. Means and methods to improve regeneration of plants include the ectopic expression of said ERF115-PAT1 complex as a suitable alternative for increasing plant transformation efficiency.

The first aspect of the invention relates to a combination of a first and second chimeric gene construct comprising the operably linked DNA elements being a) a promoter suitable for plant expression, b) a DNA region encoding an ERF with the SCL/PAT1 interaction motif, and a PAT1 transcription factor, for the first and second construct respectively, and c) a 3' end region to terminate transcription and provide polyadenylation signals to obtain functional expression of said chimeric constructs in plant tissue. Alternatively, an aspect of the invention relates to a chimeric gene construct comprising the operably linked DNA elements being a) a promoter suitable for plant expression, b) a multicistronic DNA region encoding an ERF transcription factor with the SCL/PAT1 interaction motif, coupled to a DNA region encoding PAT1 and c) a 3' end region comprising transcription termination and polyadenylation signals functioning in cells of a plant.

In one embodiment, said chimeric gene construct of the present invention comprises a b) DNA region that encodes an ERF transcription factor with SCL/PAT1 interaction motif that is ERF115. A more specific embodiment relates to said chimeric gene constructs, wherein said b) DNA region is selected from the list of SEQ ID NO: 51-100 encoding an ERF115 transcription factor protein corresponding with a protein sequence selected from the list of SEQ ID NO: 1 to 50, which is a list consisting of a number of ERF115 orthologue sequences from different plant species; and wherein said b) DNA region is selected from the list of SEQ ID NO: 126-150 encoding a PAT1 transcription factor protein that is a protein with corresponding sequence selected from the list of SEQ ID NO: 101-125, a list consisting of a number of PAT1 orthologue sequences from different plant species.

Another embodiment describes said chimeric constructs, further comprising a chimeric gene construct comprising the operably linked DNA elements being a) a plant expressible promoter, b) a DNA region encoding a site-specific recombinase that is capable of recognizing and implementing recombination at said recombination sites with the goal to remove the chimeric genes from the insertion sites, and c) a 3' end region comprising transcription termination and polyadenylation signals functioning in cells of a plant, and wherein said chimeric constructs begin and end by flanking recombination sites to allow excision of said chimeric genes.

Another embodiment relates to a set of at least one recombinant vector comprising said chimeric gene constructs. In further embodiments, a plant, plant cell or plant seed comprising said chimeric gene construct(s) or comprising said recombinant vector(s) are described. And in a particular embodiment, said plant, plant cell or plant seed co-express ERF and PAT1 transcription factors. In one embodiment, said plant is a member of the Gramineae.

In another aspect, the invention relates to the use of said chimeric gene construct(s) of the present invention, or said recombinant vector(s) or said plant, plant cell or plant seed, to obtain increased regeneration of plant tissue cells. One alternative embodiment further relates to the use of a chimeric gene construct comprising a) a plant expressible promoter, b) a DNA region encoding PAT1, and c) a 3' end region comprising transcription termination and polyadenylation signals functioning in cells of a plant, for obtaining increased regeneration of plan tissue cells.

Another embodiment relates to the use of the chimeric gene construct(s) of the present invention or said recombinant vector(s) or said plant, plant cell or plant seed, to obtain increased callus formation of plant tissue cells are described. Alternatively, the embodiment relates to the use of a chimeric gene construct comprising a) a plant expressible promoter, b) a DNA region encoding Phytochrome A Signal Transduction 1 (PAT1) and c) a 3' end region comprising transcription termination and polyadenylation signals functioning in cells of a plant, to obtain increased callus formation of plant tissue cells.

A further embodiment relates to the use of said chimeric gene construct(s) or of said recombinant vector(s) or of said plant, plant cell or plant seed, to obtain increases callus formation of plant tissue cells, wherein said recombinase is activated prior to regeneration from callus to remove said chimeric constructs from said regenerated plant tissue cells.

Another aspect of the invention relates to a method for producing a transgenic plant, whereby the method comprises introduction of a plant cell with said chimeric gene construct (s) or with said recombinant vector(s) of the present invention, and isolating a plant regenerated from said method. Alternatively, said method for producing a transgenic plant comprises transient expression of said chimeric gene construct(s) during callus formation to improve plant cell regeneration, and isolating a plant regenerated from said method. In another embodiment, the invention relates to a method for producing a plant, whereby the method comprises introducing a plant cell with said chimeric gene construct(s) or said recombinant vector according, and wherein said site-specific recombinase is expressed prior to regeneration from callus, thereby excising said chimeric constructs comprising said DNA regions encoding ERF and PAT1 transcription factors, and said recombinase.

DESCRIPTION OF THE FIGURES

The patent or application file contains at least one drawing executed in color. Copies of this patent or patent application publication with color drawing(s) will be provided by the Office upon request and payment of the necessary fee.

The drawings described are only schematic and are non-limiting. In the drawings, the size of some of the elements may be exaggerated and not drawn on scale for illustrative purposes.

a, Protein interactions identified through TAP using ERF115 and SCL21 as bait. Arrowheads point towards co-purifying proteins. b, Yeast two-hybrid interaction of ERF115 full length and fragments with SCL21 and PAT1. Growth was verified on control medium (+HIS) or selective medium (−HIS) supplemented with 15 mM 3-Amino-1,2,4-triazole (3-AT), using β-glucuronidase (GUS) as a negative control. c, Yeast two-hybrid interaction of ERF2 and ERF6 without (−) or fused to the conserved ERF115 interaction motif (+) with SCL21. The assay was performed similar to (b). d-i, Root tips expressing ERF115 (dots) (d,e), SCL21 (no expression visible) (f,g), and PAT1 (dots) (h,i) under control conditions (d,f,h) or treated with bleomycin (e,g,i). Arrowheads indicate the quiescent center (QC). Cell walls are counterstained with propidium iodide (PI). Bars=50 µm. j-l, Expression of PAT1 (green) and ERF115 (red) in root tips 10 h15 to 11 h30 after recovery from bleomycin treatment. Arrowheads indicate the dividing QC cells, inset shows detail of a dividing QC cell co-expressing ERF115 and PAT1. Cell walls are counterstained (white) by SCRI Renaissance 2200 dye. Bars=25 µm.

Figure 2:
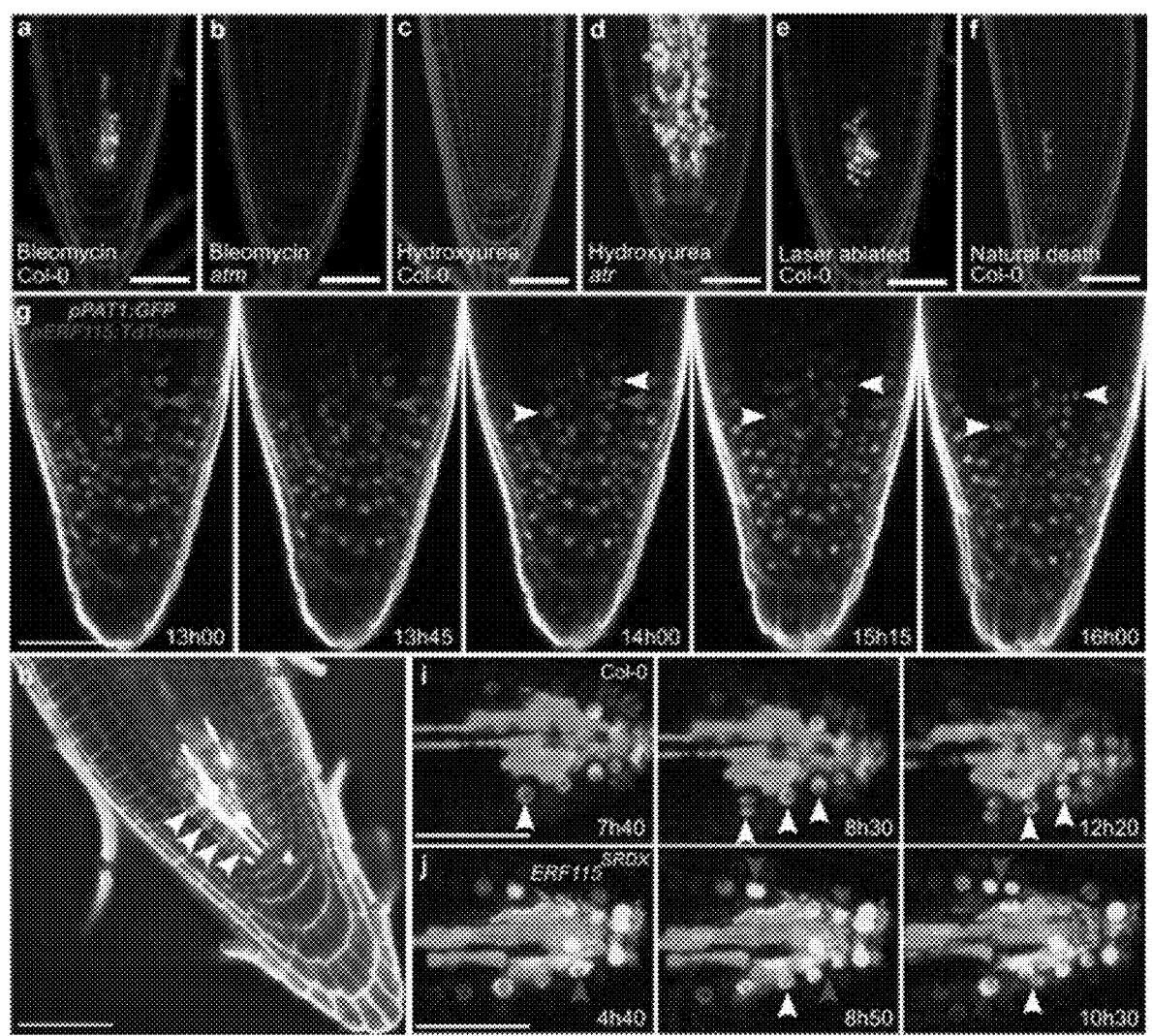

FIG. 2: ERF115 and PAT1 co-expression precedes stress-induced cell division.

a, b, ERF115 expression (green) upon bleomycin treatment of wild-type (a) and atm mutant (b) root tips. c, d, ERF115 expression (green) upon hydroxyurea treatment of wild-type (c) and atr mutant (d) root tips. e, f, Single cell death by laser ablation (e) or spontaneously occurring (f) triggers ERF115 expression (green). a-f, Cell walls are counterstained with PI. g, PAT1 (green) and ERF115 (red) expression in root tips 13 h to 16 h after recovery from bleomycin treatment. Cell walls are counterstained by SCRI Renaissance 2200 dye. h, Cells contacting dead cells express ERF115 (red) after 24-h recovery from bleomycin. Cell walls are counterstained with PI and SCRI Renaissance 2200 dye overlay. i, j, Wild-type (i) and ERF115$^{SRDX}$ mutant (j) roots recovering from bleomycin at the indicated time points, showing anticlinal and replenishing divisions indicated by expression of the WOX5 marker (white). Cell walls are counterstained in gray with PI. g-j, grey arrowheads: anticlinal divisions, white arrowheads: replenishing divisions. a-j, Bars=50 µm.

Figure 3:
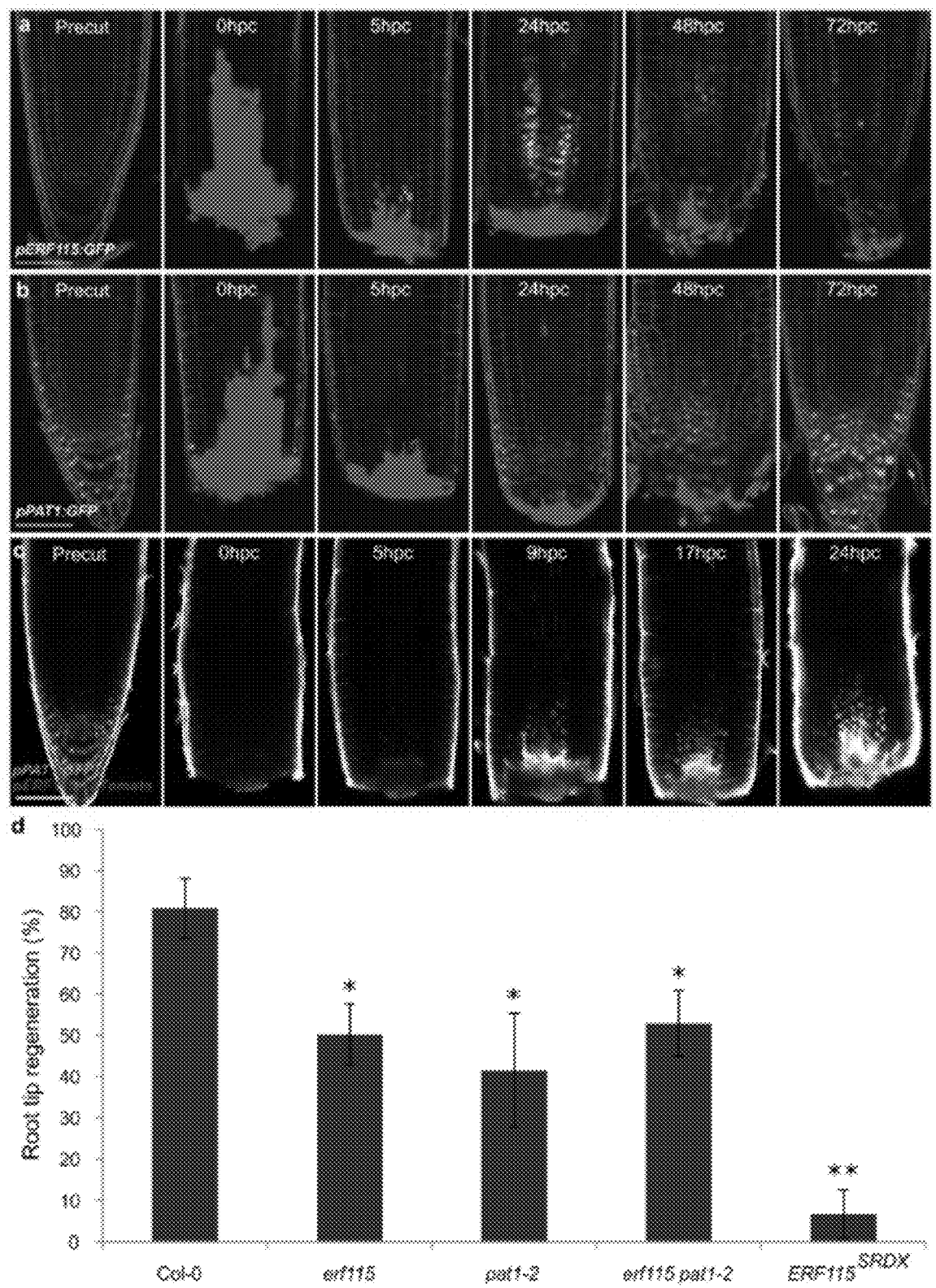

FIG. 3: ERF115-PAT1 activity is required for root tip regeneration.

a, b, Root tip excision showing the expression of ERF115 (dots) (a) and PAT1 (dots) (b) during the root tip regeneration process for the indicated time points (hpc=hours post cut). Cell walls are counterstained with PI. Bars=50 µm. c, Root tip excision showing the expression of ERF115 (red) and PAT1 (green) during the early root tip regeneration process for the indicated time points (hpc=hours post cut). Cell walls are counterstained in blue with SCRI Renaissance 2200 dye. Bar=50 µm. d, Quantification of root tip regeneration of wild-type, erf115, pat1-2, erf115-pat1-2 and ERF115$^{SRDX}$ seedlings 72 h after excision. Data indicate mean±s.e.m. for n=4 with >11 technical repeats each (* indicates p-value <0.01 compared with wild type, ** indicates p-value <0.01 compared with *, Fisher's exact test).

Figure 4:
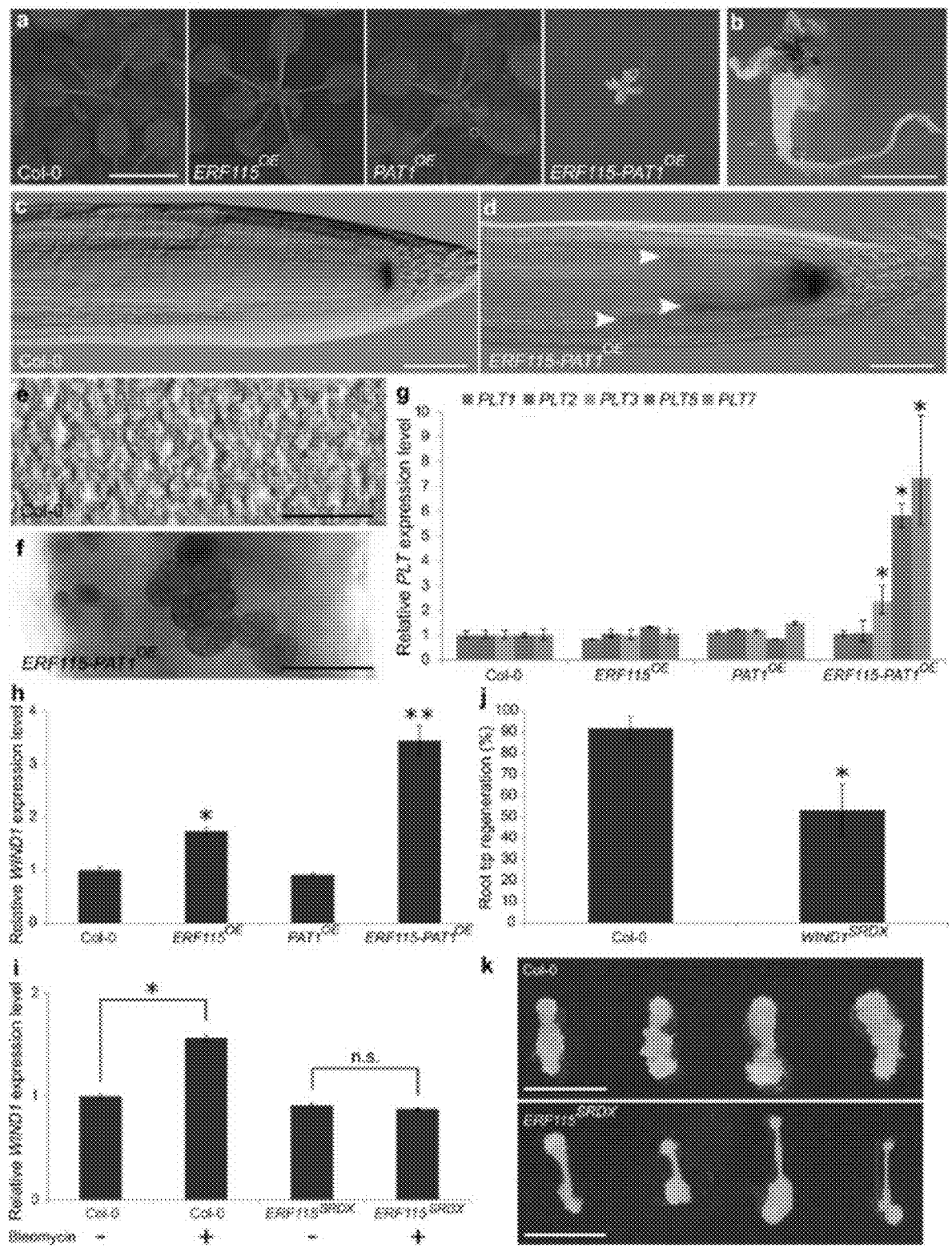

FIG. 4: ERF115-PAT1 activity triggers uncontrolled cell division.

a, Wild-type (Col-0), ERF115$^{OE}$, PAT1$^{OE}$ and ERF115-PAT1$^{OE}$ 3-week-old seedlings. Bar=1 cm. b, Three-week-old ERF115-PAT1$^{OE}$ seedling. Bar=0.5 cm. c, d, WOX5-positive cells (blue) are visualized by the β-glucuronidase (GUS) staining in wild-type (c) and ERF115-PAT1$^{OE}$ (d) roots at six days after stratification. Arrowheads indicate ectopic WOX5 expression. Bars=50 µm. e, f, Wild-type (e) and ERF115-PAT1$^{OE}$ (f) cotelydon. Blue GUS staining indicates cells ectopically expressing WOX5. Bars=0.1 mm. g, Relative PLT expression level in wild-type, ERF115$^{OE}$, PAT1$^{OE}$ and ERF115-PAT1$^{OE}$ 1-week-old seedlings. Data indicate mean±s.e.m. for n=3 (* indicates p-value <0.05 compared with wild type, Student's t-test). h, Relative WIND1 expression level in wild-type, ERF115$^{OE}$, PAT1$^{OE}$ and ERF115-PAT1$^{OE}$ 1-week-old seedlings. Data indicate mean±s.e.m. for n=3 (* indicates p-value <0.01 compared with wild type, ** indicates p-value <0.01 compared with *, Student's t-test). i, Relative WIND1 expression level in wild-type and ERF115$^{SRDX}$ root tips control treated or treated with 0.6 mg/L bleomycin for 24 h. Data indicate mean±s.e.m. for n=3 (* indicates p-value <0.01 compared, n.s. indicates not significant, Student's t-test). j, Quantification of root tip regeneration of wild-type and WIND1$^{SRDX}$ seedlings 72 h after excision. Data indicate mean±s.e.m. for n=4 with >35 technical repeats each (* indicates p-value <0.01 compared with wild type, Fisher's exact test). k, Callus generated from wild-type and ERF115$^{SRDX}$ hypocotyl segments. Bars=5 mm.

Figure 5:
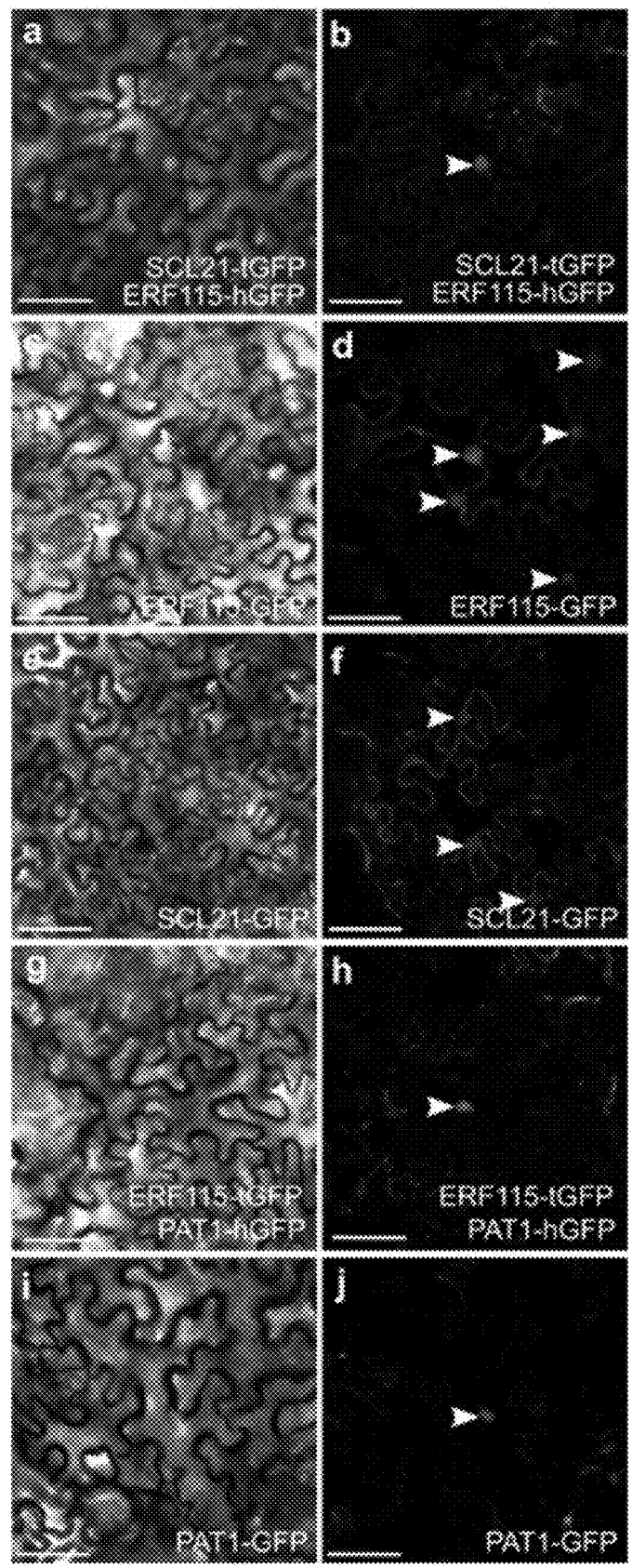

FIG. 5: ERF115, PAT1, and SCL21 protein localization in tobacco.

a, b, Bimolecular fluorescence complementation using ERF115-headGFP and SCL21-tailGFP reveals interaction in the nucleus in N. benthamiana leaf pavement cells by fluorescence and light microscope overlay (a) or solely fluorescence signal (b). c, d, Localization of the ERF115-GFP fusion protein in N. benthamiana leaf pavement cells by fluorescence and light microscope overlay (c) or solely fluorescence signal (d). e, f, Localization of the SCL21-GFP fusion protein in N. benthamiana leaf pavement cells by fluorescence and light microscope overlay (e) or solely fluorescence signal (f). g, h, Bimolecular fluorescence complementation using ERF115-tailGFP and PAT1-headGFP reveals interaction in the nucleus in N. benthamiana leaf pavement cells by fluorescence and light microscope overlay (g) or solely fluorescence signal (h). i, j, Localization of the PAT1-GFP fusion protein in N. benthamiana leaf pavement cells by fluorescence and light microscope overlay (i) or solely fluorescence signal cp. White arrowheads indicate GFP positive nuclei. Bars=50 µm.

Figure 6:
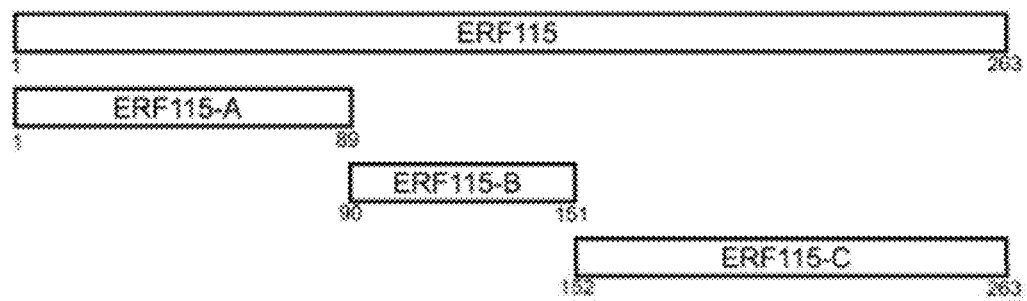
Figure 6:
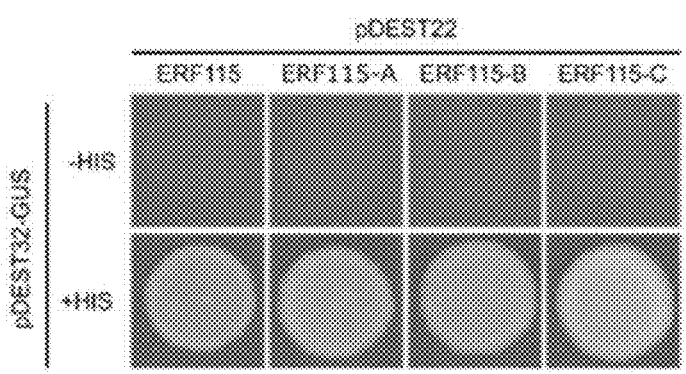
Figure 6:
Figure 6:
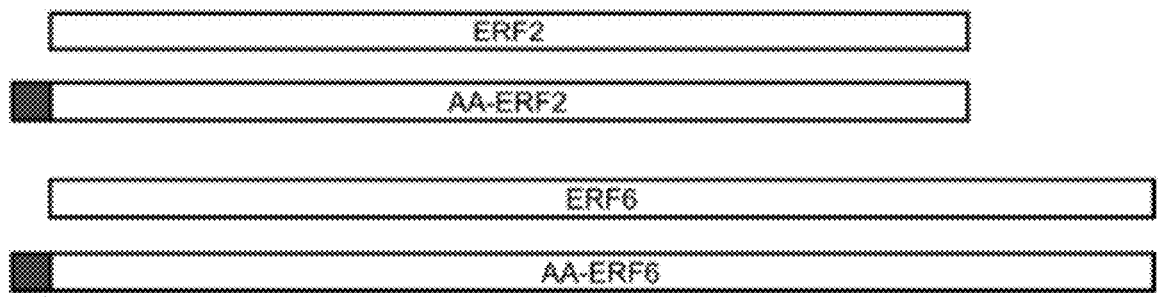

FIG. 6: Mapping of the ERF115 interaction domain.

a, Schematic overview of the ERF115 full-length protein and A-, B- and C-fragments. The B-fragment corresponds to the conserved AP2 DNA-binding domain. b, Negative control of the ERF115 fragment Y2H interaction using the GUS gene. c, Sequence alignment of the N-termini of the B-4 ERF subfamily revealing a (partially) conserved motif (box) in ERF115 (amino acids 1-89 of SEQ ID NO: 1), ERF114 (amino acids 1-87 of SEQ ID NO: 160), ERF113 (amino acids 1-37 of SEQ ID NO: 159), ERF111 (amino acids 1-182 of SEQ ID NO: 156), ERF110 (amino acids 1-74 of SEQ ID NO: 155), ERF109 (amino acids 1-133 of SEQ ID NO: 154), and ERF108 (amino acids 1-58 of SEQ ID NO: 153) as well as the schematic depicting the location of the motif (MV-SALTQVIGN (amino acids 44-54 of SEQ ID NO: 1)) in ERF115. d, Schematic overview of the chimeric ERF2 and ERF6 proteins harboring the ERF115-conserved domain (depicted in grey colored box) at their N-termini.

Figure 7:
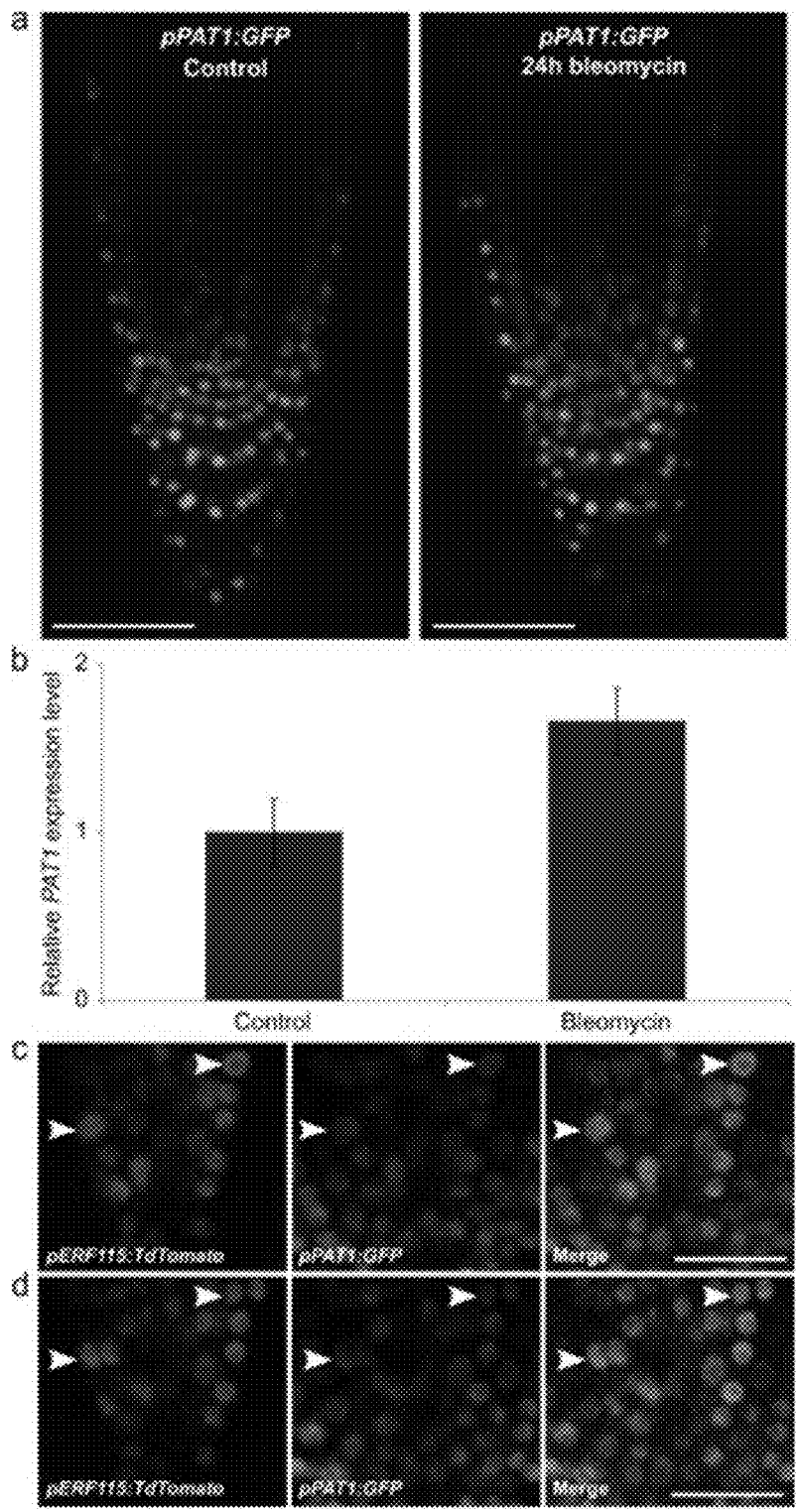

FIG. 7: PAT1 and ERF115 expression upon bleomycin treatment a, Expression of PAT1 (dots) under control conditions or treated with 0.6 mg/M bleomycin for 24 h. Bars=50 µm. b, Relative PAT1 expression level in wild-type root tips control treated or treated with 0.6 mg/L bleomycin for 24 h. Data indicate mean±s.e.m. for n=3. c, d, Detail of the meristematic region of the root presented in FIG. 2 g for the 14 h (c) and 16 h (d) time points showing the separate ERF115 (red) and PAT1 (green) expression profiles together with the merged image. White arrowheads indicate dividing cells. Bars=25 µm.

Figure 8:
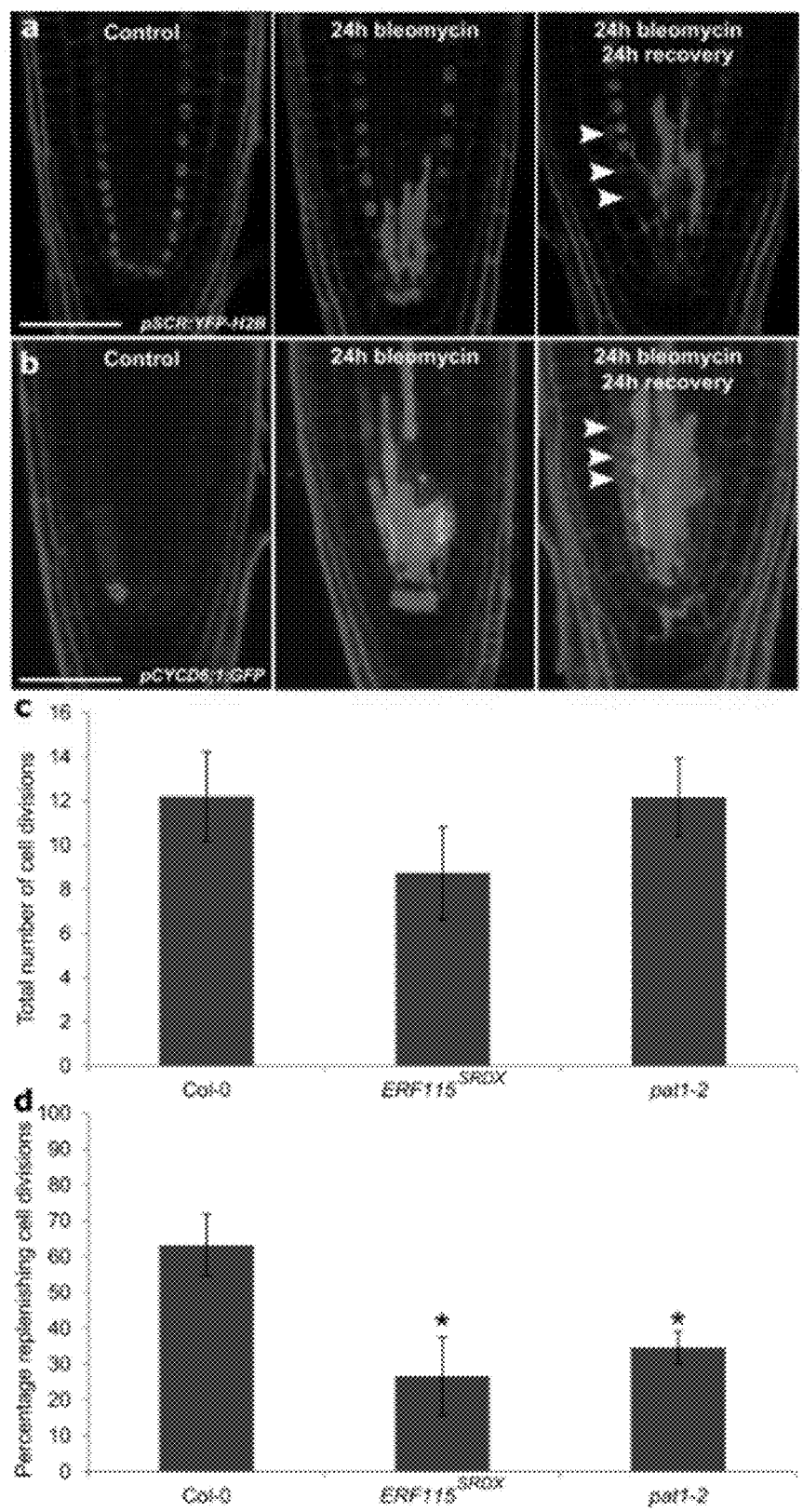

FIG. 8: Bleomycin triggers replenishing cell divisions.

a, Seedlings marked for endodermis (dots) were treated with 0.6 mg/L bleomycin and allowed to recover from the stress for 24 h. Cell walls are counterstained using PI. Arrowheads indicate replenishing cell divisions. Bar=50 µm. b, pCYCD6;1:GFP roots under control conditions are treated for 24 h with 0.6 mg/L bleomycin. Cell walls are counterstained using PI. Arrowheads indicate replenishing cell divisions. Bar=50 µm. c, Quantification of the total number of WOX5-positive cell divisions in wild-type (Col-0), ERF115$^{SRDX}$ and pat1-2 seedlings during the first 14 h of recovery after treatment with 0.6 mg/L bleomycin for 24 h. Data indicate mean±s.e.m. for n >3 (no significant differences were found, Student's t-test). d, Quantification of replenishing versus anticlinal divisions of WOX5-positive cells in wild-type (Col-0), ERF115$^{SRDX}$ and pat1-2 seedlings during the first 14 h of recovery after treatment with 0.6 mg/L bleomycin for 24 h. Data indicate mean±s.e.m. for n>3 (* indicates p-value <0.05 compared with wild type, Student's t-test).

Figure 9:
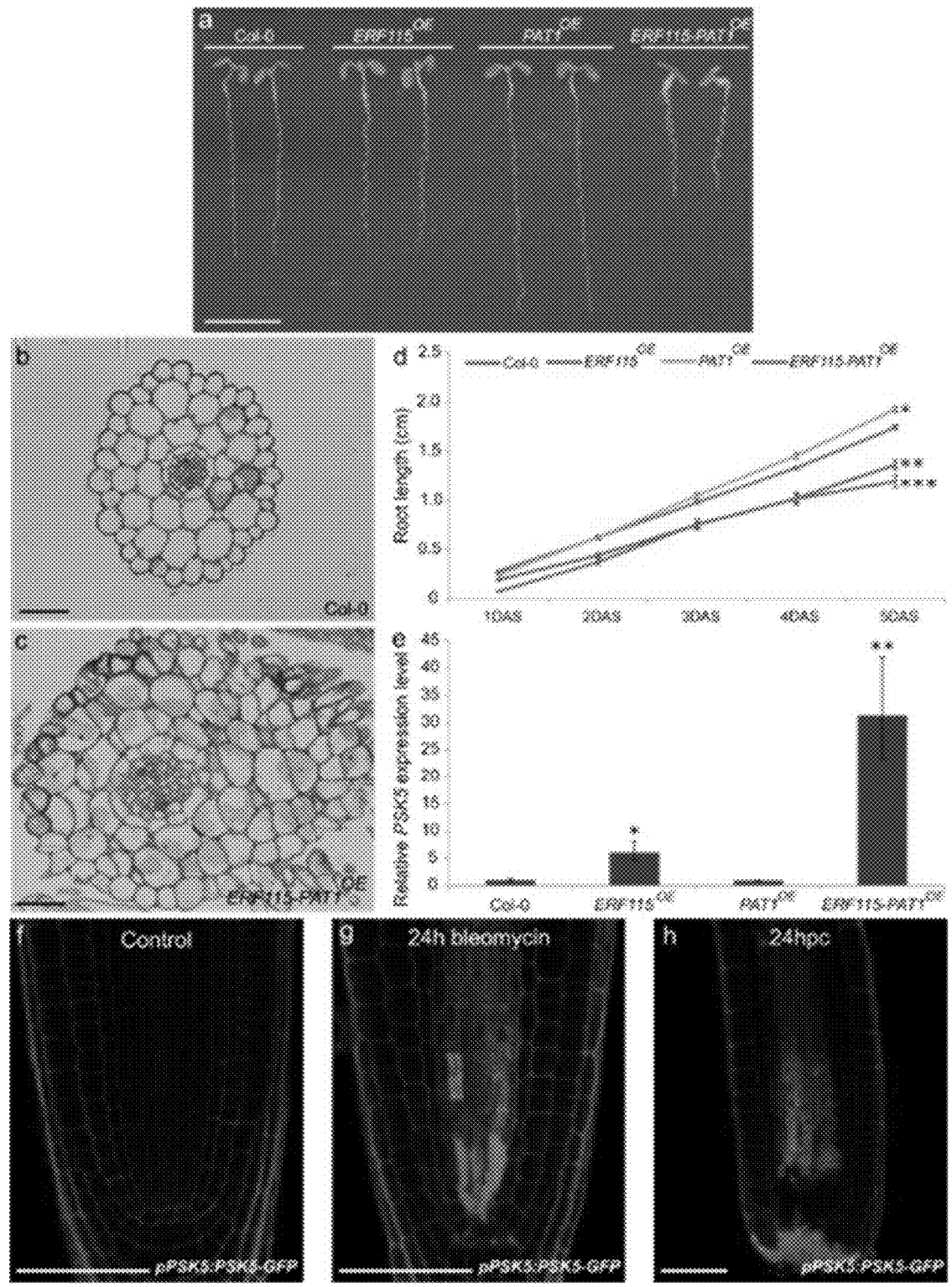

FIG. 9: Phenotypic data of ERF115-PAT1$^{OE}$ seedlings.

a, Wild-type (Col-0), ERF115$^{OE}$, PAT1$^{OE}$ and ERF115-PAT1$^{OE}$ seedlings at 7 DAS. Bar=1 cm. b, c Hypocotyl sections of 2 days after germination old wild-type (Col-0) (b) and ERF115-PAT1$^{OE}$ (c) seedlings. Bars=0.1 mm. d, Root length of wild-type (Col-0), ERF115$^{OE}$, PAT1$^{OE}$ and ERF115-PAT1$^{OE}$ plants at the indicated time points. Data indicate mean±s.e.m. for n>14 (* indicates p-value <0.01 at 7 DAS compared with wild type, ** indicates p-value <0.01 compared with wild type and *, * indicates p-value <0.01 compared with , Student's t-test). e, Relative PSK5 expression levels in wild-type (Col-0), ERF115$^{OE}$, PAT1$^{OE}$ and ERF115-PAT1$^{OE}$ 1-week-old seedlings. Data indicate mean±s.e.m. for n=3 (* indicates p-value <0.01 compared with wild type, ** indicates p-value <0.01 compared with *, Student's t-test). f-h, PSK5:PSK5-GFP roots under control conditions, treated for 24 h with 0.6 mg/L bleomycin and 24 h post cut. Cell walls are counterstained using PI. Arrowheads indicate replenishing cell divisions. Bar=50 µm.

Figure 10:
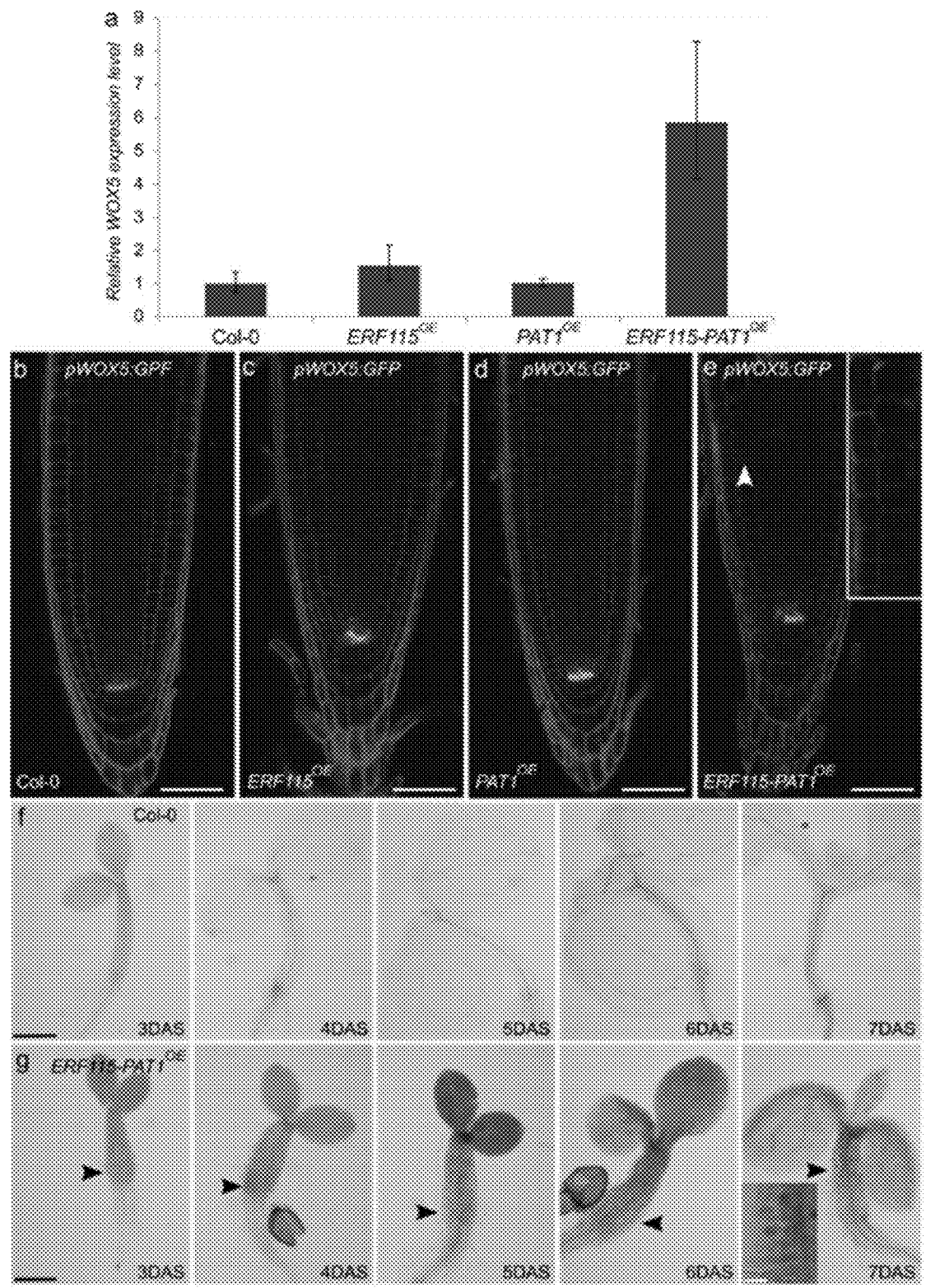

FIG. 10: Ectopic WOX5 expression in ERF115-PAT1$^{OE}$ seedlings.

a, Relative WOX5 expression levels in wild-type (Col-0), ERF115$^{OE}$, PAT1$^{OE}$ and ERF115-PAT1$^{OE}$ 1-week-old seedlings. Data indicate mean±s.e.m. for n=3. b-e, Confocal microscope images of 1-week-old root tips of wild-type (Col-0) (b), ERF115$^{OE}$ (c), PAT1$^{OE}$ (d) and ERF115-PAT1$^{OE}$ (e) seedlings. WOX5 expression is visualized by the green fluorescence (white dots). The white arrowhead indicates ectopic WOX5-expressing cells in ERF115-PAT1$^{OE}$ roots (e), shown in the enlargement. Bars=50 µm. f, g, Images of WOX5-positive cells in wild-type (f) and ERF115-PAT1$^{OE}$ (g) seedlings visualized by GUS staining on the indicated time points. Black arrowheads indicate ectopic WOX5 expression. Bars=0.5 mm. The inset in the final image represents a magnification of the WOX5-positive cells in the hypocotyl. Bar=50 µm.

Figure 11:
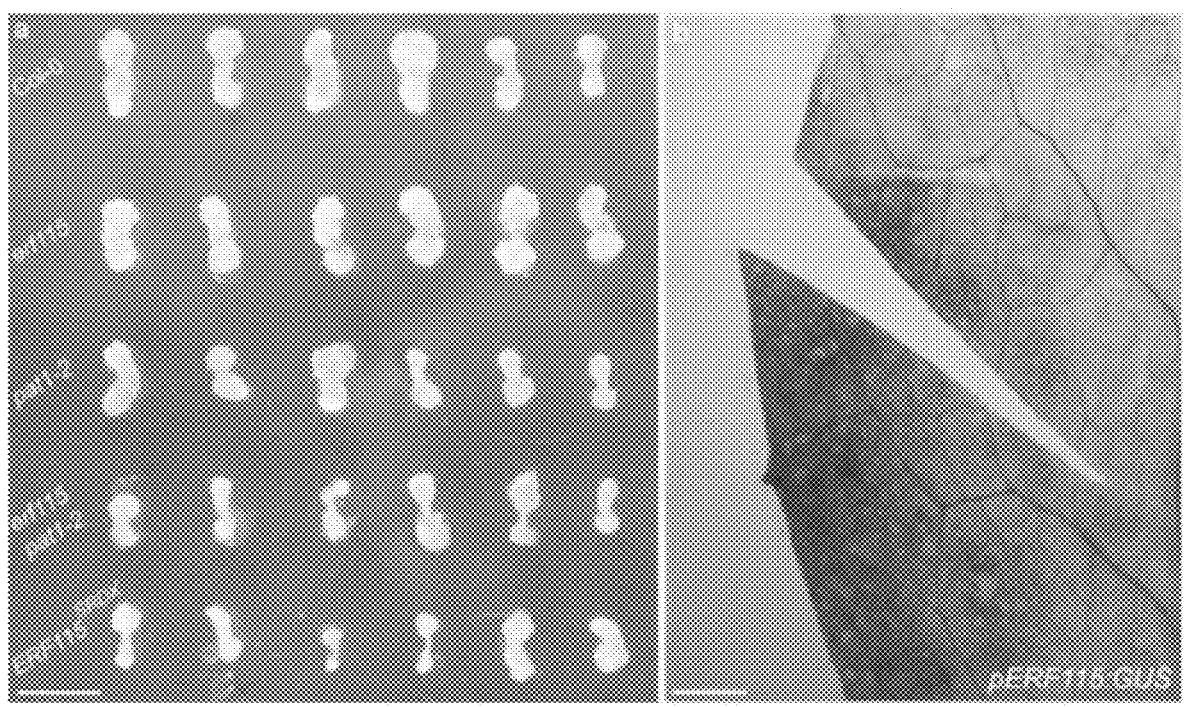

FIG. 11: Absence of ERF115 induction in regeneration incompetent tissue.

a, Callus generated from wild-type (Col-0), erf115, pat1-2, erf115 pat1-2 and ERF115$^{SRDX}$ hypocotyl segments shows reduction in callus formation in erf115 pat1-2 and ERF115$^{SRDX}$ seedlings. Bar=5 mm. b, Leaf blade cut of the pERF115:GUS reporter reveals the absence of ERF115 activation near the cut site at 24 hours post cut. Bar=1 mm.

Figure 12:
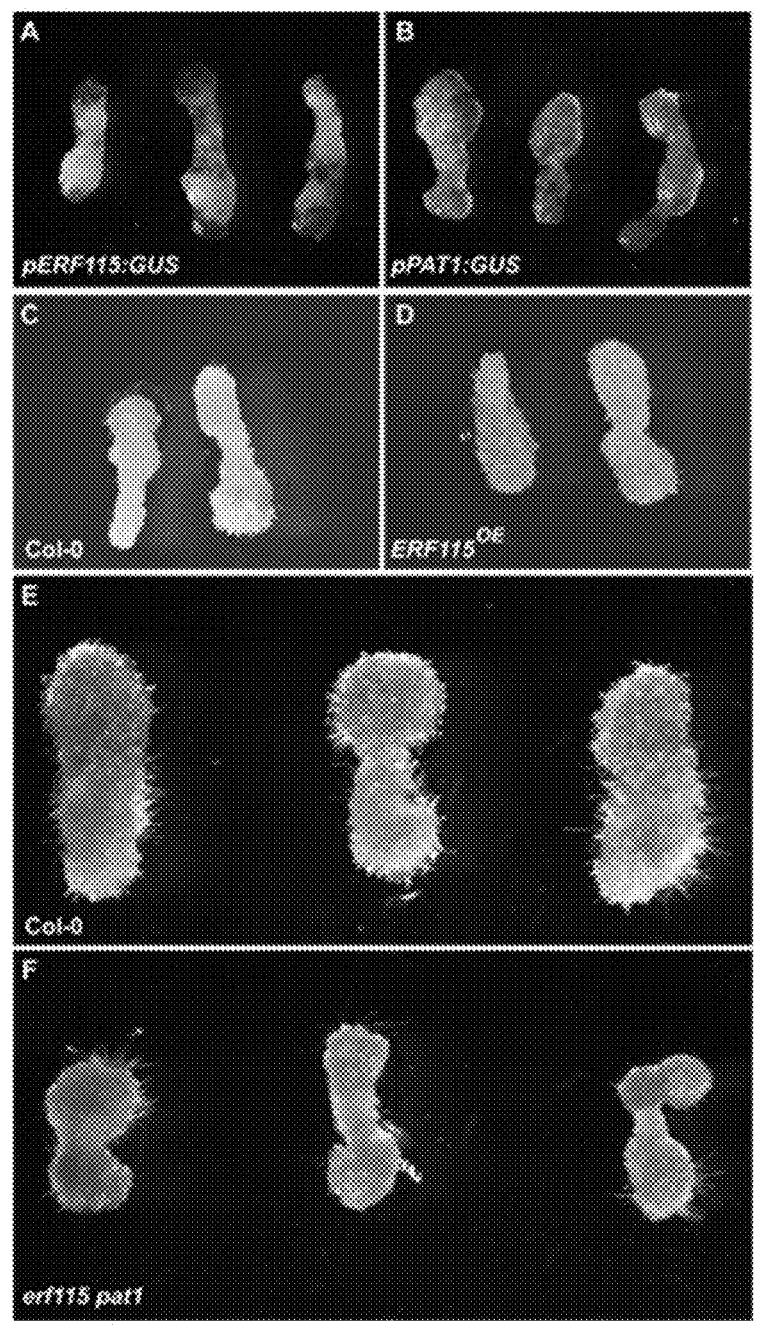

FIG. 12: ERF115 and PAT1 are both essential for callus formation.

a, b, GUS stained 3-week old hypocotyls grown on CIM after cutting them from 1-week old etiolated seedlings of ERF115(pERF115:GUS) and PAT1 (pPAT1:GUS) reporter lines. c,d, calli regenerated from ERF115 (ERF115$^{OE}$) overexpressor lines were not larger than those obtained from control plants (Col-0)

e,f, co-requirement of ERF115 and PAT1 for bigger callus induction was demonstrated by the observation that erf115 pat1-2 double mutants development poorly into calli, compared to those of the control plants.

Figure 13:
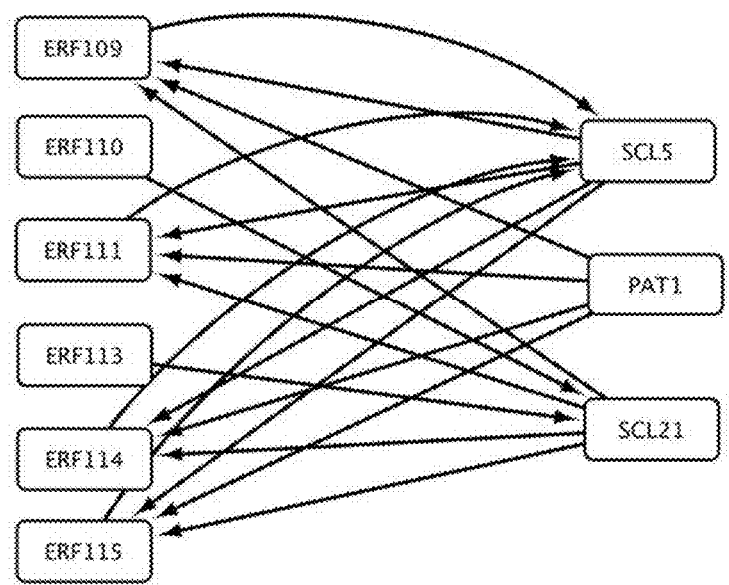

FIG. 13: Yeast two-hybrid interaction network of ERF A fragments with SCL and PAT1 proteins.

Growth was verified on selective medium (–HIS) supplemented with 15 mM 3-Amino-1,2,4-triazole (3-AT). Arrows point to interaction from bait to prey.

Figure 14:
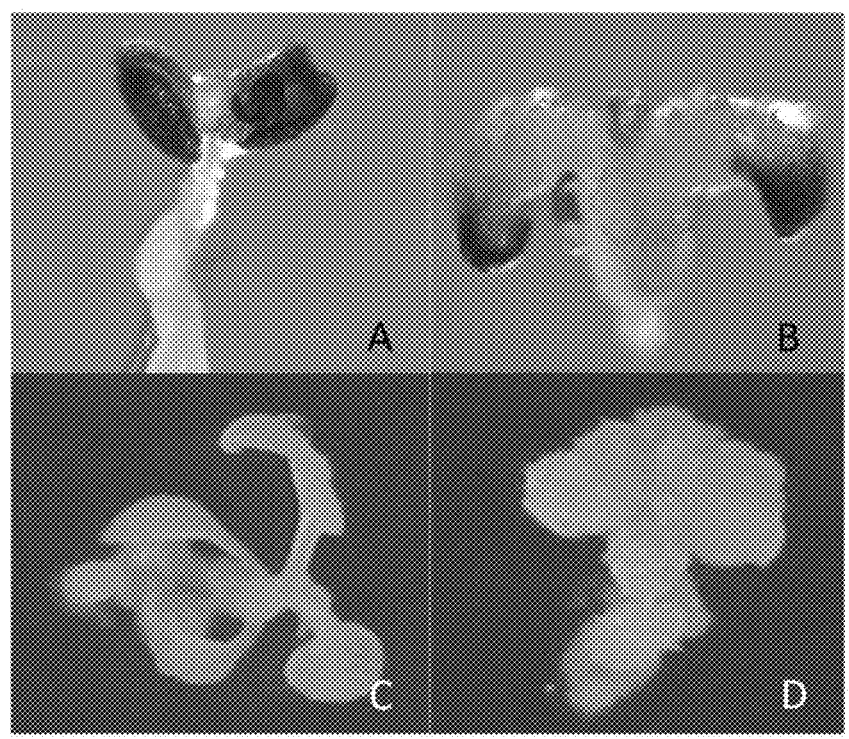

FIG. 14: PAT1 overexpressor lines induce callus in the presence of auxin.

Wild type (A,C) and PAT1 overexpressing (B,D) plants grown for two weeks on 10 µM 2,4-Dichlorophenoxyacetic acid (2,4D) (A,B) or six weeks on ½ MS media containing 1 µM 2,4D (C,D).

Figure 15:
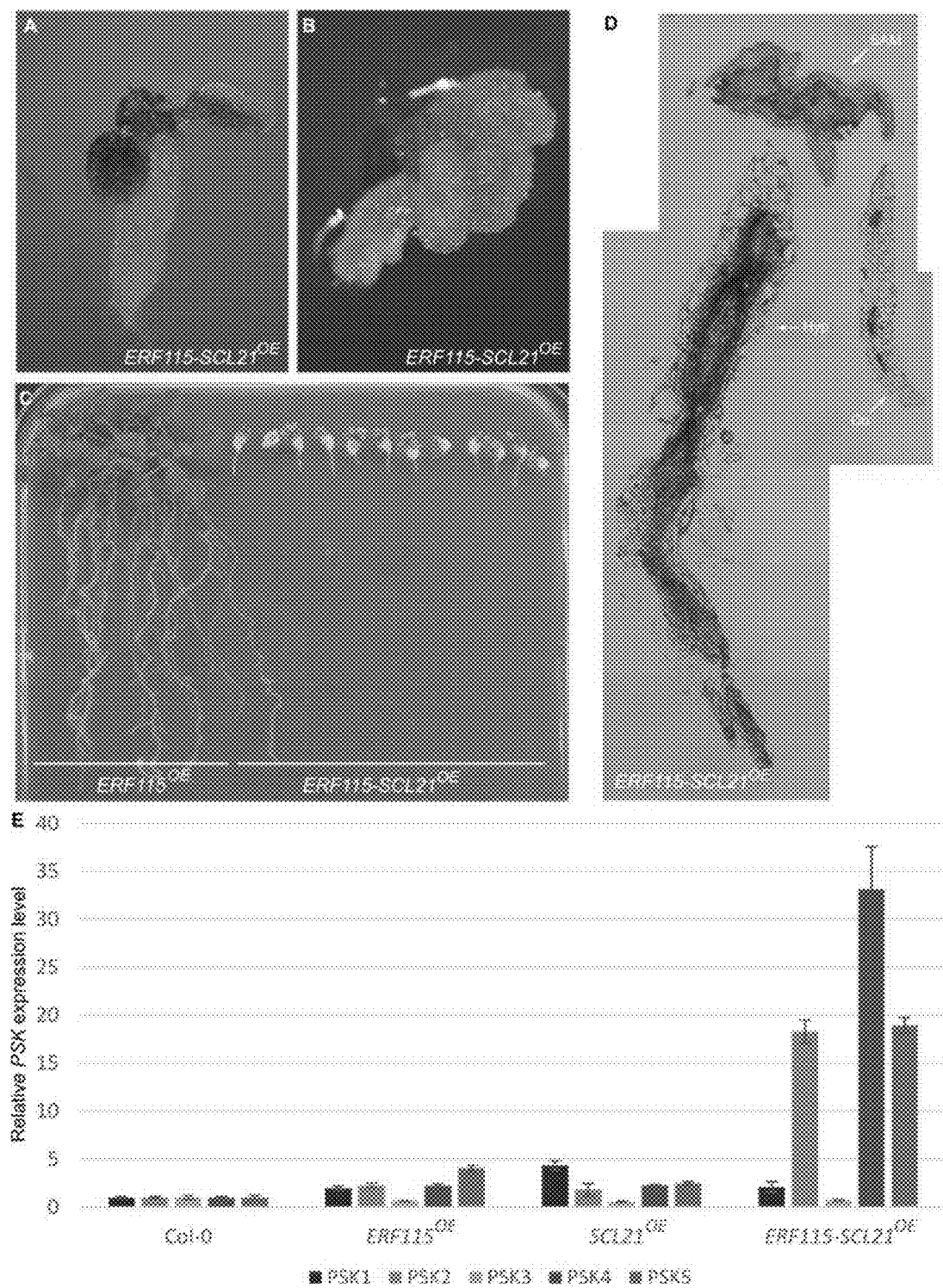

FIG. 15: Spontaneous callus formation upon co-expression of ERF115 and SCL21.

(A) 12-days-old ERF115-SCL21-overexpressing seedling. (B) 3-weeks-old ERF115-SCL21-overexpressing seedling displaying severe spontaneous callus formation. (C) In vitro grown 3-week-old ERF115$^{OE}$ (left) and ERF115-SCL21-overexpressing (right) seedlings. (D) Longitudinal section of a 12-days-old ERF115-SCL21-overexpressing seedling. SAM, shoot apical meristem; Co, cotelydon; Hyp, hypocotyl. (E) Relative PSK expression levels in one-week-old control (Col-ERF115$^{OE}$, SCL21$^{OE}$ and ERF115-SCL21-overexpressing seedlings. Bars represent standard error (n=3).

Figure 16:
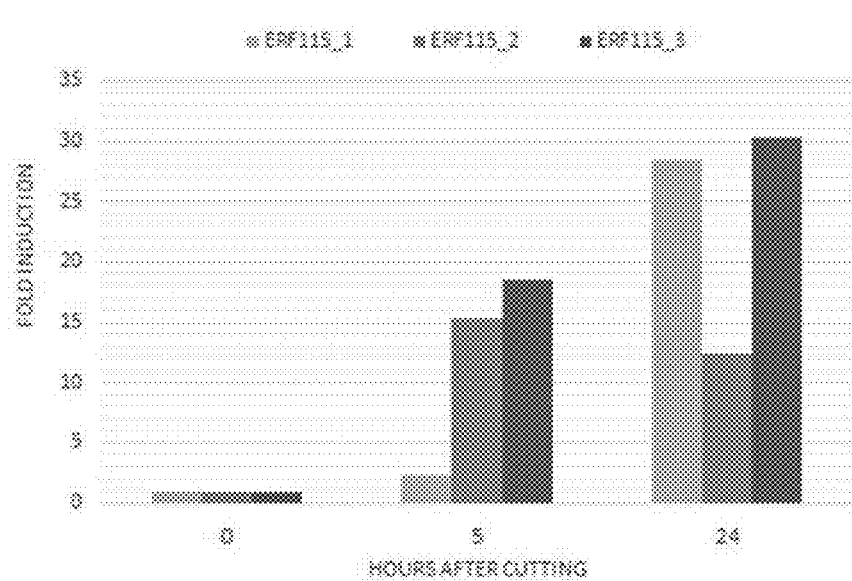
Figure 16:
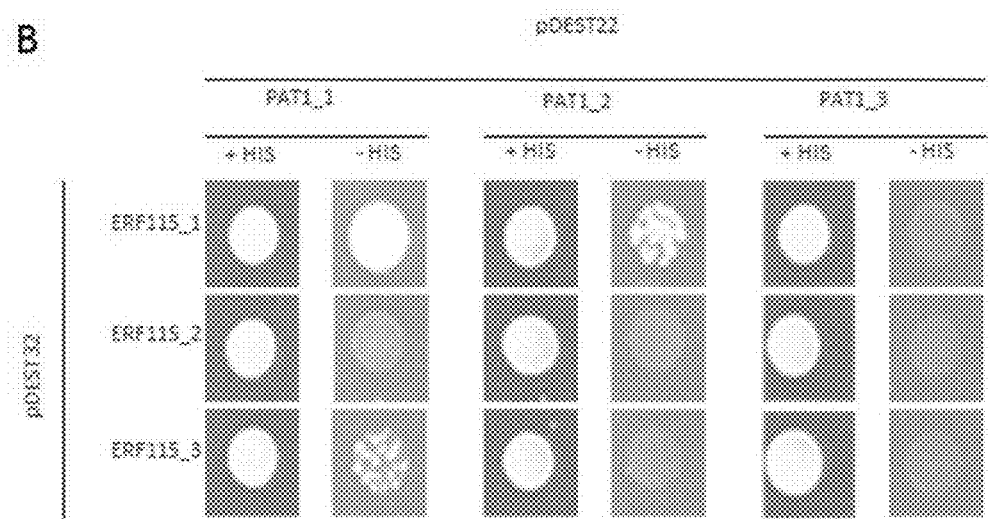

FIG. 16: ERF115 and PAT1 maize orthologues react to wounding and interact.

(A) 7 d-old seedlings of the B73 maize ecotype had their root tip excised. After 0.5 and 24 hours, the lower 1 mm of the root was taken for RT-qPCR analysis to analyse ERF115 expression levels of 3 maize candidate orthologues ERF115_1 (Zm10g15700), ERF115_2 (Zm02g16850) and ERF115_3 (Zm03g25810). (B) Yeast two-hybrid shows interaction between maize candidate orthologues of ERF115 and PAT1. Growth was verified on control medium (+HIS) or selective medium (–HIS).

DETAILED DESCRIPTION TO THE INVENTION

The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention.

Practitioners are particularly directed to Sambrook et al., Molecular Cloning: A Laboratory Manual, 4$^{th}$ ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

"About" as used herein when referring to a measurable value such as an amount, a temporal duration, and the like, is meant to encompass variations of ±20% or ±10%, more preferably ±%, even more preferably ±1%, and still more preferably ±0.1% from the specified value, as such variations are appropriate to perform the disclosed methods.

"Gene" as used here includes both the promoter region of the gene as well as the coding sequence. It refers both to the genomic sequence (including possible introns) as well as to the cDNA derived from the spliced messenger, operably linked to a promoter sequence.

"Coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

The terms "protein", "polypeptide", "peptide" are interchangeably used further herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. This term also includes post-translational modifications of the polypeptide, such as glycosylation, phosphorylation and acetylation. By "recombinant polypeptide" is meant a polypeptide made using recombinant techniques, i.e., through the expression of a recombinant or synthetic polynucleotide. When the chimeric polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

For the purposes of the invention, "transgenic", "transgene" or "recombinant" means with regard to, for example, a nucleic acid sequence, an expression cassette, chimeric gene construct or a vector comprising the nucleic acid sequence or an organism transformed with the nucleic acid sequences, expression cassettes or vectors according to the invention. A "transgenic plant" for the purposes of the invention is thus understood as meaning that the nucleic acids used in the method or use of the invention are not present in, or originating from, the genome of said plant, or are present in the genome of said plant but not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, heterologous expression of the nucleic acids takes place.

The current invention relates to the heterodimeric transcription factor complex ETHYLENE RESPONSE FACTOR115 (ERF115)-PHYTOCHROME A SIGNAL TRANSDUCTION1 (PAT1), which sustains meristem function by promoting cell renewal after stem cell loss, but moreover plays an important role in the high regenerative potential of plants, granting them the ability to improve their transformation efficiency by ectopic expression of the ERF115-PAT1 complex. In fact, the observed physical interaction between ERF115 and PAT1, combined with the co-expression of their genes and additive effects of the double mutants and overexpression lines on tissue regeneration, callus formation, and target gene expression (as exemplified below), strongly support the idea that ERF115 and PAT1 cooperate in determining the regeneration potential of cells. It is striking to note that the activation of the ERF115-PAT1 complex in response to neighbouring dead cells conceptually may be reminiscent to the regeneration process in decapitated Hydra, in which apoptosis is both necessary and sufficient to induce the regeneration-required Wnt3 production 24, indicating that plants and animals use the same general mechanism to repair injured tissues. Nevertheless, in view of their high regenerative power, plants appear to have evolved unique and more potent regeneration abilities that might be due to constant attack by herbivorous plants and insects 1-3. Together, the present invention relates to the finding that the ERF115-PAT1 complex plays a crucial role in granting plants their regenerative potential, in particular for the recovery of the root meristem, hence ensuring its indeterminate growth. Moreover, the interaction motif of ERF115 to allow complex formation with PAT1 was narrowed down to an 11-amino acid conserved region in its N-terminal part, and was named further herein as the "SCL/PAT1 interaction motif". Said interaction motif has also been identified in other ERF proteins (see FIG. 6, as well as bold-labeled residues in ERF amino acid sequences of the examples), and therefore forms the essential feature to interact with GRAS TFs, and subsequently lead to spontaneous regeneration of plant cells with an active ERF-GRAS complex.

So, in a first aspect, the invention relates to a combination of a first and second chimeric gene construct, with both gene constructs comprising the following operably linked DNA elements: a) a plant expressible promoter, b) a DNA region encoding an Ethylene Response Factor (ERF) comprising the SCL/PAT1 interaction motif, or a DNA region encoding PAT1, for the first and second construct respectively, and c) a 3' end region comprising transcription termination and polyadenylation signals functioning in cells of a plant. With "a combination" is meant that both, the first and the second gene construct, will be required to come to the invention. By combining said first and second chimeric gene constructs, one skilled in the art will obtain the desired outcome of an increased regeneration potential for plants in the present invention. With a "chimeric gene" or "chimeric construct" or "chimeric gene construct" is meant a recombinant nucleic acid sequence in which a promoter or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence. The regulatory nucleic acid sequence of the chimeric gene is not operatively linked to the associated nucleic acid sequence as found in nature.

The term "operatively" or "operably" "linked" as used herein refers to a functional linkage between the promoter sequence and the gene of interest, such that the promoter sequence is able to initiate transcription of the gene of interest, and refers to a functional linkage between the gene of interest and the transcription terminating sequence to assure adequate termination of transcription in plant cells. In the present invention a "plant expressible promoter" comprises regulatory elements, which mediate the expression of a coding sequence segment in plant cells. For expression in plants, the nucleic acid molecule must be linked operably to or comprise a suitable promoter which expresses the gene at the right point in time and with the required spatial expression pattern. A "constitutive promoter" is used in some embodiments, and is a promoter that is transcriptionally active during most, but not necessarily all, phases of growth and development and under most environmental conditions, in at least one cell, tissue or organ. Examples of plant expressible promoters for constitutive expression are the Cauliflower mosaic virus (CaMV) 35S promoter. Specific expression patterns can be obtained by using tissue-preferred promoters to target enhanced expression of a sequence of interest within a particular plant tissue. Where low-level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels. Such weak constitutive promoters include, for example, the core CaMV 35S promoter. Finally, in this application, also inducible promoter elements could be used in some embodiments. For instance, wound-inducible promoters include potato proteinase inhibitor (pin II) gene[40]; and systemin[41]. Another inducible promoter is the maize In2-2 promoter[42]. Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners[42], the maize GST promoter (GST-II-27, WO 93/01294), which is activated by hydrophobic electrophilic compounds that are used as pre-emergent herbicides, the PR-1 promoter[43], which is activated by BTH or benxo(1,2,3)thiaidazole-7-carbothioic acid s-methyl ester, the tobacco PR-1a promoter[44], which is activated by salicylic acid, the copper inducible ACE1 promoter[45], the ethanol-inducible promoter AlcA[46], an estradiol-inducible promoter[47], the XVE estradiol inducible promoter[48].

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

The ERF115 transcription factor has a function as a rate-limiting factor of quiescent center (QC) cell division, acting as a transcriptional activator of the phytosulfokine PSK5 peptide hormone. ERF115 marks QC cell division but is restrained through proteolysis, whereas QC proliferation is driven by brassinosteroid-dependent ERF115 expression, leading to two antagonistic mechanisms for regulation of ERF115 activity upon stem cells damage[14]. ERF115 is a member of the AP2/ERF family of proteins, which is a plant-specific class of putative transcription factors that regulate a wide variety of developmental processes and are characterized by the presence of an AP2 DNA binding domain that is predicted to form an amphipathic alpha helix that binds DNA (PFAM Accession PF00847). The AP2 domain was first identified in APETALA2, an *Arabidopsis* protein that regulates meristem identity, floral organ specification, seed coat development, and floral homeotic gene expression. The AP2/ERF proteins have been subdivided into distinct subfamilies based on the presence of conserved domains, one of these subfamilies concerning the ERF proteins[49]. The ERF transcription factor comprising an SCL/PAT1 interaction motif of the present invention comprises a number of ERF transcription factors, for instance most of the ERFs that belong to the ERF115 subfamily contain said SCL/PAT1 interaction motif. The SCL/PAT1 interaction or binding motif is defined and used herein with reference to the 11 amino acid stretch present in the *Arabidopsis thaliana* ERF115 (see FIG. 6) starting at position 44 of SEQ ID NO:1. Said amino acid stretch has been demonstrated to be required for interaction with PAT1. In addition, said SCL/PAT1 interaction motif, as indicated (in bold) in all ERF115 protein sequences disclosed in the Example section, can be determined by a person skilled in the art by simply aligning the ERF sequences present in the public amino acid databases, with the At ERF115 as a reference (see Methods). As shown in FIG. 6, as a non-limiting example, said SCL/PAT1 interaction motif is also present in ERF108, ERF109, ERF110, ERF111, ERF113, and ERF114. In some embodiments, said DNA regions that encode the ERFs comprising such an SCL/PAT1 interaction motif comprise ERFs that are not ERF115, but that can be ERF114, ERF113, ERF111, ERF110, ERF109, or ERF108, but not ERF112, as the latter transcription factor does not contain an SCL/PAT1 interaction motif. The DNA region (nucleotide sequence) encoding ERF is therefore meant to include a sequence encoding a member of the ERF protein family, preferably described, annotated as or homologous to the ERF115 protein, and at least comprising the SCL/PAT interaction motif. The *Arabidopsis thaliana* ERF115 DNA sequence comprising At ERF115 is provided in SEQ ID NO: 51, whereas the amino acid sequence annotated as *A. thaliana* ERF115 is provided in SEQ ID NO: 1. The *Arabidopsis thaliana* ERF108, ERF109, ERF110, ERF111, ERF112, ERF113, and ERF114 DNA sequences comprising At ERF108-At ERF 114 is provided in SEQ ID NO: 167-173, whereas the amino acid sequences annotated as *A. thaliana* ERF108-ERF114 are provided in SEQ ID NO: 153-160. Functional plant candidate orthologues for ERF115 are depicted in Example 6. The correspondence between the DNA sequence (nucleotide sequence) for ERF115 and the encoded ERF115 protein is as follows: SEQ ID NO:51 codes for the *Arabidopsis thaliana* ERF115 amino acid sequence presented in SEQ ID NO:1, SEQ ID NO: 52 encodes the protein in SEQ ID NO: 2, SEQ ID NO: 53 codes for SEQ ID NO:3, . . . until SEQ ID NO: 100 encodes for SEQ ID NO: 50.

The PAT1 protein encodes a cytoplasmic protein of 490 amino acids with sequence homologies to the plant-specific GRAS regulatory protein family. The GRAS protein family seems unique to plants and presently consists of >20 members. PAT1 shows the highest homology (45%-70% identity) to the protein sequences of the Scarecrow-like (SCL)1/5/13 subgroup of the GRAS family and to SCL21 (SEQ ID NOs: 161-164). The protein functions in an early step of phyA signal transduction. Light signaling via the phytochrome A (phyA) photoreceptor controls basic plant developmental processes including de-etiolation and hypocotyl elongations. The DNA region encoding PAT1 is therefore meant to include a sequence encoding a member of the PAT protein family, preferably described, annotated or homologous to the PAT1 protein or belonging to the PAT1 branch[17]. The *Arabidopsis thaliana* PAT1 DNA sequence including At PAT1 is provided in SEQ ID NO: 126, whereas the amino acid sequence annotated as *A. thaliana* PAT1 is provided in SEQ ID NO: 101. Functional plant candidate orthologues are depicted in Example 7. The correspondence between the DNA sequence (nucleotide sequence) for PAT1 and the encoded PAT1 protein is as follows: SEQ ID NO:101 codes for the *Arabidopsis* PAT1 amino acid sequence presented in SEQ ID NO:126, SEQ ID NO: 102 encodes the protein in SEQ ID NO: 127, SEQ ID NO: 103 codes for SEQ ID NO:128, . . . until SEQ ID NO: 125 encodes for SEQ ID NO: 150.

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. "Homologue", "Homologues" of a protein encompass peptides, oligopeptides, polypeptides, proteins and enzymes having amino acid substitutions, deletions and/or insertions relative to the unmodified or wild-type protein in question and having similar biological and functional activity as the unmodified protein from which they are derived.

Functional orthologous ERF115 or PAT1 genes can be isolated from the (publically) available sequence databases. The "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch (1970) *J Mol Biol.* 48: 443-453). The computer-assisted sequence alignment above, can be conveniently performed using standard software program such as GAP which is part of the Wisconsin Package Version 10.1 (Genetics Computer Group, Madision, Wisconsin, USA) using the default scoring matrix with a gap creation penalty of 50 and a gap extension penalty of 3. Sequences are indicated as "essentially similar" when such amino acid sequences have a sequence identity of at least about 75%, particularly at least about 80%, more particularly at least about 85%, quite particularly about 90%, especially about 95%, more especially about 100%, quite especially are identical. Alternatively, the skilled person can isolate orthologous plant ERF115 or PAT1 genes through methods of genetic hybridization. Such methods are well known to the skilled (plant) molecular biologist. Several examples of functional plant candidate orthologous ERF115 and PAT1 genes are represented in Examples 6 and 7, respectively. The co-expression of multiple genes can be valuable in transgenic plants. The current invention relates to the co-expression of ERF and GRAS transcription factors, leading to the formation of a heterodimeric protein complex, in particular here for ERF115 and PAT1. It was demonstrated that this protein complex is active in *Arabidopsis* SCN cells nearby wounded cells to induce renewal of stem cells upon DNA damage. Moreover, the protein complex was shown to induce spontaneous callus formation and regeneration of plant cells. Hence, co-expression of ERF and PAT1 or PAT1-related GRAS transcription factors such as the SCL21 or SCL-TFs belonging to the PAT1 branch[17], in particular co-expression of ERF115 and PAT1 is aimed for in order to gain regeneration competence in plant cells. To achieve co-expression within the plant cells, a multitude of techniques is known to the skilled person. These techniques include, but are not limited to co-transformation of multiple chimeric genes (here a first chimeric gene comprising ERF and a second chimeric gene comprising PAT1, either simultaneously or subsequently), crossing of transgenic plants (or 'gene stacking') wherein said transgenic plants each have one of the transgenes (one plant comprising a chimeric gene encoding ERF with another plant comprising a chimeric gene encoding PAT1), the use of multiple or bidirectional promoters to direct the expression of ERF115 and PAT1 on the same construct, the creation of a bicistronic or multicistronic construct wherein ERF115 and PAT1 are operably linked and under control of the same promoter. Multicistronic vectors or chimeric constructs can be made with IRES elements. However, these elements are quite large (500-600 bp). Alternative multicistronic vectors are made by using self-cleaving 2A peptides codes between the genes in the multicistronic vector or construct. Examples of commonly used 2A peptides used are T2A, P2A, E2A and F2A.

In one embodiment, a chimeric gene construct comprising the operably linked DNA elements: a) a plant expressible promoter, b) a multicistronic DNA region encoding an ERF comprising the SCL/PAT1 interaction motif, coupled to a DNA region encoding PAT1 and c) a 3'end region comprising transcription termination and polyadenylation signals functioning in cells of a plant is used. In said multicistronic DNA region, the above-mentioned elements can be used to obtain such a chimeric construct.

A particular embodiment relates to a chimeric gene construct of the present invention, wherein said DNA region encoding an ERF comprising the SCL/PAT1 interaction motif is ERF115.

In an alternative embodiment, said described chimeric gene constructs are flanked by recombination sites, and further comprise a chimeric gene construct wherein the DNA region encodes a site-specific recombinase protein which actively recognizes and exerts recombinase activity at those recombination sites within its reach to excise all DNA elements within the flanked sites. In an embodiment with said chimeric construct containing a DNA region encoding the site-specific recombinase, the DNA elements introduced by the chimeric gene constructs are all flanked by site-specific recombination sites that are directly repeated and are recognized by the site-specific recombinase whose expression is regulated by a presently disclosed promoter construct, such that expression of the site-specific recombinase results in the excision of the chimeric gene constructs. Examples of said site-specific recombinase are Cre or FLP recombinases.

The flanking recombination site sequences are defined to be the region of the gene on either side of the transcribed region, or alternatively in order to excise the full chimeric gene constructs the flanked recombination site sequences are present at the 5' and 3' end of the chimeric construct itself.

In one embodiment, the chimeric gene constructs are designed to contain DNA elements operably linked and flanked by recombination sites, as such that the chimeric construct with the site-specific recombinase DNA region, expressing the recombinase, specifically recognizes and implements recombination at the recombination sites flanking the chimeric constructs comprising the DNA region encoding ERF or PAT1, thereby excising the chimeric genes. The chimeric constructs can further comprise any of the operably linked sequences as those described herein. In an alternative embodiment, the chimeric gene construct comprising the DNA region encoding the site-specific recombinase as well contains flanking recombination site sequences. This allows to excise not only the chimeric gene constructs encoding the ERF and PAT1 proteins, but also to excise the chimeric gene construct enabling the recombination reaction by expression of the recombinase.

In some embodiments, the activity and/or amount of the ERF-PAT1 complex is reduced prior to regenerating a plant from a cell or tissue. In some of these embodiments, the polynucleotides encoding the ERF-PAT1 proteins are excised prior to the regeneration of a plant. In certain embodiments, the promoter and other regulatory elements that are operably linked to the heterologous polynucleotide encoding the ERF-PAT1 complex are excised along with the recombinase coding sequence. The polynucleotides encoding the ERF-PAT1 complex may be flanked by recombination sites and an appropriate site-specific recombinase is introduced into the mature embryo explant or callus grown therefrom to excise the polynucleotides encoding the ERF-PAT1 complex prior to regeneration of the mature embryo explant or callus into a plant. In some of those embodiments wherein an ERF, a PAT1, and a recombinase protein are provided to the plant cell upon expression of all three DNA regions, all three regions can be excised. The two, ERF and PAT1, can be present on the same or different chimeric gene constructs and, therefore, can be excised in one or two different excision reactions. In some of these embodiments, the DNA region encoding the site-specific recombinase for excising the ERF and PAT1 encoding chimeric genes can be located on the same chimeric gene as the ERF and PAT1 DNA region and all three polynucleotides can be excised through the activity of the site-specific recombinase. In order to control the excision of the ERF-PAT1 encoding chimeric genes, the expression of the site-specific recombinase that is responsible for the excision can be controlled by a late embryo promoter or an inducible promoter. The late embryo promoter may be GZ (Uead et al. (1994) Mol Cell Biol 14:4350-4359), ZM-LEG1 (U.S. Pat. No. 7,211,712). The inducible promoter that regulates the expression of the site-specific recombinase may also be a heat-shock, light-induced promoter, a drought-inducible promoter, including but not limited to Hva1[51], Dhn, and WSI18.

In a number of embodiments, in addition to the ERF-PAT1 protein complex, other proteins of interest (e.g., traits) may also be introduced along with or following the chimeric gene constructs comprising a presently disclosed design. In some embodiments, it might be of interest to include chimeric gene constructs comprising a DNA region encoding a protein of interest for stable introduction or transformation in the plant. In another embodiment, even such chimeric gene constructs comprising a DNA region encoding a protein of interest might be of interest to be flanked by recombination sites, and allow excision.

In the current invention, in some embodiments, the chimeric constructs comprising the DNA regions encoding PAT1, and/or an ERF comprising an SCL/PAT1 interaction motif, will be of interest for use in expression and activity during plant transformation and callus formation, to improve the regeneration and transformation efficiency. In other embodiments, the chimeric constructs comprising the DNA regions encoding a PAT1-related GRAS transcription factor part of the PAT1 branch (according to 17) and/or an ERF comprising an SCL/PAT1 interaction motif, will be of interest for use in expression and activity during plant transformation and callus formation, to improve the regeneration and transformation efficiency. In particular, said PAT1 branch transcription factors include SCL21, SCL13, SCL5 and SCL1. Depending on the desired outcome, the chimeric gene constructs for expression of ERF-PAT1 will be of use for transient utility, such as during callus formation, after which the expression is lowered or omitted.

In yet another embodiment the invention relates to a set of at least one recombinant vector comprising said chimeric gene or chimeric genes of the invention. The chimeric gene construct(s) can be part of a vector that comprises multiple chimeric gene constructs or multiple genes, such as a selectable marker gene. Selectable marker genes may be used to identify transformed cells or tissues. The chimeric gene or chimeric genes to be expressed are preferably cloned into a vector, or recombinant vector, which is suitable for transforming *Agrobacterium tumefaciens*, for example pBin19 (Bevan et al (1984) *Nucl. Acids Res.* 12-8711). In one embodiment, the first chimeric construct comprising the DNA region encoding ERF comprising an SCL/PAT1 interaction motif, and the second chimeric construct comprising the DNA region encoding PAT1 are both cloned in a different recombinant vector. In a specific embodiment, the first chimeric construct comprising the DNA region encoding ERF115, and the second chimeric construct comprising the DNA region encoding PAT1 are both cloned in a different recombinant vector. In said cases, co-transformation using both vectors is required to obtain co-expression and complex formation. In particular, when a third chimeric construct comprising a DNA region encoding a recombinase is added, or even a chimeric construct comprising a DNA region encoding a polynucleotide of interest, several recombinant vectors are necessary for introducing said genes. Alternatively, said first, second, and optionally third chimeric gene constructs can be cloned into the same recombinant vector, allowing the need of just one vector for expression of said chimeric genes. In another embodiment, the chimeric construct comprises the DNA region encoding both, an ERF comprising an SCL/PAT1 interaction motif and PAT1, whereby it will be sufficient to clone said chimeric construct into one recombinant vector to express the ERF-PAT1 complex from said chimeric construct.

In a specific embodiment, the chimeric construct comprises the DNA region encoding both, ERF115 and PAT1, whereby it will be sufficient to clone said chimeric construct into one recombinant vector to express the ERF115-PAT1 complex from said chimeric construct.

In yet another embodiment, a plant, plant cell or plant seed comprises said chimeric construct(s) or recombinant vector. Moreover, in one embodiment, a plant, plant cell, or plant seed is co-expressing ERF and PAT1. The term "plant"

as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the invention include in particular monocotyledonous and dicotyledonous plants including fodder or forage legumes, ornamental plants, food crops, trees or shrubs selected from the list comprising Acer spp., Actinidia spp., Abelmoschus spp., Agave sisalana, Agropyron spp., Agrostis stolonifera, Allium spp., Amaranthus spp., Ammophila arenaria, Ananas comosus, Annona spp., Apium graveolens, Arachis spp, Artocarpus spp., Asparagus officinalis, Avena spp. (e.g. Avena sativa, Avena fatua, Avena byzantina, Avena fatua var. sativa, Avena hybrida), Averrhoa carambola, Bambusa sp., Benincasa hispida, Bertholletia excelsea, Beta vulgaris, Brassica spp. (e.g. Brassica napus, Brassica rapa ssp. [canola, oilseed rape, turnip rape]), Cadaba farinosa, Camellia sinensis, Canna indica, Cannabis sativa, Capsicum spp., Carex elata, Carica papaya, Carissa macrocarpa, Carya spp., Carthamus tinctorius, Castanea spp., Ceiba pentandra, Cichorium endivia, Cinnamomum spp., Citrufius lanatus, Citrus spp., Cocos spp., Coffea spp., Colocasia esculenta, Cola spp., Corchorus sp., Coriandrum sativum, Corylus spp., Crataegus spp., Crocus sativus, Cucurbita spp., Cucumis spp., Cynara spp., Daucus carota, Desmodium spp., Dimocarpus longan, Dioscorea spp., Diospyros spp., Echinochloa spp., Elaeis (e.g. Elaeis guineensis, Elaeis oleifera), Eleusine coracana, Eragrostis tef, Erianthus sp., Eriobotrya japonica, Eucalyptus sp., Eugenia uniflora, Fagopyrum spp., Fagus spp., Festuca arundinacea, Ficus carica, Fortunella spp., Fragaria spp., Ginkgo biloba, Glycine spp. (e.g. Glycine max, Soja hispida or Soja max), Gossypium hirsutum, Helianthus spp. (e.g. Helianthus annuus), Hemerocallis fulva, Hevea brasiliensis, Hibiscus spp., Hordeum spp. (e.g. Hordeum vulgare), Ipomoea batatas, Juglans spp., Lactuca sativa, Lathyrus spp., Lens culinaris, Linum usitatissimum, Litchi chinensis, Lotus spp., Luffa acutangula, Lupinus spp., Luzula sylvatica, Lycopersicon spp. (e.g. Lycopersicon esculentum, Lycopersicon lycopersicum, Lycopersicon pyriforme), Macrotyloma spp., Malus spp., Malpighia emarginata, Mammea americana, Mangifera indica, Manihot spp., Manilkara zapota, Medicago sativa, Melilotus spp., Mentha spp., Miscanthus sinensis, Momordica spp., Morus nigra, Musa spp., Nicotiana spp., Olea spp., Opuntia spp., Ornithopus spp., Oryza spp. (e.g. Oryza sativa, Oryza latifolia), Panicum miliaceum, Panicum virgatum, Passiflora edulis, Pastinaca sativa, Pennisetum sp., Persea spp., Petroselinum crispum, Phalaris arundinacea, Phaseolus spp., Phleum pratense, Phoenix spp., Phragmites australis, Physalis spp., Pinus spp., Pistacia vera, Pisum spp., Poa spp., Populus spp., Prosopis spp., Prunus spp., Psidium spp., Punica granatum, Pyrus communis, Quercus spp., Raphanus sativus, Rheum rhabarbarum, Ribes spp., Ricinus communis, Rubus spp., Saccharum spp., Salix sp., Sambucus spp., Secale cereale, Sesamum spp., Setaria sp., Sinapis sp., Solanum spp. (e.g. Solanum tuberosum, Solanum integrifolium or Solanum lycopersicum), Sorghum bicolor, Spinacia spp., Syzygium spp., Tagetes spp., Tamarindus indica, Theobroma cacao, Trifolium spp., Tripsacum dactyloides, Triticosecale rimpaui, Triticum spp. (e.g. Triticum aestivum, Triticum durum, Triticum turgidum, Triticum hybernum, Triticum macha, Triticum sativum, Triticum monococcum or Triticum vulgare), Tropaeolum minus, Tropaeolum majus, Vaccinium spp., Vicia spp., Vigna spp., Viola odorata, Vitis spp., Zea mays, Zizania palustris, Ziziphus spp., amongst others.

In a specific embodiment, said plant, plant cell or plant seed species for (co-)expression of said chimeric constructs or recombinant vectors is selected from the family of the Gramineae. This family, also called the Poaceae, are the large and nearly ubiquitous family of monocotyledonous flowering plants known as grasses. The Poaceae include the cereal grasses, bamboos and the grasses of natural grassland and cultivated lawns (turf) and pasture. Grasses have stems that are hollow except at the nodes and narrow alternate leaves borne in two ranks. The lower part of each leaf encloses the stem, forming a leaf-sheath. Grasses are unusual in that the meristem is located near the bottom of the plant; hence, they can quickly recover from cropping at the top. Many grasses demonstrate economic importance in food production, industry, and lawns. They have been grown as food for domesticated animals for up to 6,000 years and due to their grains, crops such as wheat, rice, maize (corn), oats, rye, sorghum, millet and barley have been the most important human food crops.

In yet another embodiment the invention provides the use of said chimeric genes, or recombinant vectors, or plant, plant cell, or plant seed to obtain increased regeneration of plant tissue cells. The terms "increased", "improved" or "enhanced" are interchangeable and shall mean in the sense of the application at least a 3%, 4%, 5%, 6%, 7%, 8%, 9% or 10%, preferably at least 15% or 20%, more preferably 25%, 30%, 35%, 40%, 50%, 60%, 70%, 80%, 90%, 95% or more e.g. callus formation or transformed cells in comparison to control plants as defined herein. The choice of suitable control plants is a routine part of an experimental setup and may include corresponding wild type plants or corresponding plants without the chimeric constructs. The control plant is typically of the same plant species or even of the same variety as the plant to be assessed, following the same treatment. A "control plant" as used herein refers not only to whole plants, but also to plant parts, including embryos and tissue used for plant transformation. The term "regeneration" of plant tissue cells as used herein refers to a morphogenic response that results in the production of new tissues, organs, embryos, whole plants or parts of whole plants that are derived from a single cell or a group of cells. Regeneration may proceed indirectly via a callus phase or directly, without an intervening callus phase. "Regenerative capacity" refers to the ability of a plant cell to undergo regeneration.

In one embodiment, said use of said chimeric construct to obtain increased regeneration of plant tissue cells, relates to the chimeric construct(s) of the present invention comprising a DNA region encoding PAT1 and/or a DNA region encoding an ERF comprising an SCL/PAT1 interaction motif. In another embodiment, said use of said chimeric construct to obtain increased regeneration of plant tissue cells, relates to the chimeric construct(s) of the present invention comprising a DNA region encoding a GRAS transcription factor of the PAT1 branch[17], and/or a DNA region encoding an ERF comprising an SCL/PAT1 interaction motif. In another embodiment, said use of said chimeric construct to obtain increased regeneration of plant tissue cells, relates to the chimeric construct(s) of the present invention comprising a DNA region encoding PAT1 and/or a DNA region encoding ERF115.

Alternatively, one embodiment provides the use of said chimeric genes to obtain increased callus formation of plant cells. Said increased callus formation will be the result of (temporary) expression and activity of the ERF-PAT1 complex, and will allow to improve the transformation efficiency, which is of massive importance in plant species that are currently experiencing difficulties in regeneration capacities or for species which currently require long and laborious hormone treatment to regenerate new plants from plant tissue cells. In one embodiment, said use of said chimeric construct to obtain increased callus formation of plant tissue cells, relates to the chimeric construct(s) of the present invention comprising a DNA region encoding PAT1 and/or a DNA region encoding an ERF comprising an SCL/PAT1 interaction motif. In another embodiment, said use of said chimeric construct to obtain increased callus formation of plant tissue cells, relates to the chimeric construct(s) of the present invention comprising a DNA region encoding a GRAS transcription factor of the PAT1 branch[17], and/or a DNA region encoding an ERF comprising an SCL/PAT1 interaction motif. In another embodiment, said use of said chimeric construct to obtain increased callus formation of plant tissue cells, relates to the chimeric construct(s) of the present invention comprising a DNA region encoding PAT1 and/or a DNA region encoding ERF115.

The invention alternatively provides in the use of said chimeric genes and recombinant vector or plant, plant cell or plant seed to activate said recombinase just prior to regeneration of the formed callus tissue, leading to excision and removal of the chimeric gene constructs from the transformed calli, to allow further regeneration of said plant tissue into full plants or plant organs. Said use allows to obtain regenerated plants lacking any non-natural DNA, as all chimeric gene constructs that were at first introduced in order to increase regeneration potential, have been removed by the activity of said recombinase. Alternatively, said use will allow to obtain transgenic plants in which only additional chimeric constructs, lacking any flanking recombination sites, were introduced (meant for stable expression), and wherein the chimeric genes comprising DNA regions encoding ERF and PAT1 were only shortly introduced and expressed, just to allow higher regeneration competence, followed by excision via the flanking recombination sites.

In another aspect, the invention indeed also relates to a method for producing a transgenic plant, whereby the method comprises introducing a plant cell with said chimeric gene construct(s) or recombinant vector(s), and isolating a plant regenerated from said method. "Introducing" is intended to mean presenting to the organism, such as a plant, or the cell the chimeric gene or recombinant vector in such a manner that the sequence gains access to the interior of a cell of the organism or to the cell itself. Hence, the term "introduction" or "transformation" as referred to herein encompass the transfer of an exogenous polynucleotide or chimeric gene into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The chimeric gene may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation methods include, but are not limited to, stable transformation methods, transient transformation methods, virus-mediated methods, and sexual breeding. In one embodiment, the chimeric genes will be inserted by "Stable transformation", which is intended to mean that the chimeric construct introduced into a plant integrates into a genome of the plant and is capable of being inherited by the progeny thereof. Protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) Biotechniques 4:320-334), electroporation (Riggs et al. (1986) Proc. Natl. Acad. Sci. USA 83:5602-5606), *Agrobacterium*-mediated transformation (U.S. Pat. Nos. 5,563,055 and 5,981,840), direct gene transfer (Paszkowski et al. (1984) EMBO J. 3:2717-2722), and ballistic particle acceleration.

In another embodiment, the invention provides a method for producing a transgenic plant, whereby the method comprises transient expression of said chimeric gene construct(s) during callus formation to improve regeneration, and isolating a plant regenerated from said method. In such a method, one can make use of transient expression of the genes via inducible or temporal expression by selecting a suitable promoter, or one can also apply a "transient transformation" method, which is intended to mean that a chimeric gene is introduced into the plant and does not integrate into a genome of the plant or a polypeptide is introduced into a plant. The sequences can be provided to a plant using a variety of transient transformation methods. Such transient transformation methods include, but are not limited to, the introduction of the polypeptide of interest directly into the plant or the introduction of a polynucleotide encoding the polypeptide of interest into the plant. Such methods include, for example, microinjection or to particle bombardment. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include these particles coated with polyethylimine (PEI; Sigma #P3143). The chimeric gene may also be introduced into plants by contacting plants with a virus or viral nucleic acids. Generally, such methods involve incorporating a nucleotide construct within a viral DNA or RNA molecule.

The transfer of foreign genes into the genome of a plant is called transformation. Transformation of plant species is now a fairly routine technique. Advantageously, any of several transformation methods may be used to introduce the chimeric gene into a suitable ancestor cell. The methods described for the transformation and regeneration of plants from plant tissues or plant cells may be utilized for transient or for stable transformation. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, (e.g. Aldemita and Hodges, Planta 199: 612-617, 1996; Chan et al. Plant Mol Biol 22 (3): 491-506, 1993). In the case of corn transformation, exemplified methods are described in either Ishida et al. (Nat. Biotechnol 14(6): 745-50, 1996) or Frame et al. (Plant Physiol 129(1): 13-22, 2002. Said methods are further described by way of example in B. Jenes et al., Techniques for Gene Transfer, in: Transgenic Plants, Vol. 1, Engineering and Utilization, eds. S.D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al (1984) *Nucl. Acids Res.* 12-8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S.D. Kung and R. Wu, Academic Press, 1993, pp. 15-38.

The genetically modified plant cells can be regenerated via all methods with which the skilled worker is familiar. Suitable methods can be found in the abovementioned publications by S.D. Kung and R. Wu, Potrykus or Hofgen and Willmitzer. Generally, after transformation, plant cells or cell groupings are selected for the presence of one or more markers which are encoded by plant-expressible genes co-transferred with the gene of interest, following which the transformed material is regenerated into a whole plant. To "isolate" or "select" transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. Following DNA transfer and regeneration, putatively transformed plants may also be evaluated, and isolated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art. The (re)generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

In the method provided in the present invention, introduction of said chimeric gene(s) will allow to improve plant regeneration during callus formation, due to the activity of the ERF-PAT1 complex, providing that introducing the chimeric genes will involve a callus-derived regeneration step. Hence said method is applicable to the above-mentioned transformation method comprising at least a step wherein dedifferentiated cells are present, and are regenerated into new plant tissue or organs, which can be isolated from said callus.

In an alternative embodiment of the invention, a method is provided for producing a plant, whereby the method comprises introducing a plant cell with said chimeric gene construct(s) or said recombinant vector according, and wherein said site-specific recombinase is expressed to prior to regeneration from callus, thereby excising said chimeric constructs comprising said DNA regions encoding ERF and PAT1, and said recombinase. The chimeric gene constructs encoding the ERF-PAT1 complex may be flanked by recombination sites in some embodiments, as well as a chimeric gene construct comprising a DNA region encoding a site-specific recombinase which upon expression will recognize said flanking recombination sites and when introduced into the mature embryo explant or callus grown therefrom be activated to excise the chimeric constructs encoding the ERF-PAT1 complex prior to regeneration of the mature embryo explant or callus into a plant. In some of those embodiments wherein an ERF, a PAT1, and a recombinase protein are provided to the plant cell upon expression of all three DNA regions, all three regions can be excised. The two coding sequences, ERF and PAT1, can be present on the same or different chimeric gene constructs and, therefore, can be excised in one or two different excision reactions. In some of these embodiments, the DNA region encoding the site-specific recombinase for excising the ERF115 and PAT1 encoding chimeric genes can be located on the same chimeric gene as the ERF and PAT1 DNA region and all three polynucleotides can be excised through the activity of the site-specific recombinase. In said method, the produced regenerated plant will not be a transgenic plant when recombinase activity was adequately and fully functional, as the chimeric genes have been removed prior to regeneration of the transformed calli into new plant organs.

Said methods provided by the current invention are applicable to all plant species for which transformation/regeneration protocols involve a stage with callus formation or dedifferentiated transformed cells which are subsequently regenerative.

Such methods for improved regeneration capability involve the (transient) co-expression of ERF (comprising an SCL/PAT1 interaction motif) and PAT1 at a particular phase, wherein the ERF and PAT1 genes of the chimeric construct(s) can be of the same origin or homologous to the transformed or regenerated plant species, or in some embodiments, the ERF and PAT1 genes of the chimeric construct(s) can be of different origin or heterologous to the transformed or regenerated plant species.

If for instance in maize, the proposed functional candidate orthologue sequences for ERF115 and PAT1 are tested for their ability to improve the transformation protocol, the *Arabidopsis* ERF115 and PAT1 can be applied, or the functional corn orthologues can be applied for optimal improvement of regeneration during transformation of this crop. Based on phylogenetics, protein domain analysis and reciprocal BLAST analysis, ERF115 and PAT1 maize homologs were identified (see Example 6 and 7; ERF115 candidates encoded by SEQ ID NO: 52-54 with resulting amino acid sequences SEQ ID NO: 2-4; PAT1 candidates encoded by SEQ ID NO: 127-129 with resulting amino acid sequences SEQ ID NO: 102-104). Their coding sequence was optimized for synthesis and cloning, and the resulting nucleotide sequences (SEQ ID NO:178-183) were cloned in a transformation cassette driving ERF115 and PAT1 from the UBIL and EF1a promoter, respectively. Also, vectors expressing either ERF115 or PAT1 only were applied. Next, the chimeric constructs are transformed in maize (*Zea mays* L.) cv. B104 immature embryos by *Agrobacterium tumefaciens* transformation. Briefly, 12-14 days after fertilization in the greenhouse, ears of B104 plants are surface-sterilized (5% NaOCl with Tween$^{20}$, rinsed five times with sterile water); immature embryos are isolated and cocultivated with Agrobacteria for 3 days on cocultivation medium at pH 5.2 at 21° C. in the dark, with the scutellum side uppermost. After cocultivation and one week growth on non-selective resting medium, transformed embryogenic calli are selected on medium containing 1.5 mg/L phosphinothricin. After 3 weeks, transformation frequency is calculated by counting the number of calli generated per embryo, and regeneration potential is analysed through calli size and weight measurements. Such an experiment is applicable in many crops, and will allow to estimate the translatability and valorization potential for this unique ERF115-PAT1 complex regenerative function in planta.

An embodiment relates to the co-expression of the *Arabidopsis thaliana* ERF115 and *Arabidopsis thaliana* PAT1 in maize, leading to increased regeneration potential. Another embodiment relates to the induction of spontaneous callus formation in maize through the complex formation of maize ERF115_1 (SEQ ID NO:2) and PAT1_1 (SEQ ID NO:102). Another embodiment relates to the induction of spontaneous callus formation in maize through the complex formation of maize ERF115_1 (SEQ ID NO:2) and PAT1_2 (SEQ ID NO:103). Another embodiment relates to the induction of spontaneous callus formation in maize through the complex formation of maize ERF115_1 (SEQ ID NO:2) and PAT1_3 (SEQ ID NO:104). Another embodiment relates to the induction of spontaneous callus formation in maize through the complex formation of maize ERF115_2 (SEQ ID NO:3) and PAT1_1 (SEQ ID NO:102). Another embodiment relates to the induction of spontaneous callus formation in maize through the complex formation of maize ERF115_2 (SEQ ID NO:3) and PAT1_2 (SEQ ID NO:103). Another embodiment relates to the induction of spontaneous callus formation in maize through the complex formation of maize ERF115_2 (SEQ ID NO:3) and PAT1_3 (SEQ ID NO:104). Another embodiment relates to the induction of spontaneous callus formation in maize through the complex formation of maize ERF115_3 (SEQ ID NO:4) and PAT1_1 (SEQ ID NO:102). Another embodiment relates to the induction of spontaneous callus formation in maize through the complex formation of maize ERF115_3 (SEQ ID NO:4) and PAT1_2 (SEQ ID NO:103). Another embodiment relates to the induction of spontaneous callus formation in maize through the complex formation of maize ERF115_3 (SEQ ID NO:4) and PAT1_3 (SEQ ID NO:104). Another embodiment relates to the induction of callus formation in maize through the expression of PAT1_1 (SEQ ID NO:102). Another embodiment relates to the induction of callus formation in maize through the expression of PAT1_2 (SEQ ID NO:103). Another embodiment relates to the induction of callus formation in maize through the expression of PAT1_3 (SEQ ID NO:104). In a particular embodiment said induction of callus formation in maize through the expression of PAT1 alone occurs in the presence of low auxin concentrations.

It is to be understood that although particular embodiments, specific configurations as well as materials and/or molecules, have been discussed herein for compounds and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

1. ERF115 Interacts with SCL21 and PAT1

By means of tandem affinity purification (TAP), the SCARECROW-LIKE 21 (SCL21) protein was found to copurify with ERF115 (FIG. 1a). SCL21 is a member of the GIBBERELLIN-INSENSITIVE, REPRESSOR of ga1-3, SCARECROW (SCR) (GRAS) transcription factor family, including the known stem cell regulators SCARECROW (SCR) and SHORTROOT (SHR) that control the periclinal division of the endodermis/cortex initial daughter cell[16]. A reverse TAP experiment using SCL21 as bait verified copurification with ERF115, and also revealed interaction with ERF114, being the closest homolog of ERF115 (FIG. 1a). Bimolecular fluorescence complementation (BiFC) confirmed protein interaction between ERF115 and SCL21. Similarly, the SCL21 phylogenetically closest-related PHYTOCHROME A SIGNAL TRANSDUCTION1 (PAT1) protein 17 interacted with ERF115 (FIG. 5g-j). Using the yeast two-hybrid system, the SCL21/PAT1 interaction domain of ERF115 was mapped to the N-terminal sequence that precedes the conserved APETALA2 domain (FIG. 1b FIG. 6a, b). Interaction with the full-length ERF115 was weak (with SCL21) or negative (with PAT1), suggesting intramolecular control of binding affinity. Sequence alignment of the ERF115 subclass B-4 of ERF transcription factors 18 identified a conserved 11-amino-acid (AA) motif in the N-terminal region (FIG. 6c) that appeared sufficient for interaction, because chimeric protein fusions of this 11-AA domain with the distantly related ERF115 family members, ERF2 and ERF6, granted them the ability to interact with SCL21 (FIG. 1c, FIG. 6d).

2. Endogenous Expression of ERF115 and PAT1 in the Root SCN

Figure 1:
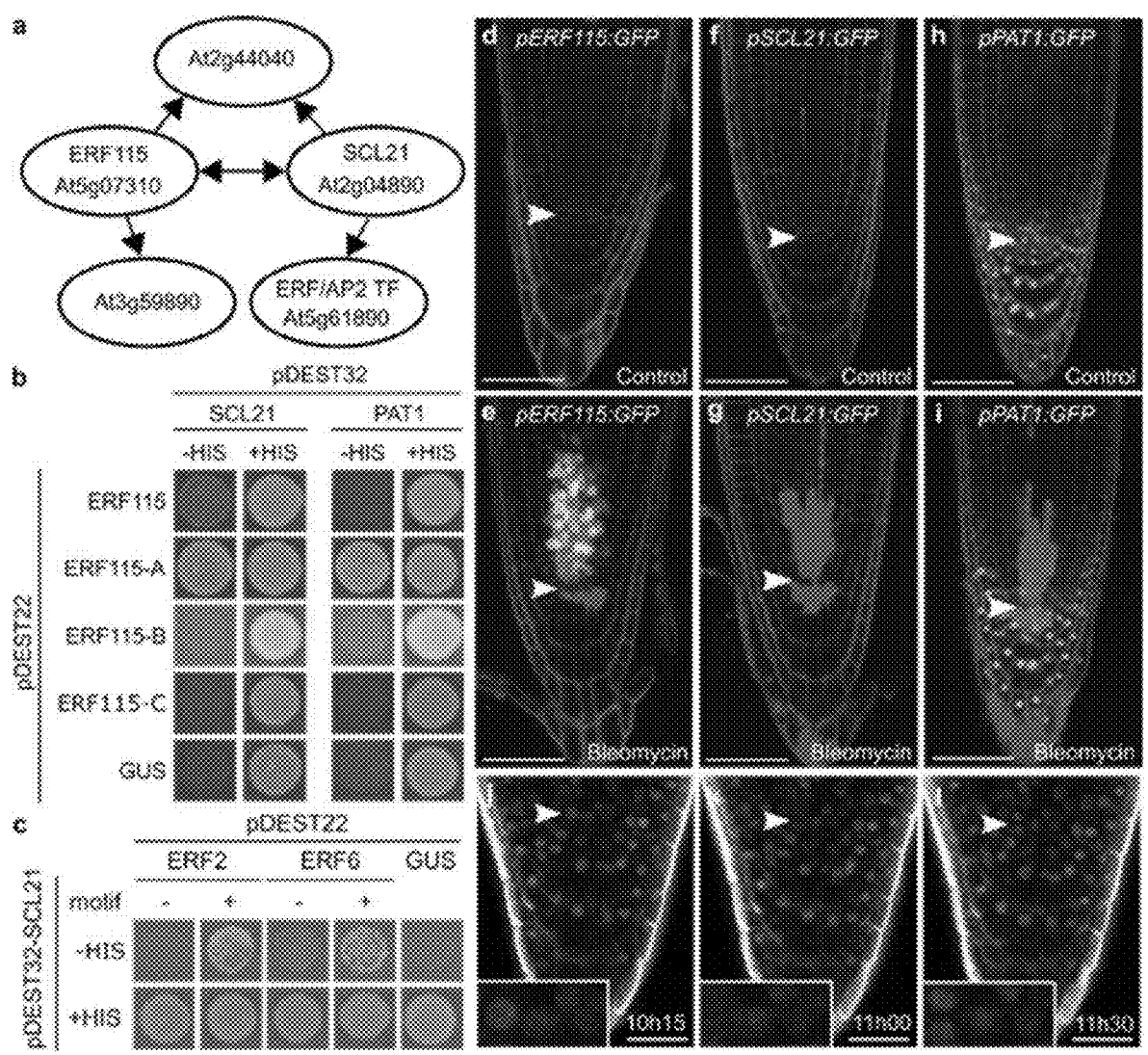
FIG. 1. ERF115 interacts with SCL21 and PAT1.

Whereas ERF115 transcripts are highly abundant in the stem cell niche (SCN) upon exposure to radiomimetic drugs such as bleomycin 14,13 (FIG. 1d, e), transcriptional reporter lines failed to detect SCL21 expression in the root SCN under both control and DNA stress conditions (FIG. 1f, g), suggesting that SCL21 might not be a genuine interaction partner of ERF115 in the root meristem. On the contrary, PAT1 is transcribed in the SCN under both conditions (FIG. 1h, i) and showed a slight increase in expression in the meristem cells upon bleomycin treatment (FIG. 7a, b). Because ERF115 has been demonstrated to promote QC cell division after death of non-QC stem cells, ERF115 and PAT1 were expected to be co-expressed in cells engaged into a cell division cycle, a hypothesis confirmed through time-lapse imaging of dual reporter lines that allowed simultaneous visualization of ERF115 and PAT1 (FIG. 1j-1). Remarkably, ERF115 expression was not confined to the QC cells upon bleomycin treatment, but occurred as well in non-QC cells in direct contact with dead cells, which can be recognized through the uptake of propidium iodide (FIG. 2a). These data suggest an intimate relationship between cell death and ERF115 activity. Indeed, ERF115 was not induced in ataxia telangiectasia (atm) knockout plants that do not undergo meristematic cell death upon bleomycin treatment 13 (FIG. 2b). Reciprocally, ERF115 hyperinduction could only be seen in ataxia telangiectasia and Rad3-related (atr) mutants displaying massive cell death upon treatment with the replication inhibitory drug hydroxyurea (FIG. 2d), in contrast to wild-type plants showing no cell death or ERF115 activation (FIG. 2c). Even a single cell death event, induced through cell-specific laser ablation (FIG. 2e) or naturally occurring (FIG. 2f), coincided with ERF115 expression in the cells in direct contact with the damaged cell. Time-lapse imaging demonstrated that the cell death events were tightly correlated with ERF115 induction, implying a yet to be identified communication from the dying cell to its neighbor.

Spatial expression analysis suggested that ERF115 activity might not be restricted to the QC cells, such as observed under control conditions 14, but might also be required in non-QC cells following meristematic cell death. By means of time tracking, these cells were captured to express PAT1 as well and to undergo cell divisions being perpendicular to the cell surface, being rarely observed in plants grown under control conditions (FIG. 2g, FIG. 7c, d). These cell divisions occurred predominantly in endodermal cells being in direct contact to the bleomycin killed cells (FIG. 2h and FIG. 8a) and were preceded by CYCD6;1 expression, being a cyclin controlling periclinal endodermal cell divisions 19,20 (FIG. 8b). These replenishing cell divisions depended on ERF115 and PAT1 activity, because they occurred less frequently after bleomycin treatment of seedlings overexpressing the dominant-negative ERF115$^{SRDX}$ or being knockout for PAT1 (FIG. 2i, j, and FIG. 8c, d).

Bleomycin treatment mainly triggers vascular cell death and activates ERF115 expression in the neighboring non-dead vascular and endodermal cells (FIG. 2h). To study any tissue-specific response of ERF115 activation, we selectively killed a single cortex cell within the root meristem through laser ablation. Similar to the bleomycin treatment, ERF115 activation could be observed in the endodermal cells, but was absent in the epidermal cells being in direct contact with the ablated cortex cell, indicating that ERF115 induction following cell death required a tissue-specific input signal. PAT1 expression could also be detected in the cells surrounding ablated to ones.

3. ERF115-PAT1 Function

The induction of replenishing cell divisions following ERF115 expression raised the possibility that the ERF115-PAT1 transcription factor complex might play a generic role in tissue regeneration. Previously, it has been found that an excised root tip regenerates a fully functional SCN within less than three days[21]. Root tip excision triggered a rapid transcriptional induction of both ERF115 (FIG. 3a) and PAT1 (FIG. 3b) adjacent to the excision site. Co-expression of ERF115 and PAT1 is confined to the vascular and endodermal cell files (FIG. 3c), being the predominant tissues involved the regeneration of the excised root tissue[22]. De novo root meristem formation appeared to be dependent on the ERF115-PAT1 complex, because only 50 and 41% of erf115-1 and pat1-2 cut roots, respectively, were able to regenerate a novel SCN, compared with 81% for wild-type roots (FIG. 3d). The erf115-1 pat1-2 double mutant showed 53% root tip recovery, similar to that of the erf115-1 and pat1-2 single mutants, suggesting that the two proteins operate as an active complex in SCN regeneration, rather than in two independent pathways. The reason for the lack of a complete regeneration inhibition might be a functional gene redundancy, because ERF115$^{SRDX}$ plants displayed a regeneration frequency of only 7% (FIG. 3d). Pre-cut roots displayed a growth phenotype being identical to that of control plants, excluding the possibility that the regeneration defects are a secondary consequence of impaired root growth.

The root excision experiments suggest the ERF115-PAT1 complex to be not only responsible for the replacement of dead root (stem) cells in response to DNA damage, but for the regeneration process in general. The potent role of the ERF115-PAT1 complex in plant cell regeneration was confirmed through its ectopic overexpression. Whereas plants either overexpressing ERF115 or PAT1 displayed no outspoken growth phenotypes, seedlings expressing both (hereafter referred to as ERF115-PAT1$^{OE}$) displayed clear neoplastic growth, including hypocotyl thickening due to an increased number of cell layers, reduced root growth, and aberrant leaf formation (FIG. 4a-b, and FIG. 9a-d). Expression of the PHYTOSULFOKINE 5 (PSK5) peptide precursor gene, a known direct ERF115 target[14], was hyperactivated in ERF115-PAT1 DE plants compared with control and single overexpression lines (FIG. 9e), indicative for a boosted activity of the ERF115-PAT1 complex. Correspondingly, PSK5 induction could as well be seen in the cells that display ERF115 and PAT1 expression following cell death, such as observed following bleomycin treatment or root tip excision (FIG. 9f-h) Strikingly, in ERF115-PAT1 DE seedlings, the QC-marker WOX5 was expressed ectopically (FIG. 4c-f, and FIG. 10a-e), preceding the development of callus-like structures, suggestive of the uncontrolled activation of regenerative divisions (FIG. 10f, g). Similarly, ERF115-PAT1 DE plants displayed a strong expression of the stem cell marker genes PLT3, PLT5 and PLT7 (FIG. 4g), known to play a crucial role in the initial plant regeneration stages 23.

4. WIND1 is Involved in ERF115-PAT1-Mediated Regeneration

Next to PSK5, WOUND INDUCED DEDIFFERENTIATION 1 (WIND1) was identified as a putative ERF115 target gene through Tandem Chromatin Affinity Purification analysis[14]. WIND1 encodes a transcription factor involved in callus formation in response to woundings. Correspondingly, WIND1 expression was found to be upregulated in ERF/15$^{OE}$ seedlings, which could be hyper-induced upon ERF115-PAT1 co-overexpression (FIG. 4h). Similarly, bleomycin-induced stem cell death also activates WIND1 (FIG. 4i), which appeared to be ERF115-dependent as this induction was abolished in ERF115$^{SRDX}$ seedlings (FIG. 4i). In agreement with ERF115 and WIND1 operating in the same pathway, WIND1$^{SRDX}$ dominant negative seedlings display impaired regenerative capacities upon root tip excision (FIG. 4j), identical to erf115 and pat1-2 mutants. Conversely, whereas spontaneous callus is formed upon ERF115-PAT1$^{OE}$, ERF115$^{SRDX}$ seedlings displayed impaired callus generation capacities when placed on callus inducing medium (FIG. 4k), similar to WIND1$^{SRDX}$ mutants 9. A less pronounced effect on callus formation was observed for the pat1-2 single mutant, whereas the erf115 single mutant showed no callus phenotype. Contrary, the erf115 pat1-2 double mutant appeared to show impaired callus formation similar to ERF115$^{SRDX}$ seedlings (FIG. 11a), again suggesting the co-involvement of ERF115 and PAT1 in callus formation. Combined, these observations suggest that WIND1 activity is at least in part involved in ERF115-PAT1-dependent tissue regeneration. However, in contrast to WIND1, ERF115 expression was not detected upon a mature leaf blade cut that does not trigger regenerations (FIG. 11b), suggesting that WIND1 activation can occur as well independent of ERF115 and suggesting that ERF115 activation upon injury is rather specific to tissues that are able to activate a regeneration program.

5. ERF115 and PAT1 are Required for Granting Regeneration Competence

To test the need for co-presence of ERF115 and PAT1 to efficiently induce callus formation, it was initially tested whether both genes are expressed in developing calli. Seedlings of ERF115 (pERF115:GUS) and PAT1 (pPAT1:GUS) reporter lines were grown for callus induction (see methods). Histochemical GUS staining revealed both reporter lines to be strongly expressed in the calli (FIG. 12 a,b).

Subsequently, it was tested whether ectopic ERF115 or PAT1 expression do trigger enhanced callus formation. Similar as described above, calli were generated from ERF115 (35S:ERF115) and PAT1 (35S:PAT1) overexpression lines. In both cases, no calli bigger being than those obtained from control plants (Col-0) were observed (FIG. 12 c,d, data not shown), fitting with the observation that spontaneous callus formation was only observed in plants co-overexpression both ERF115 and PAT1. Co-requirement of ERF115 and PAT1 was finally demonstrated by the observation that called of erf115 pat1-2 double mutants development poorly into calli, compared to those of the control plants (FIG. 12 e,f).

6. ERF115 Orthologue Sequences

SEQ ID NO: 1 depicts the amino acid sequence of the *Arabidopsis thaliana* Ethylene-responsive transcription factor ERF115 (263 aa).

Orthologue sequence search was supported by phylogenetic tree, orthologue searches in PLAZA (http://bioinformatics.psb.ugent.be/plaza/), and presence of putative SCL/PAT1-interaction domain (indicated in bold) (see also FIG. 6c).

The following species for identification of candidate ERF115 orthologue sequences were evaluated:

*Zea mays* (corn), *Vitis vinifera* (grape), *Populus trichocarpa* (poplar tree), *Solanum lycopersicum* (tomato), *Solanum tuberosum* (potato), *Glycine max* (soy bean), *Gossypium raimondii* (cotton), *Brassica rapa* (turnip), *Hordeum vulgare* (barley), *Oryza sativa* ssp. Indica,& *Japonica* (rice), *Setaria italic* (millet), *Sorghum bicolor* (sorghum), *Theobroma cacao* (cacao), *Elaeis guineensis* (oil palm), *Malus domestica* (apple), *Fragaria vesca* (strawberry), *Eucalyptus grandis* (eucalyptus), *Citrus sinensis* (orange tree), *Carica papaya* (papaya), *Musa acuminate* (banana)

```
> SEQ ID NO: 1: Arabidopsis thaliana ERF115-AT5G07310
MANSGNYGKRPFRGDESDEKKEADDDENIFPFFSARSQYDMRAMVSALTQVIGNQSSSHDNNQHQPVVY

NQQDPNPPAPPTQDQGLLRKRHYRGVRQRPWGKWAAEIRDPQKAARVWLGTFETAEAAALAYDNAALKF

KGSKAKLNFPERAQLASNTSTTTGPPNYYSSNNQIYYSNPQTNPQTIPYFNQYYYNQYLHQGGNSNDAL

SYSLAGGETGGSMYNHQTLSTTNSSSSGGSSRQQDDEQDYARYLRFGDSSPPNSGF*

> SEQ ID NO: 51: Arabidopsis thaliana ERF115-AT5G07310 coding sequence

> SEQ ID NO: 2: Zea mays ERF115 candidate orthologue-ZM10G15700
MERVKYCDCTVCSVQRSLCSTRRRRRRRQIDRQLTKVDPRRRHGKRPLPAAEVEEEEEEALPPGPPP

AKHEQLEEPHHAAVSQLQGATFSGGGGSSSSSVIGGPSPPQAYAQYYYSARADNDASAVASALAHVIRA

SPDQLPPQQAPALYGAGVPGSLRLGDHPQASAHHYPGPGGHVAAAEEEQGRRRHYRGVRQRPWGKWAAE

IRDPKKAARVWLGTFDTAEDAAIAYDEAALRFKGTKAKLNFPERVQGRTDLGFLVTRGIPDHRHPSAAV

TLAAMPPPHHQHGHQTVVPYPDLMQYAQLLQGGRGGGHAEAAVQQAHRQQQQQQLMTMMGGRPGVNLP

STFSPSSSASAPQILDFSTQQLIRPGPPSPSPPRAAAMPSSSAAAAPSTPSSTTTASSPSGGAWPYGGE

RHRNKKDA*

> SEQ ID NO: 52: Zea mays ERF115 candidate orthologue-ZM10G15700 coding
sequence > SEQ ID NO: 3: Zea mays ERF115 candidate orthologue-ZM02G16850
MRISLRVLISSELGTSLCTAAPSLARASVRKSKSSALSLTHARIDRSSSTHRRRRQINGQLTKVDPRRR

HGKRPLPADEEEEEEEELPPPPAKYEQLDQEEKHHVVVSQLQAGATFSGGRGSSSSSVAGPSPEAYAQY

YYSARADHDASAVASALAHVIRASPDQLPPQQAACLYGAAGAPVLRQGEGDHPQPQAAAHHHPGGHVAA

EEEQGLRRHYRGVRQRPWGKWAAEIRDPKKAARVWLGTFDTAEDAAIAYDEAALRFKGTKAKLNFPERV

QGRTDLGFVVTRGIPDHHRHPRAAAVNLAAMPQAQAQPHLQHGRPTVMPYPYPYPDLMQYAQLLQGGRG

GGDHAAAVQQQLMMMGGRGGNLPFSFSPPSSWSAPPQILDFSARQLITQPGPPSSPAAPGGAAPSTPSS

TTTASSPSASASGSAWPYGGEHHRNKKDA*
```

> SEQ ID NO: 53: *Zea mays* ERF115 candidate orthologue-ZM02G16850 coding sequence > SEQ ID NO: 4: *Zea mays* ERF115 candidate orthologue-ZM3G25810
MCFELADQRGPQGGGGAGWPAKRRAGGVQDEGAAAAAGMAMAAAGPGEVMSEYYQAQELSTMVSALTHV

VAGAPMGSAPAQRPMHGASGYYAHEMGSYRGAPSPELAGSELSSDTQSAGAAAMEEHQSAAALSSQEGP

ETPRRRYRGVRQRPWGKWAAEIRDPHKAARVWLGTFETAELAARAYDEAALRFRGSRAKLNFPEDARLY

PASTAGAAAPLAAAASTSPPVYSGGVQGSSDYLRYHQMLLQASTGSQGTLLPFYGGGMSNPYGGGAAMT

GSYGGAGGGNTSGSLGSYYSFPASSVSVATVPSSTSSASGYYYSSPHDSQHSEASAAADWNWESALAWP

DSSQYPPPPHTQ*

> SEQ ID NO: 54: *Zea mays* ERF115 candidate orthologue-ZM3G25810 coding sequence > SEQ ID NO: 5: *Vitis vinifera* ERF115 candidate orthologue-VV17G09050
MSAMVSALTQVIGNTDKNPLHDLGNPSPISHHSATTPHDQPSQLLQDQGNQLRRRHYRGVRQRPWGKWA

AEIRDPNKAARVWLGTFDTAEDAALAYDEAALRFKGNKAKLNFPERVQGRSELGYLTNPPSRWRW*

> SEQ ID NO: 55: *Vitis vinifera* ERF115 candidate orthologue-VV17G09050 coding sequence > SEQ ID NO: 6: *Vitis vinifera* ERF115 candidate orthologue-VV17G09050
MSAMVSALTQVIGNIDKNPLHDLGNPSPISHHSATTPHDQPSQLLQDQGNQLRRRHYRGVRQRPWGKWA

AEIRDPNKAARVWLGTFDTAEDAALAYDEAALRFKGNKAKLNFPERVQGRSELGYLTNRQDFLLPQQQQ

LPNPAVPPLPHPSLPRPSYPNLHHYAQLLPGGGGDLNHAMSSLYGREASTIQSLSTISSSSSITSHPQH

HQRRRQREEEELQQPQLLQFSSLFGSSSSNDPHNNRRDD

> SEQ ID NO: 56: *Vitis vinifera* ERF115 candidate orthologue-VV17G09050 coding sequence > SEQ ID NO: 7: *Populus trichocarpa* ERF115 candidate orthologue-PT12G10850
MDVMVSALAQVIGSSHNSSAQVQENPLTSTQSSTENDQTQPAVQDQGNARRRHYRGVRQRPWGKWAAEI

RDPKKAARVWLGTFETAEAAALAYDEAALRFKGSKAKLNFPERVPSGGTELGFFTRGQGLHTVTEPVEN

HIMAPLARSQRSQEAINPNNFQYPQFLGTTSGYGLSHVMPPAVPFGGETFLSPTSSSASSNSWPISSQQ

QQQQQEELLRLSMQFGSSYNSRYDPSKYKDEGL*

> SEQ ID NO: 57: *Populus trichocarpa* ERF115 candidate orthologue-PT12G10850 coding sequence > SEQ ID NO: 8: *Solanum lycopersicum* ERF115 candidate orthologue-SL06G068830
SDRIRRGKRRYESEEKEDRNYNHMYSSARSQHDMSTMVAVLSQVIGNKSTTNTNSSSSSSAHHKPLLTL

NHQSNTTAAMQNQLPQLNQQQGNNEKRRRQYRGVRQRPWGKWAAEIRDPEKAARVWLGTFHTAEDAAIA

YDEAALKFKGNKAKLNFPERVQSTTDQFGISYLITNTNHQQHQFQPTNFLPNSDQLQQHHYSNHNADDL

KFGVSPSFYHPTGFNPKALDLVEPSKSSSMTYLVQQASSHQVQEEPRYINHQQEDENNLKFSSYFGTYS

SSGPTLGEFEDQK*

> SEQ ID NO: 58: *Solanum lycopersicum* ERF115 candidate orthologue-SL06G068830 coding sequence > SEQ ID NO: 9: *Solanum lycopersicum* ERF115 candidate orthologue-SL03G118190
MKRSSSNNDQRDEKDTSNIFPIYSSARSQHDMSAMVSALSQVIGNSSSSASGDSSSVHVNPLTLIQQHQ

SQSSTQDQERRRYRGVRQRPWGKWAAEIRDPKKAARVWLGTFETAEGAALAYDEAALRFKGNKAKLNFP

ERVQGQFFQCYDQPATSSNNTSEQNYPNVHHYADLLLRTDNNIDLNFDVSPNTFYHSFDISQSSMEVPV

YHEEQQQVITTHEEEEEDFVKYRGSHFGNSTSSGGTK*

> SEQ ID NO: 59: *Solanum lycopersicum* ERF115 candidate orthologue-
SL03G118190 coding sequence > SEQ ID NO: 10: *Solanum tuberosum* ERF115 candidate orthologue-
ST06G025710
MDRTRHGKRPYESEEKEDTNNNQMYSSARSQHDMSTMVSVLSQVIGNKSRTNTNSSSSSSAHHKPLLTL

NHRSSTTAAMQNQLPQLNQQQGNNERRRRQYRGVRQRPWGKWAAEIRDPEKAARVWLGTFHTAEDAAIA

YDEAALKFKGNKAKLNFPERVQSATDQFGISYLITTTNQFPANNFLPNSDQLQHHYAPAGGSNHNADDL

NFGVSPSSYHPTGKSTVNDLSTQ*

> SEQ ID NO: 60: *Solanum tuberosum* ERF115 candidate orthologue-
ST06G025710 coding sequence > SEQ ID NO: 11: *Glycine max* ERF115 candidate orthologue-GM06G17180
MEGRSISHSSEREEEYDLFPIYSERSQQDMSAMVSALTQVIGGSNSDSLQQHEGLLTSSHNNTSTQNNN

EQSQAPQQEQGSVRRRHYRGVRQRPWGKWAAEIRDPKKAARVWLGTFETAEAAALAYDEAALRFKGSKA

KLNFPERVQGTASEFGYHLTNQHSTSSHDQQASNPIITPHFATTQETYSPSHHFQYAQQQLMGGGSNSF

NNNQDMLRFYGGHNNFVSSQQSASSSSSTALSQNQQDELLRFSMQFGASSHSDHSGNWRGGQ*

> SEQ ID NO: 61: *Glycine max* ERF115 candidate orthologue-GM06G17180
coding sequence > SEQ ID NO: 12: *Gossypium raimondii* ERF115 candidate orthologue-
GR08G21060
MNAMVHALAQVIGNNNSNPLLQLHDDQHPNPTAQQNQSHQQPQPQDQGNARRRHYRGVRQRPWGKWAAE

IRDPKKAARVWLGTFETAEAAALAYDDAALRFKGSKAKLNTPERVQGRLESSYLTTTRQELERTEAPPH

PPPTYPNISQYAQLLSGGLPNTAFNYAMPSGAAYGSWPAFTTSSHSSSSSSSSTTLTSQQQGYMGGFSL

HFGGSSPTSDHTNNMGDYDYYYSRDQ*

> SEQ ID NO: 62: *Gossypium raimondii* ERF115 candidate orthologue-
GR08G21060 coding sequence > SEQ ID NO: 13: *Brassica rapa* ERF115 candidate orthologue-BR03G02730
MNNGKRPFRAGESEEKKEADDDENIFPFFSARSEYDTRAMVSALTQVIGNQSSTHDNNLHHPVEYDQQD

PIQHVPPTQDHGNLRKIHYRGVRQRPWGKWAAEIRDPQKAARVWLGTFETAEAAALAYDEAALKFKGSK

AKLNFPERAQLASNTSTITGLPNYYSSNNQTYYSNPQTNPQNIPYYNQYYYNQYLQQGGNSNDALSYSL

AGGETGGSIYSQTLSNTTSSPAGGSLRQQEDYTRFWHFGDSSPNSGV*

> SEQ ID NO: 63: *Brassica rapa* ERF115 candidate orthologue-BR03G02730
coding sequence > SEQ ID NO: 14: *Brassica rapa* ERF115 candidate orthologue-BR10G25380
MMPFGAGESDERKEADDEENIFPFLSARSQYDTRAMVSALTQVIGNQSSTHDSNQHHPVEYNQQDPIQH

VPPTQDQGNLRKRHYRGVRQRPWGKWAAEIRDPQKAARVWLGTFETAEAAALAYDEAALKFKGSKAKLN

FPERAQLASNASTITGLPNYHSSNNQMYYSNPQTNPQTMPYYNQYYYNQYLQQGGNSNDALSYSLAGGE

TGGSMYNHQSISNTTSSSSGGSSRPQQEQDYARFWHFGDSSPSSGF*

> SEQ ID NO: 64: *Brassica rapa* ERF115 candidate orthologue-BR10G25380
coding sequence > SEQ ID NO: 15: *Hordeum vulgare* ERF115 candidate orthologue-
HV53830G00010
MVSALSHVIRATPDQEPAYYPAGPAAVSREQQHQHAAAIAEEQGRKRHYRGVRQRPWGKWAAEIRDPKK

AARVWLGTFDTAEDAAIAYDEAALRFKGTKAKLNFPERVQGRTDLGFVVTRGIPDRLQQQQHYPAAVGA

PAMRPPLHQQQAVVPYPDLLRYAQLLQGAGSAGGAVNLPFGAMSPPSMSSSSSPHILDFSTQQLIRVSP

ASPAAAISGSATTGPSTSSSTTTASSPGAAWPYTGEQKNNKDS*

> SEQ ID NO: 65: *Hordeum vulgare* ERF115 candidate orthologue-
HV53830G00010 coding sequence > SEQ ID NO: 16: *Oryza sativa* ssp. *Indica* ERF115 candidate orthologue-
OSINDICA_04G24720
MVTALAHVIRAAPDLHLPHHPSSSASAAAHPQQASSFYPTAAAAASSPSDQLAAAAAAAEEQGRRRHYR

GVRQRPWGKWAAEIRDPKKAARVWLGTFDTAEDAAIAYDEAALRFKGTKAKLNFPERVQGRTDLGFLVT

RGIPPAATHGGGYYPSSSPAAGACPPPRQQQTVVPYPDLMRYAQLLQGGVGGSYMPFGGAATMSSSTVS

SSSAPQILDFSTQQLIRAGPPSPMPSSGSGSATAAASSTTSASSPGAWPYGGSERKKKDSSS*

> SEQ ID NO: 66: *Oryza sativa* ssp. *Indica* ERF115 candidate orthologue-
OSINDICA_04G24720 coding sequence > SEQ ID NO: 17: *Oryza sativa* ssp. *Japonica* ERF115 candidate orthologue-
OSINDICA_04G24720
MVTALAHVIRAAPDLHLPHHPSSSASAAAHPQQASSFYPTAAAAASSPSDQLAAAAAAAEEQGRRRHYR

GVRQRPWGRWAAEIRDPKKAARVWLGTFDTAEDAAIAYDEAALRFKGTKAKLNTPERVQGRTDLGFLVT

RGIPPALTHGGGYYPSSSPAAGACPPPRQQQTVVPYPDLMRYAQLLQGGVGGSYMPFGGAATMSSSTVS

SSSAPQILDFSTQQLIRAGPPSPMPSSGSGSATAAASSTTSASSPGAWPYGGSERKKEDSSS*

> SEQ ID NO: 67: *Oryza sativa* ssp. *Japonica* ERF115 candidate orthologue-
OSINDICA_04G24720 coding sequence > SEQ ID NO: 18: *Setaria italica* ERF115 candidate orthologue-
SI007G08350
MPGSIDPAPSADGRRRRRQIDRQLTKVDPRRHGKRPLPADKEEEDQPPPPPPAKHEQLEIEEHRYHVSQ

LQQGATFSAGGGGGGSSSSSAAGAAAGPSPEAYAQYYYSARADHDASAVASALAHVIRASPDQLPPHAF

GGGGGAPPGQGDYQQAAPPAAAAAAAEEEQAAGRRRHYRGVRQRPWGKWAAEIRDPKKAARVWLGTFDTA

EDAAIAYDEAALRFKGTKAKLNFPERVQGRTDMGFLVTRGIPDRHHHQGGAAVTLAAMPPPHRQHHQTV

VPYPDLMQYAQLLQGGGRGGGGAGDHHAEAAAQQAQARLMMMARGGVSLPFGAASFSSSSSSAPQILDF

STQQLIRPGPPSPAAAAPSTPSSTTTASSPGGSAWPYGGEHHRNKKDA*

> SEQ ID NO: 68: *Setaria italica* ERF115 candidate orthologue-
SI007G08350 coding sequence > SEQ ID NO: 19: *Sorghum bicolor* ERF115 candidate orthologue-
SB02G026630
MTKKLISAMAGKQGFKEQQFNDQRRQQASIQGDDIAKSLVGFGGGGGRLISHEQEDAIIVAALRHVVSG

YSTPPPEVVTVAGGEPCGVCGIDGCLGCDFFGAAPELTQQEAVNFGTGQMVATAAAAAAGGEHGQRTRR

RRKKNMYRGVRQRPWGKWAAEIRDPRRAARVWLGTFDTAEEAARAYDCAAIEFRGARAKLNFPGHEALL

PFQGHGHGGDACATAAANAETQTTPMLMTPSPCSADAAAAAPGDWQLGGGVDGGEGDEVWEGLLQDLMK

QDEADLWFLPFSGAASSF*

> SEQ ID NO: 69: *Sorghum bicolor* ERF115 candidate orthologue-
SB02G026630 coding sequence > SEQ ID NO: 20: *Theobroma cacao* ERF115 candidate orthologue-
LOC18608834
MTAMVTALTHVMGTGGSDEQLSFTPSSVPLSQSAVKEEPDPPQPVQDQENTRRRHYRGVRQRPWGKWAA

EIRDPKKAARVWLGTFDTAEDAALAYDRAALKFKGTKAKLNFPERVQGNTEVSYFTGHGDSSTVRPDQN

PTPAATPPSWSQDSYPHLFQYAQLLSSSNDADISYYTSNLFNQEPLSPQFPSMAASPNISSQYHHQDQT

RFSTKYESSSGSDYPEQYGKDSDPSNRSE*

> SEQ ID NO: 70: *Theobroma cacao* ERF115 candidate orthologue-
LOC18608834 coding sequence > SEQ ID NO: 21: *Elaeis guineensis* ERF115 candidate orthologue-
LOC105060414
MVSALAHVISSSLSGVGVGVGRSESVVIQSELNPAMAGPESGSMERELSQPSEEQGNVRRRHYRGVRQR

PWGKWAAEIRDPRKAARVWLGTYNTAEEAAIAYDEAALRFKGTKAKLNFPERVQGRTDLGFLVSRGIPE

-continued

RPPQPITPPPTASYPDLLQYAQLLQSRDEDLHSVASGLFVTDSFTSGSSQVSYHSTSGSSQEFLDFFSQ

MRSSSSSSSRQPRGDQKDKDSNQQQ*

> SEQ ID NO: 71: *Elaeis guineensis* ERF115 candidate orthologue-
LOC105060414 coding sequence > SEQ ID NO: 22: *Elaeis guineensis* ERF115 candidate orthologue-
LOC105051098
MVSALAHVISSSSPGVGVGVGVGGGETREIQPELSPAMAGTGSGSMEIRELSQPSQEQGNVRRRHYRGV

RQRPWGKWAAEIROPKKAARVWLGTFDTAEQAAIAYDEAALRFKGTKAKLNFPERVQGRTDLGFLLSRG

IPERQPEPITPSAAATYPDLLQYAQLLQSRDEDFHNVASGLYIGGSFASGSSQMSPASMSGSSQEFLDF

SSQFGTSSSSTSWPHGDQKDKDSSQHP*

> SEQ ID NO: 72: *Elaeis guineensis* ERF115 candidate orthologue-
LOC105051098 coding sequence > SEQ ID NO: 23: *Malus domestica* ERF115 candidate orthologue-
LOC103433166
MSAMVSALTQVIGTTDDHAAVQPNPTSISDSSLLVKQEPDRSQPVQDQEPVRRRHYRGVRQRPWGKWAA

EIRDPKKAARVWLGTFETAEDAAIAYDNAALKFKGTKAKLNFPERVQGKTDLGILMGSSGSGAASTQRT

QNLMTPAGHIVNPQPAPAPLMMSQQPETFPDLYQYARLLSGNDADFYNYSSYPFNQDPRFTSRFLPSST

HFSSSTASQDSQPPQQGQQDHEEDGGNEDRNWSNPRE*

> SEQ ID NO: 73: Malus domestica ERF115 candidate orthologue-
LOC103433166 coding sequence > SEQ ID NO: 24: Malus domestica ERF115 candidate orthologue-
LOC103420552
MIFDPFCSSARSQHEMSAMVSALAQVLGSNNSQTPAVQEPVEPPLITPQSSAMELHDGQSPQQAQDQGN

VRRRHYRGVRQRPWGKWAAEIRDPKKAARVWLGTFETAEAAAISYDEAALRFKGSKAKLNFPERVQGRI

TELGYLTTTSTQQNLPAEAQSITDHHQPLPDHQYQLQAFPNNVATPHDQYAPYFLSGNEGVNYDDLPTN

LSERERFAFQTSETTSSSLLPFLPSHQQEDQQHPLNYSMPAFGSSSSSSSSNPPPRNRNRRP*

> SEQ ID NO: 74: *Malus domestica* ERF115 candidate orthologue-
LOC103420552 coding sequence > SEQ ID NO: 25: *Malus domestica* ERF115 candidate orthologue-
LOC103454881
MIFEPFCSSARSQHEMSAMVSALSQVLGSTNNQTPAVQVPMEPPMIAPQSSAMESHDDQSPQHARDQGT

ARRRHYRGVRQRPWGKWAAEIRDPKKAARVWLGTFETDEAAALAYDEAALRFKGSKAKLNFPERVQGRI

TELGSLTATSTQQMLPAGTSQGVITDHHHPLSDXQYQLQAFPNNVVTPPHDQYAQYFRSGHECISYDLP

ATLYEREIFAXQTSETTTSSSSLLPFLPSHQQEDQQHPLSYSMPGFGSSSSSSSNPPPRNRNRRP*

> SEQ ID NO: 75: *Malus domestica* ERF115 candidate orthologue-
LOC103454881 coding sequence > SEQ ID NO: 26: *Malus domestica* ERF115 candidate orthologue-
LOC103438752
MYDIATNSQFDVHKVDRKHGKRLLASVESEEKEEDQIFPVYSTRSQQDTSAMVSALAQVIGKNSDQINN

PLDQVQGINPLITSQSSPTETQSQTVLQDQGNLRRQHYRGVRRRPXGKWAAEIRDPVKAARVWLGTFDT

AEAAALAYDKAALKFKGSKAKLNFPERVQGISESGCLALITTDQQDSLNINPPQPNITRPTSSSVFDCT

QYNNVTSSTSLLSSSSMPSQQAAELPSFSMQFGSSFSSSSSGPPHKYRKDFDSSHSR*

> SEQ ID NO: 76: *Malus domestica* ERF115 candidate orthologue-
LOC103438752 coding sequence > SEQ ID NO: 27: *Malus domestica* ERF115 candidate orthologue-
LOC103438754
MVSALAQVIGKNSDQINNPLGQVQGINPLTTSQSSPTETQSQPVLLQDQGNLRRQHYRGVRRRPSGKWA

AEIRDPVKAARVWLGTFDTAEAAALAYDKAALKFKGSKAKXNFPERVQGSSESGCLTLITTDQQDSLNI

NPPQPNITRPTSSSVFDCTQHNNVIYCTSLLSSSSMPSQQAAELPSFSMQFGSSFSSSSSGPPHKYRKD

FDSRHSR*

> SEQ ID NO: 77: *Malus domestica* ERF115 candidate orthologue-
LOC103438754 coding sequence > SEQ ID NO: 28: *Malus domestica* ERF115 candidate orthologue-
LOC103415143
MFFRYTFLLGIRAVSSVVFRSSVVEAILVTTTALQYVQTTRTTISAATSTCSRVKLDKVDLKHGKRPLA

SVESEEKEEDQIFPVYSARSQQDTSAMVSALAQVIGNNSDQINNPLDQVQGISSLITSQSSPTETQSQP

VLLQDQGNLRRQHYRGVRRRPWGKWAAEIRDPIKAARVWLGTFNTAEAAALAYDGAALRFKGSKAKLNF

PERVVQGSSESGCLTITTQLQHSLNNIPPEANISRPTYSNVFDYARYNNVTSTSSSSMPSQQAAELRSF

SMQFGSSSSSSSGPPYKYRKDFDRSHSR*

> SEQ ID NO: 78: *Malus domestica* ERF115 candidate orthologue-
LOC103415143 coding sequence > SEQ ID NO: 29: *Fragaria vesca* ERF115 candidate orthologue-
LOC101303581
MSAMVSALTQVIGNPEEDNKQVQSNPASVKDEPDRSQPVQDQESTVRRRHYRGVRQRPWGKWAAEIRDP

KKAARVWLGTFETAEDAAIAYDNAALKFKGTKAKLNFPERVQGNSSILIQGSSGTTSSGSSVSTERNRS

RPALTVPHHDASYVAPSQPQQESSSFPDLYQYAQLLQSNDIDFSSNYQYPPNNPFNQDYHPQYSTPQFP

PSTYYPSHQQQGQQDDHVQEDHQNENKNWNRRNPSE*

> SEQ ID NO: 79: *Fragaria vesca* ERF115 candidate orthologue-
LOC101303581 coding sequence > SEQ ID NO: 30: *Fragaria vesca* ERF115 candidate orthologue LOC101309928
MSAMVSVLSRVISGDSSTDTDPNPALLQLPQQSSTATPELDQSHQQAAPDQAGSVRRRHYRGVRQRPWG

KWAAEIRDPKKAARVWLGTFETAEAAALAYDEAALRFKGSKAKLNFPERVQGTSESGGYLTTQTVAHQP

LISDYHQQQLVYPNNITTTDQYYPQFYGNLNYGQPDRFYNQPATSSYPPFIPISQAQEEDRQQQPALS

SPMPDFGSPSSSLHPEYPQYDTTRNFDNSHWRG*

> SEQ ID NO :80: *Fragaria vesca* ERF115 candidate orthologue LOC101305928
coding sequence > SEQ ID NO: 31: *Fragaria vesca* ERF115 candidate orthologue-LOC101292641
MAKEQEHAIMVSALEQVIGGGIATRTSGTSQNHCQYATSAAEAGTNKKVVILVSDGDTCQVCKIDGCLG

CEFFPPSNKHGKGKRVKKSKYRGVRQRPWGKWAAEIRDPRRAVRVWLGTFQTAEEAARAYDKAAVEFRG

EKAKLNFPRISSEAGTSTAALTKQSMETDDEVHNQVNPSNEKSANQELGQGSDVKDDEIDRFIWKMLKD

DDGDEDLSTMVNSNMLN*

> SEQ ID NO: 81: *Fragaria vesca* ERF115 candidate orthologue-LOC101292641
coding sequence > SEQ ID NO: 32: *Fragaria vesca* ERF115 candidate orthologue-LOC101309634
MVSALTQVIGNTTHEQNPLQVIDHQVLGNPQVFSAENPVEQSQPAVVLQAQGNVRQHYRGVRRRPWGKW

AAEIRDPHKAARVWLGTFETAEAAALAYDEAALRFKGSKAKLNFPERVQGISPSTSSGLYLAISTSTGH

DHRLANSAPPAAPISRPTTYSINPNNVNIDYDALVSSSQNHGQERTMPQINVQTTLSSTSSASSMPSHH

QQERVQQQEDQQQLLKFPIMPFGGSSSSSSDPPTKYRRDSSGSGDFRR*

> SEQ ID NO: 82: *Fragaria vesca* ERF115 candidate orthologue-LOC101309634
coding sequence > SEQ ID NO: 33: *Eucalyptus grandis* ERF115 candidate orthologue-
LOC104433731
MVSALSRVISTSDDAPSSADDPAAPVQEEHGDPPQQAPDQESVRKKHYRGVRQRPWGKWAAEIRDPKKA

ARVWLGTFETAEDAALAYDRAALKFKGTKAKLNFPERVQGKPEYAAYSNPSHQNSGVNVLPEQINPQPA

PFVPYPHAAFPDLAQYAQLLSSNDAEFPYYVSNLYGQEPFGSQQSSTSSSSISSSSYHYNQQQQQQEP

QNEPSRTSFGWSPSNYDFQGYGDGFDPRNQGQ*

-continued

> SEQ ID NO: 83: *Eucalyptus grandis* ERF115 candidate orthologue-
LOC104433731 coding sequence > SEQ ID NO: 34: *Eucalyptus grandis* ERF115 candidate orthologue-
LOC104426218
MEGRNWKRSKSQAGHVSEETEDGDRKRNNYAYPSSLMETARSQQDTSAIVSALAQVIANPAAAASHHAS

LSSSASLSQSSLHDHQAPDAQVGKNKKLEVSRNYRGVRQRPWGKYAAEIRDPKKAARVWLGTFDTAEGA

ALAYDEAALRFKGNKAKLNFPERVHSLPPPYGPACNASQPQSQLLPPAFSSCDNHVGAQLMDGCAMPPP

RPSYVRGQGPTSSASASDYFQSLQPTPSLSSSSSMPSPFHQHDPQHSFDGFSSSWRSSHE*

> SEQ ID NO: 84: *Eucalyptus grandis* ERF115 candidate orthologue-
LOC104426218 coding sequence > SEQ ID NO: 35: *Eucalyptus grandis* ERF115 candidate orthologue-
LOC104425760
MEGRNWKRSKSQAGHVSAEREDGDKKRNNYAYPSSLMETGRSQQDTSAIVSALAQVIANPAAAESHHAS

LSSSASLSQSSLHDHQAPDAQVGKNKKLEVSRNYRGVRQRPWGKYAAEIRDPKKAARVWLGTFDTAEGA

ALAYDEAALRFKGNKAKLNFPERVHSLPPPYGPASNASQPQSQQLPPAFSSCDNHVGAQLMDGCAMPPP

CPSFVRGQGPTSSASASDYFQSLQPTPSSSSSSSTTSPFHQHDPQHSFDGFSSSWRSSQE*

> SEQ ID NO: 85: *Eucalyptus grandis* ERF115 candidate orthologue-
LOC104425760 coding sequence > SEQ ID NO: 36: *Eucalyptus grandis* ERF115 candidate orthologue-
LOC104415849
MSGLKVADRGDKAPILYPGLDRERETSAMVLALARVVAGEVPGDAEESCPFPFPSGVLRLKRGHGDLSA

EPSAEAQLRRAPGRESSVDDAARGIMEGPSMKTTNHATPTYEYSNSTAAMSMSNDEHQPRRKYRGVRQR

PWGKWAAEIRDPVKAARVWLGTFETAEGAAQAYDVAALKYRGNKAKLNFPENvvARLSLAAPPATQMTV

PDAARTHVTVPADTEHQLASGPDHGCGEWCSWLSPDPDLAHSNLLPSSSSPSSSSSSVSKAASFAFPTR

SGSWPF*

> SEQ ID NO: 86: *Eucalyptus grandis* ERF115 candidate orthologue-
LOC104415849 coding sequence > SEQ ID NO: 37: *Eucalyptus grandis* ERF115 candidate orthologue-
LOC104450834
MEEAVMPMYSPYCPPGETSAIVSALTHVVTGTRGGQHGGAYQSTLAPSFAYDSASAGSSSQLPWTYIGQ

KRERDEAGSSSQFLAEPPLSQRDYYGIYGGSFALRETSAISASLPGLQARTVAATSNVPPPPSGAGPPP

YEGGERRRYRGVRQRPWGKWAAEIRDPQKAARVWLGTFDTAEAAARAYDEAALRFGNRAKLNFPENV

RVIPPNVPTYGSPAAAAATLAAGSAPPAIAAGQLAPPYAGAVPLYPRGSEGFNLGDYWEYSQLLQGHHH

HQPASLMEQMMYSSQMASSHSSLSLPSSSPPQPPPPPPSFPSSDLYGSSSSSGFGGASSFSSSVPLFFP

QQPPLGYFRPPPPRPPHDQGSGGEDSEPPPSSDSSHYHSSTS*

> SEQ ID NO: 87: *Eucalyptus grandis* ERF115 candidate orthologue-
LOC104450834 coding sequence > SEQ ID NO: 38: *Eucalyptus grandis* ERF115 candidate orthologue-
LOC104418178
MSIMVSALRRVVSGEVLSGDDQQQQFNLSGGYEPAALLGRSSSLDSVGVGQKRGRGDSTSSSEFLVSQD

SVAFGGFPQAGSSSSSDARGHAGSTTVETAKADTADGTAPKYEYNYEAPTTMAASRLDPTVRRKYRGVR

QRPWGKWAAEIRDPFKASRVWLGTFDTAEGAARAYDRAALQFRGSKAKLNFPENVRLRQQPAPVASAAF

PSATHFTISRELPASGNFDATGYDGQAPMQQFPENDFREYHRDVAAHQERLQGRTMSLYEQMLFSNSSF

GSQFQPAFSLSPSSSSSSSSVLARSPNSSLFMPSPPNVTSRSQESRRGSGDGAAVFSQHPWTDSSHYSS

SSG*

> SEQ ID NO: 88: *Eucalyptus grandis* ERF115 candidate orthologue-
LOC104418178 coding sequence > SEQ ID NO: 39: *Eucalyptus grandis* ERF115 candidate orthologue-
LOC104416633
MQQLHDLGMTRDDEHGIMVNALQHVISGSSSTRPEPIPAFRSSTPSHLSADGTAAEQRAPGLLSLPDVA

TCQVCRIDGCLGCNFFAPGRVAMAVQGGGDPAKAAQALGVGQSNKSAGRKRKGFYRGVRQRPWGKWAAE

IRDPRRAARVWLGTFETAEQAARAYDRAALEFRGARAKLNFPLLPNDCTSTGAGKSRDMMEDGEAEETI

KARAEGGESNDVREKAPSFERDDERGASEFWEKLEKEELEQWPVMHLPP*

> SEQ ID NO: 89: *Eucalyptus grandis* ERF115 candidate orthologue-
LOC104416633 coding sequence > SEQ ID NO: 40: *Citrus sinensis* ERF115 candidate orthologue-
LOC102629317
MYGTAVVSALSQVIGNTQNSPTSLQLSQNPNFTTSSPNTSERDLSQRVEDQGNVRRRHYRGVRQRPWGK

WAAEIRDPKKAARVWLGTFDTAEAAALAYDEAALRFKGSKAKLNFPERVQANLTTHRYQDHYYHAAAAT

TSQQVSNPPPPPPPRPLPLTQEVMYSNLFQYQQANYGIPSGFYGEYRYLPVTLPTTSSSSSSSSATSSQ

QPQQHELLRYGMQLESSSSSASDPHESTRRNSDTSHPGD*

> SEQ ID NO: 90: *Citrus sinensis* ERF115 candidate orthologue-
LOC102629317 coding sequence > SEQ ID NO: 41: *Citrus sinensis* ERF115 candidate orthologue-
LOC102620304
MSAMVSALTQVIGTTTTDADADPSPAAVKEESSDNPLQQTQTQTQDQDQGTRRRHYRGVRQRPWGKWAA

EIRDPKKAARVWLGTFETAEDAAMAYDKAALKFKGTKAKLNFPERVQGTTEFVYLDSSSSSSAFHHHHE

SVMPAPPPRPTSMHHGAYPDLLQYAQILSSDDATFNYYTSNLFNPQSSSSSSSTPSTFSSSTTSLEQQQ

EMTRFSSNYESLSGSDFQDHSNNPNG*

> SEQ ID NO: 91: *Citrus sinensis* ERF115 candidate orthologue-
LOC102620304 coding sequence > SEQ ID NO: 42: *Citrus sinensis* ERF115 candidate orthologue-
LOC102620304
MSAMVSALTQVIGTTTTDADADPSPAAVKEESSDNPLQQTQTQTQDQDQEGTRRRHYRGVRQRPWGKWA

AEIRDPKKAARVWLGTFETAEDAAMAYDKAALKFKGTKAKLNFPERVQGTTEFVYLDSSSSSSAFHHHH

ESVMPAPPPRPTSMHHGAYPDLLQYAQILSSDDATFNYYTSNLFNPQSSSSSSSTPSTFSSSTTSLEQQ

QEMTRFSSNYESLSGSDFQDHSNNPNG*

> SEQ ID NO: 92: *Citrus sinensis* ERF115 candidate orthologue-
LOC102620304 coding sequence > SEQ ID NO: 43: *Carica papaya* ERF115 candidate orthologue-KM453703.1
MCGGAIISDFIPTATTRSCKLTADYLWPDLNRNRKSKKSSKRSEVVDLDDDFEADFQGFKDDESDIDVD

EDLDDIDAVFSDIKPFAFSATPLPRKTTASALSNGSKPVKAVEFNGLAEKSAKRKRKNQYRGIRQRPWG

KWAAEIRDRRKGVRVWLGTFNTAEEAARAYDAEARRIRGKKAKVNFPDESPRASPKRAVNSMKPVAKAI

LNSAQPNLSQNVNYFNNLGQDYYNTMVFVDEKPQMNQFASMNSFPPRRNAGVKPFVPSDNTHMYFSSDP

GSNSFGCSEFGWGDQATKTPEISSVLLDQPQFVEDCNPEKKLKCSSETMVPVQGNANKSLSEELLAFDN

QMKYLQVPHLDSNWDSSLDAFLNGDAPQDAGNSMDLWAFDDLPSLVGGVF*

> SEQ ID NO: 93: *Carica papaya* ERF115 candidate orthologue-KM453703.1
coding sequence > SEQ ID NO: 44: *Musa acuminata* subsp. *malaccensis* ERF115 candidate
orthologue-LOC103988289
MAACSSGTAKWKLREGKRKRARGWEKAKSKQECRAHQSRRPAQSSERLFLSQSRIIHSLSFLLLRLLLD

RLPLSPLSAVNISVSLSRCCIYLRLSVVFLCRRRCHHQRISPDPLSGRRKEEERSRNDKVDRRPGKRP

LPPDELEKKEGDQQQAVSRFASSRADHDASAMVSALAKVISSSSSVVDTRGGEPASTQQGIKLEEAAGR

GDTEAAQVSEEQGNVRRRHYRGVRQRPWGKWAAEIRDPRKAARVWLGTFDTAEDAAVAYDEAALRFKGT

KAKLNFPERVQGRTDLGFLVSPGVPERQPPRVPLQLPATSYPDLLQYAQLLQSRDEDLQNVASGLYVGG

TFTPVSSQTPTTSALGSSQHFLDFSSQSQYTNFSSSSSSSSSSSWVHGEQKDKDGSRPP*

> SEQ ID NO: 94: *Musa acuminata* subsp. *malaccensis* ERF115 candidate
orthologue-LOC103988289 coding sequence > SEQ ID NO: 45: *Musa acuminata* subsp. *malaccensis* ERF115 candidate
orthologue-LOC104000654
MVSALSRVISSSSSVIDASAGEPTVNQQGIKLEGADPGEKQAIQISEEQGTVRRHYRGVRQRPWGKWAA

EIRDPKKAARVWLGTFDTAEDAAVAYDEAALRFKGSKAKLNFPQRVQGRAELSFLASPGIPRRQPQPPT

RPPASSYPDLFRYAQLLQSGDDNLQSVASGLYVGSAFTSAPSQAPPSSTGSLPQFLGFSSHSPYSSSS

SSSGSWVYGDHKDKDSSRPP*

> SEQ ID NO: 95: *Musa acuminata* subsp. *malaccensis* ERF115 candidate
orthologue-LOC104000654 coding sequence > SEQ ID NO: 46: *Musa acuminata* subsp. *malaccensis* ERF115 candidate
orthologue-LOC103970805
MDRRHGKRPLPPDEAAPEEKAGELSCSPLARADQDASAIVSALAHVIGSCSPVAGVGGGEMRQDVSGSG

TGSVENRTQPSEEQGNAGRRHYRGVRQRPWGKWAAEIRDPQKAARVWLGTFDTAVDAAIAYDEAALRFK

GCKAKLNFPERVQGRSDLGFLTHRWQAQPPVQLPATSYPDLLRYARLLQSRDDDLHNRAVGLHPAGSSF

MSTSSHTTPTSSLSGSSQELVGFSHHWQLRSSSSSSSWPQVDLQDEDED*

> SEQ ID NO: 96: *Musa acuminata* subsp. *malaccensis* ERF115 candidate
orthologue-LOC103970805 coding sequence > SEQ ID NO: 47: *Musa acuminata* subsp. *malaccensis* ERF115 candidate
orthologue-LOC103977129
MVSALSHVISSRSPPVGAGGGEPVMVQHDGKLSGSGSGSAEIRTQPSGEQGRRHYRGVRQRPWGKWAAE

IRDPRKAARVWLGTFDTAEDAAIAYDEAALRFKGTKAKLNFPERVQGRTDLGFLVSGGGSERQPQPPTQ

RLPAANSYPNLLQYAQLLQSRDQDLHQAAFGLYAGSTFTSTSSQTSPTSMSAASSQEMLDFTCQSHFKS

SSSSSSWPHGGHKHEDQQPPGM*

> SEQ ID NO: 97: *Musa acuminata* subsp. *malaccensis* ERF115 candidate
orthologue-LOC103977129 coding sequence > SEQ ID NO: 48: *Musa acuminata* subsp. *malaccensis* ERF115 candidate
orthologue-LOC103976772
MVSALTHVISSVSPVVGAGGDELVAEPDASCGSGPGSMEIGTQASEEQGRRHYRGVRQRPWGKWAAEIR

DPKKAARVWLGTFDRAEDAAMAYDEAALRFKGTKAKLNFPERVQGRTDLGFLVTRAAPERQPQPPATSY

PDLRQYAQLLQSGDADVHNAALGLYAGSTITSTSLSGSSQETQDLSSRSQFTSSSASSSWPQSGQKEKD

QRPPTM*

> SEQ ID NO: 98: *Musa acuminata* subsp. *malaccensis* ERF115 candidate
orthologue-LOC103976772 coding sequence > SEQ ID NO: 49: *Musa acuminata* subsp. *malaccensis* ERF115 candidate
orthologue-LOC103979104
MCHNVANPHQLPDDSFAAEGSDGAPLSSYHRAQEISTIVSALAHVMASERRPRPVGMAVDSVSVVSSSS

SSSSSSSSSLSCISSSYSSPSLGGQGGGARSQNRTRRVPSPPDLALRHHQGLGEFARYRGDASPDVAAT

EQYPQGGPLPILGYPVPAAAMEEPSPASSNPEEAERSEPRRKYRGVRQRPWGKWAAEIRDPHKAARVWL

GTFETAEEAARAYDAAALRFRGRRAKLNFPENVRLQPSLSVPLATSNSPATTSDTITDYLAYTRLLQGG

EEHPRIPPTSLLDQYMYSNYASPMCSTVNDGSSLPAPSIPTYSSVVSSSSTPYSPFYASSTTEQQTNWS

GVSDIPETSWMGSSQFPPSSSGS*

> SEQ ID NO: 99: *Musa acuminata* subsp. *malaccensis* ERF115 candidate orthologue-LOC103979104 coding sequence > SEQ ID NO: 50: *Musa acuminata* subsp. *malaccensis* ERF115 candidate orthologue-LOC103993551
MCLKVANPHQSSDGSFAAAGSDEMEEDAAAAAGMMYSSVTAQAALLSGHRRSRETSTMVSALTRVMAGE

QRPRPVPMAVDSMSAVSSSSSFSYIFSPPPSYSSPSTGGQSGGASSQTRTRPELPSHLALRYYRCLGEF

GSYYGGASPDVAAVEQYPQAFLPMLQSPAPAAAAVEEASPASSNQEERERAAPKRKYRGVRQRPWGKWA

AEIRDPYKAARVWLGTFETAEEAARAYDEAALRFRGSRAKLNFPENVRLQPSHSVALAAQVPPSNSPAT

SSGAVSDYLAYSRLLQGASEYQRLPPASLLDPFVHSGVNDSSSLPASSFHANSVPSSTVISPSSSSSSS

YPPSYASSTPTERQMIWGGASGFPETSWTHSSQFPPSSSGDS*

> SEQ ID NO: 100: *Musa acuminata* subsp. *malaccensis* ERF115 candidate orthologue-LOC103993551 coding sequence 7. PAT1 Orthologue Sequences SEQ ID NO: 101 depicts the amino acid sequence of the *Arabidopsis thaliana* Phytochrome A Signal Transduction 1 (PAT)1 (490 aa).

Orthologue sequence search was supported by phylogenetic tree, orthologue searches in PLAZA (http://bioinformatics.psb.ugent.be/plaza/).

The following species for identification of candidate PAT1 orthologue sequences were evaluated:

*Zea mays* (corn), *Vitis vinifera* (grape), *Populus trichocarpa* (poplar tree), *Solanum lycopersicum* (tomato), *Solanum tuberosum* (potato), *Glycine max* (soy bean), *Gossypium raimondii* (cotton), *Brassica rapa* (turnip), *Hordeum vulgare* (barley), *Oryza sativa* ssp. Indica,& *Japonica* (rice), *Setaria italic* (millet), *Sorghum bicolor* (sorghum), *Theobroma cacao* (cacao), *Elaeis guineensis* (oil palm), *Malus domestica* (apple), *Fragaria vesca* (strawberry), *Beta vulgaris* (beet), *Eucalyptus grandis* (eucalyptus), *Citrus sinensis* (orange tree), *Carica papaya* (papaya), *Musa acuminate* (banana)

> SEQ ID NO: 101: *Arabidopsis thaliana* PAT1-At5g48150
MYKQPRQELEAYYFEPNSVEKLRYLPVNNSRKRFCTLEPFPDSPPYNALSTATYDDTCGSCVTDELNDF

KHKIREIETVMMGPDSLDLLVDCTDSFDSTASQEINGWRSTLEAISRRIDLRADVSCAKAMSENDLMMA

HSMMEKLRQMVSVSGEPIQRLGAYLLEGLVAQLASSGSSIYNALNRCPEPASTELLSYMHILYEVCPYF

KFGYMSANGAIAEAMKEENRVHIIDFQIGQGSQWVTLIQAFAARPGGPPRIRITGIDDMTSAYARGGGL

SIVGNRLAKLAKQFNVPFEFNSVSVSVSEVKPKNLGVRPGEALAVNFAFVLHHMPDESVSTENHRDRLL

RMVKSLSPKVVTLVEQESNTNTAAFFPRFMETMNYYAAMFESIDVTLPRDHKQRINVEQHCLARDVVNI

IACEGADRVERHELLGKWRSRFGMAGFTPYPLSPLVNSTIKSLLRNYSDKYRLEERDGALYLGWMHRDL

VASCAWK*

> SEQ ID NO: 126: *Arabidopsis thaliana* PAT1-At5g48150 coding sequence

> SEQ ID NO: 102: *Zea mays* PAT1 candidate orthologue-ZM01G25390

> SEQ ID NO: 127: *Lea mays* PAT1 candidate orthologue-ZM01G25390 coding sequence > SEQ ID NO: 103: *Zea mays* PAT1 candidate orthologue-ZM02G37800

> SEQ ID NO: 128: *Zea mays* PAT1 candidate orthologue-ZM02G37800 coding sequence > SEQ ID NO: 104: *Zea mays* PAT1 candidate orthologue-ZM07G25570

> SEQ ID NO: 129: *Lea mays* PAT1 candidate orthologue-ZM07G25570 coding sequence > SEQ ID NO: 105: *Vitis vinifera* PAT1 candidate orthologue-VV12G09370

> SEQ ID NO: 130: *Vitis vinifera* PAT1 candidate orthologue-VV12G09370 coding sequence > SEQ ID NO: 106: *Populus trichocarpa* PAT1 candidate orthologue-PT01G36170

-continued

> SEQ ID NO: 131: *Populus trichocarpa* PAT1 candidate orthologue-PT01G36170 coding sequence > SEQ ID NO: 107: *Solanum lycopersicum* PAT1 candidate orthologue-SL04G014830

> SEQ ID NO: 132: *Solanum lycopersicum* PAT1 candidate orthologue-SL04G014830 coding sequence > SEQ ID NO: 108: *Solanum tuberosum* PAT1 candidate orthologue-ST04G011980

> SEQ ID NO: 133: *Solanum tuberosum* PAT1 candidate orthologue-ST04G011980 coding sequence > SEQ ID NO: 109: *Glycine max* PAT1 candidate orthologue-GM02G46730

> SEQ ID NO: 134: *Glycine max* PAT1 candidate orthologue-GM02G46730 coding sequence > SEQ ID NO: 110: *Gossypium raimondii* PAT1 candidate orthologue-GR02G08060

> SEQ ID NO: 135: *Gossypium raimondii* PAT1 candidate orthologue-GR02G08060 coding sequence > SEQ ID NO: 111: *Brassica rapa* PAT1 candidate orthologue-BR01G18810

> SEQ ID NO: 136: *Brassica rapa* PAT1 candidate orthologue-BR01G18810 coding sequence > SEQ ID NO: 112: *Hordeum vulgare* PAT1 candidate orthologue-HV50736G00010

> SEQ ID NO: 137: *Hordeum vulgare* PAT1 candidate orthologue-HV50736G00010 coding sequence > SEQ ID NO: 113: *Oryza sativa ssp. Indica* PAT1 candidate orthologue-OSINDICA_10G14210

> SEQ ID NO: 138: *Oryza sativa ssp. Indica* PAT1 candidate orthologue-OSINDICA_10G14210 coding seuuence > SEQ ID NO: 114: *Oryza sativa ssp. Japonica* PAT1 candidate orthologue-OS10G22430

> SEQ ID NO: 139: *Oryza sativa ssp. Japonica* PAT1 candidate orthologue-OS10G224.30 coding sequence > SEQ ID NO: 115: *Setaria italic* PAT1 candidate orthologue-SI009G27720

> SEQ ID NO: 140: *Setaria italic* PAT1 candidate orthologue-SI009G27720 coding sequence > SEQ ID NO: 116: *Sorghum bicolor* PAT1 candidate orthologue-SBO2G037650

> SEQ ID NO: 141: *Sorghum bicolor* PAT1 candidate orthologue-SB02G037650 coding sequence > SEQ ID NO: 117: *Theobroma cacao* PAT1 candidate orthologue-TC0007G05450

> SEQ ID NO: 142: *Theobroma cacao* PAT1 candidate orthologue-TC0007G05450 coding sequence > SEQ ID NO: 118: *Elaeis guineensis* PAT1 candidate orthologue-LOC105032539

> SEQ ID NO: 143: *Elaeis guineensis* PAT1 candidate orthologue-LOC105032539 coding sequence > SEQ ID NO: 119: *Elaeis guineensis* PAT1 candidate orthologue-LOC105034289

> SEQ ID NO: 144: *Elaeis guineensis* PAT1 candidate orthologue-LOC105034289 coding sequence > SEQ ID NO: 120: *Malus domestica* PAT1 candidate orthologue-LOC103442977

-continued

> SEQ ID NO: 145: *Malus domestica* PAT1 candidate orthologue-LOC103442977 coding sequence > SEQ ID NO: 121: *Fragaria vesca* subsp. *Vesca* PAT1 candidate orthologue-LOC101291701

> SEQ ID NO: 146: *Fragaria vesca* subsp. *Vesca* PAT1 candidate orthologue-LOC101291701 coding sequence > SEQ ID NO: 122: *Beta vulgaris* subsp. *vulgaris* PAT1 candidate orthologue-LOC104891820

> SEQ ID NO: 147: *Beta vulgaris* subsp. *vulgaris* PAT1 candidate orthologue-LOC104891820 coding sequence > SEQ ID NO: 123: *Eucalyptus grandis* PAT1 candidate orthologue-LOC104434750

> SEQ ID NO: 148: *Eucalyptus grandis* PAT1 candidate orthologue-LOC104434750 coding sequence > SEQ ID NO: 124: *Citrus sinensis* PAT1 candidate orthologue-LOC102621664

> SEQ ID NO: 149: *Citrus sinensis* PAT1 candidate orthologue-LOC102621664 coding sequence > SEQ ID NO: 125: *Musa acuminata* subsp. *Malaccensis* PAT1 candidate orthologue-LOC103974444

> SEQ ID NO: 150: *Musa acuminata* subsp. *Malaccensis* PAT1 candidate orthologue-LOC103974444 coding sequence 8. The N-Terminal a Fragment of Several *A. thaliana* ERFs Also Interacts with PAT1 or SCL transcription factors in yeast.

Besides the ERF115-PAT1 and the ERF115-SCL21 interaction that was demonstrated in previous Example 1, the GRAS-domain transcription factors that belong to the PAT1 branch[17] were analysed for interaction with a number of ERFs that contain the SCL-PAT1 interaction motif. As presented in FIG. 13, the *A. thaliana* ERF transcription factors ERF115 (SEQ ID NO: 1), ERF114 (SEQ ID NO: 160), ERF113 (SEQ ID NO: 159), ERF111 (SEQ ID NO: 156), ERF110 (SEQ ID NO: 155), and ERF109 (SEQ ID NO: 154), which all contain the SCL/PAT1 interaction motif in their A-fragment (see FIG. 6, or bold labelled motif in SEQ ID as provided), showed interaction with PAT1 (SEQ ID NO: 101), SCL5 (SEQ ID NO: 164) and/or SCL21 (SEQ ID NO: 161) in Y2H, whereas no interaction was observed for ERF112 (SEQ ID NO: 57, or SEQ ID NO:58), which lacks the ERF/PAT1 interaction domain.

9. PAT1 Overexpression in the Presence of Auxin Triggers Hyperplasia

Although spontaneous callus formation requires the presence of active ERF-PAT1 complex as shown in the present invention, we here also demonstrate for the first time that upon overexpression of PAT1 in seedling grown in medium containing a rather low auxin concentration, increased callus formation resulting in hyperplasia is observed, as compared to wild-type seedlings. Already two weeks post germination, a remarkable difference was observed (FIG. 14b as compared to WT FIG. 14a). Six weeks after germination, the seedlings of the PAT1 overexpression line incubated in low 2,4D containing medium was fully covered by callus tissue (FIG. 14d). This observation suggests that for some crops, or in some transformation protocols, an introduction of PAT1 is sufficient to allow regeneration in a more rapid and more pronounced form.

10. Complex Formation Between ERF115 and SCL21 Leads to Spontaneous Callus Formation As shown in FIG. 15 *a-d*, the *Arabidopsis* seedlings overexpressing ERF115 together with SCL21, for which it was shown that both proteins interact (FIGS. 1 and 5), were also found to induce callus in a spontaneous manner, i.e. without additional hormones such as cytokinin or auxin in the growth medium. Although no biological role in relation to regeneration competence has been identified for the ERF115-SCL21 complex before, the current observation led to the insight that the presence of the interaction motif in the ERF115, and the consequent in vivo interaction with SCL21- or PAT1-related transcription factors is sufficient to provide a bio-tool for increased regeneration of plant cells. Moreover, the expression of the Phytosulfokine peptide precursor genes PSK2, 4 and 5 was also shown to be significantly higher in the co-expressing ERF115-SCL21 overexpression line, indicating that the ERF115 complex activity is triggered, and that the callus induction is not an artefact, but might be linked to responses induced by wounding.

11. Maize ERF115 Orthologues are Induced Upon Wounding, and Shown to Interact with Maize PAT1 Orthologues in Yeast.

We have shown that the ERF115-PAT1 transcription factor complex appears to play a generic role in tissue regeneration, due to the induction of replenishing cell divisions following ERF115 expression induced by wounding. To identify the orthologues in maize, the expression level was analysed via qRT-PCR in 7 day old B73 maize seedlings upon wounding (i.e. after removal of the root tip). Already few hours after wounding, the expression level of *Zea mays* ERF115_1 (SEQ ID NO: 2) slightly increased, and more prominently increased more than 10-fold for *Zea mays* ERF115_2 (SEQ ID NO: 3) and *Zea mays* ERF115_3 (SEQ ID NO: 4). Twenty four hours after root tip excision, the *Zea mays* ERF115_2 expression remained around 10-fold higher as compared to before excision, and the *Zea mays* ERF115_1 expression was induced over 25-fold, as well as the *Zea mays* ERF115_3 expression (FIG. 16a). This result suggests that the ERF115 potential of cell regeneration induction is retained in maize.

In a Y2H experiment, the interaction of the full length ERF115 maize orthologues with the 3 PAT1 maize orthologues was analysed (FIG. 16b). ERF115_1 showed interaction with PAT1_1 (SEQ ID NO: 102) and PAT1_2 (SEQ ID NO:103), but not with PAT1_3 (SEQ ID NO:104). ERF115_2 did not show interaction with any of the 3 PAT1 maize orthologues. And ERF115_3 showed the clearest growth signal, referring to interaction, with maize PAT1_1, although weaker compared to the ERF115_1/PAT1_1 interaction. These results demonstrate that the protein complex between maize orthologues is also formed in yeast, even for some of the full length maize ERF115 orthologues. In *Arabidopsis*, the full length ERF115 did not interact with PAT1 in Y2H, but only the A fragment did, indicating that A-fragment interaction is sufficient for activity towards regeneration competence. The functional complex in maize is hence possibly formed by those ERF115_1,ERF115_2, or ERF115_3 A fragments, since these all contain the SCL/PAT1 interaction motif.

Materials and Methods

Mutant Lines

The PAT1$^{OE}$ transgenic line was generated by inserting the respective cDNA ORF into the pH7GW2 expression vector under control of the CaMV 35S promoter via Gateway recombination and subsequent *Agrobacterium tumefaciens*-mediated transformation of *Arabidopsis thaliana* plants. For GFP reporter constructs, the 2000-bp, 2437-bp, 2163-bp, 3021-bp and 2500-bp promoter regions upstream of the ERF115[14], PAT1, SCL21, WOX5 and PLT5 start codons, respectively, were inserted into the pMK7S*NFm14GW plasmid, driving the NLS-GUS/GFP ORF, yielding a nuclear localized GFP/GUS dual reporter. The pERF115:TdTomato line was generated by recombining the respective promoter fragment in front of the NLS-TdTomato ORF into the pB7m24GW,3 plasmid. The pPSK5:PSK5-GFP line was generated by combining the PSK5 genomic ORF in front of the GFP reporter sequence, under control of the 2548-bp PSK5 promoter region into the pK7m34GW plasmid. The erf115, ERF115$^{OE}$, ERF115$^{Srdx}$ pat1-2, pCYCD6;1:GFP, pSCR:YFP-H2B, atm-1, atr-2, and WIND1$^{SRDX}$ lines were described previously[14,17,19,23,25,26]. Double mutants or reporter line combinations were generated by crossing. In all experiments, the Col-0 ecotype was used as wild type. Primers used for cloning can be found in Table 1.

Plant Medium and Growth Conditions.

Plants were grown under a long-day regime (16 h light/8 h darkness) at 21° C. on agar-solidified culture medium (Murashige and Skoog [MS] medium, 10 g/L saccharose, 0.215 g/L 2-(N-morpholino)ethanesulfonic acid [MES], and 1% plant tissue culture agar). The PAT1OE transgenic line was selected using 15 mg/L hygromycin, the pWOX5:NLS-GUS/GFP, pSCL21:NLS-GUS/GFP, pPAT1:NLS-GUS/GFP and pPSK5:PSK5-GFP transgenic lines using 50 mg/L kanamycin, the pERF115:NLS-TdTomato line using 10 mg/L glufosinate-ammonium. For all treatments, 5-day-old seedlings were transferred to culture medium supplemented with 0.6 mg/L bleomycin sulphate (Calbiochem) or 1 mM hydroxyurea (Sigma) for 24 h.

Callus Induction.

Seedlings were grown in the dark for 1 week in order to obtain etiolated seedlings. Cotyledons and roots were removed with a pair of fine scissors and about 5 mm long hypocotyl segments were placed on callus inducing medium (CIM) (1×MS salts, 1% sucrose, 0.5 g/L MES, 100 mg myo-inositol, 3% Phytagel, 30 mg/L 2,4-D, 1 g/L kinetin) for another 3 weeks.

Cloning and Chimeric Construct Generation.

For chimeric ERF2 and ERF6 allele generation, the 11-AA conserved motif of *Arabidopsis thaliana* ERF115 was fused N-terminally to the full-length ORFs (SEQ ID NO: 165 for ERF2, and SEQ ID NO: 166 for ERF6; also see FIGS. 6c and d) using primer adaptor ligation. Basically, the motif-encoding sequence was incorporated 5' upstream of the ORFs' forward gene-specific primer sequences; as reverse primer, a plasmid-specific primer in which the wild-type ORF was inserted was used.

Bimolecular Fluorescence Complementation and Protein Localization.

The ERF115, SCL21 and PAT1 ORFs were C-terminally tagged with the head- and tail-fragments of the GFP ORF as indicated in the text and inserted into the pK7m34GW plasmid under control of the CaMV 35S constitutive promoter using Gateway cloning. For *Nicotiana benthamiana* leaf blade infiltration, equal concentrations (final OD 600=0.5) of a 2-day-old liquid grown *Agrobacterium tumefaciens* culture containing the respective constructs were incubated in infiltration buffer (10 mM MgCl$_2$, 10 mM MES [pH5.6], 0.1 mM acetosyringone) for 2 h prior to infiltration of 6-week-old plants. Plants were further grown for two days before interaction analysis. As a negative control for the BiFC, single constructs were infiltrated, yielding no detectable GFP signal.

Confocal Microscopy.

Infiltrated *N. benthamiana* leaf segments were analyzed by an Axiovert 100M Confocal Laser Scanning Microscope (Zeiss). *Arabidopsis* material was counterstained using propidium iodide (PI) or SCRI Renaissance 2200 dye (REN). For PI staining, seedlings were incubated in a 10-μM solution for 3 min prior to imaging. For REN staining, seedlings were grown on culture medium supplemented with the SCRI Renaissance 2200 dye in a final dilution of 1/50.000. For treatments, culture medium was supplemented with the REN dye in combination with the respective compound.

For multicolor confocal microscopy, a Zeiss LSM5 Exciter Confocal was used. GFP fluorescence was observed after excitation using a 488-nm laser and detected using the band-pass 505 nm-530 nm emission filter setting, TdTomato fluorescence was observed after excitation using a 543-nm laser and detected using the band-pass 560 nm-615 nm emission filter, PI fluorescence was observed after excitation using a 543-nm laser and detected using the 650 nm long-pass emission filter, REN fluorescence was observed after excitation using a 405-nm laser and detected using the band-pass 420 nm-480 nm emission filter. For cell specific laser ablation, a ten second pulse was given by the UV-laser (405 nm) at full power using a completely open pinhole with a Zeiss LSM710 Confocal.

For time-tracking, excitation using the 488-nm laser at 5% output was used to reduce laser-dependent tissue damage. Images were acquired by 10 min intervals. The number of anticlinal and replenishing type of divisions of each movie were scored independently by two persons and averaged prior to analysis in order to reduce putative discrepancy.

Qrt-PCR Analysis.

RNA was isolated from the respective tissues with the RNeasy isolation kit (Qiagen). DNase treatment with the RQ1 RNase-Free DNase (Promega) was performed prior to cDNA synthesis with the iScript cDNA Synthesis Kit (Bio-Rad). Relative expression levels were determined by qRT-PCR with the LightCycler 480 Real-Time SYBR Green PCR System (Roche). The *Arabidopsis thaliana* ACT, CAK2 and EMB2386 and maize 18S and EFalpha reference genes were used for normalization. In three biological repetitions, total RNA was isolated by means of the RNeasy Plant mini kit (Qiagen). For the root tips, seedlings were sown and grown for 5 days on nylon meshes (Prosep) to facilitate transfer to medium containing 0.6 mg/L bleomycin for 24 h, and subsequent harvesting using a scalpel. Quantitative PCR data were analyzed using the $2^{(-\Delta\Delta C(t))}$ method. Primer sequences can be found in Table 1.

Tandem Affinity Purification.

Cloning of a GS-TAP-tagged ERF115 and SCL21 fusion under the control of the constitutive cauliflower mosaic virus 35S promoter and transformation of *Arabidopsis* cell suspension cultures were performed as described previously[27]. TAP of protein complexes was done using the GS tag[28] followed by protein precipitation and separation[29]. Proteolysis and peptide isolation, acquisition of mass spectra by a 4800 MALDI TOF/TOF Proteomics Analyzer (AB SCIEX), and mass spectrometry-based protein homology identification based on the TAIR genomic data-base, performed as described previously[30]. Experimental background proteins were subtracted based on 40 TAP experiments on wild-type cultures and cultures expressing TAP-tagged mock proteins GUS, RFP, and GFP 29.

Histochemical Staining Assay.

GUS staining was performed as described previously[31]. Following staining, samples were cleared in a 75%/25% ethanol/acetic acid solution before mounting on slides using lactic acid. Samples were observed under a BX51 microscope (Olympus).

Root Cutting Assays.

Root cutting experiments were performed as described previously[7]. Root tip regeneration after 72 hours post cut was scored negative when a collapse of the root meristem was observed.

Yeast Two-Hybrid.

The Y2H assay was performed as described previously 31,32.

Hypocotyl Sections.

Sections were performed as previously described[33,34].

In silico analysis of PAT1 and ERF115 orthologues Reciprocal blast searches in combination with phylogenetics and protein domain analysis identified three putative ERF115 and three putative PAT1 maize orthologous sequences (as depicted in SEQ ID NOs:2-4 for ERF115 and SEQ ID NOs:102-104 for PAT1, respectively). The presumptive maize ERF115 genes all contain the conserved amino acid motif in the N-terminal domain that has been identified as the PAT1 interaction motif, as revealed by sequence alignment.

Sequences Listed as Reference

In the ERF sequences, the presence of the SCL/PAT1-interaction domain is indicated in bold.

> SEQ ID NO: 151: Arabidopsis thaliana ERF2-AT5G47220
MYGQCNIESDYALLESITRHLLGGGGENELRLNESTPSSCFTESWGGLPLKENDSEDMLVYGLLKDAFH
FDTSSSDLSCLFDFPAVKVEPTENFTAMEEKPKKAIPVTETAVKAKHYRGVRQRPWGKFAAEIRDPAKN
GARVWLGTFETAEDAALAYDIAAFRMRGSRALLNFPLRVNSGEPDPVRITSKRSSSSSSSSSSSTSSSE
NGKLKRRRKAENLTSEVVQVKCEVGDETRVDELLVS*

> SEQ ID NO: 165: Arabidopsis thaliana ERF2-AT5G47220 coding sequence

> SEQ ID NO: 152: Arabidopsis thaliana ERF6-AT4G17490
MATPNEVSALFLIKKYLLDELSPLPTTATTNRWMNDFTSFDQTGFEFSEFETKPEIIDLVTPKPEIFDF
DVKSEIPSESNDSFTFQSNPPRVTVQSNRKPPLKIAPPNRTKWIQFATGNPKPELPVPVVAAEEKRHYR
GVRMRPWGKFAAEIRDPTRRGTRVWLGTFETAIEAARAYDKEAFRLRGSKAILNFPLEVDKWNPRAEDG
RGLYNKRKRDGEEEEVTVVEKVLKTEESYDVSGGENVESGLTAIDDWDLTEFLSMPLLSPLSPHPPFGY
PQLTVV*

> SEQ ID NO: 166: Arabidopsis thaliana ERF6-AT4G17490 coding sequence

> SEQ ID NO: 153: Arabidopsis thaliana ERF108-AT1G43160
MVSMLTNVVSGETEPSASATWTMGHKREREEFSLPPQPLITGSAVTKECESSMSLERPKKYRGVRQRPW
GKWAAEIRDPHKATRVWLGTFETAEAAARAYDAAALRFRGSKAKLNFPENVGTQTIQRNSHFLQNSMQP
SLTYIDQCPTLLSYSRCMEQQQPLVGMLQPTEEENHFFEKPWTEYDQYNYSSFG*

> SEQ ID NO: 167: Arabidopsis thaliana ERF108-AT1G43160 coding sequence

> SEQ ID NO: 154: Arabidopsis thaliana ERF109-AT4G34410
MHYPNNRTEFVGAPAPTRYQKEQLSPEQELSVIVSALQHVISGENETAPCQGFSSDSTVISAGMPRLDS
DTCQVCRIEGCLGCNYFFAPNQRIEKNHQQEEEITSSSNRRRESSPVAKKAEGGGKIRKRKNKKNGYRG
VRQRPWGKFAAEIRDPKRATRVWLGTFETAEDAARAYDRAAIGFRGPRAKLNFPFVDYTSSVSSPVAAD
DIGAKASASASVSATDSVEAEQWNGGGGDCNMEEWMNMMMMMDFGNGDSSDSGNTIADMFQ > SEQ ID NO: 168: Arabidopsis thaliana ERF109-AT4G34410 coding sequence > SEQ ID NO: 155: Arabidopsis thaliana ERF110-AT5G50080
MSAMVSALTQVVSARSQTEAEGAHSSSSSAGHKRGWLGIDSAPIPSSFARVDSSHNPIEESMSKAFPEE
AREKKRRYRGVRQRPWGKWAAEIRDPHRAARVWLGTFPDTAEAAARAYDEAALRFRGNKAKLNFPEDVRI
LPPPPPLLRSPADTVANKAEEDLINYWSYTKLLQSSGQRSFLERGQEESSNIFEHSPMEQPLPPSSSGP
SSSNFPAPSLPNT*

> SEQ ID NO: 169: Arabidopsis thaliana ERF110-AT5G50080 coding sequence

> SEQ ID NO: 156: Arabidopsis thaliana ERF111-AT5G64750
MCVLKVANQEDNVGKKAESIRDDDHRTLSEIDQWLYLFAAEDDHHRHSFPTQQPPPSSSSSSLISGFSR
EMEMSAIVSALTHVVAGNVPQHQQGGGEGSGEGTSNSSSSSGQKRRREVEEGGAKAVKAANTLTVDQYF
SGGSSTSKVREASSNMSGPGPTYEYTTTATASSETSSFSGDQPRRRYRGVRQRPWGKWAAEIRDPFKAA -continued RVWLGTFDNAESAARAYDEAALRFRGNKAKLNFPENVKLVRPASTEAQPVHQTAAQRPTQSRNSGSTTT
LLPIRPASNQSVHSQPLMQSYNLSYSEMARQQQQFQQHHQQSLDLYDQMSFPLRFGHTGGSMMQSTSSS
SSHSRPLFSPAAVQPPPESASETGYLQDIQWPSDKTSNNYNNSPSS*

> SEQ ID NO: 170: *Arabidopsis thaliana* ERF111-AT5G64750 coding sequence

> SEQ ID NO: 157: *Arabidopsis thaliana* ERF112-AT2G33710
MHSGKRPLSPESMAGNREEKKELCCCSTLSESDVSDFVSELTGQPIPSSIDDQSSSLTLQEKSNSRQRN
YRGVRQRPWGKWAAEIRDPNKAARVWLGTFDTAEEAALAYDKAAFEFRGHKAKLNFPEHIRVNPTQLYP
SPATSHDRIIVTPPSPPPPIAPDILLDQYGHFQSRSSDSSANLSMNMLSSSSSSLNHQGLRPNLEDGEN
VMTTISTEDDRRRQQHASPDRPIK*

> SEQ ID NO: 158: *Arabidopsis thaliana* ERF112-AT2G33710-alternatively
spliced
MHSGKRPLSPESMAGNREEKKELCCCSTLSESDVSDFVSELTGQPIPSSIDDQSSSLTLQEKSNSRQRN
YRGVRQRPWGKWAAEIRDPNKAARVWLGTFDTAEEAALAYDKAAFEFRGHKAKLNFPEHIRVNPTQLYP
SPATSHDRIIVTPPSPPPPIAPDILLDQYGHFQSRSSDSSANLSMNMLSSSSSSLNHQGLRPNLEDGEN
VKNISIHKRRK*

> SEQ ID NO: 171: *Arabidopsis thaliana* ERF112-AT2G33710 coding sequence

> SEQ ID NO: 159: *Arabidopsis thaliana* ERF113-AT5G13330
MVSALSRVIENPTDPPVKQELDKSDQHQPDQDQPRRRHYRGVRQRPWGKWAAEIRDPKKAARVWLGTFE
TAEEAALAYDRAALKFKGTKAKLNFPERVQGPTTTTTISHAPRGVSESMNSPPPRPGPPSTTTTSWPMT
YNQDILQYAQLLTSNNEVDLSYYTSTLFSQPFSTPSSSSSSSQQTQQQQLQQQQQQREEEEKNYGYNYY
NYPRE*

> SEQ ID NO: 172: *Arabidopsis thaliana* ERF113-AT5G13330 coding sequence

> SEQ ID NO: 160: *Arabidopsis thaliana* ERF114-AT5G61890
MYGKRPFGGDESEEREEDENLFPVFSARSQHDMRVMVSALTQVIGNQQSKSHDNISSIDDNYPSVYNPQ
DPNQQVAPTHQDQGDLRRRHYRGVRQRPWGKWAAEIRDPKKAARVWLGTFETAESAALAYDEAALKFKG
SKAKLNFPERVQLGSNSTYYSSNQIPQMEPQSIPNYNQYYHDASSGDMLSFNLGGGYGSGTGYSMSHDN
STTTAATTSSSSGGSSRQQEEQDYARFWRFGDSSSSPHSGY*

> SEQ ID NO: 173: *Arabidopsis thaliana* ERF114-AT5G61890 coding sequence

> SEQ ID NO: 161: *Arabidopsis thaliana* Scarecrow-Like 21-AT2G04890

> SEQ ID NO: 174: *Arabidopsis thaliana* Scarecrow-Like 21-AT2G04890
coding sequence > SEQ ID NO: 162: *Arabidopsis thaliana* Scarecrow-Like 1-AT1G21450

> SEQ ID NO: 175: *Arabidopsis thaliana* Scarecrow-Like 1-AT1G21450
coding sequence > SEQ ID NO: 163: *Arabidopsis thaliana* Scarecrow-Like 13-AT4G17230

> SEQ ID NO: 176: *Arabidopsis thaliana* Scarecrow-Like 13-AT4G17230
coding sequence > SEQ ID NO: 164: *Arabidopsis thaliana* Scarecrow-Like 5-AT1G50600,
depicted here as shorter annotated protein (as compared to TAIR)

> SEQ ID NO: 177: *Arabidopsis thaliana* Scarecrow-Like 5-AT1G50600,
depicted here as shorter annotated encoding nucleotide sequence (as
compared to TAIR)

> SEQ ID NO: 178: *Zea mays* ERF115_1 synthetic CDS used for cloning

> SEQ ID NO: 179: *Zea mays* ERF115_2 synthetic CDS used for cloning

> SEQ ID NO: 180: *Zea mays* ERF115_3 synthetic CDS used for cloning

> SEQ ID NO: 181: *Zea mays* PAT1_1 synthetic CDS used for cloning

> SEQ ID NO: 182: *Zea mays* PAT1_2 synthetic CDS used for cloning

> SEQ ID NO: 183: *Zea mays* PAT1_3 synthetic CDS used for cloning

TABLE 1

Primer sequences

| cloning primers | Sequence |
| --- | --- |
| ERF115_A_Fragment_FW | ATGGCGAATTCAGGAAATTATGG |
| ERF115_A_Fragment_REV | TCACTTCCTCAATAGCCCTTG |
| ERF115_B_Fragment_FW | ATGAGGCACTATAGAGGGGTAAG |
| ERF115_B_Fragment_REV | TCAAGCTCTCTCAGGGAAATTG |
| ERF115_C_Fragment_FW | ATGCAACTAGCAAGTAACACTAG |
| ERF115_C_Fragment_REV | TCAAAAACCAGAATTAGGAGGTG |
| ERF2_motif_fusion_FW | ATGGTCTCAGCCTTGACTCAAGTCATTGGAAACATGTACGGACAGTGCAATATAG |
| ERF2_motif_fusion_REV | GGGGACAAGTTTGTACAAAAAAGCAGGCTTG |
| ERF6_motif_fusion_FW | ATGGTCTCAGCCTTGACTCAAGTCATTGGAAACATGGCTACACCAAACGAAGTATC |
| ERF6_motif_fusion_REV | GGGGACAAGTTTGTACAAAAAAGCAGGCTTG |
| PLT5_promoter_FW | TCTTATATCTAGTGTATTTTCACC |
| PLT5_promoter_REV | CTTTGGGAATAGGTTTTTTTTTTC |
| PAT1_promoter_FW | GACCAATAGATGATATACAAGTG |
| PAT1_promoter_REV | TTCTAGTCACTTCAATGATCTGC |
| PAT1_ORF_FW | ATGTACAAGCAGCCTAGACAAGAGC |
| PAT1_ORF_STOP_REV | TCATTTCCAAGCACACGAGGCAACC |
| PAT1_ORF_withoutSTOP_REV | TTTCCAAGCACACGAGGCAACCAAATC |
| PSK5_promoterWFW | CCTGAGTTGCAGAGTGGAGA |
| PSK5_promoterWREV | TCTTTTATATGACTACTTATGATACAATTC |
| PSK5_ORF_FW | ATGGTTAAGTTCACAACTTTCCTC |
| PSK5_ORF_withoutSTOP_REV | GGGATTGTGGTTTTGAGTGTAG |
| SCL21_promoterWFW | TAGGTCACGATTCGTGCC |
| SCL21_promoterWREV | CACAAATAAGCAAGTAAGAATCTTT |
| SCL21_ORF_FW | ATGGACAATGTAAGAGGTTCAATAA |
| SCL21_ORF_STOP_REV | TCACTTCCATGCACAAGATGAG |
| SCL21_ORF_withoutSTOP_REV | CTTCCATGCACAAGATGAGAC |
| WOX5_promoterWFW | AGTAGTTAGAGCCACCATACCCAA |
| WOX5_promoterWREV | GTTCAGATGTAAAGTCCTCAACTG |
| RT-qPCR | |
| ACT_FW | GGCTCCTCTTAACCCAAAGGC |
| ACT_REV | CACACCATCACCAGAATCCAGC |
| CAK2_FW | ACCACCATTAACGTGCGTCAAC |
| CAK2_REV | GATCTTGGCGAGAGAATCGGTATC |
| EMB2386_FW | CTCTCGTTCCAGAGCTCGCAAAA |
| EMB2386_REV | AAGAACACGCATCCTACGCATCC |
| PAT1_FW | TTTGCCTTTGTGCTTCATCA |
| PAT1_REV | CATCGCGGCATAGTAGTTCA |
| PLT1_FW | ACGAAAACCAATCCAACCAC |

TABLE 1-continued

Primer sequences

| | |
|---|---|
| PLT1_REV | ATTGGACGCTAGGCATCAAG |
| PLT2_FW | GAGGTTCCAAAAGTGGCTGA |
| PLT2_REV | CGTTGGTTTGATGAATGTCG |
| PLT3_FW | GGACGGGAAGATATGAAGCA |
| PLT3_REV | AGGGAAATTGGTGGTAGCAG |
| PLT5_FW | CAGGCACGAATTGGAAGAGT |
| PLT5_REV | AGGCATTAGTCCACCCACAG |
| PLT7_FW | GGATATGACAAGGAAGATAGAGCA |
| PLT7_REV | TGCAATAAACTCTTGCTTGGTC |
| PSK5_FW | GCATCAGCTCGGCTCAAT |
| PSK5_REV | GCATTCTTCTTCTCCAACACC |
| WIND1_FW | CCCGGCTTAACTTCCCTAAC |
| WIND1_REV | TAGATCTGGCGACGAAACCT |
| WOX5_FW | GGCTAGGGAGAGGCAGAAAC |
| WOX5_REV | TCCACCTTGGAGTTGGAGTC |
| ERF115_1 FW | AAAGACGCGTGATCGAGAGCTG |
| ERF115_1 REV | ACGTGTTGCTCAATCTTGTCTCAC |
| ERF115_2 FW | AAGTAGCTGTGCGGAGGAATGG |
| ERF115_2 REV | GGGTAAGTGGCAGCGACGATTT |
| ERF115_3 FW | TGATGACACCCGAGTGGTCTTTG |
| ERF115_3 REV | ACACCGATGGAGTCTTGGAGAAC |
| 18S FW | ACCTTACCAGCCCTTGACATATG |
| 18S REV | GACTTGACCAAACATCTCACGAC |
| EF alpha FW | AGTCCGTTGAGATGCACCATG |
| EF alpha REV | CACATACCCACGCTTCAGATCC |

REFERENCES

1. Sena, G. & Birnbaum, K. D. Built to rebuild: in search of organizing principles in plant regeneration. Curr. Opin. Genet. Dev. 20, 460-465 (2010).
2. Birnbaum, K. D. & Sánchez Alvarado, A. Slicing across kingdoms: regeneration in plants and animals. Cell 132, 697-710 (2008).
3. Stappenbeck, T. S. & Miyoshi, H. The role of stromal stem cells in tissue regeneration and wound repair. Science 324, 1666-9 (2009).
4. Melnyk, C. W. & Meyerowitz, E. M. Plant grafting. Curr. Biol. 25, R183-R188 (2015).
5. Thorpe, T. A. History of plant tissue culture. Mol. Biotechnol. 37, 169-180 (2007).
6. Sugimoto, K., Gordon, S. P. & Meyerowitz, E. M. Regeneration in plants and animals: dedifferentiation, transdifferentiation, or just differentiation? Trends Cell Biol. 21, 212-218 (2011).
7. Ikeuchi, M., Sugimoto, K. & Iwase, A. Plant callus: mechanisms of induction and repression. Plant Cell 25, 3159-3173 (2013).
8. Vogel, G. How does a single somatic cell become a whole plant? Science 309, 86 (2005).
9. Iwase, A. et al. The AP2/ERF transcription factor WIND1 controls cell dedifferentiation in Arabidopsis. Curr Biol. 21, 508-14 (2011).
10. van den Berg, C., Willemsen, V., Hendriks, G., Weisbeek, P. & Scheres, B. Short-range control of cell differentiation in the Arabidopsis root meristem. Nature 390, 287-289 (1997).
11. Sarkar, A. K. et al. Conserved factors regulate signalling in Arabidopsis thaliana shoot and root stem cell organizers. Nature 446, 811-814 (2007).
12. Haecker, A. et al. Expression dynamics of WOX genes mark cell fate decisions during early embryonic patterning in Arabidopsis thaliana. Development 131, 657-668 (2004).
13. Fulcher, N. & Sablowski, R. Hypersensitivity to DNA damage in plant stem cell niches. Proc. Natl. Acad. Sci. USA 106, 20984-20988 (2009).
14. Heyman, J. et al. ERF115 controls root quiescent center cell division and stem cell replenishment. Science 342, 860-863 (2013).

15. Zhang, Y. et al. TOPOISOMERASE1a acts through two distinct mechanisms to regulate stele and columella stem cell maintenance in the *Arabidopsis* root. Plant Physiol. 171, 483-93 (2016).
16. Heidstra, R., Welch, D. & Scheres B. Mosaic analyses using marked activation and deletion clones dissect *Arabidopsis* SCARECROW action in asymmetric cell division. Genes Dev. 18, 1964-9 (2004).
17. Torres-Galea, P., Hirtreiter, B. & Bolle, C. Two GRAS proteins, SCARECROW-LIKE21 and PHYTOCHROME A SIGNAL TRANSDUCTION1, function cooperatively in phytochrome A signal transduction. Plant Physiol. 161, 291-304 (2013).
18. Nakano, T., Suzuki, K., Fujimura, T. & Shinshi, H. Genome-wide analysis of the ERF gene family in *Arabidopsis* and rice. Plant Physiol. 140, 411-432 (2006).
19. Sozzani, R. et al. Spatiotemporal regulation of cell-cycle genes by SHORTROOT links patterning and growth. Nature 466, 128-32 (2010).
20. Koizumi, K., Hayashi, T., Wu, S., Gallagher, K. L. The SHORT-ROOT protein acts as a mobile, dose-dependent signal in patterning the ground tissue. Proc. Natl. Acad. Sci. U.S.A. 109, 13010-5 (2012).
21. Sena, G., Wang, X., Liu, H.-Y., Hofhuis, H. & Birnbaum, K. D. Organ regeneration does not require a functional stem cell niche in plants. Nature 457, 1150-1153 (2009).
22. Efroni, I. et al. Root Regeneration Triggers an Embryo-like Sequence Guided by Hormonal Interactions. Cell 165, 1721-33 (2016).
23. Kareem, A. et al. PLETHORA genes control regeneration by a two-step mechanism. Curr. Biol. 25, 1017-1030 (2015).24.
24. Chera, S. et al. Apoptotic cells provide an unexpected source of Wnt3 signaling to drive hydra head regeneration. Dev. Cell 17, 279-289 (2009).
25. Garcia, V. et al. AtATM is essential for meiosis and the somatic response to DNA damage in plants. Plant Cell. 1, 119-32 (2003)
26. Culligan, K., Tissier, A., & Britt, A. ATR regulates a G2-phase cell-cycle checkpoint in *Arabidopsis thaliana*. Plant Cell. 5, 1091-104 (2004)
27. Van Leene, J. et al. A tandem affinity purification-based technology platform to study the cell cycle interactome in *Arabidopsis thaliana*. Mol Cell Proteomics. 6, 1226-38 (2007)
28. BurckstOmmer, T. et al. An efficient tandem affinity purification procedure for interaction proteomics in mammalian cells. Nat Methods. 3, 1013-9 (2006)
29. Van Leene, J., Witters, E., Inzé, D. & De Jaeger, G. Boosting tandem affinity purification of plant protein complexes. Trends Plant Sci. 13, 517-520 (2008)
30. Van Leene, J. et al. Targeted interactomics reveals a complex core cell cycle machinery in *Arabidopsis thaliana*. Mol Syst Biol. 10, 397 (2010)
31. Lammens, T. et al. Atypical E2F activity restrains APC/CCCS52A2 function obligatory for endocycle onset. Proc Natl Acad Sci. 38, 14721-6 (2008)
32. Heyman, J. et al. *Arabidopsis* ULTRAVIOLET-B-INSENSITIVE4 maintains cell division activity by temporal inhibition of the anaphase-promoting complex/cyclosome. Plant Cell. 12, 4394-410 (2011)
33. Gietz, D., St Jean, A., Woods, R. A. & Schiestl, R. H. Improved method for high efficiency transformation of intact yeast cells. Nucleic Acids Res. 20, 1425 (1992)
34. Beeckman, T. and Viane R. Embedding Thin Plant specimens for oriented Sectionings. Biotechn. Histochem. 75, 23-26 (1999)
35. De Smet, I. et al. An Easy and Versatile Embedding method for transverse sections. Journal of Microscopy. 213, 76-80 (2004)
36. Sugiyama, M. Organogenesis in vitro. Curr Opin Plant Biol. 2: 61-64 (1999)
37. Grafi G (2004) How cells dedifferentiate: a lesson from plants. Dev Biol. 268:1-6
38. Mehrnia M., Balazadeh S, Zanor M I, Mueller-Roeber B. EBE, an AP2/ERF transcription factor highly expressed in proliferating cells, affects shoot architecture in *Arabidopsis*. Plant Physiol. 162(2), 842-857 (2013)
39. Boutilier K, Offringa R, Sharma V K, Kieft H, Ouellet T, Zhang L, Hattori J, Liu C M, van Lammeren A A, Miki B L, Custers J B, van Lookeren Campagne M M. Ectopic expression of BABY BOOM triggers a conversion from vegetative to embryonic growth. The Plant Cell. 14, 1737-1749 (2002)
40. Duan et al. Transgenic rice plants harboring an introduced potato proteinase inhibitor II gene are insect resistant. Nat Biotechnol 14:494-498 (1996)
41. McGurl et al. Structure, expression, and antisense inhibition of the systemin precursor gene. Science 225:1570-1573 (1992)
42. De Veylder et al. Herbicide safener-inducible gene expression in *Arabidopsis thaliana*. Plant Cell Physiol 38:568-577 (1997)
43. Cao et al. *Bacillus thuringiensis* protein production, signal transduction, and insect control in chemically inducible PR-1a/cry1Ab broccoli plants. Plant Cell Reports 6:554-60 (2006)
44. Ono et al. Transient assay system for the analysis of PR-1a gene promoter in tobacco BY-2 cells. Biosci. Biotechnol. Biochem. 68:803-7 (2004)
45. Mett et al. Copper-controllable gene expression system for whole plants. PNAS 90:4567-4571 (1993)
46. Caddick et al. An ethanol inducible gene switch for plants used to manipulate carbon metabolism. Nature Biotechnol 16:177-80 (1998)
47. Bruce et al. Expression profiling of the maize flavonoid pathway genes controlled by estradiol-inducible transcription factors CRC and P. Plant cell 12:65-79 (2000)
48. Zuo J, Niu Q W, Chua N H. Technical advance: An estrogen receptor-based transactivator XVE mediates highly inducible gene expression in transgenic plants. Plant J. 24(2):265-73 (2000)
49. Sakuma et al. DNA-binding specificity of the ERF/AP2 domain of *Arabidopsis* DREBs, transcription factors involved in dehydration- and cold-inducible gene expression. Biochem Biophys Res Comm 290:998-1009 (2002)
50. Bolle et al. PAT1, a new member of the GRAS family, is involved in phytochrome A signal transduction. Genes Dev. 14(10):1269-78 (2000)
51. Straub et al. Structure and promoter analysis of an ABA- and stress-regulated barley gene, HVA1 Plant Mol Biol 26:617-630 (1994)

The invention claimed is:

1. A composition comprising:
   a first chimeric gene construct and a second chimeric gene construct;
   the first chimeric gene construct comprising the following operably linked DNA elements:
   a) a plant expressible promoter,
   b) a DNA region encoding an Ethylene Response Factor (ERF) comprising an SCL/PAT1 interaction motif, and
   c) a 3' end region comprising transcription termination and polyadenylation signals functioning in cells of a plant, and the second chimeric gene construct comprising the following operably linked DNA elements:
   a) a plant expressible promoter,
   b) a DNA region encoding Phytochrome A Signal Transduction 1 (PAT1), and
   c) a 3' end region comprising transcription termination and polyadenylation signals functioning in cells of a plant wherein expression of the first chimeric gene construct and the second chimeric gene construct in a plant leads to the formation of an ERF/PAT1 complex,
   wherein the ERF comprising an SCL/PAT1 interaction motif is ERF115, and wherein the plant has increased plant cell regeneration potential without additional hormones as compared to an otherwise identical plant lacking the first chimeric gene construct and the second chimeric gene construct.

2. The composition of claim 1, wherein the DNA region encoding the ERF is selected from the group consisting of SEQ ID NOs: 51-100, and wherein the DNA region encoding the PAT1 is selected from the group consisting of SEQ ID NOs: 126-150.

3. The composition of claim 1,
wherein the first and second chimeric gene constructs are flanked by recombination sites, and
wherein the composition further comprises:
 a third chimeric gene construct comprising the following operably linked DNA elements:
  a) a plant expressible promoter,
  b) a DNA region encoding a site-specific recombinase that is capable of recognizing and implementing recombination at the recombination sites, and
  c) a 3' end region comprising transcription termination and polyadenylation signals functioning in cells of a plant.

4. A set of one or more recombinant vectors comprising the chimeric gene constructs of claim 1.

5. A plant, plant cell or plant seed comprising the chimeric gene constructs of claim 1.

6. The plant, plant cell or plant seed of claim 5, wherein ERF and PAT1 are co-expressed.

7. A method for producing a transgenic plant, the method comprising introducing into a plant cell the composition of claim 1, and regenerating a plant from the cell.

8. The method according to claim 7, further comprising transiently expressing the chimeric gene constructs.

9. The method according to claim 7, further comprising:
expressing the ERF and PAT1 encoded by the chimeric gene constructs;
forming a callus from the plant cell;
expressing a recombinase; and
excising the chimeric gene constructs with the recombinase.

10. The composition according to claim 1,
wherein the first chimeric gene construct and the second chimeric gene construct form part of a multicistronic gene region;
wherein the plant expressible promoters of the first chimeric gene construct and the second chimeric gene construct are the same and wherein the plant expressible promoter promotes transcription of the multicistronic gene region; and
wherein the 3' end regions comprising transcription termination and polyadenylation signals functioning in cells of a plant of the first chimeric gene construct and the second chimeric gene construct are the same.

11. The chimeric gene construct of claim 10, wherein the DNA region encoding the ERF is selected from the group consisting of SEQ ID NOs: 51-100, and wherein the DNA region encoding the PAT1 is selected from the group consisting of SEQ ID NOs: 126-150.

12. A recombinant vector comprising the gene construct of claim 10.

13. A method for producing a transgenic plant, the method comprising:
introducing into a plant cell the chimeric gene construct of claim 10, and
regenerating a plant from the cell.

14. The method according to claim 13, further comprising transiently expressing the chimeric gene construct.

15. The method according to claim 14, further comprising:
expressing the ERF and PAT1 encoded by the chimeric gene construct;
forming a callus from the plant cell;
expressing a recombinase; and
excising the chimeric gene construct with the recombinase.

16. A plant comprising:
a first chimeric gene construct, a second chimeric gene construct, and an ERF/PAT1 complex;
the first chimeric gene construct comprising the following operably linked DNA elements:
 a) a plant expressible promoter,
 b) a DNA region encoding an Ethylene Response Factor (ERF) comprising an SCL/PAT1 interaction motif, and
 c) a 3' end region comprising transcription termination and polyadenylation signals functioning in cells of the plant, and
the second chimeric gene construct comprising the following operably linked DNA elements:
 a) a plant expressible promoter,
 b) a DNA region encoding Phytochrome A Signal Transduction 1 (PAT1), and
 c) a 3' end region comprising transcription termination and polyadenylation signals functioning in cells of the plant
wherein the ERF comprising an SCL/PAT1 interaction motif is ERF115, and
wherein the plant has increased plant cell regeneration potential without additional hormones as compared to an otherwise identical plant lacking the first chimeric gene construct and the second chimeric gene construct.

* * * * *